(12) United States Patent
Zhang et al.

(10) Patent No.: US 11,382,971 B2
(45) Date of Patent: *Jul. 12, 2022

(54) MEVALONATE PATHWAY INHIBITOR AS HIGHLY-EFFICIENT VACCINE ADJUVANT

(71) Applicant: Tsinghua University, Beijing (CN)

(72) Inventors: Yonghui Zhang, Beijing (CN); Yun Xia, Beijing (CN); Yonghua Xie, Beijing (CN); Zhengsen Yu, Beijing (CN); Xiaoying Zhou, Beijing (CN); Xin Li, Beijing (CN); Liping Li, Beijing (CN); Yunyun Yang, Beijing (CN); Kanzhao Gao, Beijing (CN); Ke Wang, Jiangsu (CN); Wanli Liu, Beijing (CN); Meng Zhao, Beijing (CN)

(73) Assignee: Tsinghua University, Beijing (CN)

( * ) Notice: Subject to any disclaimer, the term of this patent is extended or adjusted under 35 U.S.C. 154(b) by 10 days.

This patent is subject to a terminal disclaimer.

(21) Appl. No.: 15/757,893

(22) PCT Filed: Sep. 8, 2016

(86) PCT No.: PCT/CN2016/098371
§ 371 (c)(1),
(2) Date: Mar. 6, 2018

(87) PCT Pub. No.: WO2017/041720
PCT Pub. Date: Mar. 16, 2017

(65) Prior Publication Data
US 2019/0321465 A1    Oct. 24, 2019

(30) Foreign Application Priority Data

Sep. 9, 2015 (CN) .......................... 201510570517.9
Jan. 14, 2016 (CN) .......................... 201610022707.1

(51) Int. Cl.
*A61P 37/02* (2006.01)
*A61K 39/39* (2006.01)
*A61K 31/663* (2006.01)
*A61K 39/00* (2006.01)

(52) U.S. Cl.
CPC ............ *A61K 39/39* (2013.01); *A61K 31/663* (2013.01); *A61P 37/02* (2018.01); *A61K 2039/55511* (2013.01)

(58) Field of Classification Search
CPC ...... C07F 9/65068; C07F 9/6561; C07F 9/58; A61K 39/39; A61K 31/663; A61K 2039/55511; A61P 37/02
See application file for complete search history.

(56) References Cited

U.S. PATENT DOCUMENTS

| 4,958,839 | A | 9/1990 | Guzik et al. |
| 5,064,856 | A | 11/1991 | Garrity et al. |
| 5,102,911 | A | 4/1992 | Lee et al. |
| 5,583,122 | A * | 12/1996 | Benedict .......... C07F 9/650952 514/89 |
| 7,462,733 | B2 | 12/2008 | McKenna et al. |
| 7,781,418 | B2 | 8/2010 | Ebetino et al. |
| 8,816,082 | B2 * | 8/2014 | Tsantrizos .............. A61P 19/10 546/22 |
| 9,040,563 | B2 | 5/2015 | Sebti et al. |
| 2008/0003201 | A1 | 1/2008 | Chu |

FOREIGN PATENT DOCUMENTS

| CN | 1555271 | A | 12/2004 | |
| CN | 102659840 | A | 9/2012 | |
| CN | 103768595 | A | 5/2014 | |
| EP | 0350002 | A1 | 1/1990 | |
| EP | 1658845 | A1 | 5/2006 | |
| JP | 2014040396 | A | 3/2014 | |
| WO | 2002098354 | A2 | 12/2002 | |
| WO | 2010033978 | A2 | 3/2010 | |
| WO | WO-2010033978 | A2 * | 3/2010 | ........... C07D 471/04 |
| WO | 2011147038 | A1 | 12/2011 | |
| WO | 2011148356 | A1 | 12/2011 | |
| WO | 2012054807 | A2 | 4/2012 | |

OTHER PUBLICATIONS

Park et al. BMC Struct. Biol. 2012, 12:32. (Year: 2012).*
Ghosh et al. J. Med. Chem. 2004, 47, 175-187. (Year: 2004).*
Simoni, D.. et al. "Design, synthesis, and biological evaluation of novel aminobisphosphonates possessing an in vivo antitumour activity through a gl-T lymphocytes-mediated activation mechanism," J. Med. Chem. 51(21) (Oct. 20, 2008): 6800-6807.
Agapkina, J et al. "Specific features of HIV-1 integrase inhibition by bisphosphonate derivatives," European Journal of Medicinal Chemistry. 49 (Dec. 12, 2013): 73-82.
Leon et al. "Isoprenoid biosynthesis as a drug target: bisphosphonate inhibition of *Escherichia coli* K12 growth and synergistic effects of fosmidomycin," J. Med. Chem. (Nov. 10, 2006) 49:7331-7341.
Martin et al. "Activity of bisphosphonates against trypanosoma brucei rhodesiense," J Med. Chem. (Jun. 5, 2002);45:2904-2914.

(Continued)

*Primary Examiner* — Amanda L. Aguirre

(74) *Attorney, Agent, or Firm* — Fox Rothschild LLP

(57) ABSTRACT

Disclosed are inhibitors of mevalonate pathway as an efficient vaccine adjuvant and use thereof. In particular, the inhibitor is an acetoacetyl-CoA transferase inhibitor, a HMG-CoA synthase inhibitor, a HMG-CoA reductase inhibitor, a mevalonate kinase inhibitor, a phosphomevalonate kinase inhibitor, a mevalonate-5-pyrophosphate decarboxylase inhibitor, an isopentenyl pyrophosphate isomerase inhibitor, a farnesyl pyrophosphate synthase inhibitor, a geranylgeranyl pyrophosphate synthase inhibitor or a geranylgeranyl transferase (I, II) inhibitor. Also disclosed is an immunogenic composition comprising inhibitors of mevalonate pathway as an adjuvant.

7 Claims, 51 Drawing Sheets

(56) References Cited

OTHER PUBLICATIONS

Schutter et al. "Design of potent bisphosphonate inhibitors of the human farnesyl pyrophosphate synthase via targeted interactions with the active cite 'capping' phenyls," Bioorg. Med. Chem. Lett. (Jul. 24, 2012); 20:5583-5591.

Schutter et al. "Novel bisphoshonate inhibitors of the human pyrophosphate synthase," Bioorg. Med. Chem. Lett. (Aug. 11, 2010); 20:5781-5786.

Chen et al. "Inhibition of geranylgeranyl diphosphate synthase by bisphosphonates: a crystallographic and computation investigation," J. Med. Chem. (Aug. 23, 2008); 51:5594-5607.

Szabo et al. "An investigation of bone resorption and dicytostelium discoideum growth inhibition by bisphosphonate drugs," J. Med. Chem. (Jun. 8, 2002); 45:2894-2903.

Greenspan et al., "The Inhibition of Cytoplasmic Acetoacetyl-COA Thiolase by a Triyne Carbonate (L-660,631)," Biochemical and Biophysical Research Communications (Aug. 30, 1989); 163(1):548-553.

Kamigaki et al., "Zoledronate-pulsed dendritic cell-based anticancer vaccines," OncoImmunology (2013); 2(9): 1-4.

Office Action (with English translation) dated Apr. 1, 2021 issued in related Chinese Application No. 201680051521.7; 20 pgs.

Zhang et al., "Research Progress of Antitumor Mechanism of Bisphosphonates," Chin Hosp Pharm J. (2008; 28(18): 1590-1593.

Zheng et al., "Progress of Statins in Its Anti-tumor Effect," Medical Recapitulate (2006); 12(10): 605-607.

Jahrling et al., "Passive immunization of Ebola virus-infected cynomolgus monkeys with immunoglobulin from hyperimmune horses" Archives of Virology (1996); 11:135-140.

Tan et al., "Design, Synthesis and Characterization of Peptide-Based Rab Geranylgeranyl Transferase Inhibitors," Department of Chemical Biology and Department of Physical Biochemistry, Max-Planck-Institute of Molecular Physiology and Institute for Molecular Bioscience, The University of Queensland; 1-105, (2009).

Ling et al., "Bisphosphonate Inhibitors of Toxoplasma gondi Growth: In Vitro, QSAR, and In Vivo Investigations," Journal of Medicinal Chemistry (2005); 48(9): 3130-3140.

Zhang et al., "Activity of Nitrogen-Containing and Non-Nitrogen-Containing Bisphosphonates on Tumor Cell Lines," Journal of Medicinal Chemistry (2006); 49: 5804-5814.

Szabo et al., "Inhibition of Geranylgeranyl Diphosphate Synthase by Bisphosphonates and Diphosphates: A Potential Route to New Bone Antiresportion and Antiparasitic Agents," Journal of Medicinal Chemistry (2002): 45; 2185-2196.

International Search Report dated Jan. 18, 2019 issued in related International Patent Application No. PCT/CN2018/110256.

* cited by examiner

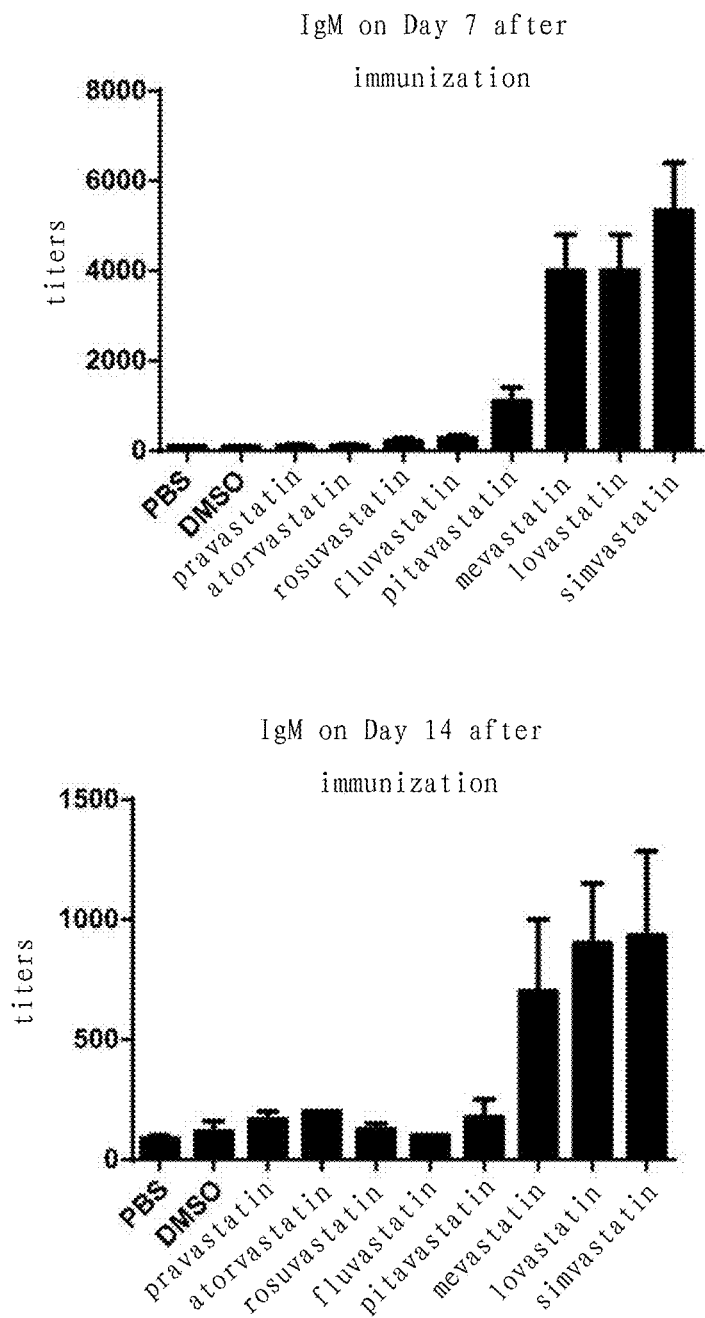
Figure. 2A-B

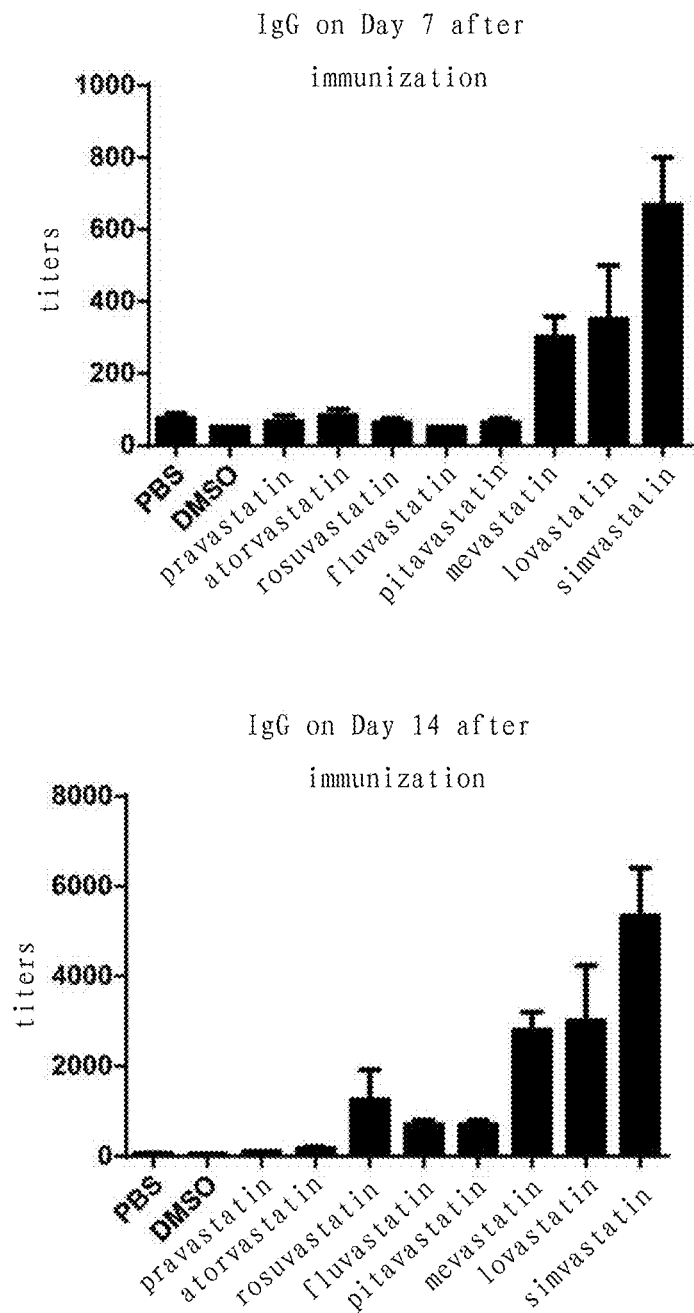
Figure. 2C-D

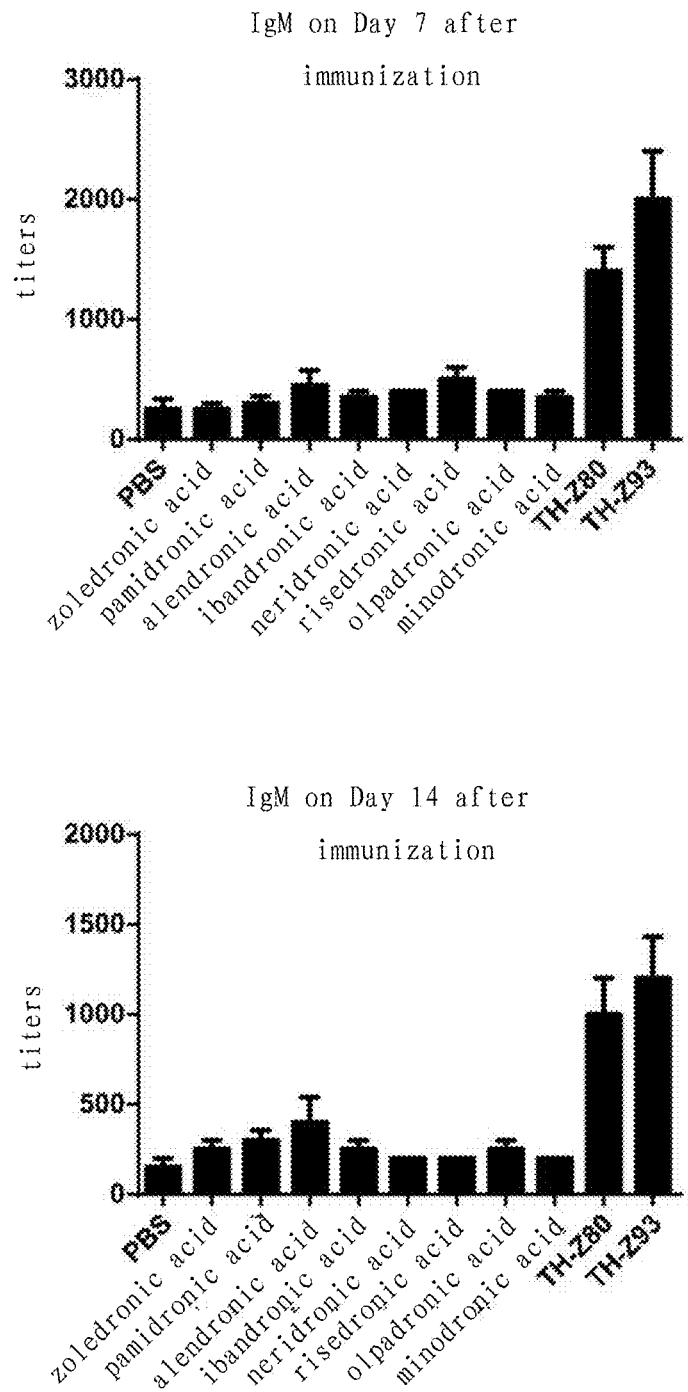
Figure. 5A-B

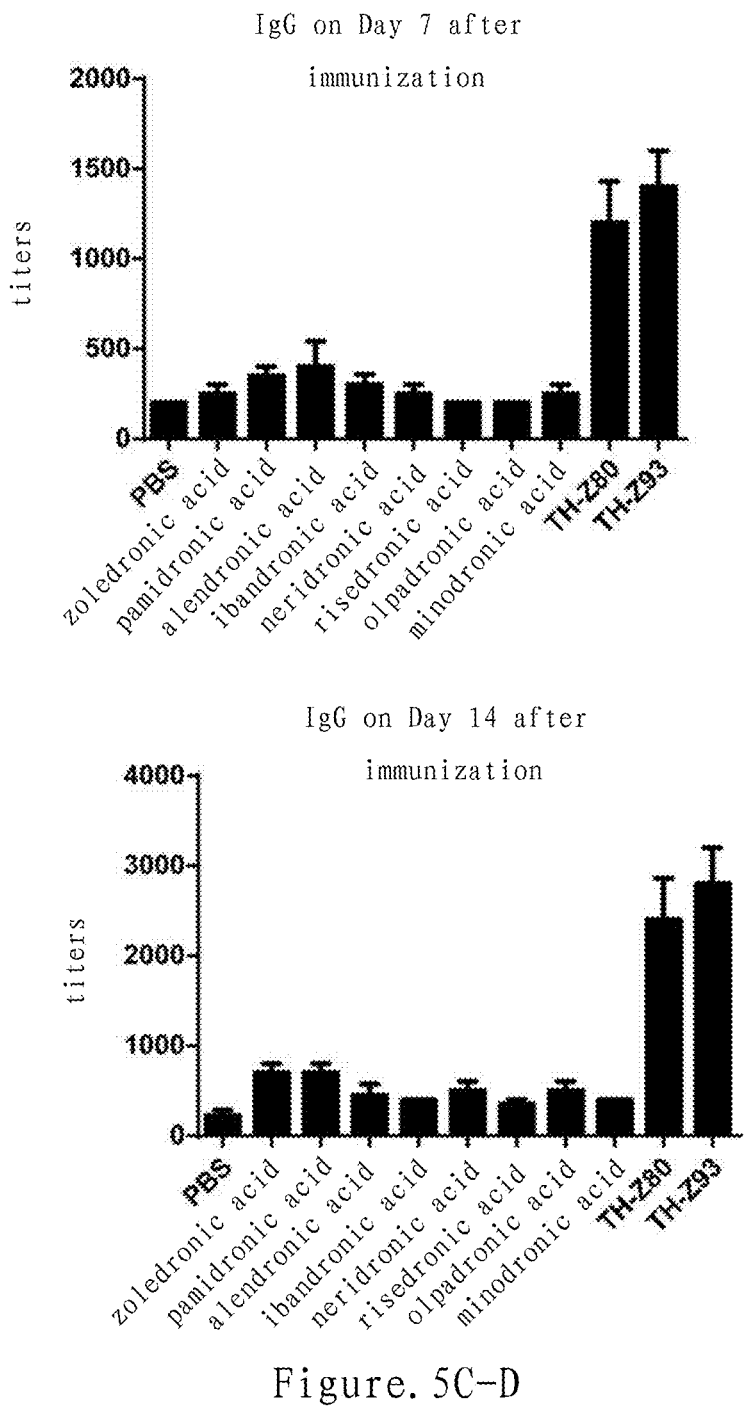
Figure. 5C-D

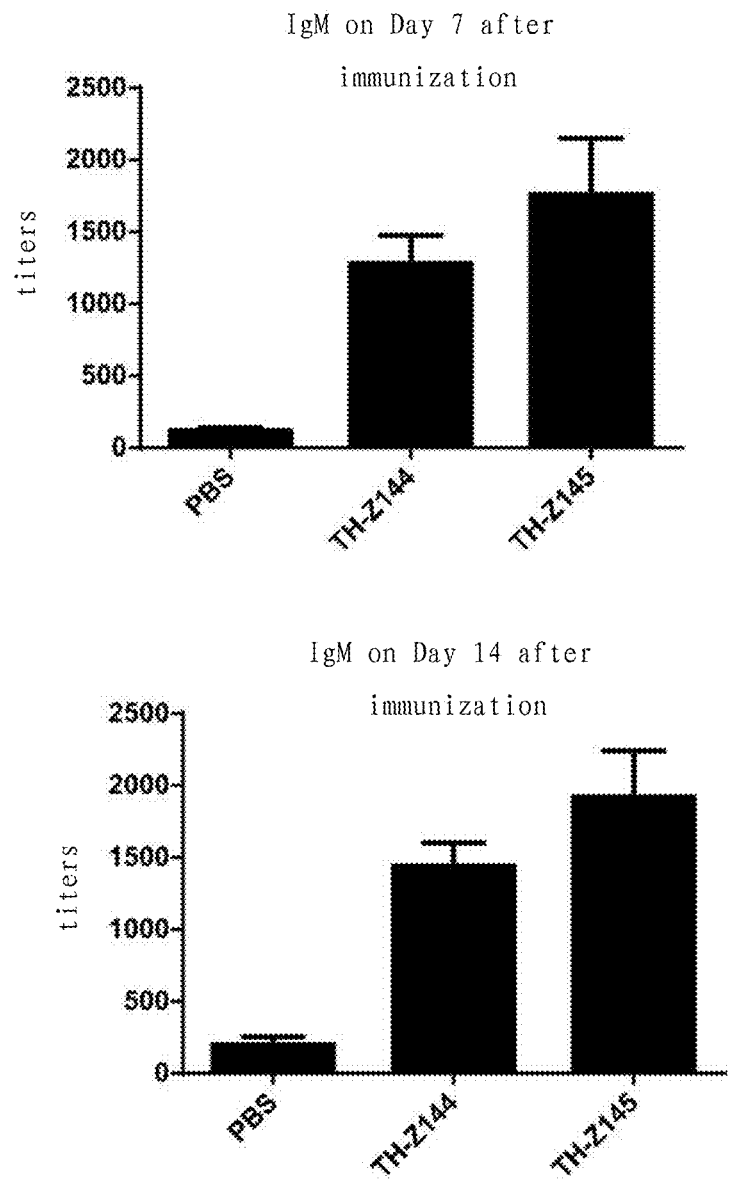
Figure. 6A-B

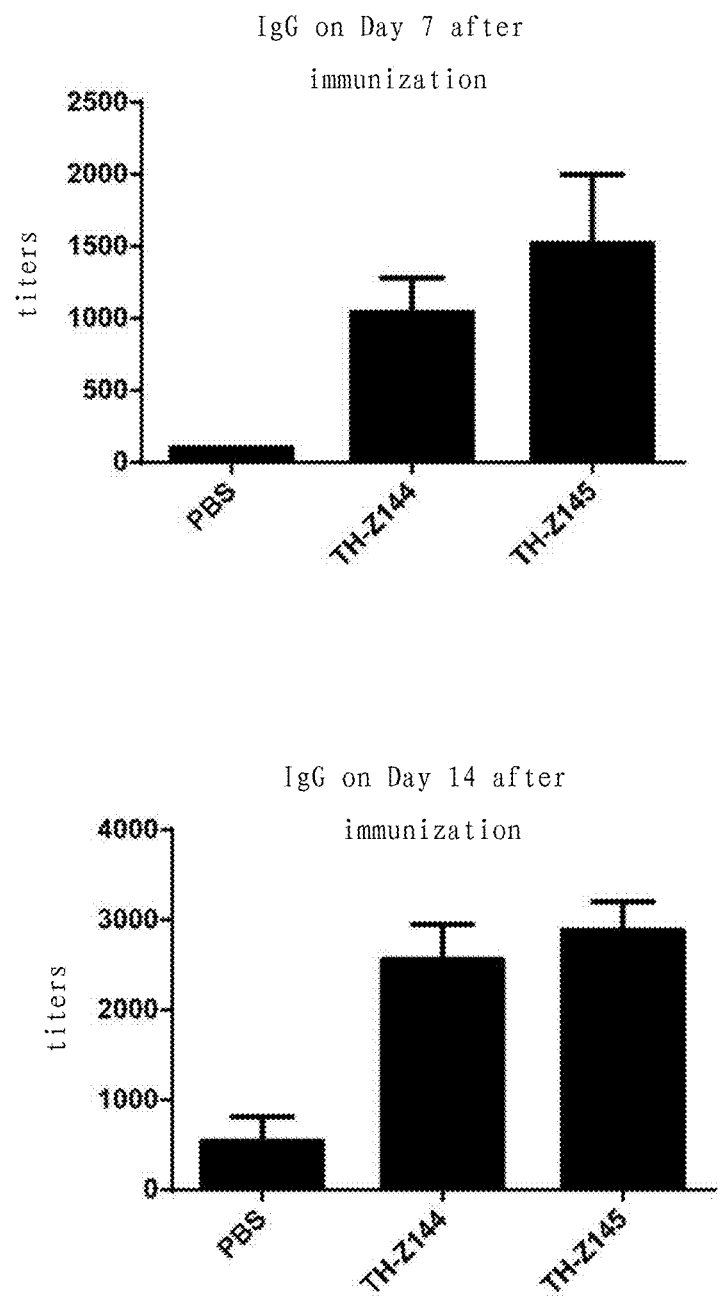
Figure. 6C-D

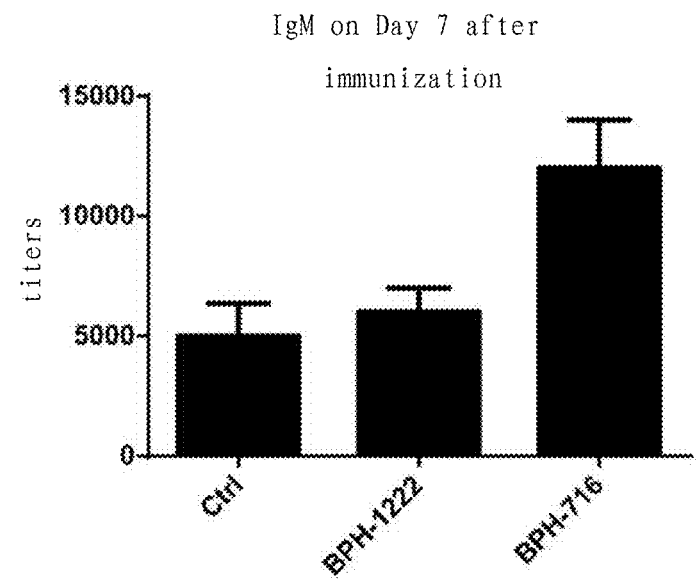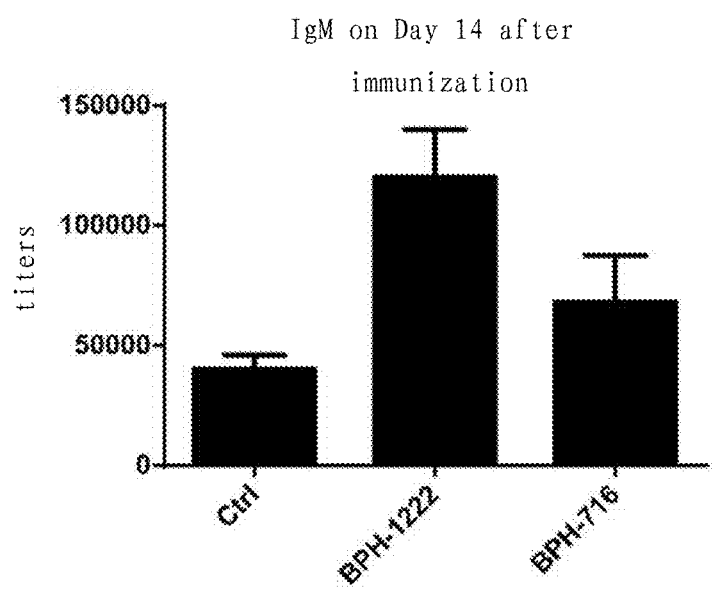
Figure. 7A-B

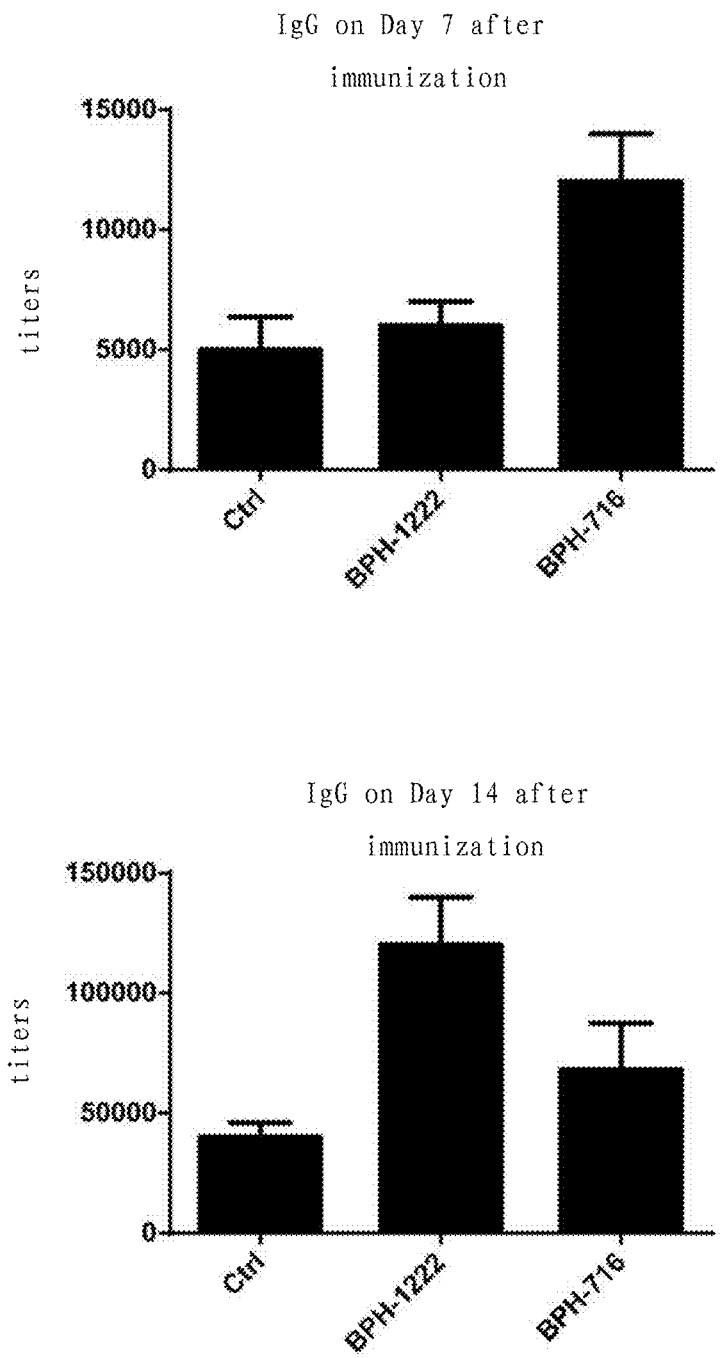
Figure. 7C-D

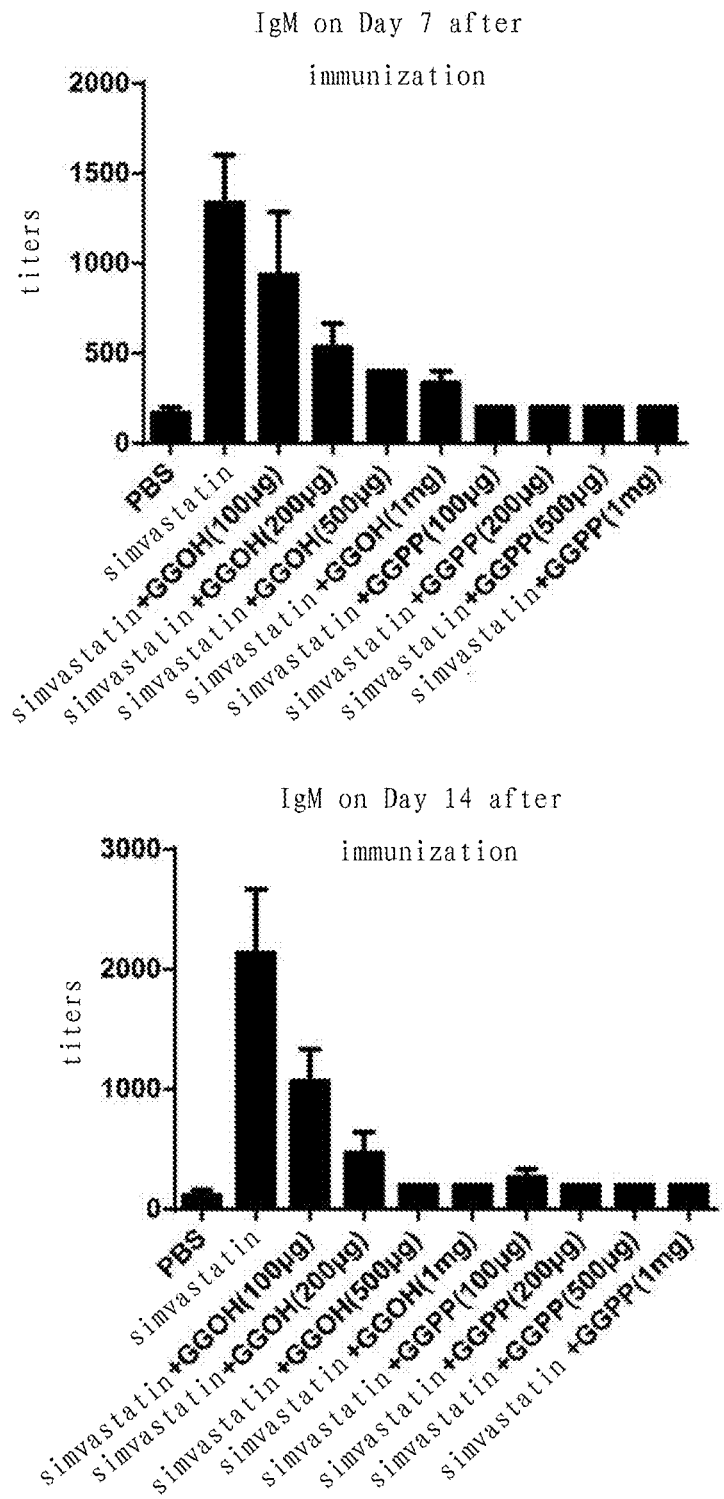
Figure. 9A-B

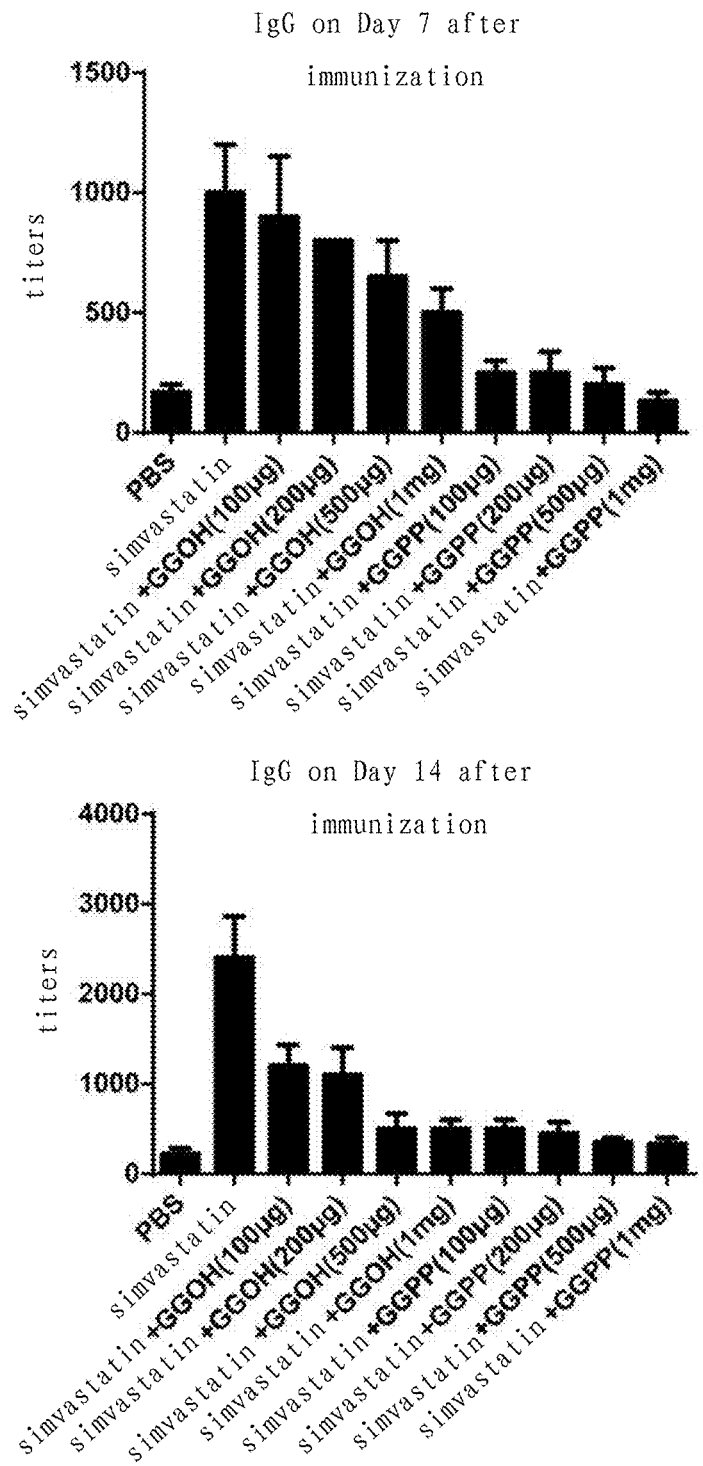
Figure. 9C-D

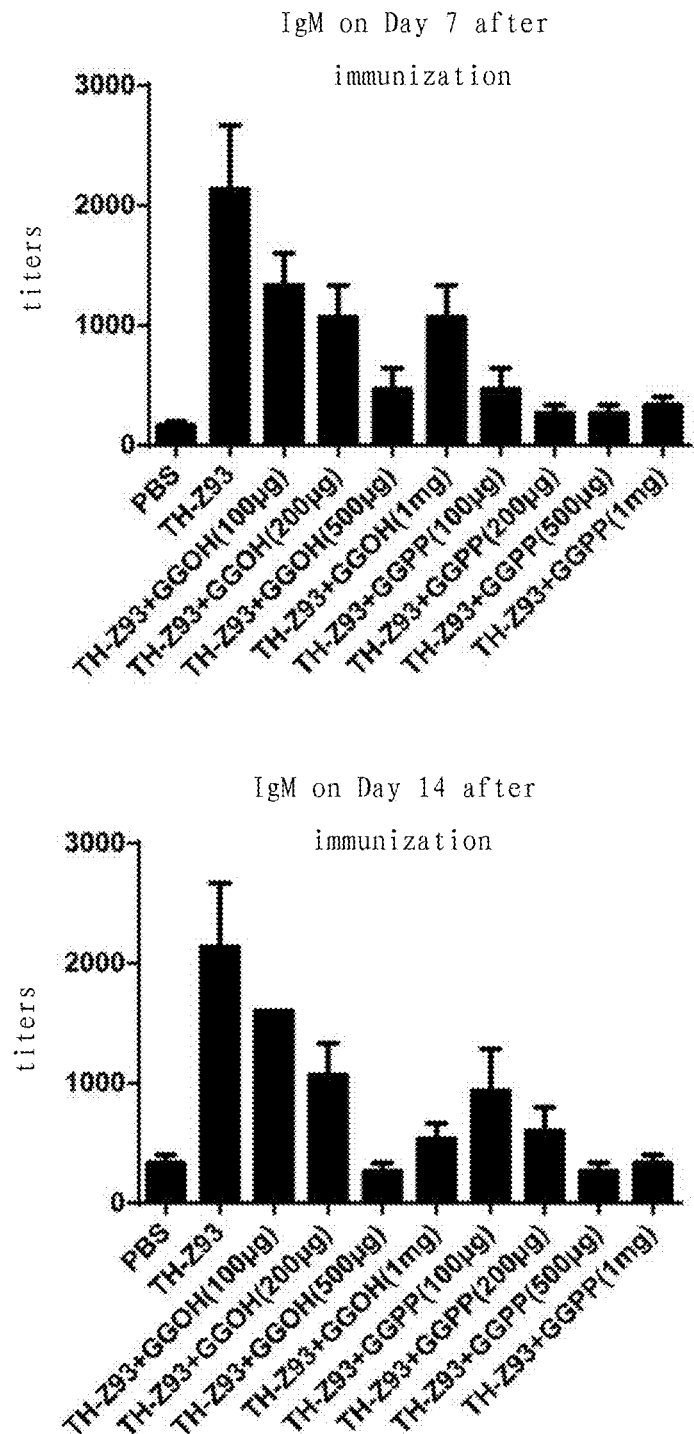
Figure. 10A-B

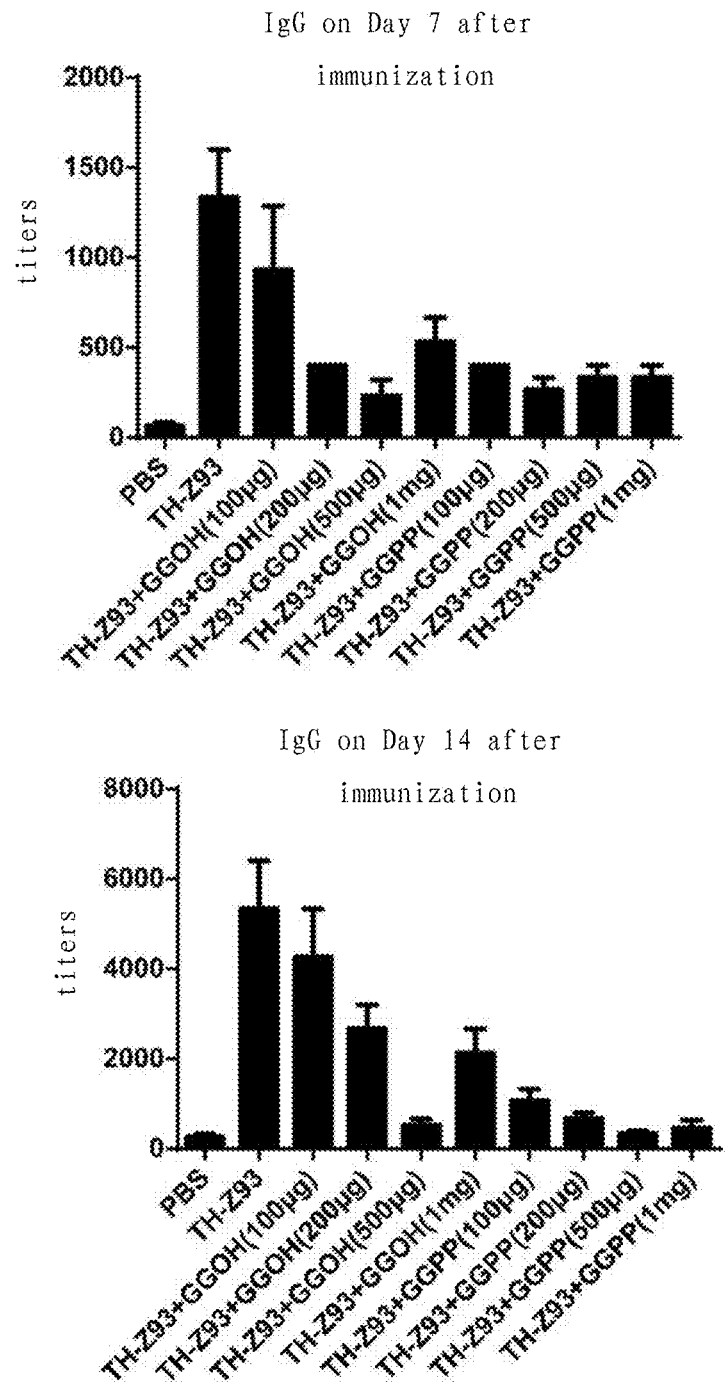
Figure. 10C-D

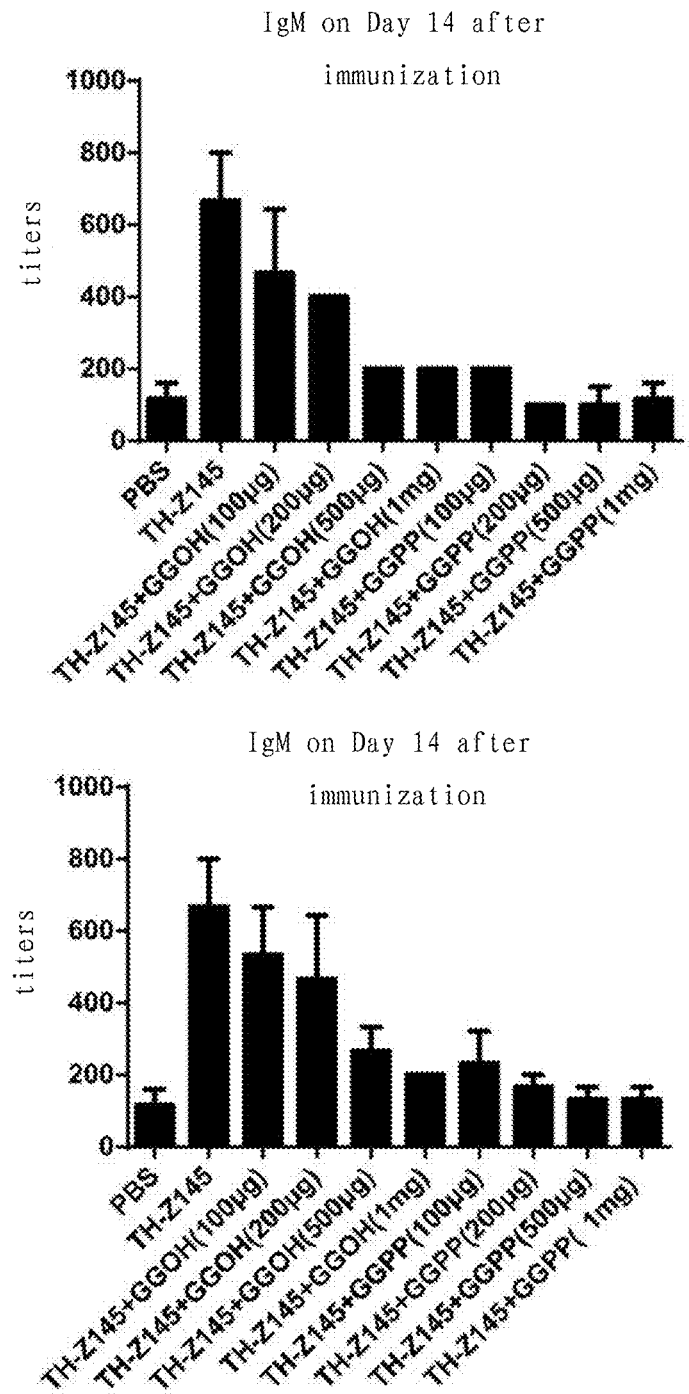
Figure. 11A-B

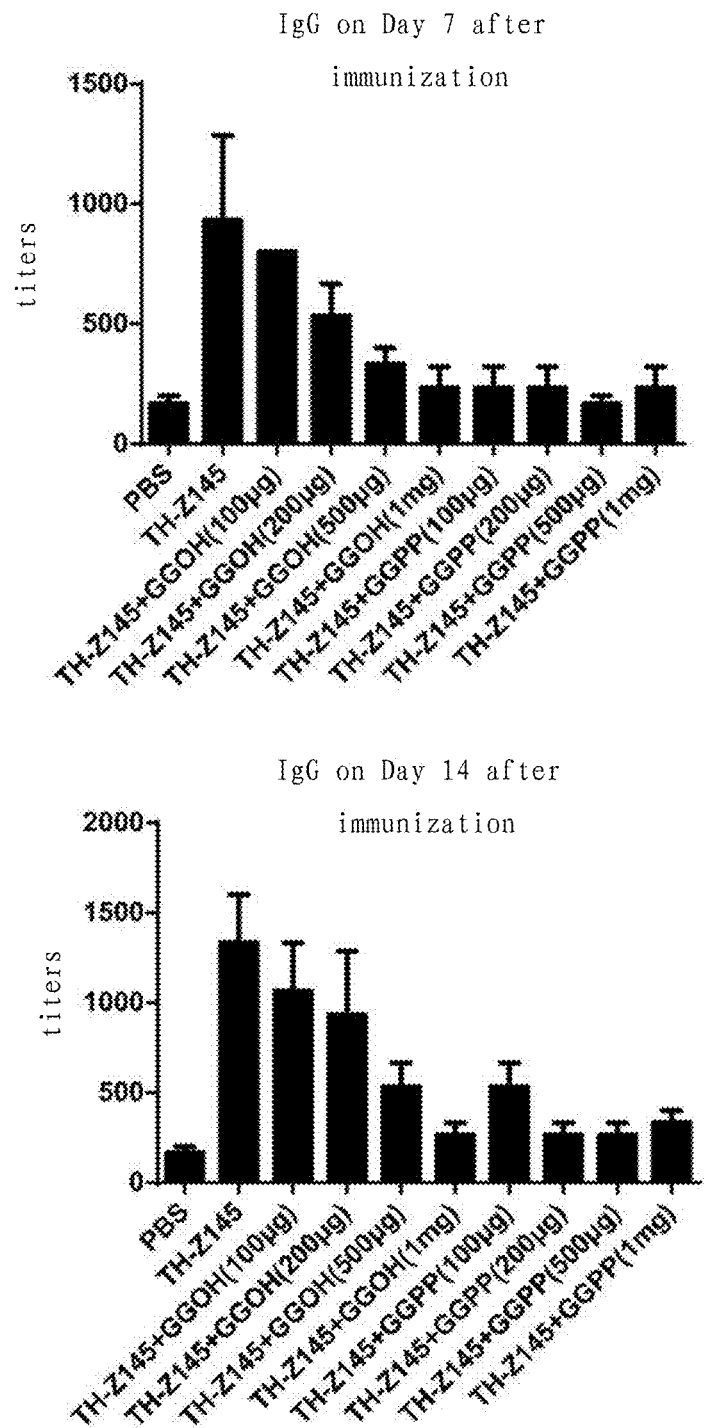
Figure. 11C-D

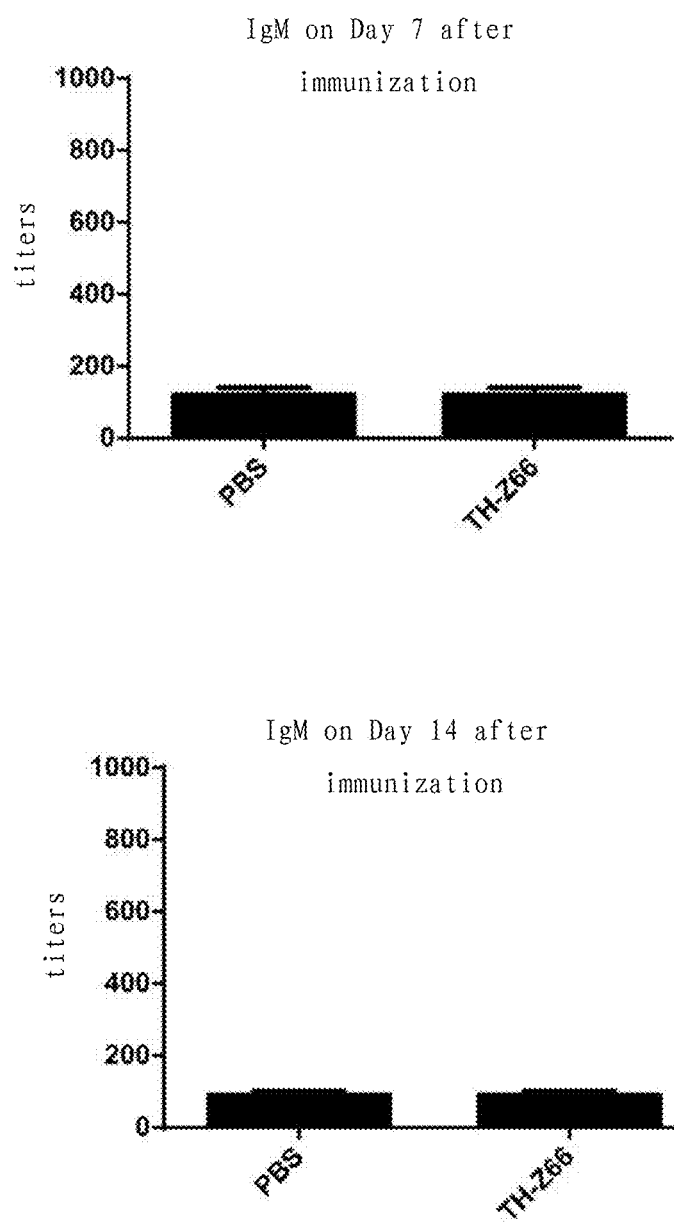
Figure. 12A-B

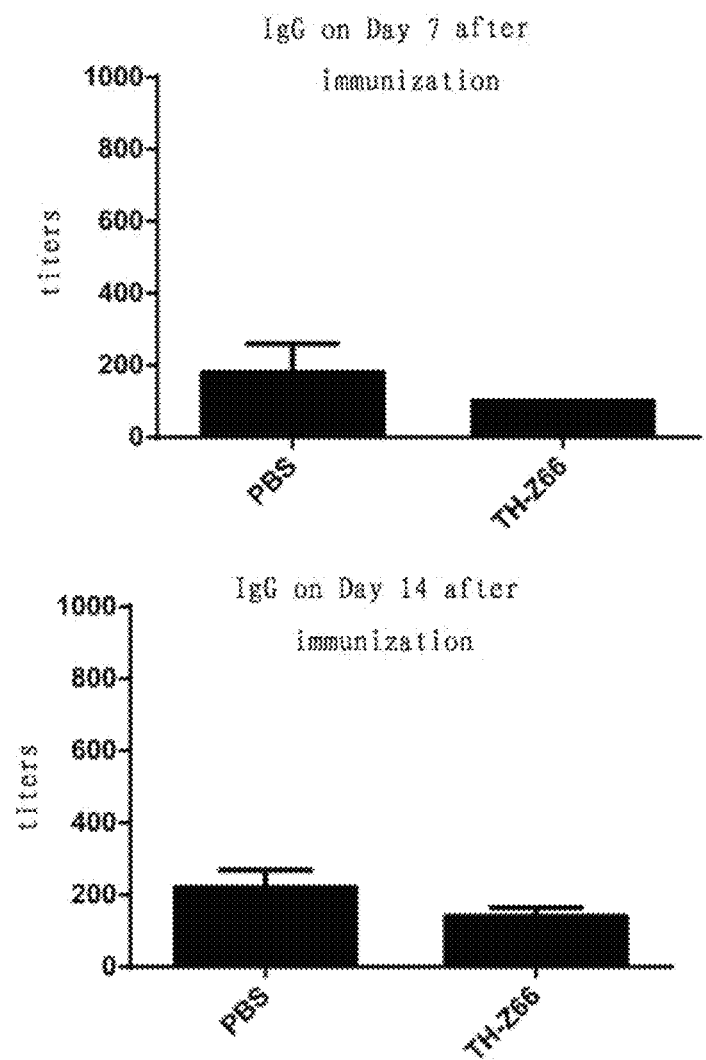
Figure. 12C-D

Figure. 16A-B

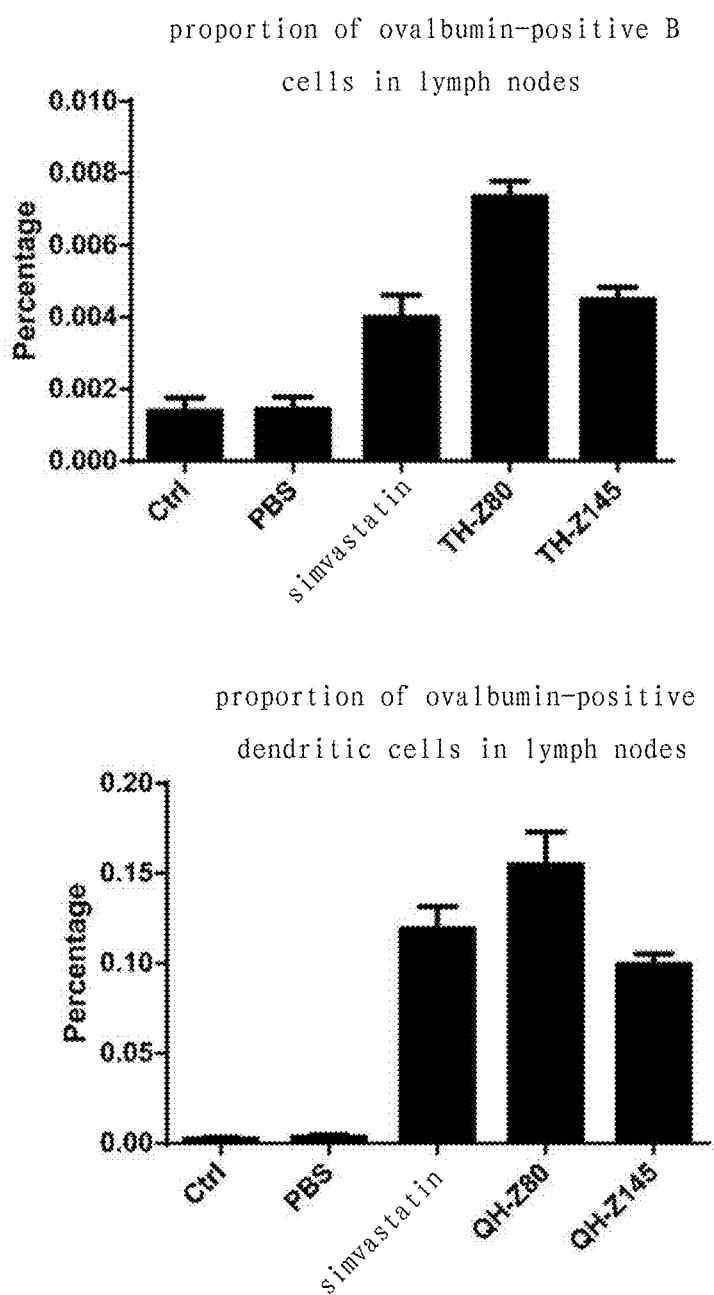
Figure. 22B-C

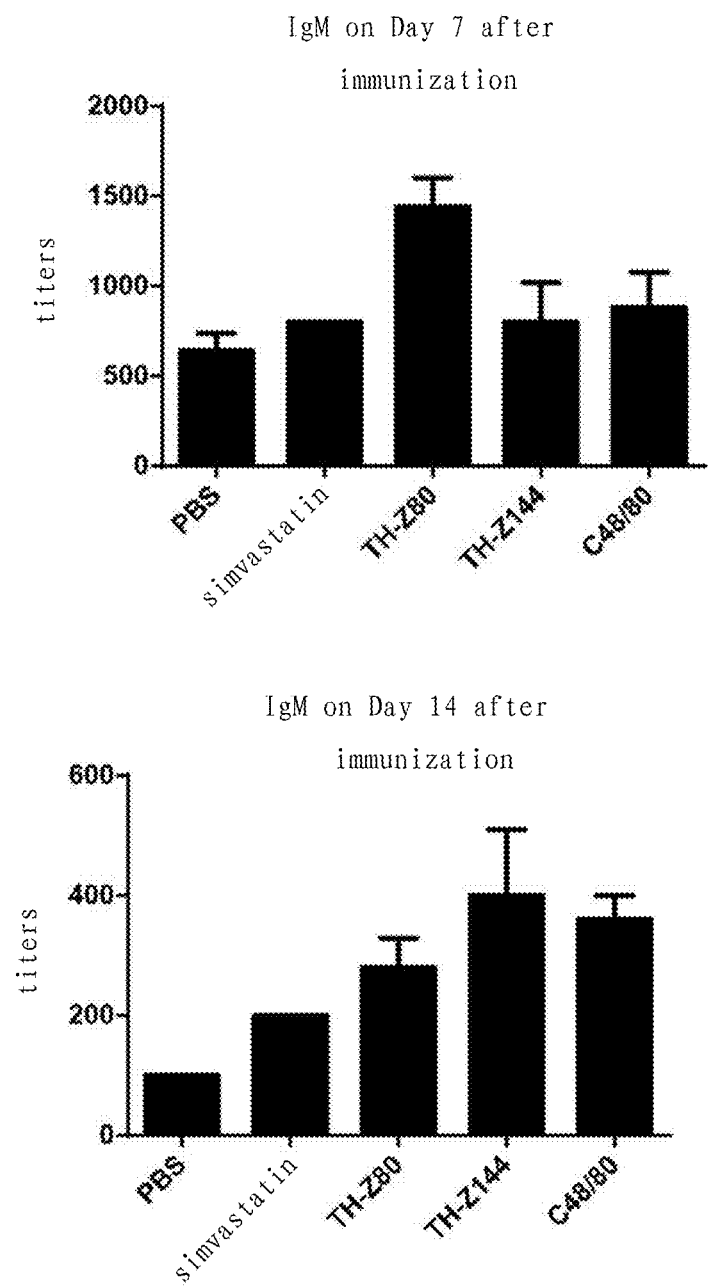
Figure. 23A-B

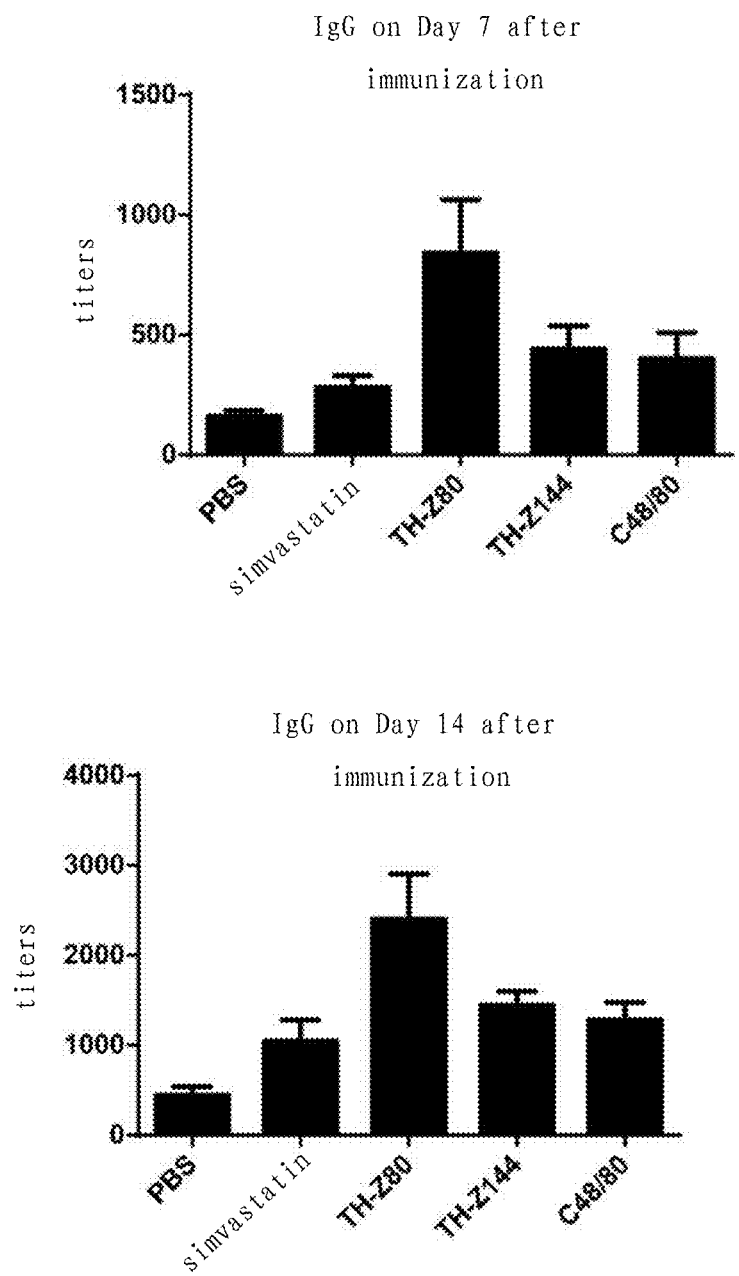
Figure. 23C-D

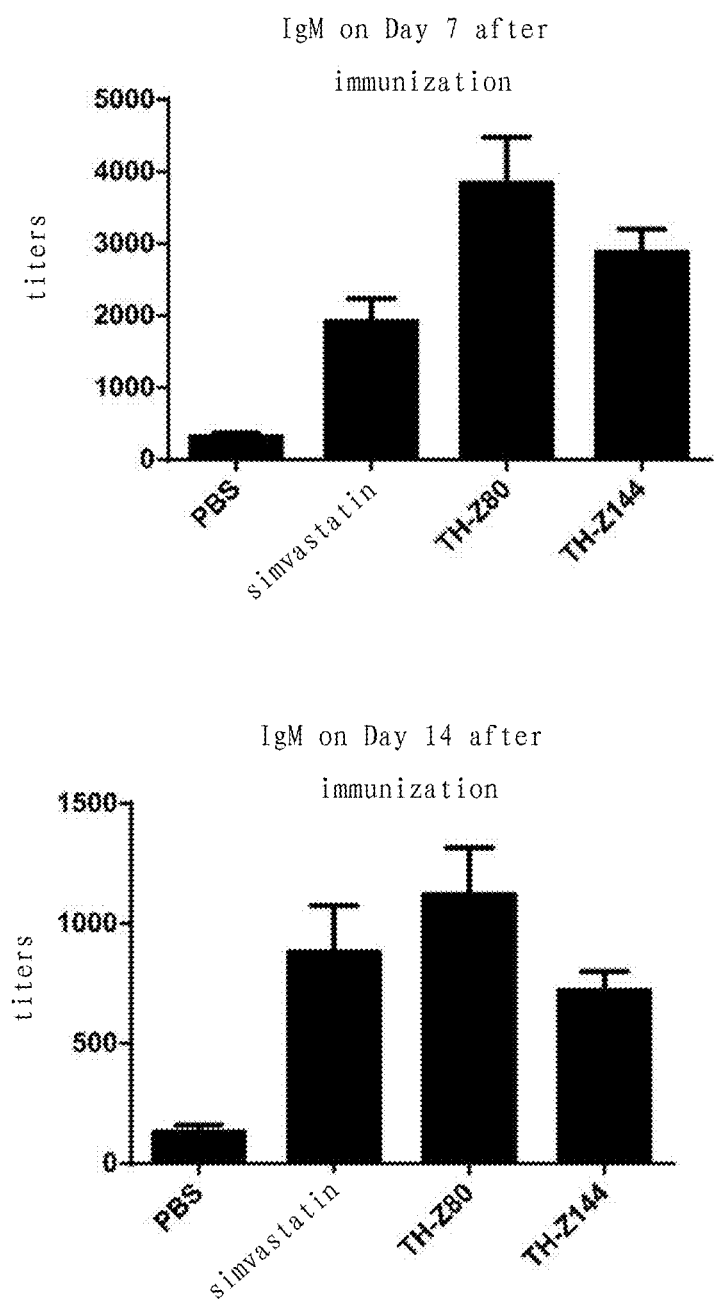
Figure. 24A-B

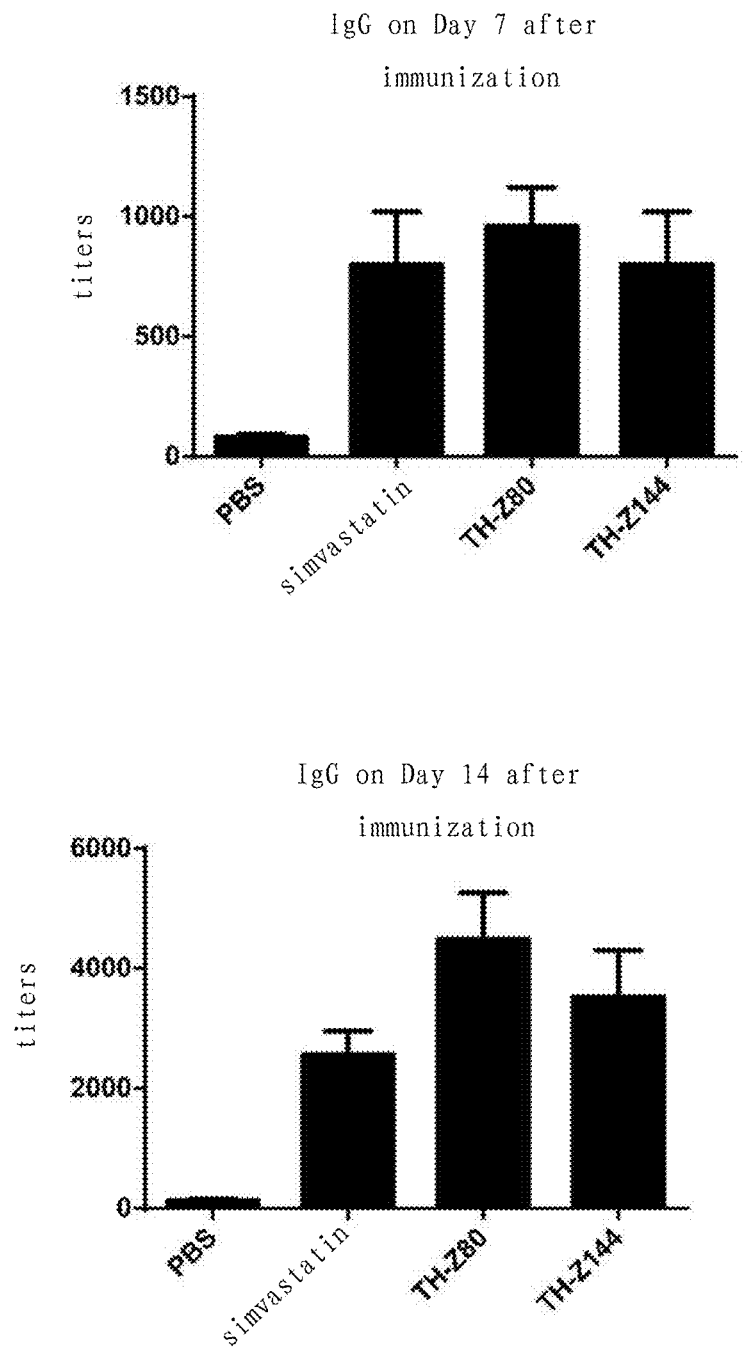
Figure. 24C-D

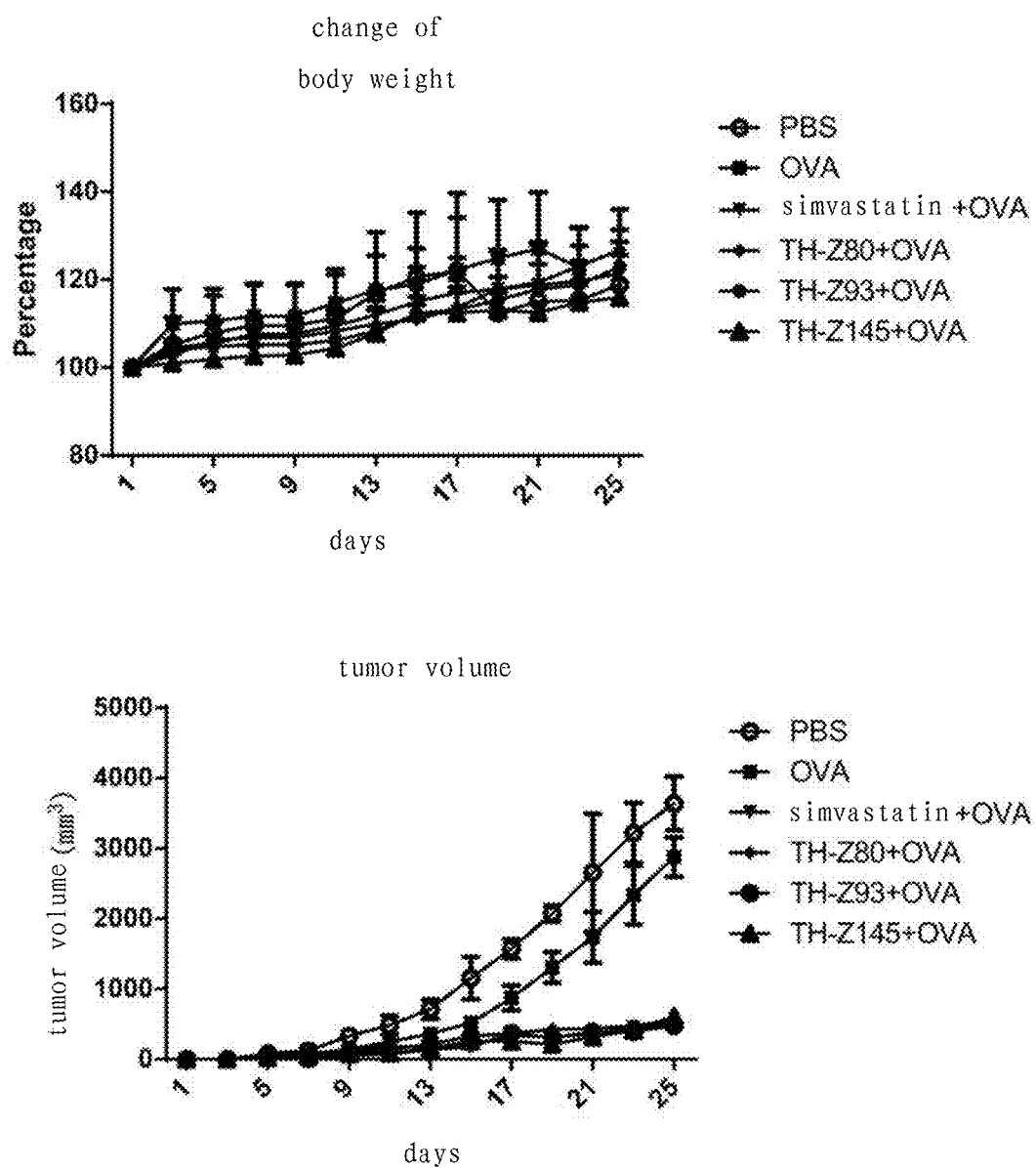
Figure. 25B-C

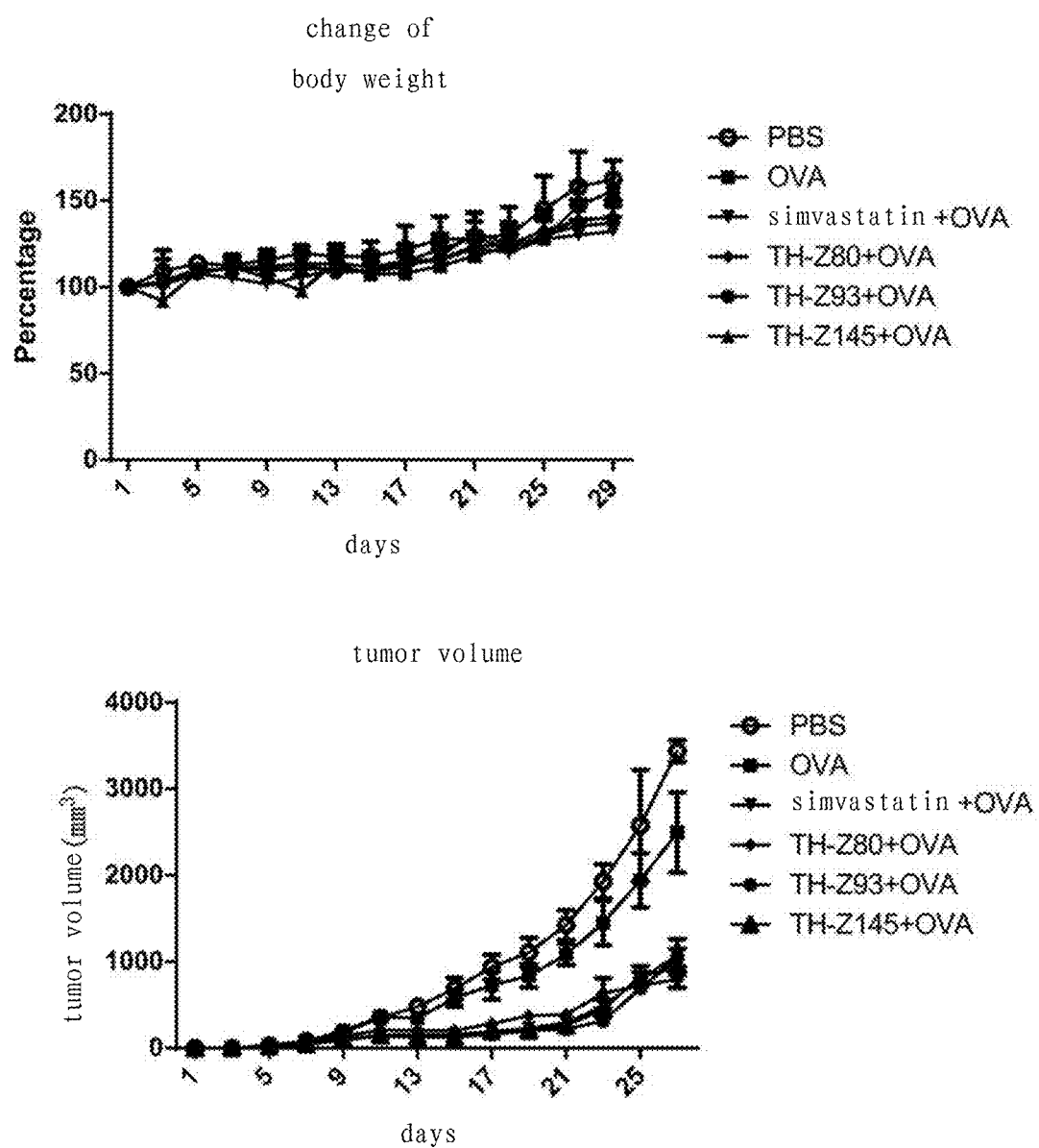
Figure. 26B-C

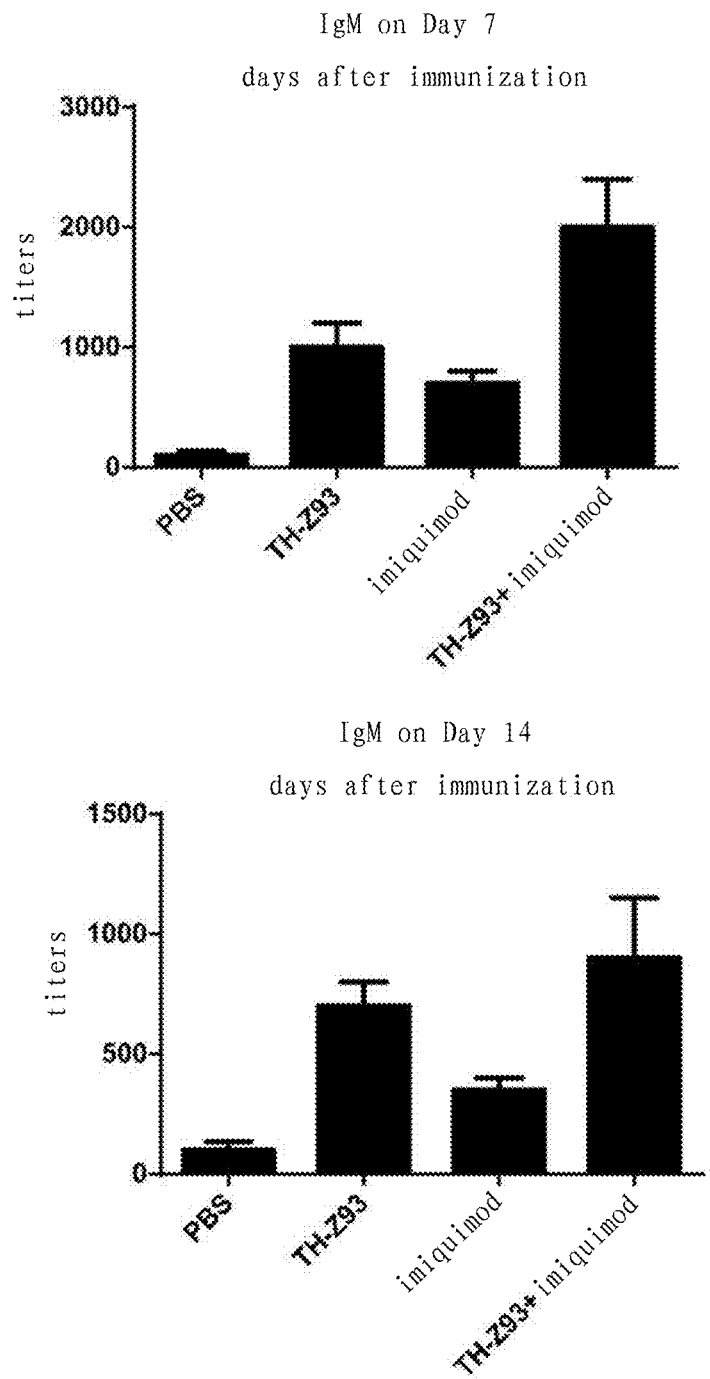
Figure. 28A-B

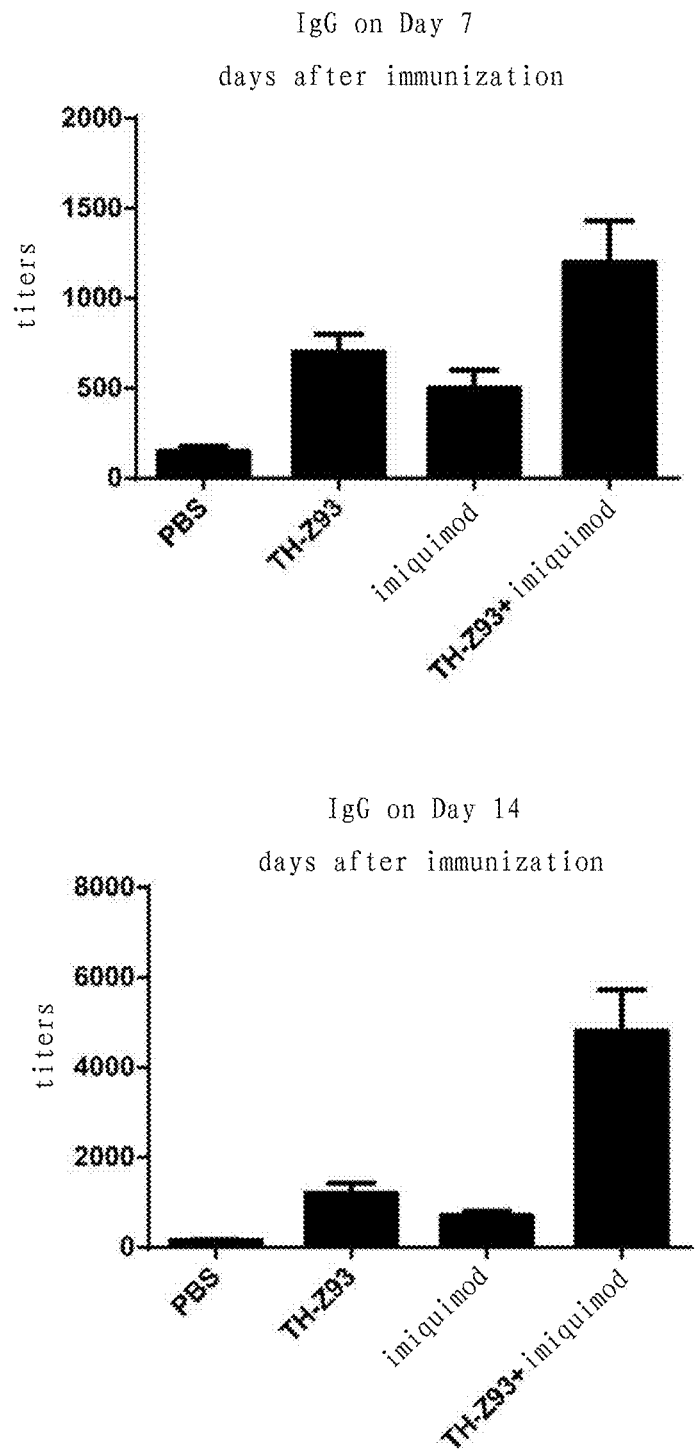
Figure. 28C-D

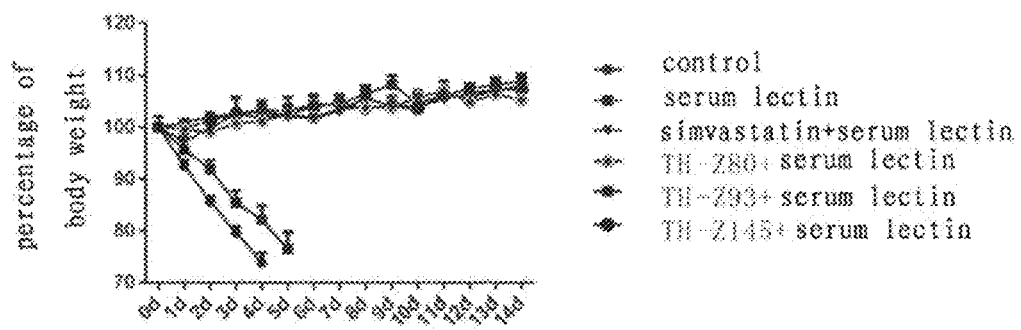
Figure. 35-A
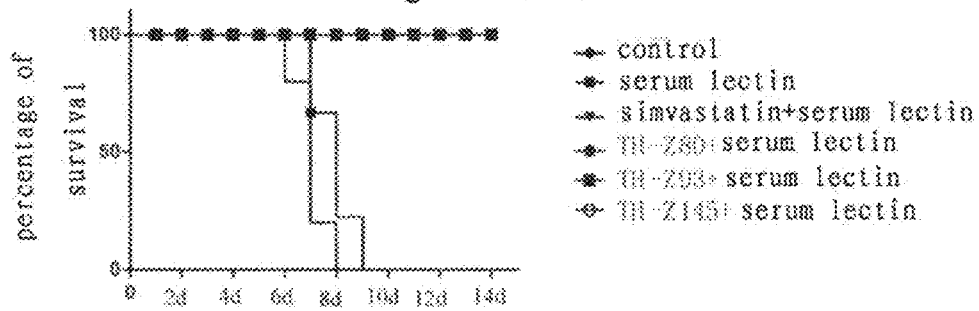
Figure. 35-B
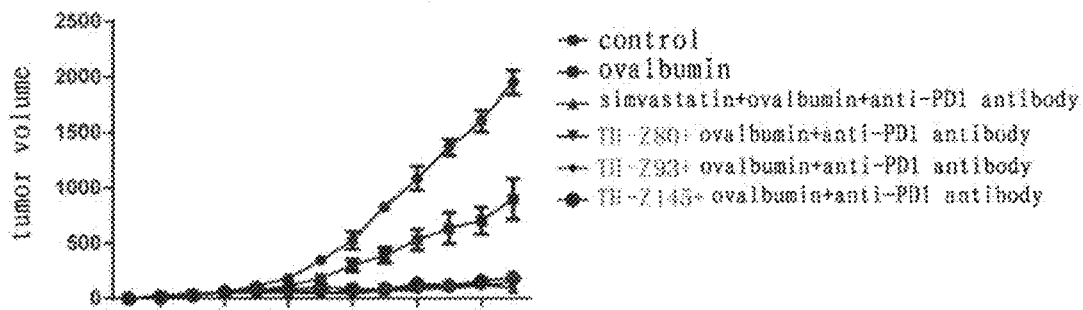
Figure. 36
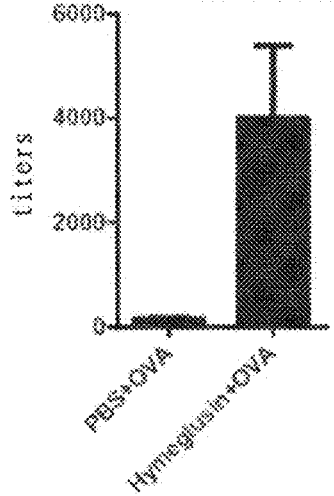
Figure. 37

MEVALONATE PATHWAY INHIBITOR AS HIGHLY-EFFICIENT VACCINE ADJUVANT

CROSS REFERENCE TO RELATED APPLICATIONS

The present application is a national application of PCT/CN2016/098371 filed on Sep. 8, 2016, which claims the priority of the Chinese Patent Application No. 201510570517.9 filed on Sep. 9, 2015 and the Chinese Patent Application No. 201610022707.1 filed on Jan. 14, 2016. The Chinese Patent Application No. 201510570517.9 and the Chinese Patent Application No. 201610022707.1 are incorporated herein by reference as part of the disclosure of the present application.

TECHNICAL FIELD

The present disclosure relates to inhibitors of mevalonate pathway as an efficient vaccine adjuvant. The present disclosure also relates to an immunogenic composition comprising inhibitors of mevalonate pathway as an adjuvant.

BACKGROUND

The adjuvant plays an important role in the development and use of vaccines. An adjuvant is also known as a non-specific immune enhancer. The adjuvant itself is not antigenic. However, an adjuvant injected into a body together with an antigen or an adjuvant pre-injected into a body can enhance the immunogenicity of the antigen or alter the type of immune response. Live attenuated and inactivated vaccines may essentially contain natural adjuvant ingredients, which may include proteins, lipids and oligonucleotides in particulate form. In fact, many attenuated or inactivated vaccines have a very strong protective effect on the body after immunization. However, due to some limitations of these attenuated and inactivated vaccines themselves (for example, attenuated pathogenic microorganisms mutate into highly pathogenic microorganisms, the inactivated vaccine is not completely inactivated in preparation), the vaccines may directly lead to illness when they act on the body. A subunit vaccine is a vaccine that is made of a component of a primary protective immunogen of a pathogenic microorganism. Due to the development of the modern molecular biology, the subunit vaccine becomes a main trend of development and application of a modern vaccine because of its convenient quality control, mass production, safety and reliability. But the subunit vaccine also has a short protective effect, slow onset and other shortcomings. Adjuvants used to compensate for these shortcomings of subunit vaccines are an important component of the development and use of modern vaccines.

The most widely used adjuvant in vaccine production is aluminum adjuvant. In 1926, an aluminum salt was first discovered to have adjuvant effects, and was first used in diphtheria vaccine in 1936. However, due to some limitations of the aluminum adjuvant such as weak effects of an adjuvant, in order to play a good role, an aluminum adjuvant needs to cooperate with highly immunogenic antigens. In particular, an aluminum adjuvant does not contribute well to a Th1 response that mediates cell immunity, resulting in the aluminum adjuvant unable to prevent diseases such as influenza, HIV, cancer, and malaria, so these vaccines urgently require new and effective adjuvants. Up to now, adjuvants approved clinically in the United States and Europe include aluminum salts, oil-in-water emulsions (MF59 AS03 and AF03) and AS04 (MPL aluminum salts). The development of adjuvants is in a "primitive" state, and currently known molecular targets are TLR (Toll-like receptors) only. There is an urgent need in the art for the discovery of new molecular targets for adjuvants.

SUMMARY OF THE INVENTION

In the present disclosure, we first discovered and demonstrated that enzymes associated with the mevalonate pathway can serve as targets for rational design of an adjuvant.

The mevalonate pathway is a metabolic pathway for the synthesis of isopentenyl pyrophosphate (IPP) and dimethallyl pyrophosphate (DMAPP) from acetyl coenzyme A as a raw material and is present in all higher eukaryotes and many viruses. The product of this pathway can be thought of as an activated isoprene unit, which is a synthetic precursor of steroids, terpenoids and other biomolecules. In this pathway, acetoacetyl-CoA is produced by two molecules of acetyl-CoA, and the resulting acetoacetyl-CoA is then reacted with acetyl-CoA to produce 3-hydroxy-3-methylglutaryl CoA, i.e., HMG-CoA, and then HMG-CoA is reduced to mevalonate under the action of HMG-CoA reductase. The mevalonate is catalyzed by two kinases and one decarboxylase to form isopentenyl pyrophosphate (IPP). Under the catalysis of FPP synthase (FPPS), IPP forms farnesyl pyrophosphate (FPP). FPP forms in different downstream pathways, for example cholesterol, ubiquinone, Heme A, sterol, dolichol and prenylated proteins. For example, FPP can form squalene under the action of squalene synthase (SQS), and squalene produces cholesterol under the catalysis of a series of enzymes. Under the action of farnesyl transferase, FPP is able to perform farnesylation modification to some proteins. On the other hand, under the catalysis of GGPP synthase (GGPPS), FPP affords geranylgeranyl pyrophosphate (GGPP), whereas under the action of geranylgeranyl transferase, GGPP is capable of carrying out geranylgeranylation modification on some proteins to form prenylated proteins.

We found that all substances that affect the geranylgeranylation of proteins can be used for the development of vaccine adjuvants. In particular, vaccine adjuvants can be developed to against the following targets: 1) thiolase (acetoacetyl-CoA transferase); 2) HMG-CoA synthase; 3) HMG-CoA reductase; 4) mevalonate kinase; 5) phosphomevalonate kinase; 6) mevalonate-5-pyrophosphate decarboxylase; 7) isopentenyl pyrophosphate isomerase; 8) farnesyl pyrophosphate synthase (FPPS); 9) geranylgeranyl pyrophosphate synthase (GGPPS); 10) geranylgeranyl transferases I and II.

We have also found that other substances that do not directly act on a mevalonate pathway but indirectly affect the geranylgeranylation can also be used for the development of vaccine adjuvants.

Therefore, in one aspect, the present disclosure relates to an immunogenic composition comprising an agent as an adjuvant that affects the geranylgeranylation of proteins. Such an agent may include, but is not limited to, 1) thiolase (acetoacetyl-CoA transferase) inhibitors; 2) HMG-CoA synthase inhibitors; 3) HMG-CoA reductase inhibitors; 4) mevalonate kinase inhibitors; 5) phosphomevalonate kinase inhibitors; 6) mevalonate-5-pyrophosphate decarboxylase inhibitors; 7) isopentenyl pyrophosphate isomerase inhibitors; 8) farnesyl pyrophosphate synthase inhibitors; 9) geranylgeranyl pyrophosphate synthase inhibitors; and 10) geranylgeranyl transferase (I, II) inhibitors.

In another aspect, the present disclosure encompasses the above-mentioned inhibitors for use as adjuvants.

In another aspect, the present disclosure encompasses the use of the above-mentioned inhibitors as adjuvants in the preparation of immunogenic compositions.

In another aspect, the present disclosure also relates to novel compounds or a pharmaceutically acceptable salt, ester, prodrug, or solvate thereof as inhibitors of farnesyl pyrophosphate synthase (FPPS), said compounds having the formula:

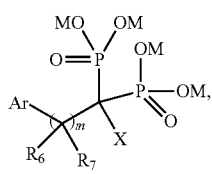

Formula I

In the Formula I, the compound has a molecular weight of less than 1000, and Ar is a benzimidazolyl-type group, or an aza-benzimidazolyl group;

X is selected from the group consisting of hydrogen, hydroxy, an aliphatic group, mercapto, halogen, alkoxy and alkyl; each M is independently selected from the group consisting of a negative charge, hydrogen, alkyl, an aliphatic group, $-(CH_2)_p-O-CO-R$, $-(CH_2)_p-CO-R$ and a positive ion; wherein p is an integer of 1 to 6, R is hydrogen, alkyl or aryl; the positive ion is $Li^+$, $Na^+$, $K^+$, $Ca^{2+}$, $Mg^{2+}$, $NH_4^+$ or $N(R')_4^+$, wherein R' is alkyl; $R_6$ and $R_7$ are each independently selected from the group consisting of hydrogen, hydroxy, mercapto, halogen, amino, an aliphatic group and alkyl; m is an integer of 1 to 6.

In another aspect, the present disclosure also relates to novel compounds or a pharmaceutically acceptable salt, ester, prodrug, or solvate thereof as inhibitors of farnesyl pyrophosphate synthase (FPPS), said compounds having the formula:

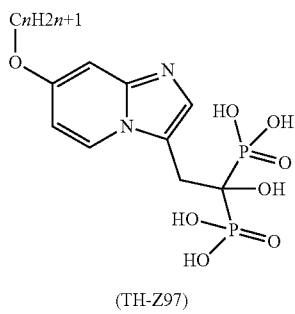

(TH-Z97)

wherein n is an integer of 1 to 24, preferably n is an integer of 1 to 20, more preferably n is an integer of 1 to 15, and even more preferably n is an integer of 1 to 12.

In another aspect, the present disclosure also relates to novel compounds or a pharmaceutically acceptable salt, ester, prodrug, or solvate thereof as inhibitors of farnesyl pyrophosphate synthase (FPPS), said compounds having the formula:

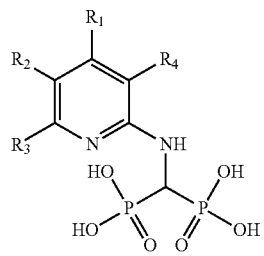

wherein $R_1$ is selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl;

$R_2$ is selected from the group consisting of hydrogen, alkyl, alkoxy, alkylamino, alkylthio, halogen, hydroxy, cycloalkyl, heterocyclyl, aryl and heteroaryl;

$R_3$ is selected from the group consisting of hydrogen, alkyl, alkoxy, alkylamino, alkylthio, halogen, hydroxy, cycloalkyl, heterocyclyl, aryl and heteroaryl;

or $R_2$ and $R_3$ together with the carbon atom to which they are attached form an aromatic or heteroaromatic ring; and $R_4$ is selected from the group consisting of hydrogen, alkyl, alkoxy, alkylamino, alkylthio, halogen, hydroxy, cycloalkyl, heterocyclyl, aryl and heteroaryl.

In a preferred embodiment of this aspect, the compound is selected from the group consisting of:

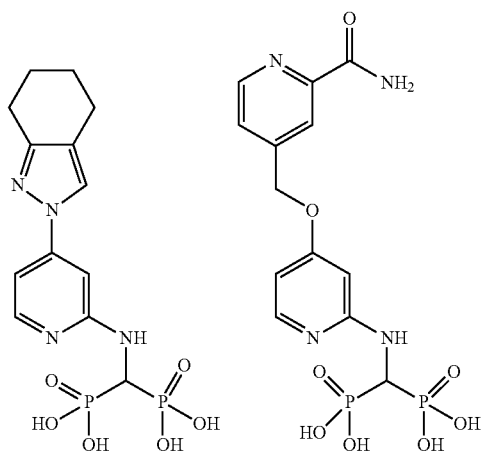

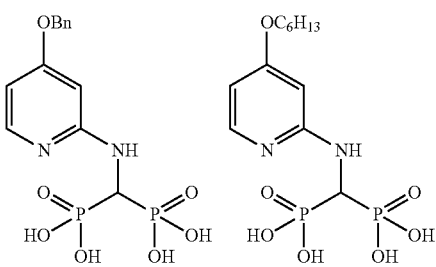

-continued

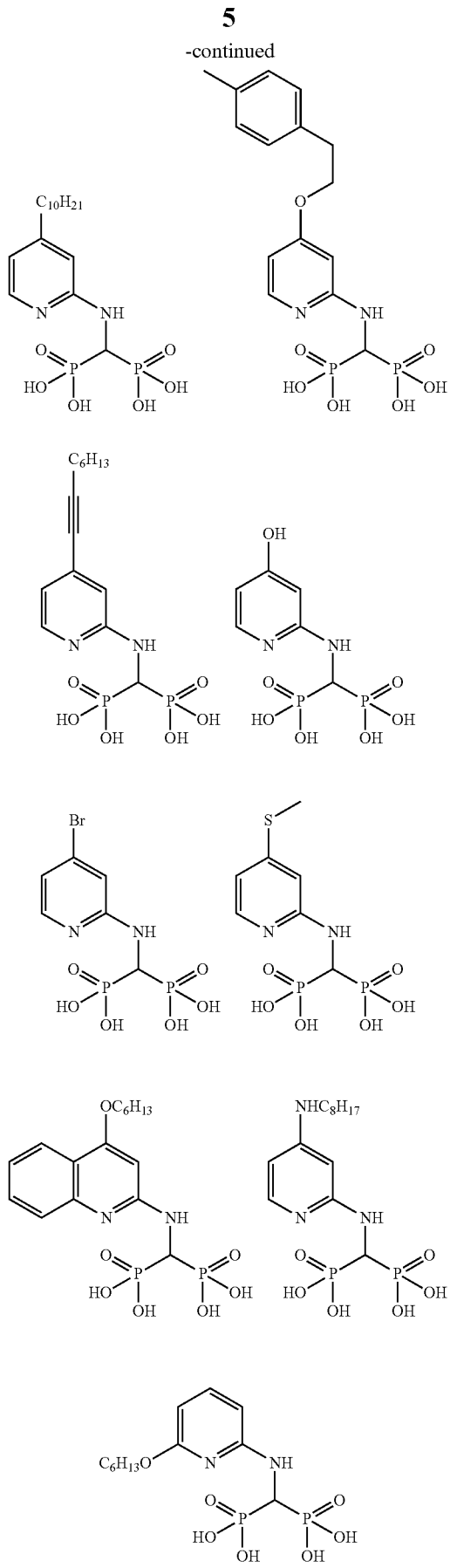

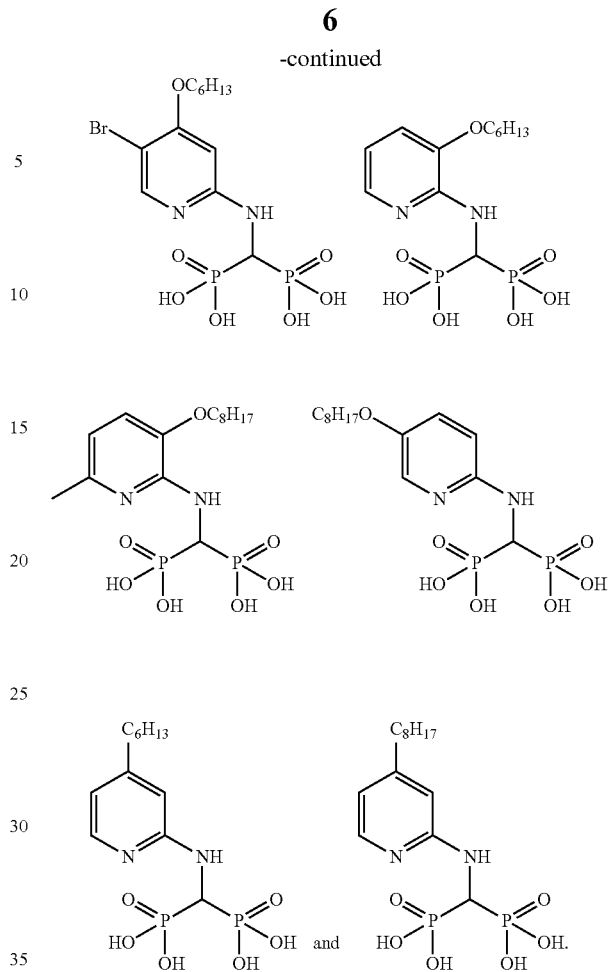

In another aspect, the present disclosure also relates to novel compounds or a pharmaceutically acceptable salt, ester, prodrug, or solvate thereof as inhibitors of farnesyl pyrophosphate synthase (FPPS), said compounds having the formula:

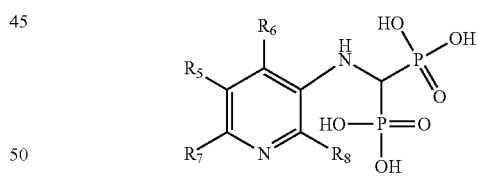

wherein:

$R_5$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_6$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_7$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and $R_8$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

In a preferred embodiment of this aspect, the compound is

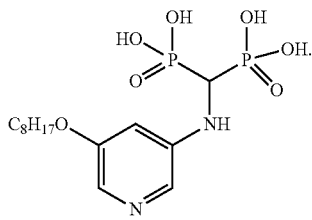

In another aspect, the present disclosure also relates to novel compounds, or a pharmaceutically acceptable salt, ester, prodrug, or solvate thereof, as inhibitors of geranylgeranyl pyrophosphate synthase, having the formula:

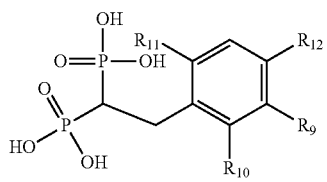

wherein:
$R_9$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_{10}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_{11}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and
$R_{12}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

In a preferred embodiment of this aspect, the compound is selected from the group consisting of:

TH-Z144

and

TH-Z145

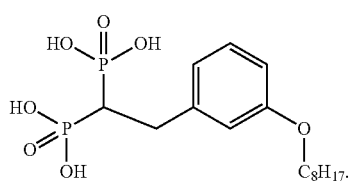

In another aspect, the present disclosure also relates to the use of said novel compounds or a pharmaceutically acceptable salt, ester, prodrug, or solvate thereof as adjuvants in the preparation of immunogenic compositions for prevention or treatment of diseases.

Another aspect of the present disclosure relates to a method of immunizing a subject or a host, which comprises administering to said subject or host an immunogenic composition as defined in the present disclosure.

BRIEF DESCRIPTION OF THE DRAWINGS

FIGS. 2A-D show adjuvant activities of eight statin drugs in OVA antibody titer assay, expressed as antibody titers of IgM and IgG on Day 7 and Day 14 after immunization.

FIGS. 5A-D show comparative results of adjuvant activities of the bisphosphonic acid compounds TH-Z80 and TH-Z93 of the present disclosure with eight commercially available bisphosphonic acid drugs for OVA antibody titer detection.

FIGS. 6A-D show adjuvant activities of the GGPPS inhibitors TH-Z144 and TH-Z145 in OVA antibody titer assay, expressed as antibody titers of IgM and IgG on Day 7 and Day 14 after immunization.

FIGS. 7A-D show adjuvant activities of FPPS and GGPPS dual inhibitors BPH-716 and BPH-1222 in OVA antibody titer assay, expressed as antibody titers of IgM and IgG on Day 7 and Day 14 after immunization, where Ctrl represents the control group wherein mice were treated with PBS.

FIGS. 9A-D show inhibitory effects of GGOH and GGPP on the adjuvant activity of simvastatin (a HMG-CoA reductase inhibitor).

FIGS. 10A-D show inhibitory effects of GGOH and GGPP on the adjuvant activity of TH-Z93 (a FPPS inhibitor).

FIGS. 11A-D show inhibitory effects of GGOH and GGPP on the adjuvant activity of TH-Z145 (a GGPPS inhibitor).

FIGS. 12A-D show the results of adjuvant activity studies of the selective squalene synthase inhibitor TH-Z66 in OVA antibody titer assay, expressed as antibody titers of IgM and IgG on Day 7 and Day 14 after immunization.

FIGS. 22A-D show the proportion of cell markers B220, F4/80, and CD11c in lymph nodes after immunization with simvastatin, TH-Z80, TH-Z145 described herein as adjuvants, where Ctrl represents mice that are not subjected to any treatment.

FIGS. 23A-D show the titers of IgM and IgG antibodies in the Middle East Respiratory Syndrome Virus Mers protein after immunization with simvastatin, TH-Z80, TH-Z144 as adjuvants, expressed as antibody titers of IgM and IgG on Day 7 and Day alkyl or aryl; the positive ion is Li$^+$, Na$^+$, K$^+$, Ca$^{2+}$, NH$_4^+$ or N(R')$_4^+$, wherein R' is alkyl; R$_6$ and R$_7$ are each independently selected from the group consisting of hydrogen, hydroxy, mercapto, halogen, amino, an aliphatic group and alkyl;

Figure 1:
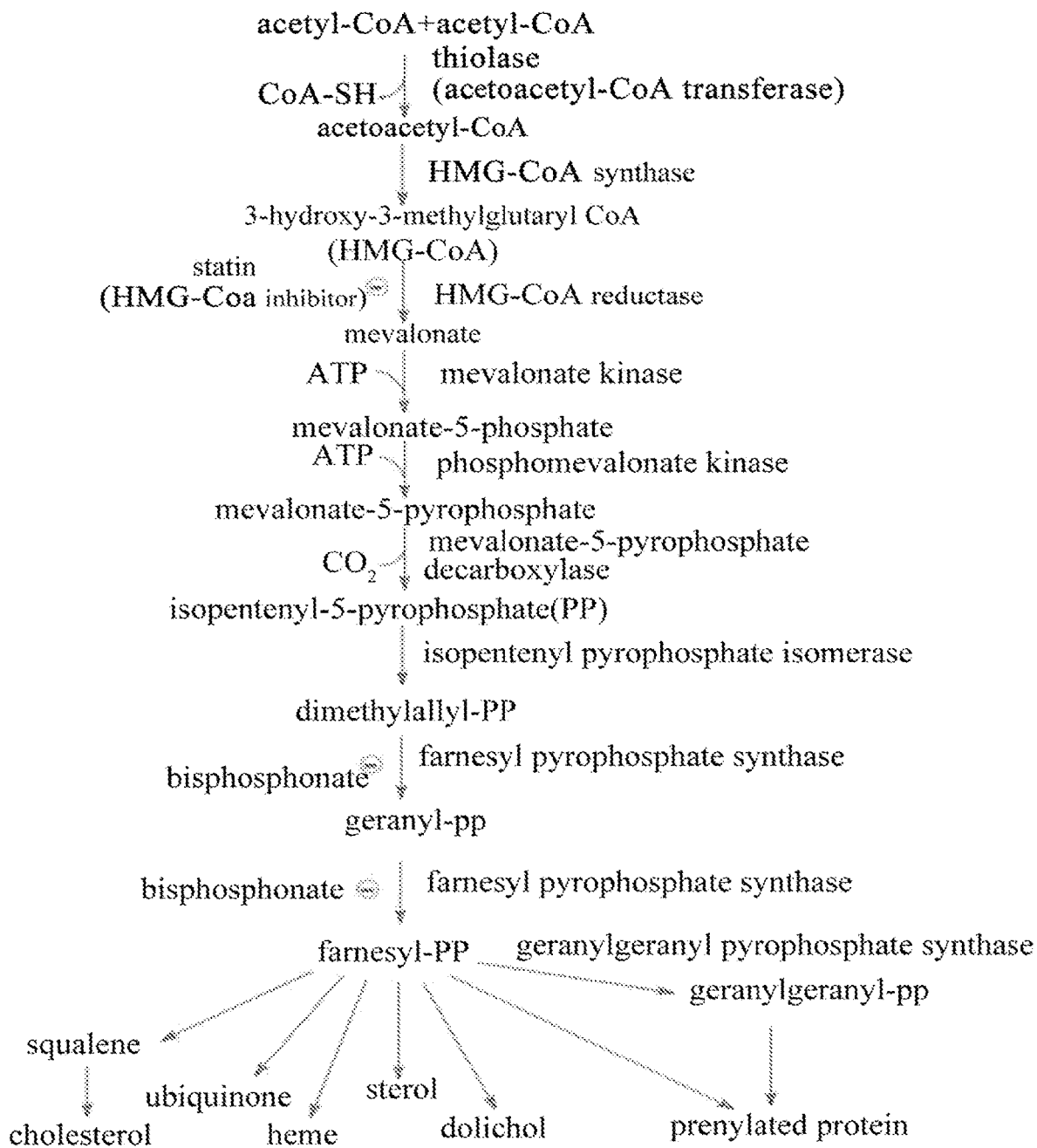
FIG. 1 is a schematic representation of the mevalonate pathway.

m is an integer of 1 to 6.

8. The immunogenic composition according to 7, wherein the compound represented by Formula I is a compound represented by the following Formulae II-X:

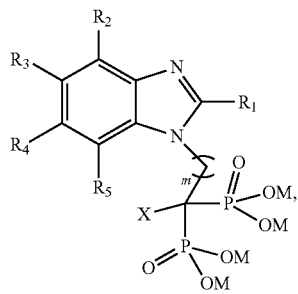

Formula II

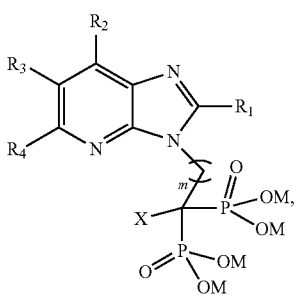

Formula III

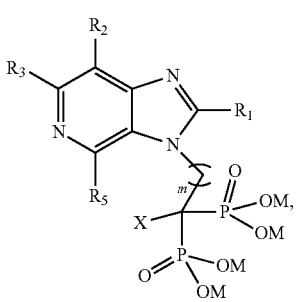

Formula IV

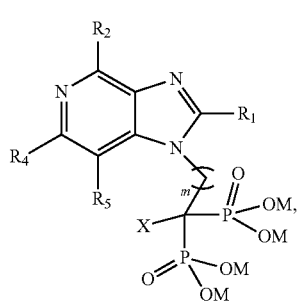

Formula V

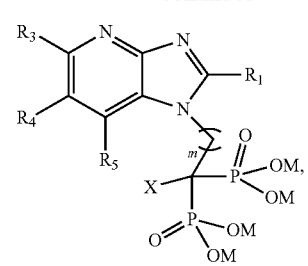

Formula VI

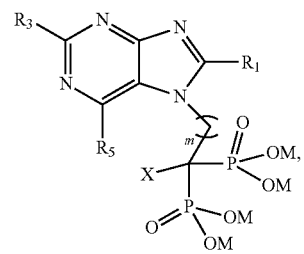

Formula VII

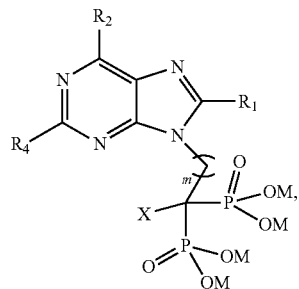

Formula VIII

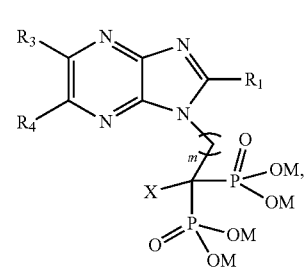

Formula IX

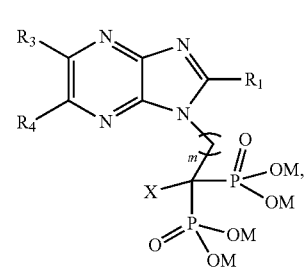

Formula X

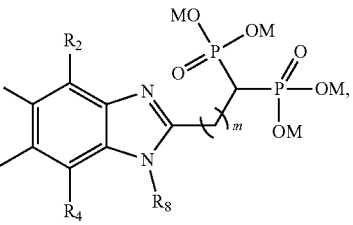

in the Formulae II-X, X is selected from the group consisting of hydrogen, hydroxy, mercapto, halogen, alkoxy and alkyl;

Each M is independently selected from the group consisting of a negative charge, hydrogen, alkyl, —(CH$_2$)$_p$—O—CO—R, —(CH$_2$)$_p$—CO—R and a positive ion; wherein p is an integer of 1 to 6, R is hydrogen, alkyl or aryl; the positive ion is Li$^+$, Na$^+$, K$^+$, Ca$^{2+}$, Mg$^{2+}$, NH$_4^+$ or N(R')$_4^+$, wherein R' is alkyl;

R$_1$, R$_2$, R$_3$, R$_4$, R$_5$ and R$_8$ are independently selected from the group consisting of hydrogen, hydroxy, an aliphatic group, mercapto, halogen, amino, alkyl, —O—(CH$_2$)$_q$CH$_3$, —NH—(CH$_2$)$_q$CH$_3$, —N[(CH$_2$)$_q$CH$_3$]$_2$, —(CH$_2$)$_p$—S—(CH$_2$)$_q$CH$_3$, —O—(CH$_2$)$_p$—S—(CH$_2$)$_q$CH$_3$, and —O—

$(CH_2)_p-O-(CH_2)_q CH_3$, wherein p is an integer of 1 to 6, q is an integer of 0 to 6; m is an integer of 1 to 6.

9. The immunogenic composition according to 7 or 8, wherein the compound is a compound represented by Formulae XI-XVIII:

Formula XI
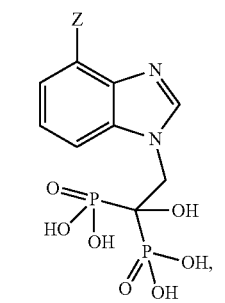

Formula XII
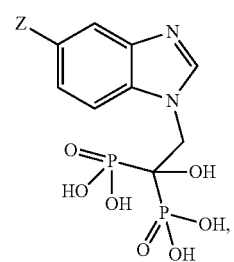

Formula XIII
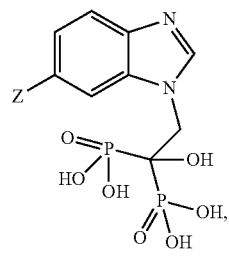

Formula IXV
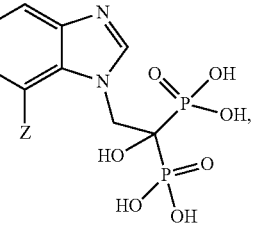

Formula XV
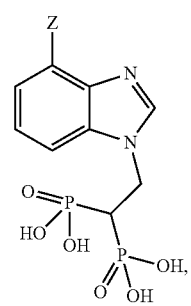

Formula XVI
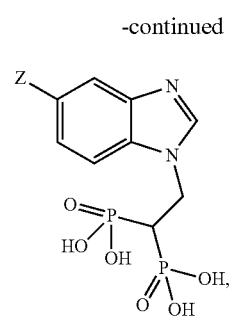

Formula XVII
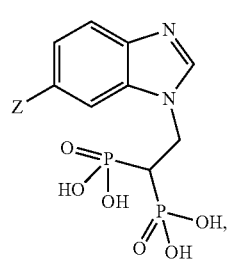

Formula XVIII
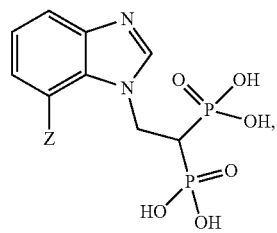

in the Formulae XI-XVIII, Z is hydrogen, hydroxy, an aliphatic group, alkoxy, amino or alkylamino.

10. The immunogenic composition according to any one of 7 to 9, wherein the compound is a compound represented by Formula IXX or XX:

Formula IXX
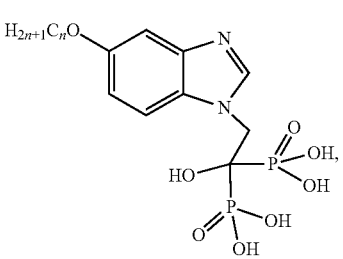

Formula XX
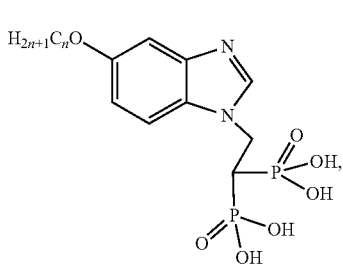

in Formulae IXX and XX, n is 0, or an integer of 1-12.

11. The immunogenic composition according to any one of 7 to 10, wherein the compound is any one of the following:
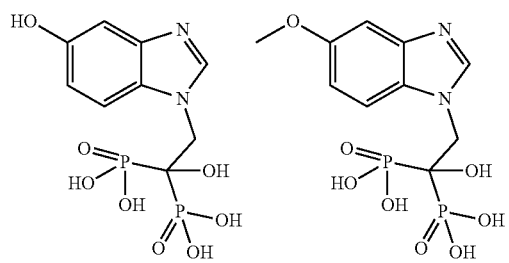
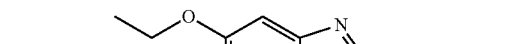
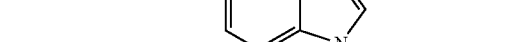
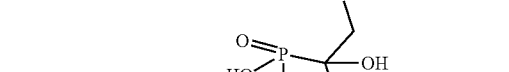
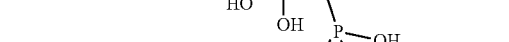
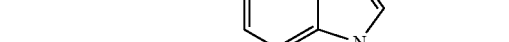
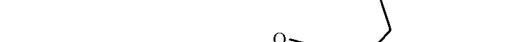
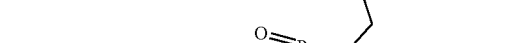
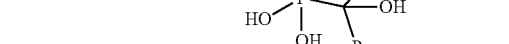
-continued
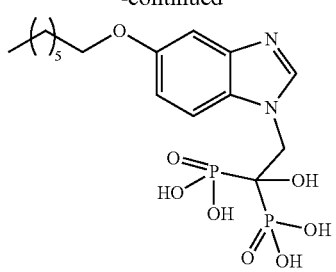
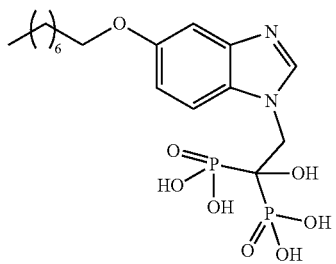
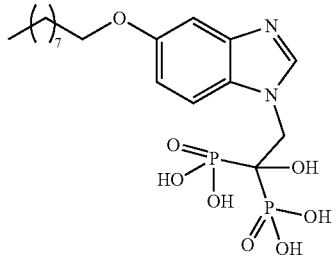
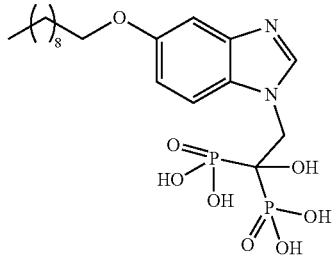
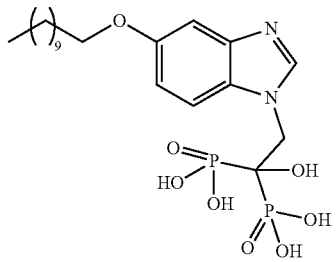
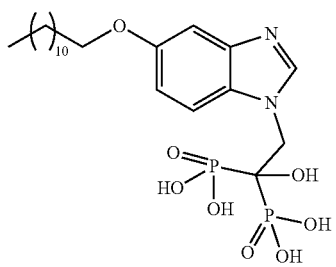

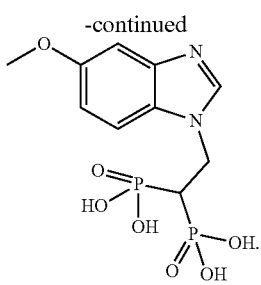

12. The immunogenic composition according to 1, wherein the farnesyl pyrophosphate synthase inhibitor is a compound of the following Formula or a pharmaceutically acceptable salt, ester, prodrug, or solvate thereof:

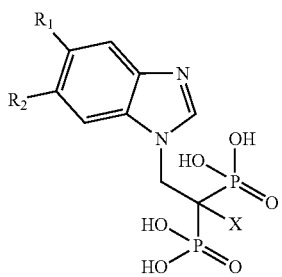

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl; X is selected from the group consisting of hydrogen, hydroxy, mercapto, and halogen.

13. The immunogenic composition according to 12, wherein the farnesyl pyrophosphate synthase inhibitor is a compound of the following Formula or a pharmaceutically acceptable salt, ester, prodrug, or solvate thereof:

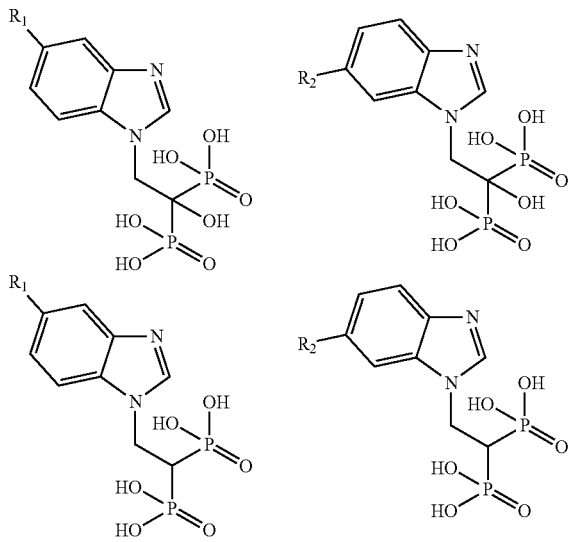

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl.

14. The immunogenic composition according to 13, wherein the farnesyl pyrophosphate synthase inhibitor is a compound of the following Formula or a pharmaceutically acceptable salt, ester, prodrug, or solvate thereof:

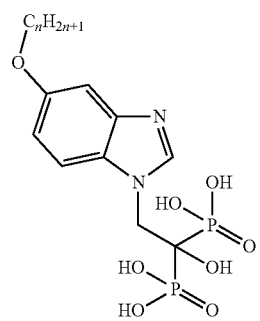

wherein n is an integer of 1 to 24, preferably n is an integer of 1 to 12.

15. The immunogenic composition according to 14, wherein n is an integer from 1 to 20.

16. The immunogenic composition according to 14, wherein n is an integer from 1 to 15.

17. The immunogenic composition according to 14, wherein the compound is selected from the group consisting of:

| n= | compound No. |
|---|---|
| 1 | TH-Z79 |
| 2 | TH-Z148 |
| 3 | TH-Z149 |
| 4 | TH-Z150 |
| 5 | TH-Z151 |
| 6 | TH-Z80 |
| 7 | TH-Z152 |
| 8 | TH-Z81 |
| 9 | TH-Z153 |
| 10 | TH-Z82 |
| 11 | TH-Z154 and |
| 12 | TH-Z155. |

18. The immunogenic composition according to 1, wherein the farnesyl pyrophosphate synthase inhibitor is a compound of the following Formula or a pharmaceutically acceptable salt, ester, prodrug, or solvate thereof:

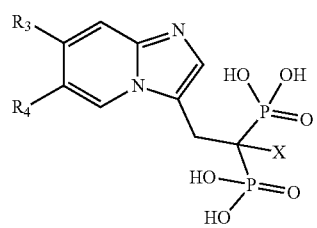

wherein $R_3$ and $R_4$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl; X is selected from the group consisting of hydrogen, hydroxy, mercapto, and halogen.

19. The immunogenic composition according to 18, wherein the farnesyl pyrophosphate synthase inhibitor is a compound of the following Formula or a pharmaceutically acceptable salt, ester, prodrug, or solvate thereof:

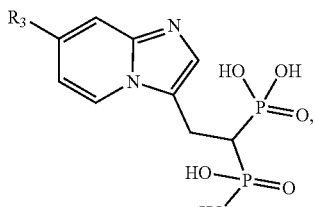

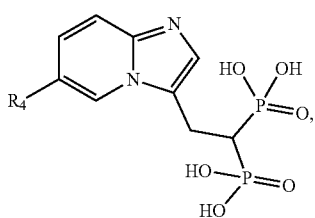

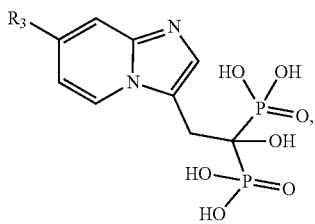

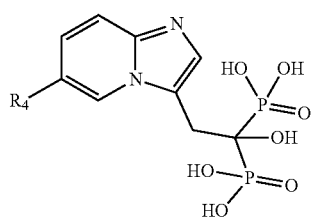

wherein $R_3$ and $R_4$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl.

20. The immunogenic composition according to 19, wherein the farnesyl pyrophosphate synthase inhibitor is a compound of the following Formula or a pharmaceutically acceptable salt, ester, prodrug, or solvate thereof:

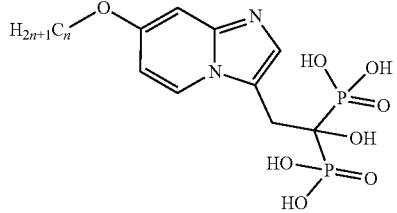

wherein n is an integer of 1 to 24, preferably n is an integer of 1 to 12.

21. The immunogenic composition according to 20, wherein n is an integer from 1 to 20.

22. The immunogenic composition according to 20, wherein n is an integer from 1 to 15.

23. The immunogenic composition according to 20, wherein the compound is selected from the group consisting of:

| n= | compound No. |
|---|---|
| 1 | TH-Z156 |
| 2 | TH-Z157 |
| 3 | TH-Z158 |
| 4 | TH-Z159 |
| 5 | TH-Z160 |
| 6 | TH-Z97 |
| 7 | TH-Z161 |
| 8 | TH-Z98 |
| 9 | TH-Z162 |
| 10 | TH-Z99 |
| 11 | TH-Z198 and |
| 12 | TH-Z163. |

24. The immunogenic composition according to 1, wherein the farnesyl pyrophosphate synthase inhibitor is a compound of the following Formula or a pharmaceutically acceptable salt, ester, prodrug, or solvate thereof:

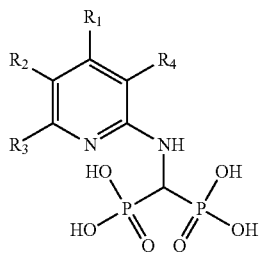

wherein:
$R_1$ is selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl;
$R_2$ is selected from the group consisting of hydrogen, alkyl, alkoxy, alkylamino, alkylthio, halogen, hydroxy, cycloalkyl, heterocyclyl, aryl and heteroaryl;
$R_3$ is selected from the group consisting of hydrogen, alkyl, alkoxy, alkylamino, alkylthio, halogen, hydroxy, cycloalkyl, heterocyclyl, aryl and heteroaryl;
or $R_2$ and $R_3$ together with the carbon atom to which they are attached form an aromatic or heteroaromatic ring; and $R_4$ is selected from the group consisting of hydrogen, alkyl, alkoxy, alkylamino, alkylthio, halogen, hydroxy, cycloalkyl, heterocyclyl, aryl and heteroaryl.

25. The immunogenic composition according to 24, wherein $R_1$ is selected from the group consisting of hydrogen, $C_{1-10}$ alkyl, $C_{1-10}$ alkynyl, $C_{1-10}$ alkylamino, $C_{1-10}$ alkylthio, halogen, hydroxy, indazolyl, $C_{1-10}$ alkoxy, and $C_{1-10}$ alkoxy substituted with phenyl or pyridyl, wherein the pyridyl is optionally substituted with carbamoyl.

26. The immunogenic composition according to 25, wherein $R_1$ is selected from the group consisting of hydrogen, 4-methylphenylethoxy, 4,5,6,7-tetrahydro-2H-indazol-2-yl, (2-carbamoylpyridin-4-yl)methoxy, benzyloxy, hexyloxy, methylthio, octylamino, hexyl, octyl, decyl, oct-1-yn-1-yl, hydroxyl, and bromo.

27. The immunogenic composition according to 24, wherein $R_2$ is selected from the group consisting of hydrogen, $C_{1-10}$ alkoxy, and halogen.

28. The immunogenic composition according to 27, wherein $R_2$ is selected from the group consisting of hydrogen, octyloxy, and bromo.

29. The immunogenic composition according to 24, wherein $R_3$ is selected from the group consisting of hydrogen, $C_{1-10}$ alkyl, and $C_{1-10}$ alkoxy.

30. The immunogenic composition according to 29, wherein $R_3$ is selected from the group consisting of hydrogen, methyl, and hexyloxy.

31. The immunogenic composition according to 24, wherein $R_2$ and $R_3$ together with the carbon atom to which they are attached form a benzene ring.

32. The immunogenic composition according to 24, wherein $R_4$ is selected from the group consisting of hydrogen, and $C_{1-10}$ alkoxy.

33. The immunogenic composition according to 32, wherein $R_4$ is selected from the group consisting of hydrogen and octyloxy.

34. The immunogenic composition according to 24, wherein the compound is selected from the group consisting of:

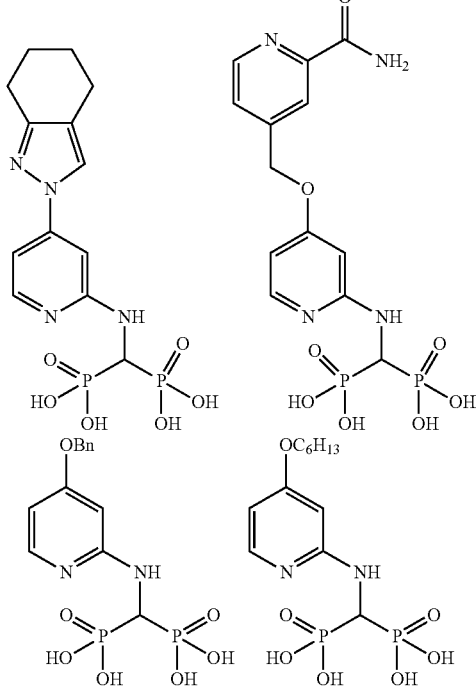

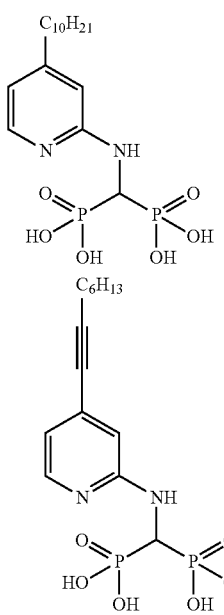

-continued

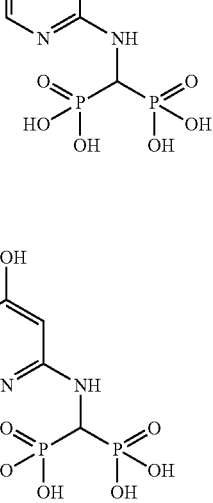

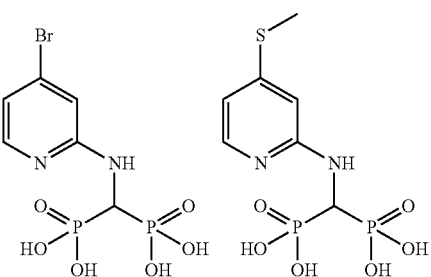

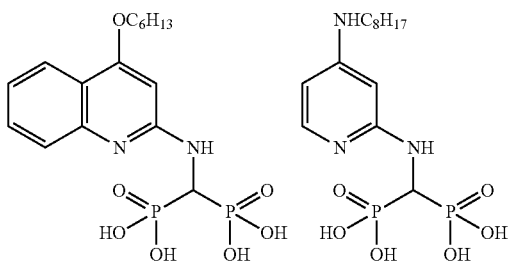

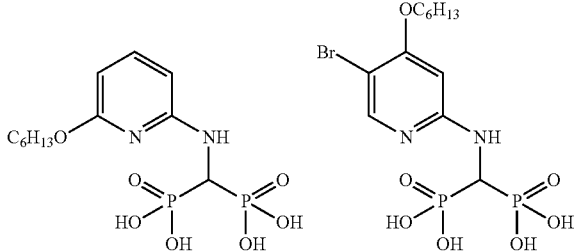

-continued

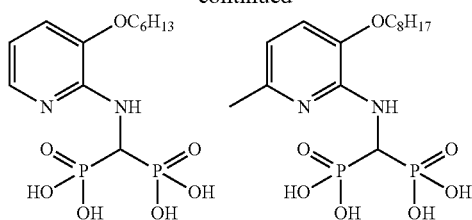

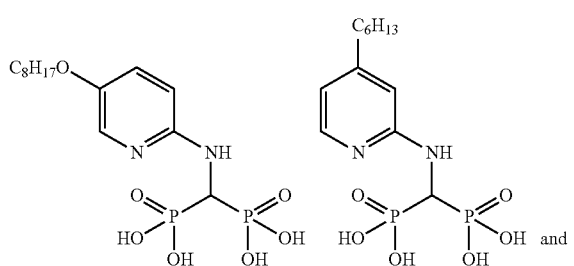

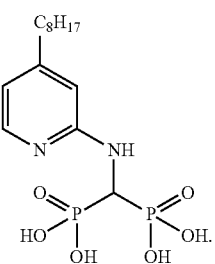

35. The immunogenic composition according to 1, wherein the farnesyl pyrophosphate synthase inhibitor is a compound of the following Formula or a pharmaceutically acceptable salt, ester, prodrug, or solvate thereof:

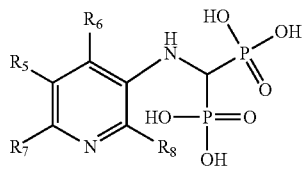

wherein:

$R_5$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_6$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_7$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and $R_8$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

36. The immunogenic composition according to 35, wherein $R_5$ is selected from $C_{1-10}$ alkoxy.

37. The immunogenic composition according to 35, wherein the compound is

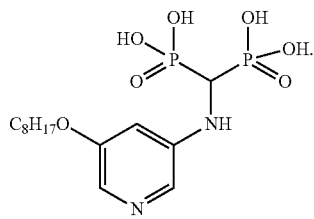

38. The immunogenic composition according to 1, wherein the geranylgeranyl pyrophosphate synthase inhibitor is a compound of the following Formula or a pharmaceutically acceptable salt, ester, prodrug, or solvate thereof:

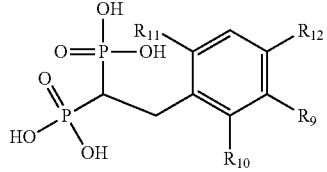

wherein:

$R_9$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_{10}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_{11}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and $R_{12}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

39. The immunogenic composition according to 38, wherein $R_9$ is selected from $C_{1-10}$ alkoxy.

40. The immunogenic composition according to 38, wherein the compound is

TH-Z144

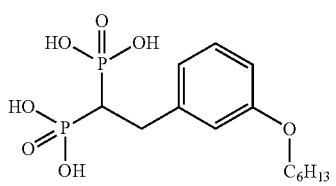

or

TH-Z145

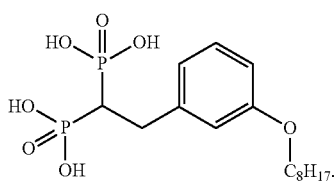

41. The immunogenic composition according to any one of 1-40, comprising one or more antigens.

42. The immunogenic composition according to 41, wherein the antigen is derived from a bacteria, a virus, a parasite or a tumor.

43. The immunogenic composition according to 41, wherein the antigen is derived from anthrax, *campylobacter*, cholera, diphtheria, enterotoxigenic *Escherichia coli*, giardia, *Neisseria gonorrhoeae, Helicobacter pylori, Haemophilus influenzae* type B, *haemophilus* influenza of an unknown type, meningitis cocci, pertussis, pneumococcus, *salmonella, shigella, streptococcus* B, *streptococcus* of a group A, tetanus, *Vibrio cholerae, yersinia, staphylococcus, pseudomonas* and *clostridium* species, or antigens derived from adenovirus, dengue serotype 1 to 4, ebola virus, enterovirus, hepatitis serotype A to E, herpes simplex virus 1 or 2, human immunodeficiency virus, influenza, Japanese equine encephalitis, measles, norwalk, papilloma virus, parvovirus B19, poliomyelitis, rabies, rotavirus, rubella, measles, vaccinia lymph, vaccinia lymph constructs containing genes encoding other antigens such as malaria antigens, chickenpox, and yellow fever, or antigens derived from *entamoeba histolytica*, malaria parasite, toxoplasmosis, and worms, or antigens derived from tumors.

44. The immunogenic composition according to 41, wherein the antigen is derived from Middle East Respiratory Syndrome (Mers) virus, hepatitis B virus, or melanoma.

45. The immunogenic composition according to any one of 1-44, for the treatment or prevention of Middle East Respiratory Syndrome, Hepatitis B Virus, or Melanoma.

46. The immunogenic composition according to any one of 1-45, further comprising another adjuvant.

47. The immunogenic composition according to 46, wherein the another adjuvant is selected from the group consisting of aluminum adjuvants, complete Freund's adjuvant, incomplete Freund's adjuvant, MF59, AS01, AS02, AS03, AS04, AS15, CAF01, ISCOMs (Immunostimulatory complex), Virosomes (virus particles), GLA-SE, liposomes, edible oils, saponins, AF03, and TLR agonists.

48. The immunogenic composition according to 47, wherein the TLR agonists are selected from the group consisting of (e.g., triacyl lipoprotein), TLR2 stimulants (e.g., peptidoglycans, yeast polysaccharides, HMGB1 (high mobility group protein 1), lipoteichoic acid), TLR3 stimulants (double-stranded RNA such as PolyI:C), TLR4 stimulants (e.g., LPS, MPL, RC529, GLA, E6020), TLR5 stimulants (flagellin), TLR6 stimulants (e.g., triacyl lipoprotein, lipoteichoic acid), TLR7/8 stimulants (single-stranded RNA, imiquimod), TLR9 stimulants (DNA, such as CPG ODN), C-lectin ligands (e.g., kelp polysaccharides), and CD1d ligands (e.g., α-galactosylceramide).

49. The immunogenic composition according to any one of 1-48, suitable for immunization by oral, topical or parenteral route.

50. The immunogenic composition according to 49, suitable for immunization by injection.

51. The immunogenic composition according to 49, suitable for immunization by sole, subcutaneous, muscular, abdominal and nasal mucosa injection in a subject.

52. The immunogenic composition according to any one of 1-51, for use in the preparation of the following vaccines: BCG vaccine, hepatitis A vaccine, hepatitis B vaccine, hepatitis C vaccine, hepatitis D vaccine, hepatitis E vaccine, influenza vaccine, polio vaccine, DPT vaccine, measles vaccine, vaccinum encephalitidis epidemicae, rabies vaccine, hemorrhage fever vaccine, pneumonia vaccine, epidemic menigitis vaccine, hepatitis A vaccine, mumps vaccine, influenza vaccine, rubella vaccine, varicella vaccine, AIDS vaccine, malaria vaccine, and vaccines for the treatment and prevention of cancers, including but not limited to melanoma therapeutic vaccines, melanoma prophylactic vaccines, lung cancer therapeutic vaccines, lung cancer prophylactic vaccines, bladder cancer prophylactic vaccines, bladder cancer therapeutic and prophylactic vaccines, cervical cancer therapeutic vaccines, cervical cancer prophylactic vaccines, bladder cancer therapeutic vaccines, bladder cancer prophylactic vaccines, breast cancer therapeutic vaccines, breast cancer prophylactic vaccines, liver cancer therapeutic vaccines, liver cancer prophylactic vaccines, prostate cancer therapeutic vaccines, and prostate cancer prophylactic vaccines.

53. A thiolase inhibitor for use as an adjuvant.

54. A HMG-CoA synthase inhibitor for use as an adjuvant.

55. A HMG-CoA reductase inhibitor for use as an adjuvant.

56. A mevalonate kinase inhibitor for use as an adjuvant.

57. A phosphomevalonate kinase inhibitor for use as an adjuvant.

58. A mevalonate-5-pyrophosphate decarboxylase inhibitor for use as an adjuvant.

59. An isopentenyl pyrophosphate isomerase inhibitor for use as an adjuvant.

60. A farnesyl pyrophosphate synthase inhibitor for use as an adjuvant.

61. A geranylgeranyl pyrophosphate synthase inhibitor for use as an adjuvant.

62. A geranylgeranyl transferase (I, II) inhibitor for use as an adjuvant.

63. The HMG-CoA reductase inhibitor according to 55, wherein the HMG-CoA reductase inhibitor is a statin compound.

64. The HMG-CoA reductase inhibitor according to 63, wherein the statin compound is selected from the group consisting of pravastatin, atorvastatin, rosuvastatin, fluvastatin, pitavastatin, mevastatin, lovastatin, simvastatin, cerivastatin, and a pharmaceutically acceptable salt, ester, prodrug, or solvate thereof.

65. The HMG-CoA reductase inhibitor according to 63, wherein the statin compound is selected from the group consisting of simvastatin, lovastatin and mevastatin, and a pharmaceutically acceptable salt, ester, prodrug or solvate thereof.

66. The farnesyl pyrophosphate synthase inhibitor according to 60, wherein the farnesyl pyrophosphate synthase inhibitor is a bisphosphonic acid compound or a pharmaceutically acceptable salt, ester, prodrug, or solvate thereof.

67. The farnesyl pyrophosphate synthase inhibitor according to 66, wherein the bisphosphonic acid compound is selected from the group consisting of zoledronic acid, pamidronic acid, alendronic acid, ibandronic acid, neridronic acid, risedronic acid, olpadronic acid, and minodronic acid.

68. The farnesyl pyrophosphate synthase inhibitor according to 60, wherein the farnesyl pyrophosphate synthase inhibitor is a compound of the following Formula or a pharmaceutically acceptable salt, ester, prodrug, or solvate thereof:

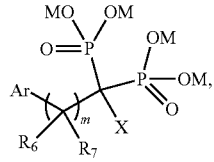

Formula I

In the Formula I, the compound has a molecular weight of less than 1000, and Ar is a benzimidazolyl-type group, or an aza-benzimidazolyl group;

X is selected from the group consisting of hydrogen, hydroxy, an aliphatic group, mercapto, halogen, alkoxy and alkyl; each M is independently any one of the following: a negative charge, hydrogen, alkyl, an aliphatic group, —$(CH_2)_p$—O—CO—R, —$(CH_2)_p$—CO—R or a positive ion; wherein p is an integer of 1 to 6, R is hydrogen, alkyl or aryl; the positive ion is $Li^+$, $Na^+$, $K^+$, $Ca^{2+}$, $Mg^{2+}$, $NH_4^+$ or $N(R')_4^+$, wherein R' is alkyl; $R_6$ and $R_7$ are each independently selected from the group consisting of hydrogen, hydroxy, mercapto, halogen, amino, an aliphatic group and alkyl;

m is an integer of 1 to 6.

69. The farnesyl pyrophosphate synthase inhibitor according to 68, wherein the compound represented by Formula I is a compound represented by the following Formulae II-X:

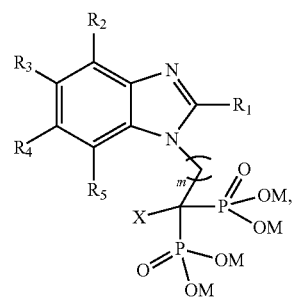

Formula II

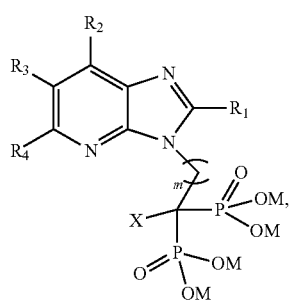

Formula III

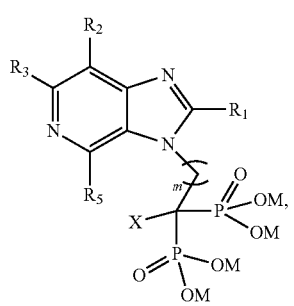

Formula IV

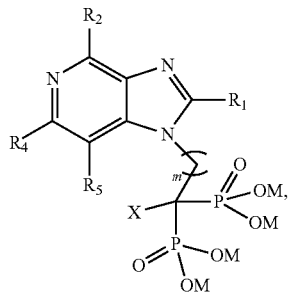

Formula V

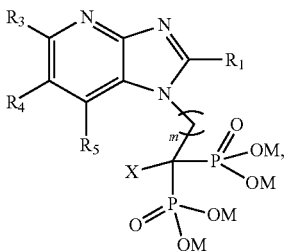

Formula VI

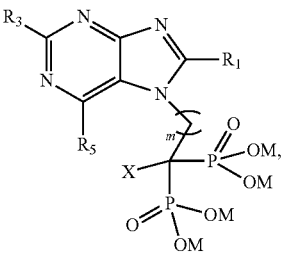

Formula VII

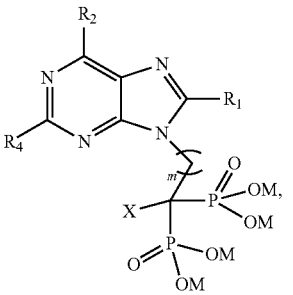

Formula VIII

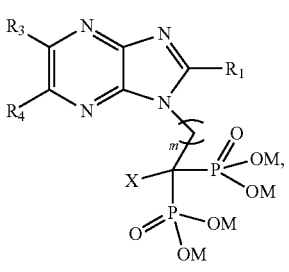

Formula IX

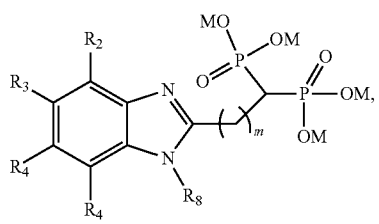

Formula X in Formulae II-X, X is selected from the group consisting of hydrogen, hydroxy, mercapto, halogen, alkoxy and alkyl;

each M is independently selected from the group consisting of a negative charge, hydrogen, alkyl, —$(CH_2)_p$—O—CO—R, —$(CH_2)_p$—CO—R and a positive ion; wherein p is an integer of 1 to 6, R is hydrogen, alkyl or aryl; the positive ion is $Li^+$, $Na^+$, $K^+$, $Ca^{2+}$, $Mg^{2+}$, $NH_4^+$ or $N(R')_4^+$, wherein R' is alkyl;

$R_1$, $R_2$, $R_3$, $R_4$, $R_5$, and $R_8$ are independently selected from the group consisting of hydrogen, hydroxy, an aliphatic group, mercapto, halogen, amino, alkyl, —O—$(CH_2)_q CH_3$, —NH—$(CH_2)_q CH_3$, —N[$(CH_2)_q CH_3$]$_2$, —$(CH_2)_p$—S—$(CH_2)_q CH_3$, —O—$(CH_2)_p$—S—$(CH_2)_q CH_3$ and —O—$(CH_2)_p$—O—$(CH_2)_q CH_3$, wherein p is an integer of 1 to 6, q is an integer of 0 to 6; m is an integer of 1 to 6.

70. The farnesyl pyrophosphate synthase inhibitor according to 68 or 69, wherein the compound is a compound represented by Formulae XI-XVIII:

Formula XI

Formula XII

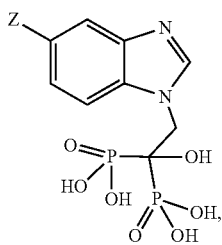

Formula XIII

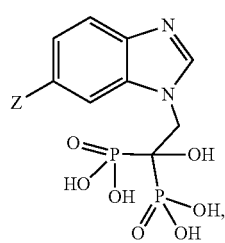

Formula IXV

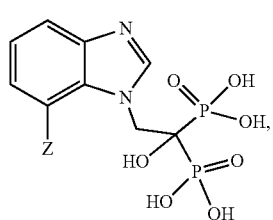

Formula XV

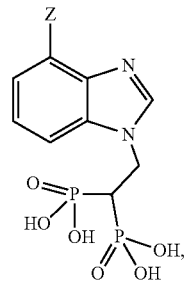

Formula XVI

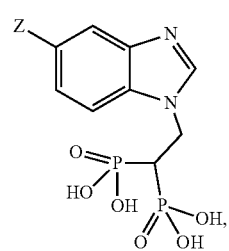

Formula XVII

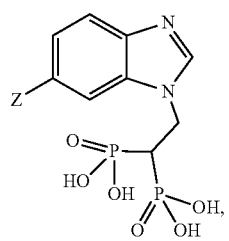

Formula XVIII

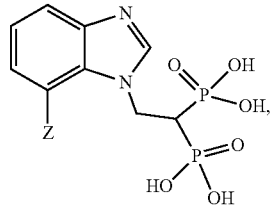

in Formulae XI-XVIII, Z is hydrogen, hydroxy, an aliphatic group, alkoxy, amino or alkylamino.

71. The farnesyl pyrophosphate synthase inhibitor according to any one of 68-70, wherein the compound is a compound represented by Formula IXX or XX:

Formula IXX

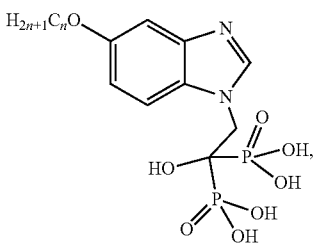

Formula XX
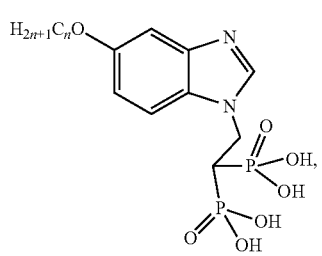
in Formulae IXX and XX, n is 0, or an integer of 1 to 12.
72. The farnesyl pyrophosphate synthase inhibitor according to any one of 68-71, wherein the compound is any one of the following:
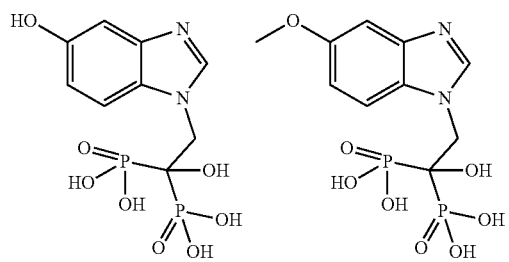
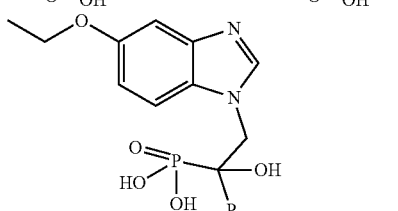
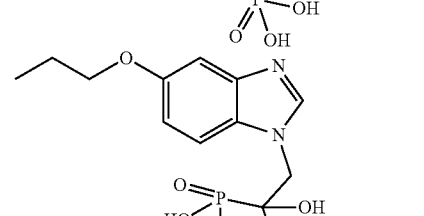
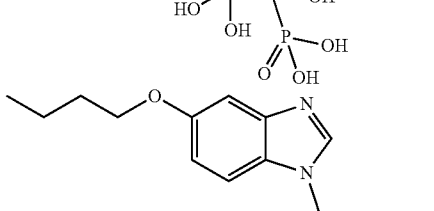
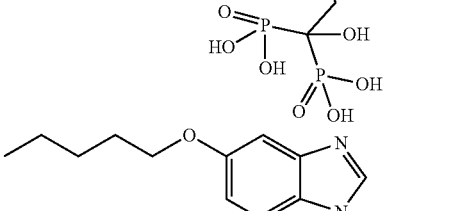
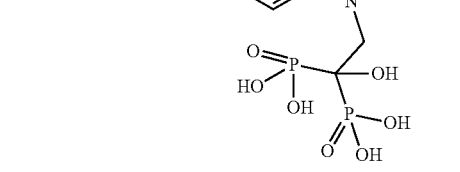
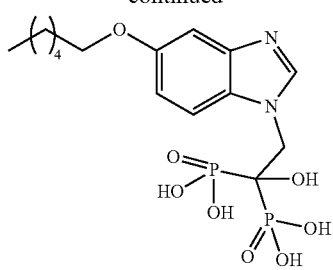
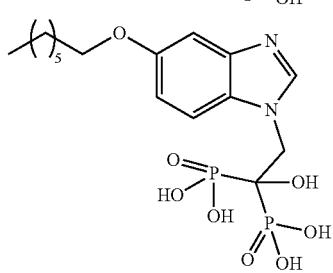
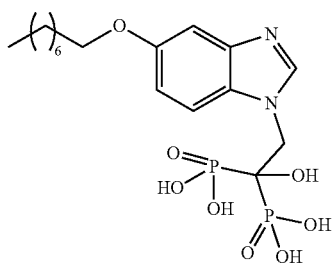
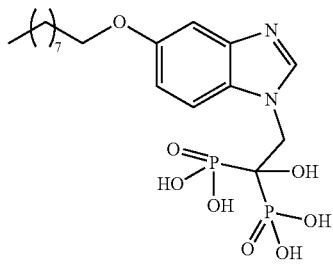
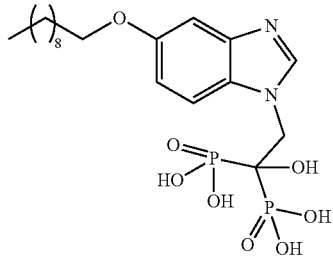
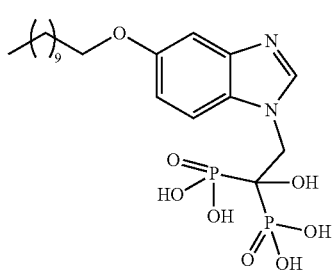

-continued

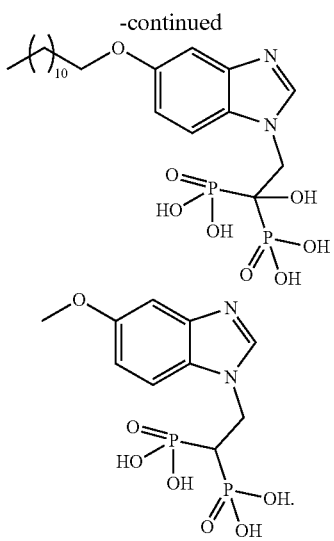

73. The farnesyl pyrophosphate synthase inhibitor according to 60, wherein the farnesyl pyrophosphate synthase inhibitor is a compound of the following Formula or a pharmaceutically acceptable salt, ester, prodrug, or solvate thereof:

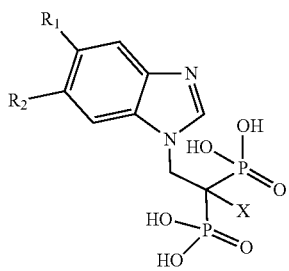

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl; X is selected from the group consisting of hydrogen, hydroxy, mercapto, and halogen.

74. The farnesyl pyrophosphate synthase inhibitor according to 73, wherein the farnesyl pyrophosphate synthase inhibitor is a compound of the following Formula or a pharmaceutically acceptable salt, ester, prodrug, or solvate thereof:

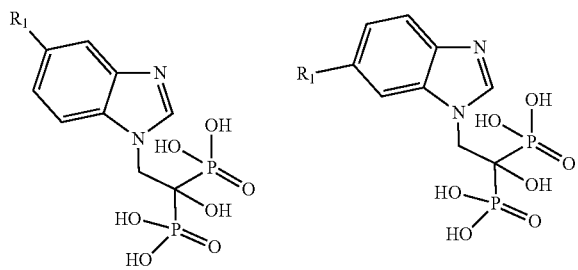

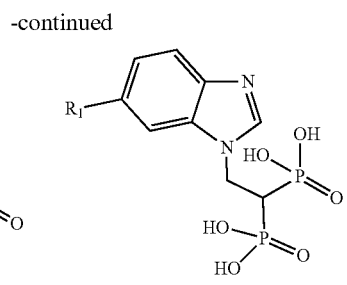

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl.

75. The farnesyl pyrophosphate synthase inhibitor according to 60, wherein the farnesyl pyrophosphate synthase inhibitor is a compound of the following Formula or a pharmaceutically acceptable salt, ester, prodrug, or solvate thereof:

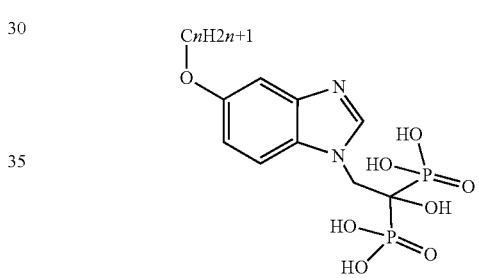

wherein n is an integer of 1 to 24, preferably n is an integer of 1 to 12.

76. The farnesyl pyrophosphate synthase inhibitor according to 75, wherein n is an integer from 1 to 20.

77. The farnesyl pyrophosphate synthase inhibitor according to 75, wherein n is an integer from 1 to 15.

78. The farnesyl pyrophosphate synthase inhibitor according to 75, wherein the compound is selected from the group consisting of:

| n= | compound No. |
|---|---|
| 1 | TH-Z79 |
| 2 | TH-Z148 |
| 3 | TH-Z149 |
| 4 | TH-Z150 |
| 5 | TH-Z151 |
| 6 | TH-Z80 |
| 7 | TH-Z152 |
| 8 | TH-Z81 |
| 9 | TH-Z153 |
| 10 | TH-Z82 |
| 11 | TH-Z154 and |
| 12 | TH-Z155. |

79. The farnesyl pyrophosphate synthase inhibitor according to 60, wherein the farnesyl pyrophosphate synthase inhibitor is a compound of the following Formula or a pharmaceutically acceptable salt, ester, prodrug, or solvate thereof:

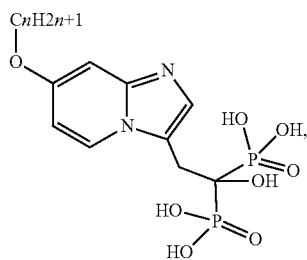

wherein n is an integer from 1 to 12.

80. The farnesyl pyrophosphate synthase inhibitor according to 60, wherein the farnesyl pyrophosphate synthase inhibitor is a compound of the following Formula or a pharmaceutically acceptable salt, ester, prodrug, or solvate thereof:

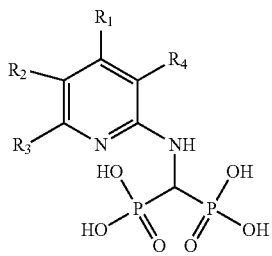

wherein $R_1$ is selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl;
$R_2$ is selected from the group consisting of hydrogen, alkyl, alkoxy, alkylamino, alkylthio, halogen, hydroxy, cycloalkyl, heterocyclyl, aryl and heteroaryl;
$R_3$ is selected from the group consisting of hydrogen, alkyl, alkoxy, alkylamino, alkylthio, halogen, hydroxy, cycloalkyl, heterocyclyl, aryl and heteroaryl;
or $R_2$ and $R_3$ together with the carbon atom to which they are attached form an aromatic or heteroaromatic ring; and
$R_4$ is selected from the group consisting of hydrogen, alkyl, alkoxy, alkylamino, alkylthio, halogen, hydroxy, cycloalkyl, heterocyclyl, aryl and heteroaryl.

81. The farnesyl pyrophosphate synthase inhibitor according to 80, wherein $R_1$ is selected from the group consisting of hydrogen, $C_{1-10}$ alkyl, $C_{1-10}$ alkynyl, $C_{1-10}$ alkylamino, $C_{1-10}$ alkylthio, halogen, hydroxy, indazolyl, $C_{1-10}$ alkoxy, and $C_{1-10}$ alkoxy substituted with phenyl or pyridyl, wherein the pyridyl is optionally substituted with carbamoyl.

82. The farnesyl pyrophosphate synthase inhibitor according to 81, wherein $R_1$ is selected from the group consisting of hydrogen, 4-methylphenylethoxy, 4,5,6,7-tetrahydro-2H-indazol-2-yl, (2-carbamoylpyridin-4-yl)methoxy, benzyloxy, hexyloxy, methylthio, octylamino, hexyl, octyl, decyl, oct-1-yn-1-yl, hydroxyl, and bromo.

83. The farnesyl pyrophosphate synthase inhibitor according to 80, wherein $R_2$ is selected from the group consisting of hydrogen, $C_{1-10}$ alkoxy, and halogen.

84. The farnesyl pyrophosphate synthase inhibitor according to 83, wherein $R_2$ is selected from the group consisting of hydrogen, octyloxy, and bromo.

85. The farnesyl pyrophosphate synthase inhibitor according to 80, wherein $R_3$ is selected from the group consisting of hydrogen, $C_{1-10}$ alkyl, and $C_{1-10}$ alkoxy.

86. The farnesyl pyrophosphate synthase inhibitor according to 85, wherein $R_3$ is selected from the group consisting of hydrogen, methyl, and hexyloxy.

87. The farnesyl pyrophosphate synthase inhibitor according to 80, wherein $R_2$ and $R_3$ together with the carbon atom to which they are attached form a benzene ring.

88. The farnesyl pyrophosphate synthase inhibitor according to 80, wherein $R_4$ is selected from the group consisting of hydrogen, and $C_{1-10}$ alkoxy.

89. The farnesyl pyrophosphate synthase inhibitor according to 88, wherein $R_4$ is selected from the group consisting of hydrogen, and octyloxy.

90. The farnesyl pyrophosphate synthase inhibitor according to 80, wherein the compound is selected from the group consisting of:

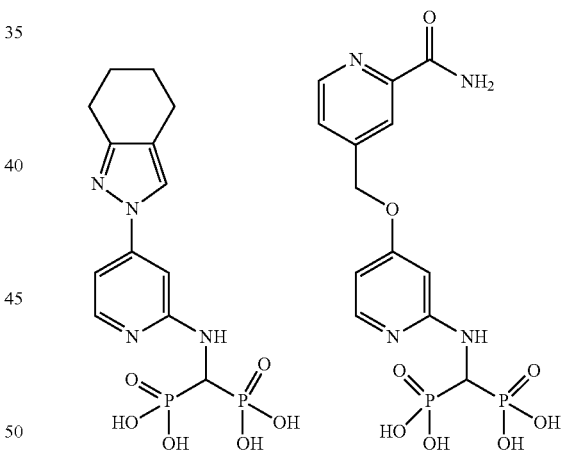

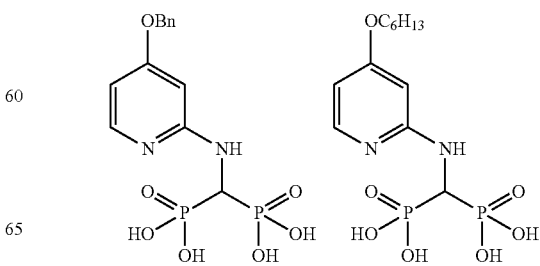

-continued

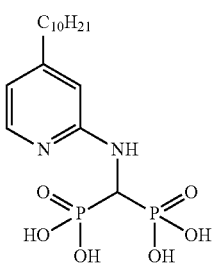
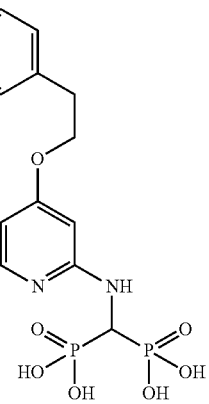
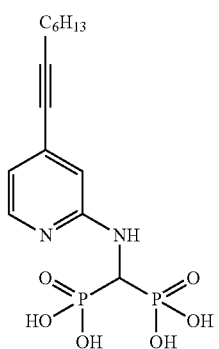
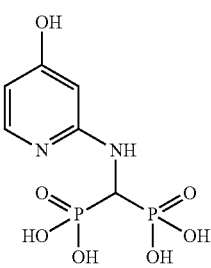
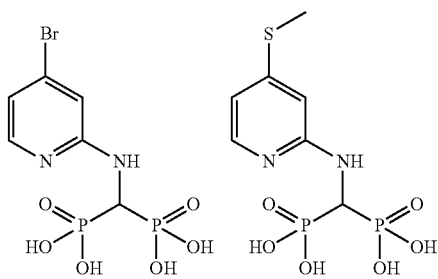
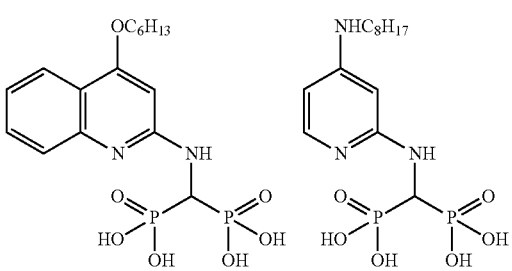
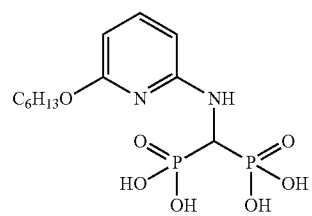

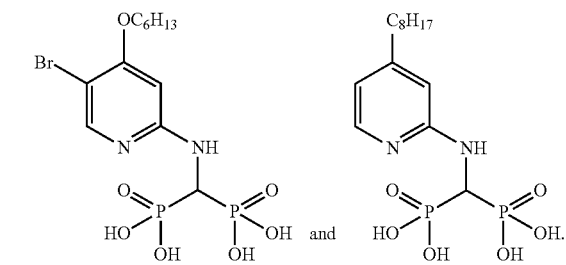

91. The farnesyl pyrophosphate synthase inhibitor according to 60, wherein the farnesyl pyrophosphate synthase inhibitor is a compound of the following Formula or a pharmaceutically acceptable salt, ester, prodrug, or solvate thereof:

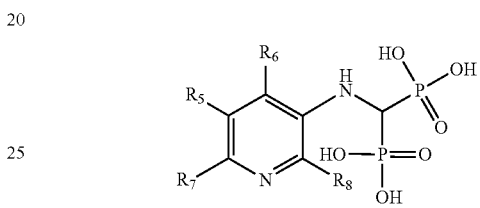

wherein:

$R_5$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_6$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_7$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and $R_8$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

92. The farnesyl pyrophosphate synthase inhibitor according to 91, wherein $R_5$ is selected from $C_{1-10}$ alkoxy.

93. The farnesyl pyrophosphate synthase inhibitor according to 91, wherein the compound is

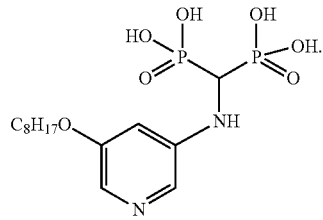

94. The geranylgeranyl pyrophosphate synthase inhibitor according to 61, wherein the geranylgeranyl pyrophosphate synthase inhibitor is a compound of the following Formula or a pharmaceutically acceptable salt, ester, prodrug, or solvate thereof:

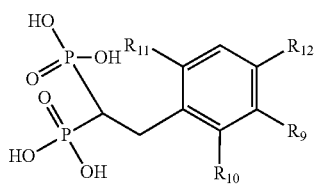

wherein:
$R_9$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_{10}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_{11}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and
$R_{12}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

95. The geranylgeranyl pyrophosphate synthase inhibitor according to 94, wherein $R_9$ is selected from $C_{1-10}$ alkoxy.

96. The geranylgeranyl pyrophosphate synthase inhibitor according to 94, wherein the compound is

TH-Z144

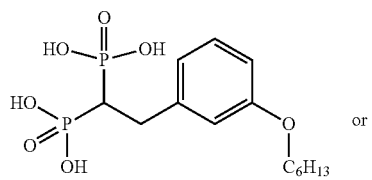

or

TH-Z145

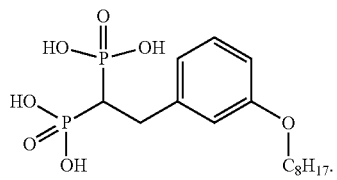

97. Use of a thiolase inhibitor as an adjuvant in the preparation of an immunogenic composition.

98. Use of a HMG-CoA synthase inhibitor as an adjuvant in the preparation of an immunogenic composition.

99. Use of a HMG-CoA reductase inhibitor as an adjuvant in the preparation of an immunogenic composition.

100. Use of a mevalonate kinase inhibitor as an adjuvant in the preparation of an immunogenic composition.

101. Use of a phosphomevalonate kinase inhibitor as an adjuvant in the preparation of an immunogenic composition.

102. Use of a mevalonate-5-pyrophosphate decarboxylase inhibitor as an adjuvant in the preparation of an immunogenic composition.

103. Use of an isopentenyl pyrophosphate isomerase inhibitor as an adjuvant in the preparation of an immunogenic composition.

104. Use of a farnesyl pyrophosphate synthase inhibitor as an adjuvant in the preparation of an immunogenic composition.

105. Use of a geranylgeranyl pyrophosphate synthase inhibitor as an adjuvant in the preparation of an immunogenic composition.

106. Use of a geranylgeranyl transferase (I, II) inhibitor as an adjuvant in the preparation of an immunogenic composition.

107. The use of 99, wherein the HMG-CoA reductase inhibitor is a statin compound.

108. The use of 107, wherein the statin compound is selected from the group consisting of pravastatin, atorvastatin, rosuvastatin, fluvastatin, pitavastatin, mevastatin, lovastatin, simvastatin, cerivastatin, and a pharmaceutically acceptable salt, ester, prodrug, or solvate thereof.

109. The use of 107, wherein the statin compound is selected from the group consisting of simvastatin, lovastatin and mevastatin, and a pharmaceutically acceptable salt, ester, prodrug or solvate thereof.

110. The use of 109, wherein the farnesyl pyrophosphate synthase inhibitor is a bisphosphonic acid compound or a pharmaceutically acceptable salt, ester, prodrug, or solvate thereof.

111. The use of 110, wherein the bisphosphonic acid compound or a pharmaceutically acceptable salt thereof is selected from the group consisting of zoledronic acid, pamidronic acid, alendronic acid, ibandronic acid, neridronic acid, risedronic acid, olpadronic acid, and minodronic acid.

112. The use of 104, wherein the farnesyl pyrophosphate synthase inhibitor is a compound of the following Formula or a pharmaceutically acceptable salt, ester, prodrug, or solvate thereof:

Formula I

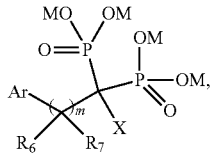

in the Formula I, the compound has a molecular weight of less than 1000, and Ar is a benzimidazolyl-type group, or an aza-benzimidazolyl group;

X is selected from the group consisting of hydrogen, hydroxy, an aliphatic group, mercapto, halogen, alkoxy and alkyl; each M is independently selected from the group consisting of a negative charge, hydrogen, alkyl, an aliphatic group, —$(CH_2)_p$—O—CO—R, —$(CH_2)_p$—CO—R and a positive ion; wherein p is an integer of 1 to 6, R is hydrogen, alkyl or aryl; the positive ion is $Li^+$, $Na^+$, $K^+$, $Ca^{2+}$, $Mg^{2+}$, $NH_4^+$ or $N(R')_4^+$, wherein R' is alkyl; $R_6$ and $R_7$ are each independently selected from the group consisting of hydrogen, hydroxy, mercapto, halogen, amino, an aliphatic group and alkyl;

m is an integer of 1 to 6.

113. The use of 112, the compound represented by the Formula I is a compound represented by the following Formulae II-X:

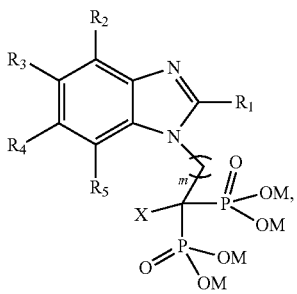

Formula II

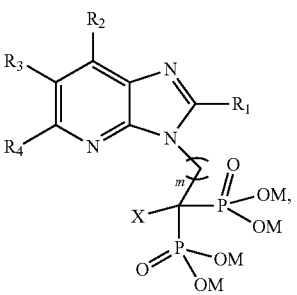

Formula III

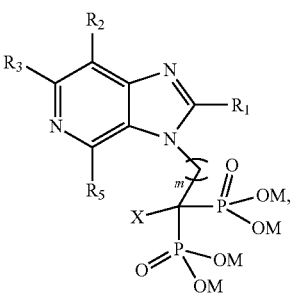

Formula IV

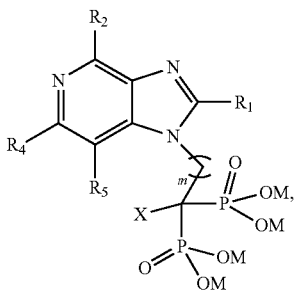

Formula V

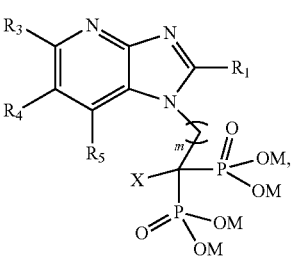

Formula VI

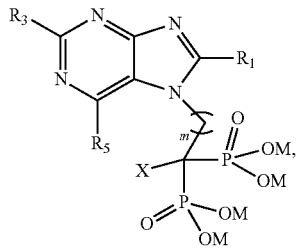

Formula VII

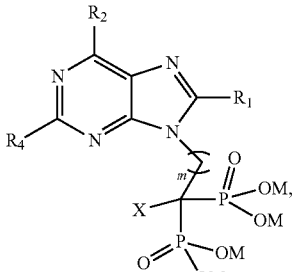

Formula VIII

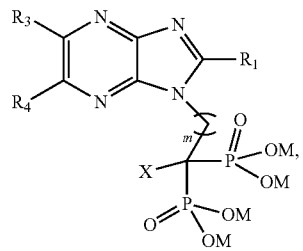

Formula IX

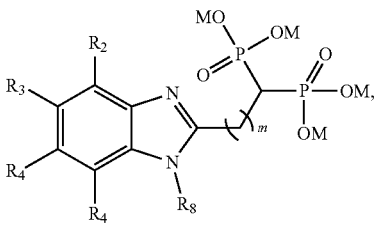

Formula X in Formulae II-X, X is selected from the group consisting of hydrogen, hydroxy, mercapto, halogen, alkoxy and alkyl;

Each M is independently selected from the group consisting of a negative charge, hydrogen, alkyl, —$(CH_2)_p$—O—CO—R, —$(CH_2)_p$—CO—R and a positive ion; wherein p is an integer of 1 to 6, R is hydrogen, alkyl or aryl; the positive ion is $Li^+$, $Na^+$, $K^+$, $Ca^{2+}$, $Mg^{2+}$, $NH_4^+$ or $N(R')_4^+$, wherein R' is alkyl;

$R_1$, $R_2$, $R_3$, $R_4$, $R_5$, and $R_8$ are independently selected from the group consisting of hydrogen, hydroxy, an aliphatic group, mercapto, halogen, amino, alkyl, —O—$(CH_2)_q CH_3$, —NH—$(CH_2)_q CH_3$, —N[$(CH_2)_q CH_3$]$_2$, —$(CH_2)_p$—S—$(CH_2)_q CH_3$, —O—$(CH_2)_p$—S—$(CH_2)_q CH_3$, and —O—$(CH_2)_p$—O—$(CH_2)_q CH_3$, wherein p is an integer of 1 to 6, q is an integer of 0 to 6; m is an integer of 1 to 6.

114. The use of 112 or 113, wherein the compound is a compound represented by Formulae XI-XVIII:

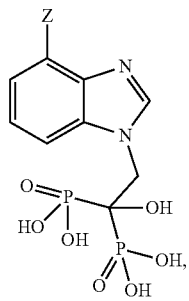

Formula XI

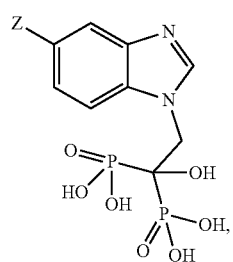

Formula XII

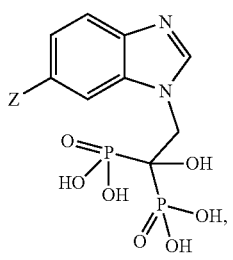

Formula XIII

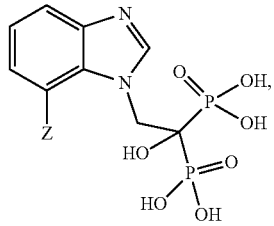

Formula IXV

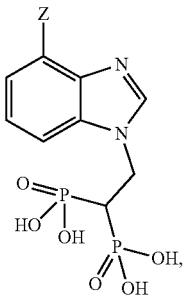

Formula XV

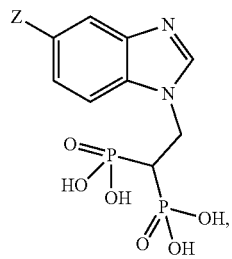

Formula XVI

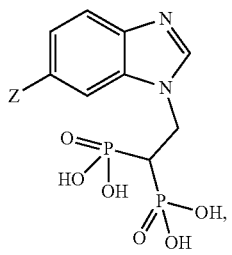

Formula XVII

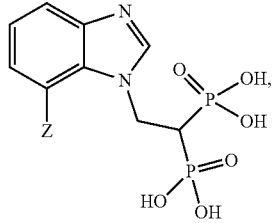

Formula XVIII in Formulae XI-XVIII, Z is hydrogen, hydroxy, an aliphatic group, alkoxy, amino or alkylamino.

115. The use of any one of 112-114, wherein the compound is a compound represented by Formula IXX or XX:

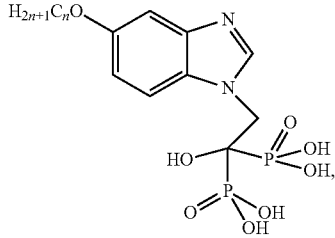

Formula IXX

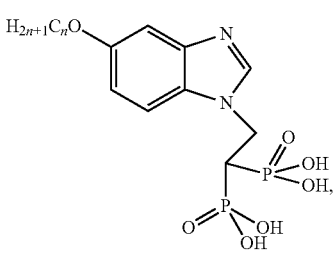

Formula XX in Formulae IXX and XX, n is 0, or an integer of 1-12.

116. The use of any one of 112-115, wherein the compound is any one of the following:
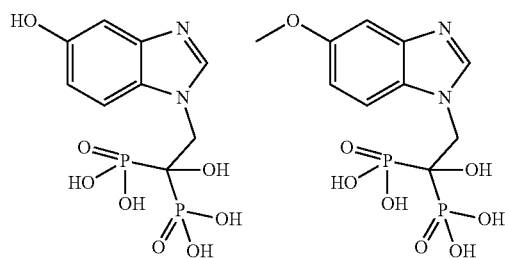
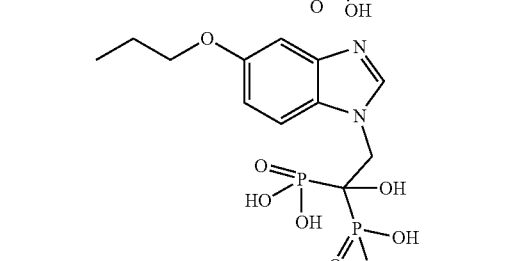
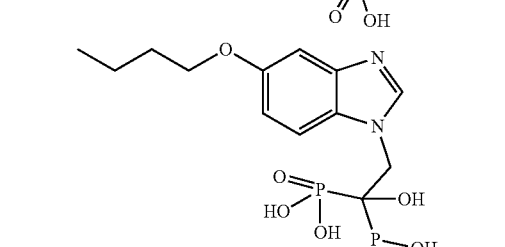
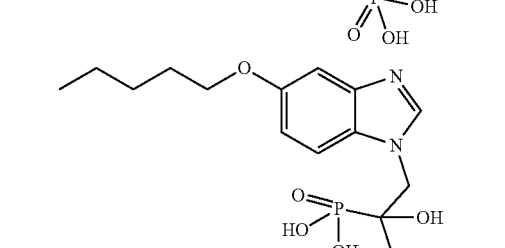
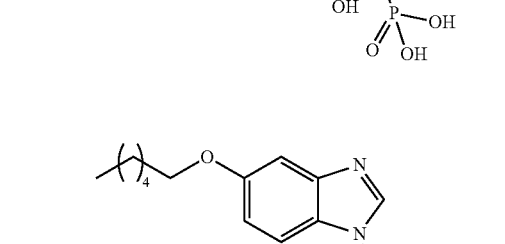
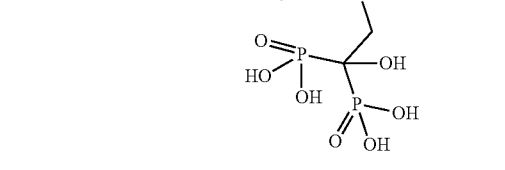
-continued
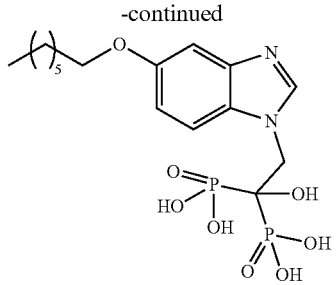
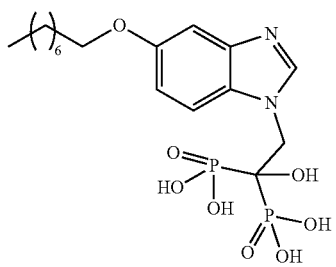
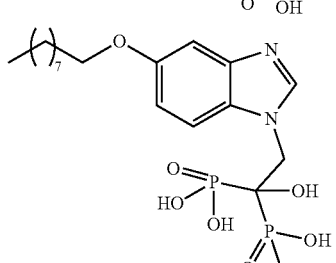
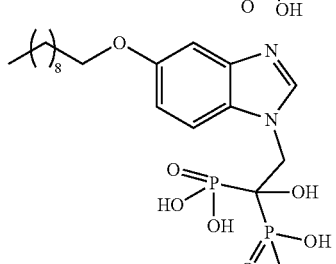
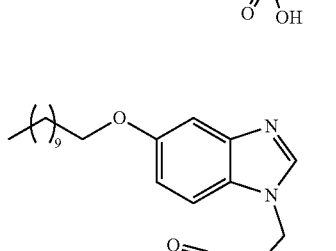
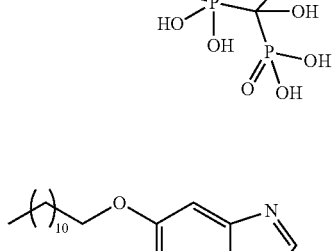
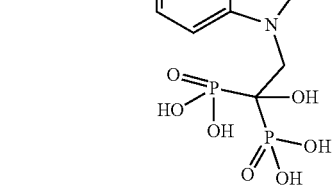

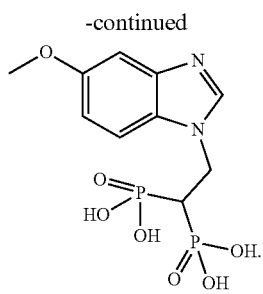

117. The use of 104, wherein the farnesyl pyrophosphate synthase inhibitor is a compound of the following Formula or a pharmaceutically acceptable salt, ester, prodrug, or solvate thereof:

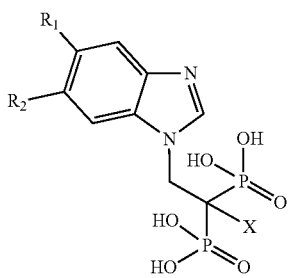

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl; X is selected from the group consisting of hydrogen, hydroxy, mercapto, and halogen.

118. The use of 117, wherein the farnesyl pyrophosphate synthase inhibitor is a compound of the following Formula or a pharmaceutically acceptable salt, ester, prodrug, or solvate thereof:

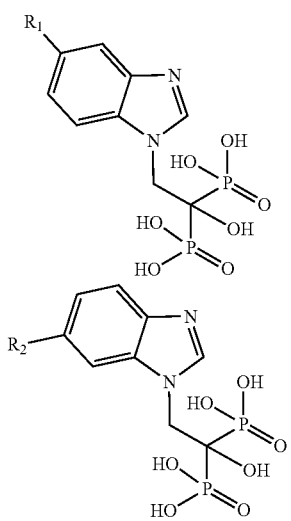

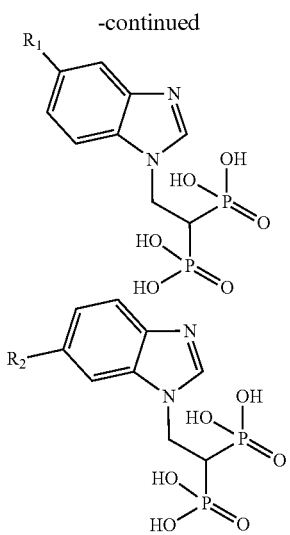

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl.

119. The use of 104, wherein the farnesyl pyrophosphate synthase inhibitor is a compound of the following Formula or a pharmaceutically acceptable salt, ester, prodrug, or solvate thereof:

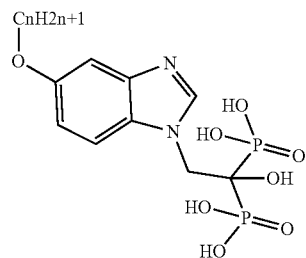

wherein n is an integer of 1 to 24, preferably n is an integer of 1 to 12.

120. The use of 119, wherein n is an integer from 1 to 20.

121. The use of 119, wherein n is an integer from 1 to 15.

122. The use of 119, wherein the compound is selected from the group consisting of:

| n= | compound No. |
|---|---|
| 1 | TH-Z79 |
| 2 | TH-Z148 |
| 3 | TH-Z149 |
| 4 | TH-Z150 |
| 5 | TH-Z151 |
| 6 | TH-Z80 |
| 7 | TH-Z152 |
| 8 | TH-Z81 |
| 9 | TH-Z153 |
| 10 | TH-Z82 |

49

-continued

| n= | compound No. |
|---|---|
| 11 | TH-Z154 and |
| 12 | TH-Z155. |

123. The use of 104, wherein the farnesyl pyrophosphate synthase inhibitor is a compound of the following Formula or a pharmaceutically acceptable salt, ester, prodrug, or solvate thereof:

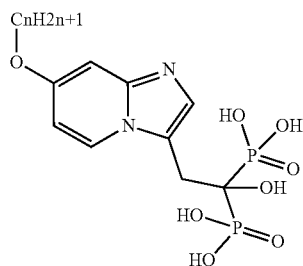

wherein n is an integer from 1 to 12.

124. The use of 104, wherein the farnesyl pyrophosphate synthase inhibitor is a compound of the following Formula or a pharmaceutically acceptable salt, ester, prodrug, or solvate thereof:

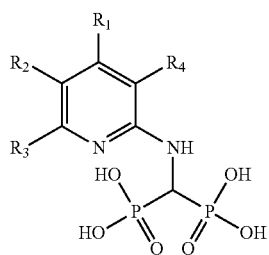

wherein $R_1$ is selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl;
$R_2$ is selected from the group consisting of hydrogen, alkyl, alkoxy, alkylamino, alkylthio, halogen, hydroxy, cycloalkyl, heterocyclyl, aryl and heteroaryl;
$R_3$ is selected from the group consisting of hydrogen, alkyl, alkoxy, alkylamino, alkylthio, halogen, hydroxy, cycloalkyl, heterocyclyl, aryl and heteroaryl;
or $R_2$ and $R_3$ together with the carbon atom to which they are attached form an aromatic or heteroaromatic ring; and
$R_4$ is selected from the group consisting of hydrogen, alkyl, alkoxy, alkylamino, alkylthio, halogen, hydroxy, cycloalkyl, heterocyclyl, aryl and heteroaryl.

125. The use of 124, wherein $R_1$ is selected from the group consisting of hydrogen, $C_{1-10}$ alkyl, $C_{1-10}$ alkynyl, $C_{1-10}$ alkylamino, $C_{1-10}$ alkylthio, halogen, hydroxy, indazolyl, $C_{1-10}$ alkoxy, and $C_{1-10}$ alkoxy substituted with phenyl or pyridyl, wherein the pyridyl is optionally substituted with carbamoyl.

50

126. The use of 125, wherein $R_1$ is selected from the group consisting of hydrogen, 4-methylphenylethoxy, 4,5,6,7-tetrahydro-2H-indazol-2-yl, (2-carbamoylpyridin-4-yl) methoxy, benzyloxy, hexyloxy, methylthio, octylamino, hexyl, octyl, decyl, oct-1-yn-1-yl, hydroxyl, and bromo.

127. The use of 124, wherein $R_2$ is selected from the group consisting of hydrogen, $C_{1-10}$ alkoxy, and halogen.

128. The use of 127, wherein $R_2$ is selected from the group consisting of hydrogen, octyloxy, and bromo.

129. The use of 124, wherein $R_3$ is selected from the group consisting of hydrogen, $C_{1-10}$ alkyl, and $C_{1-10}$ alkoxy.

130. The use of 129, wherein $R_3$ is selected from the group consisting of hydrogen, methyl, and hexyloxy.

131. The use of 124, wherein $R_2$ and $R_3$ together with the carbon atom to which they are attached form a benzene ring.

132. The use of 124, wherein $R_4$ is selected from the group consisting of hydrogen, and $C_{1-10}$ alkoxy.

133. The use of 132, wherein $R_4$ is selected from the group consisting of hydrogen and octyloxy.

134. The use of 124, wherein the compound is selected from the group consisting of:

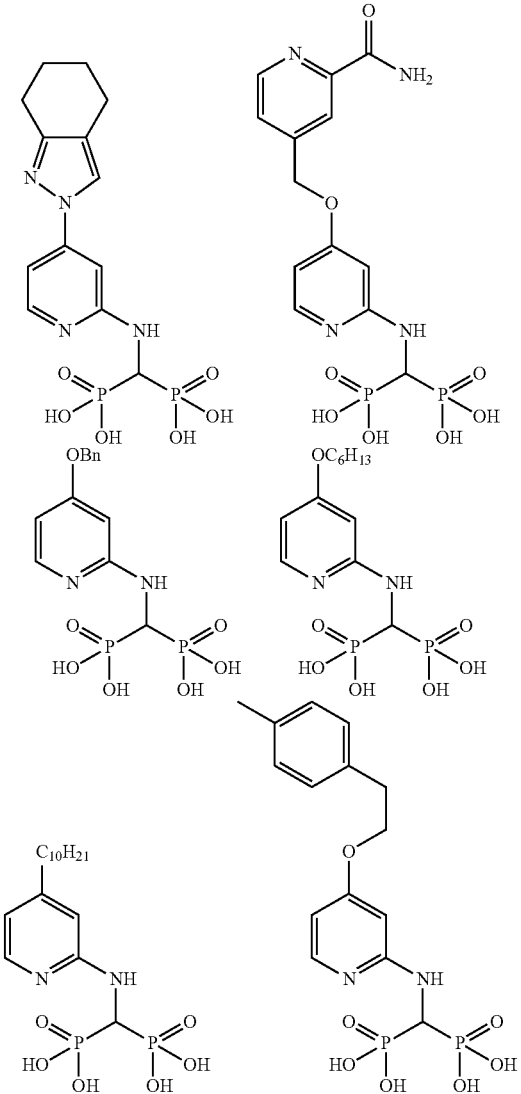

-continued

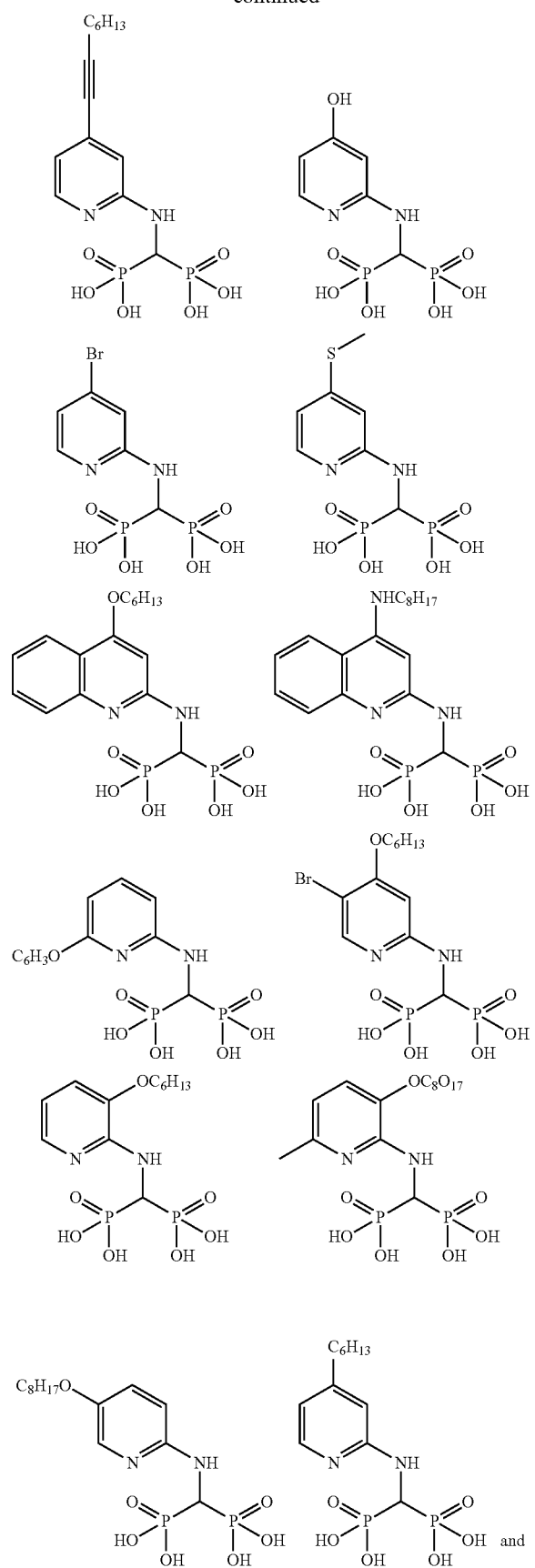

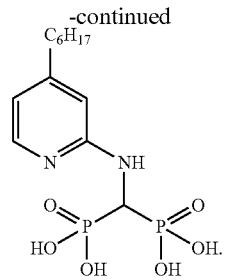

135. The use of 104, wherein the farnesyl pyrophosphate synthase inhibitor is a compound of the following Formula or a pharmaceutically acceptable salt, ester, prodrug, or solvate thereof:

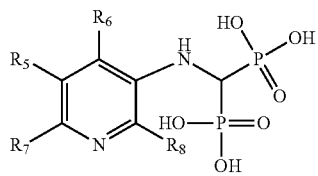

wherein:
$R_5$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_6$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_7$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and
$R_8$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

136. The use of 135, wherein $R_5$ is selected from $C_{1-10}$ alkoxy.

137. The use of 136, wherein the compound is

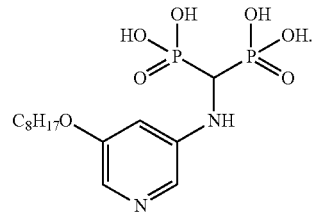

138. The use of 105, wherein the geranylgeranyl pyrophosphate synthase inhibitor is a compound of the following Formula or a pharmaceutically acceptable salt, ester, prodrug, or solvate thereof:

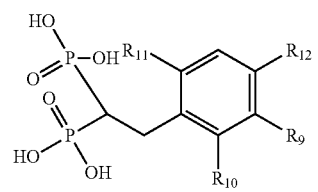

wherein:

R$_9$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

R$_{10}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

R$_{11}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and R$_{12}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

139. The use of 138, wherein R$_9$ is selected from C$_{1-10}$ alkoxy.

140. The use of 139, wherein the compound is

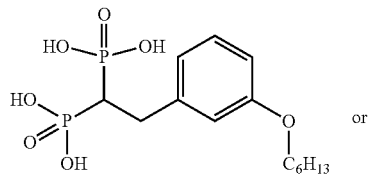

TH-Z144 or

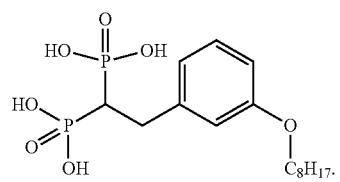

TH-Z145

141. A compound of the following Formula or a pharmaceutically acceptable salt, ester, prodrug, or solvate thereof:

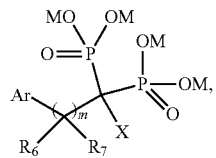

Formula I in the Formula I, the compound has a molecular weight of less than 1000, and Ar is a benzimidazolyl-type group, or an aza-benzimidazolyl group;

X is selected from the group consisting of hydrogen, hydroxy, an aliphatic group, mercapto, halogen, alkoxy and alkyl; each M is independently selected from the group consisting of a negative charge, hydrogen, alkyl, an aliphatic group, —(CH$_2$)$_p$—O—CO—R, —(CH$_2$)$_p$—CO—R and a positive ion; wherein p is an integer of 1 to 6, R is hydrogen, alkyl or aryl; the positive ion is Li$^+$, Na$^+$, K$^+$, Ca$^{2+}$, Mg$^{2+}$, NH$_4^+$ or N(R')$_4^+$, wherein R' is alkyl; R$_6$ and R$_7$ are each independently selected from the group consisting of hydrogen, hydroxy, mercapto, halogen, amino, an aliphatic group and alkyl;

m is an integer of 1 to 6.

142. The compound according to 141, the compound represented by the Formula I is a compound represented by the following Formulae II-X:

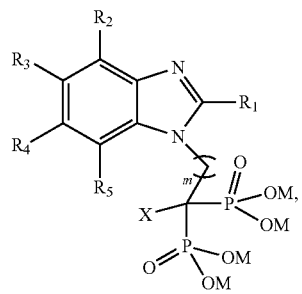

Formula II

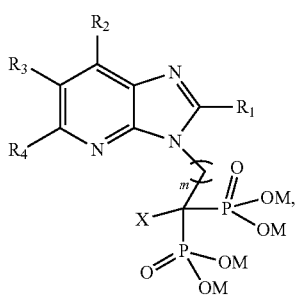

Formula III

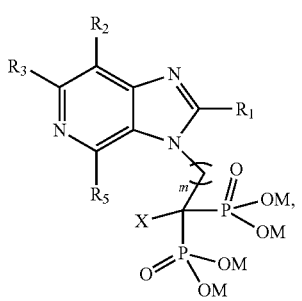

Formula IV

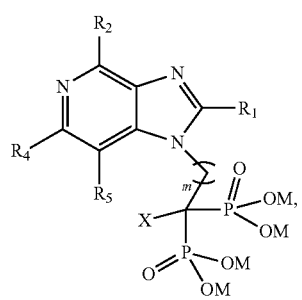

Formula V

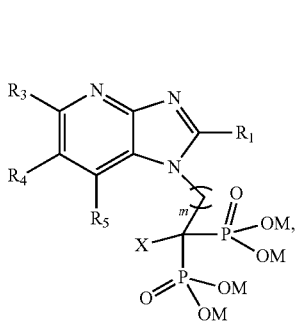

Formula VI

-continued

Formula VII

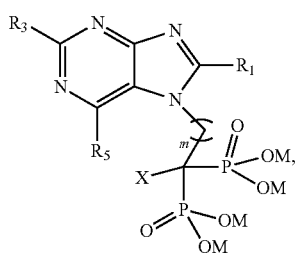

Formula VIII

Formula IX

Formula X

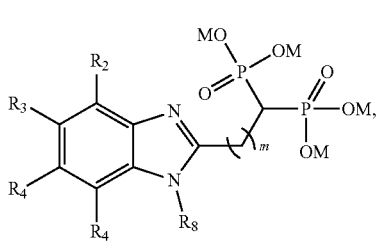

in Formulae II-X, X is selected from the group consisting of hydrogen, hydroxy, mercapto, halogen, alkoxy and alkyl;

Each M is independently selected from the group consisting of a negative charge, hydrogen, alkyl, $-(CH_2)_p-O-CO-R$, $-(CH_2)_p-CO-R$ and a positive ion; wherein p is an integer of 1 to 6, R is hydrogen, alkyl or aryl; the positive ion is $Li^+$, $Na^+$, $K^+$, $Ca^{2+}$, $Mg^{2+}$, $NH_4^+$ or $N(R')_4^+$, wherein R' is alkyl;

$R_1$, $R_2$, $R_3$, $R_4$, $R_5$, and $R_8$ are independently selected from the group consisting of hydrogen, hydroxy, an aliphatic group, mercapto, halogen, amino, alkyl, $-O-(CH_2)_qCH_3$, $-NH-(CH_2)_qCH_3$, $-N[(CH_2)_qCH_3]_2$, $-(CH_2)_p-S-(CH_2)_qCH_3$, $-O-(CH_2)_p-S-(CH_2)_qCH_3$, and $-O-(CH_2)_p-O-(CH_2)_qCH_3$, wherein p is an integer of 1 to 6, q is an integer of 0 to 6; m is an integer of 1 to 6, preferably m is 1.

143. The compound according to 141 or 142, wherein the compound is a compound represented by Formulae XI-XVIII:

Formula XI

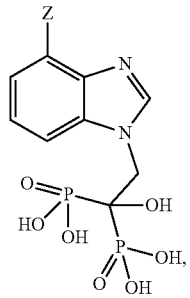

Formula XII

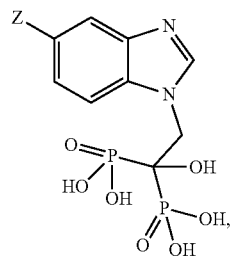

Formula XIII

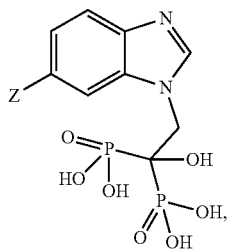

Formula IXV

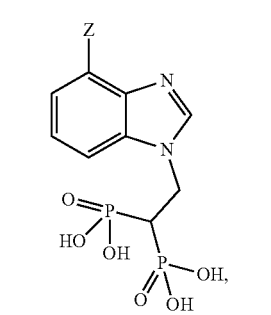

Formula XV

-continued

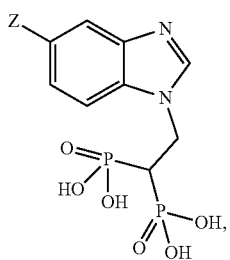
Formula XVI

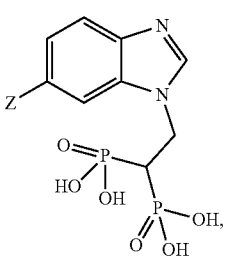
Formula XVII

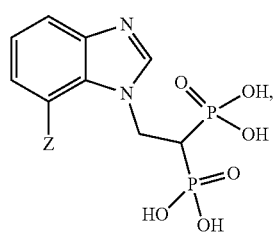
Formula XVIII in Formulae XI-XVIII, Z is hydrogen, hydroxy, an aliphatic group, alkoxy, amino or alkylamino.

144. The compound according to any one of 141-143, wherein the compound is Formula IXX or XX:

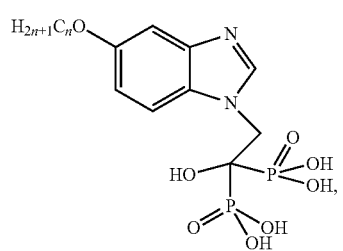
Formula IXX

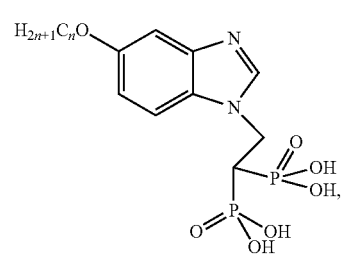
Formula XX in Formulae IXX and XX, n is 0, or an integer of 1-12.

145. The compound according to any one of 141-144, wherein the compound is any one of the following:

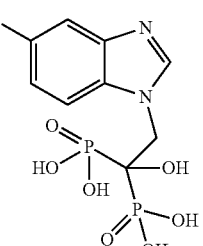 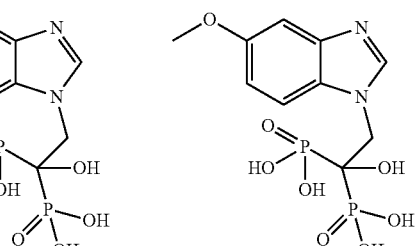

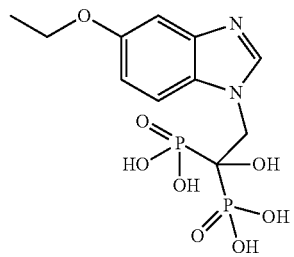

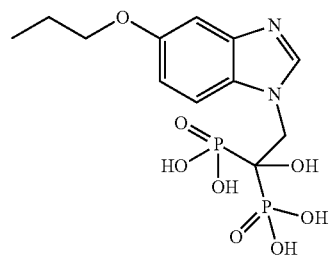

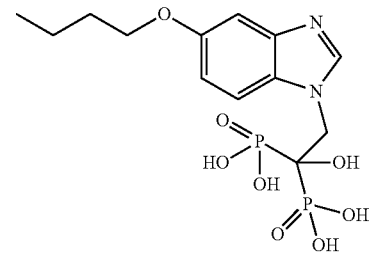

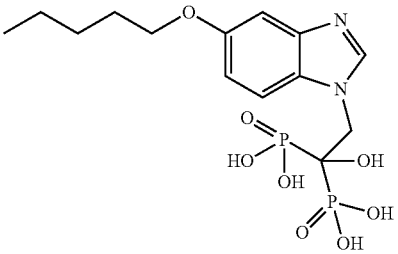

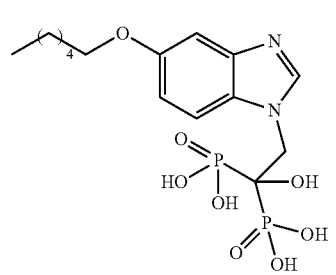

-continued

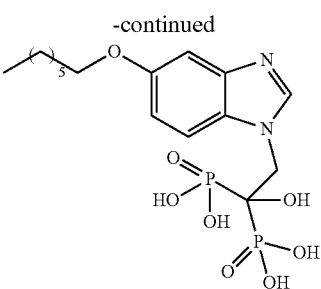
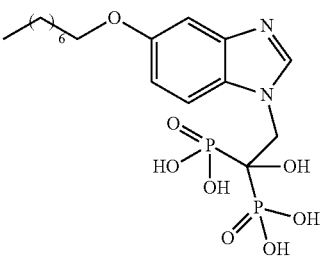
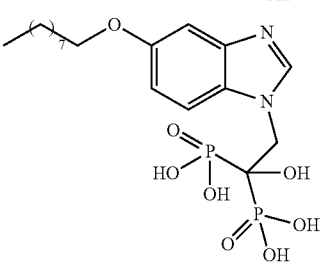
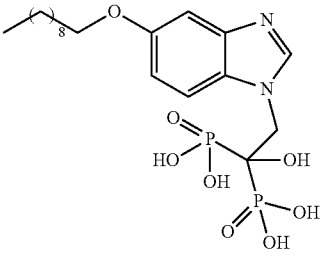
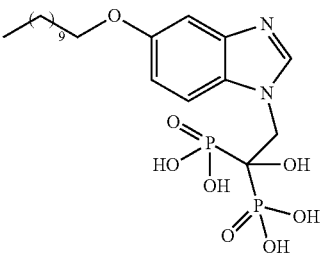
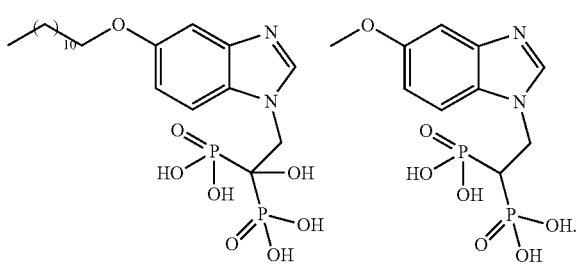

146. A compound of the following Formula or a pharmaceutically acceptable salt, ester, prodrug, or solvate thereof:

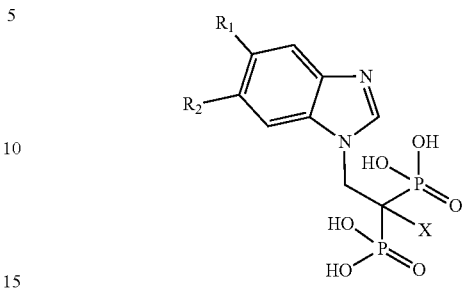

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl; X is selected from the group consisting of hydrogen, hydroxy, mercapto, and halogen.

147. The compound according to 146, or a pharmaceutically acceptable salt, ester, prodrug, or solvate thereof, which is a compound of the formula:

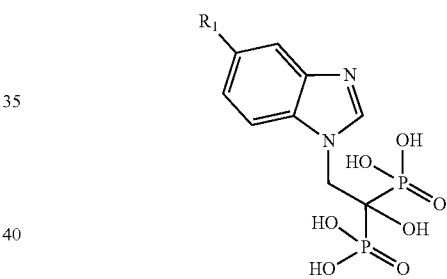

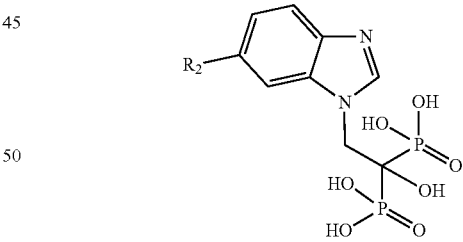

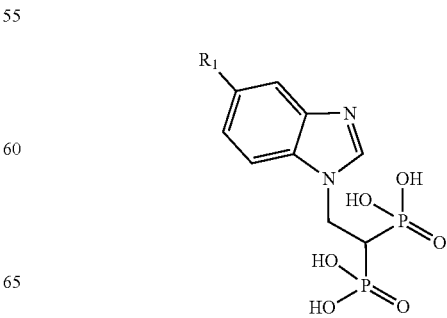

-continued

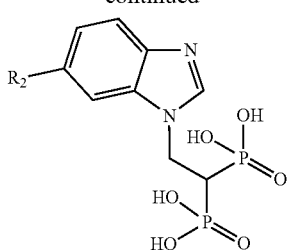

wherein $R_1$ and $R_2$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl.

148. A compound of the following Formula or a pharmaceutically acceptable salt, ester, prodrug, or solvate thereof:

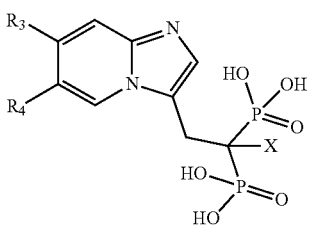

wherein $R_3$ and $R_4$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl; X is selected from the group consisting of hydrogen, hydroxy, mercapto, and halogen.

149. The compound according to 148, or a pharmaceutically acceptable salt, ester, prodrug, or solvate thereof, which is a compound of the formula:

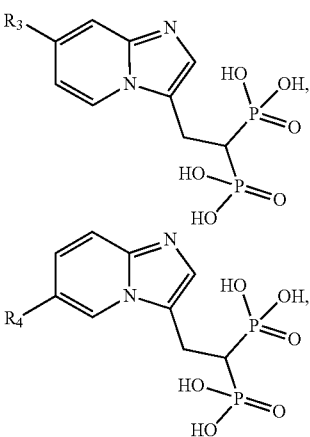

-continued

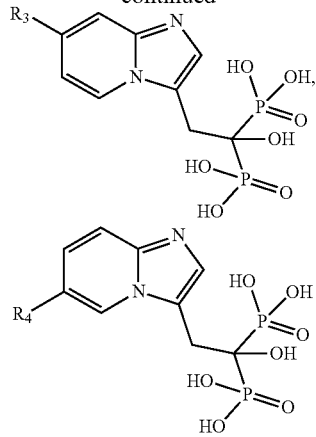

wherein $R_3$ and $R_4$ are independently selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl.

150. A compound of the following Formula or a pharmaceutically acceptable salt, ester, prodrug, or solvate thereof:

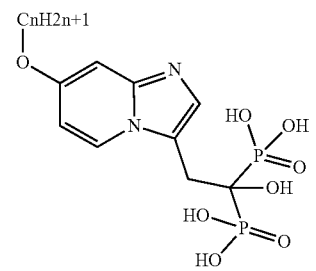

wherein n is an integer of 1 to 24, preferably n is an integer of 1 to 12.

151. A compound according to 150 or a pharmaceutically acceptable salt, ester, prodrug, or solvate thereof, wherein n is an integer from 1 to 20.

152. A compound according to 150 or a pharmaceutically acceptable salt, ester, prodrug, or solvate thereof, wherein n is an integer from 1 to 15.

153. A compound according to 150 or a pharmaceutically acceptable salt, ester, prodrug, or solvate thereof, wherein the compound is selected from the group consisting of:

| n= | Compound No. |
|---|---|
| 1 | TH-Z156 |
| 2 | TH-Z157 |
| 3 | TH-Z158 |
| 4 | TH-Z159 |
| 5 | TH-Z160 |
| 6 | TH-Z97 |
| 7 | TH-Z161 |
| 8 | TH-Z98 |
| 9 | TH-Z162 |

-continued

| n= | Compound No. |
|---|---|
| 10 | TH-Z99 |
| 11 | TH-Z198 and |
| 12 | TH-Z163. |

154. A compound of the following Formula or a pharmaceutically acceptable salt, ester, prodrug, or solvate thereof:

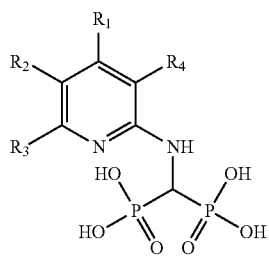

wherein $R_1$ is selected from the group consisting of hydrogen, alkyl, alkenyl, alkynyl, alkoxy, alkylamino, alkylthio, halogen, hydroxy, cycloalkyl, heterocyclyl, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl;
$R_2$ is selected from the group consisting of hydrogen, alkyl, alkoxy, alkylamino, alkylthio, halogen, hydroxy, cycloalkyl, heterocyclyl, aryl and heteroaryl;
$R_3$ is selected from the group consisting of hydrogen, alkyl, alkoxy, alkylamino, alkylthio, halogen, hydroxy, cycloalkyl, heterocyclyl, aryl and heteroaryl;
or $R_2$ and $R_3$ together with the carbon atom to which they are attached form an aromatic or heteroaromatic ring; and
$R_4$ is selected from the group consisting of hydrogen, alkyl, alkoxy, alkylamino, alkylthio, halogen, hydroxy, cycloalkyl, heterocyclyl, aryl and heteroaryl.

155. The compound according to 154, or a pharmaceutically acceptable salt, ester, prodrug, or solvate thereof, wherein $R_1$ is selected from the group consisting of hydrogen, $C_{1-10}$ alkyl, $C_{1-10}$ alkynyl, $C_{1-10}$ alkylamino, $C_{1-10}$ alkylthio, halogen, hydroxy, indazolyl, $C_{1-10}$ alkoxy, and $C_{1-10}$ alkoxy substituted with phenyl or pyridyl, wherein the pyridyl is optionally substituted with carbamoyl.

156. The compound according to 155, or a pharmaceutically acceptable salt, ester, prodrug, or solvate thereof, wherein $R_1$ is selected from the group consisting of hydrogen, 4-methylphenylethoxy, 4,5,6,7-tetrahydro-2H-indazol-2-yl, (2-carbamoylpyridin-4-yl)methoxy, benzyloxy, hexyloxy, methylthio, octylamino, hexyl, octyl, decyl, oct-1-yn-1-yl, hydroxyl, and bromo.

157. The compound according to 154, or a pharmaceutically acceptable salt, ester, prodrug, or solvate thereof, wherein $R_2$ is selected from the group consisting of hydrogen, $C_{1-10}$ alkoxy, and halogen.

158. The compound according to 157, or a pharmaceutically acceptable salt, ester, prodrug, or solvate thereof, wherein $R_2$ is selected from the group consisting of hydrogen, octyloxy, and bromo.

159. The compound according to 154, or a pharmaceutically acceptable salt, ester, prodrug, or solvate thereof, wherein $R_3$ is selected from the group consisting of hydrogen, $C_{1-10}$ alkyl, and $C_{1-10}$ alkoxy.

160. The compound according to 159, or a pharmaceutically acceptable salt, ester, prodrug, or solvate thereof, wherein $R_3$ is selected from the group consisting of hydrogen, methyl, and hexyloxy.

161. The compound according to 154, or a pharmaceutically acceptable salt, ester, prodrug, or solvate thereof, wherein $R_2$ and $R_3$ together with the carbon atom to which they are attached form a benzene ring.

162. The compound according to 154, or a pharmaceutically acceptable salt, ester, prodrug, or solvate thereof, wherein $R_4$ is selected from the group consisting of hydrogen, and $C_{1-10}$ alkoxy.

163. The compound according to 162, or a pharmaceutically acceptable salt, ester, prodrug, or solvate thereof, wherein $R_4$ is selected from the group consisting of hydrogen and octyloxy.

164. The compound according to 154, or a pharmaceutically acceptable salt, ester, prodrug, or solvate thereof, wherein the compound is selected from the group consisting of:

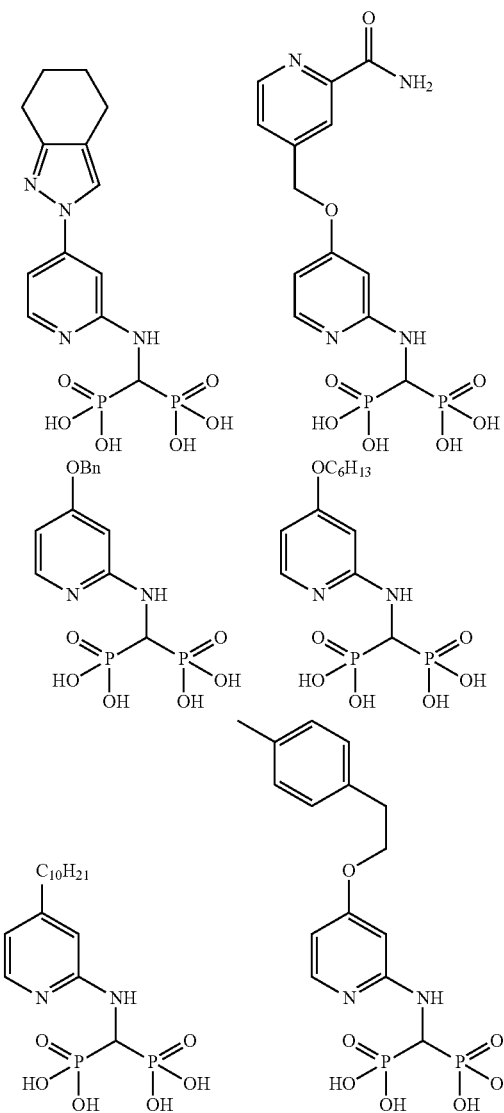

-continued

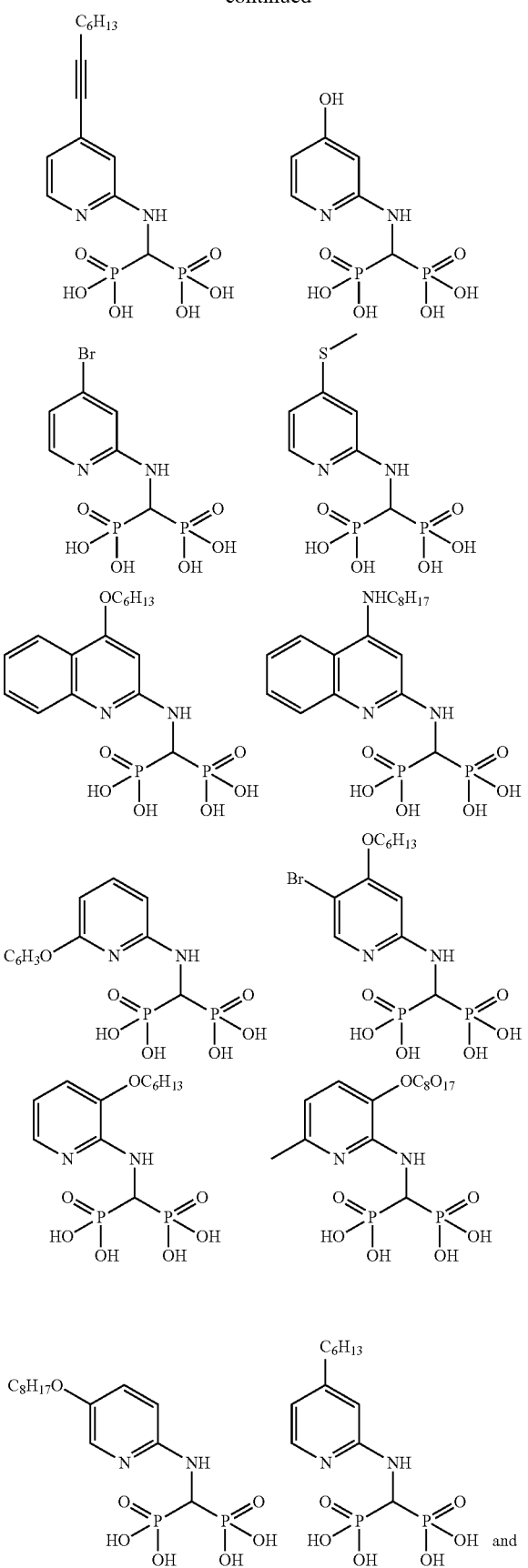

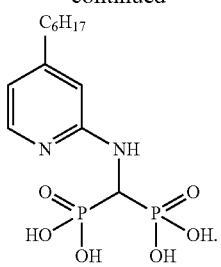

165. A compound of the following Formula or a pharmaceutically acceptable salt, ester, prodrug, or solvate thereof:

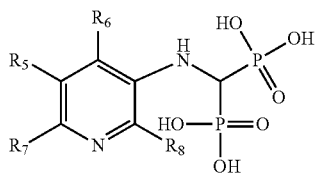

wherein:
$R_5$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_6$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;
$R_7$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and
$R_8$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

166. The compound according to 165, or a pharmaceutically acceptable salt, ester, prodrug, or solvate thereof, wherein $R_5$ is selected from $C_{1-10}$ alkoxy.

167. The compound according to 165, or a pharmaceutically acceptable salt, ester, prodrug, or solvate thereof, wherein the compound is

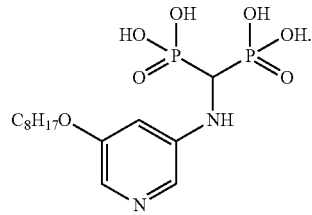

168. A compound of the following Formula or a pharmaceutically acceptable salt, ester, prodrug, or solvate thereof:

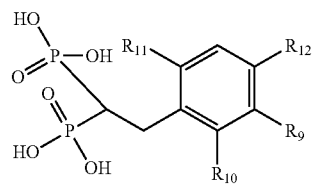

wherein:

$R_9$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_{10}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl;

$R_{11}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl; and $R_{12}$ is selected from the group consisting of hydrogen, alkyl, alkenyl, alkynyl, alkoxy, alkylamino, alkylthio, halogen, hydroxy, cycloalkyl, heterocyclyl, aryl and heteroaryl.

169. The compound according to 168, or a pharmaceutically acceptable salt, ester, prodrug, or solvate thereof, wherein $R_9$ is selected from $C_{1-10}$ alkoxy.

170. The compound according to 168, or a pharmaceutically acceptable salt, ester, prodrug, or solvate thereof, wherein the compound is

TH-Z144

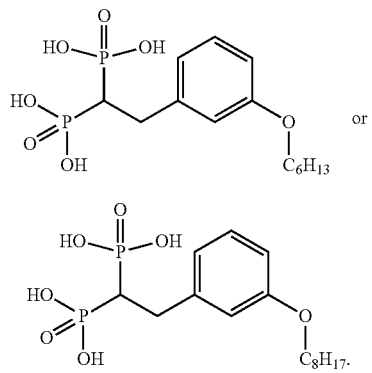

or

TH-Z145

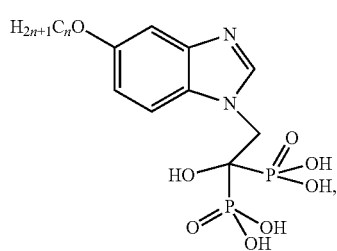

171. A method for preparing a compound represented by Formula IXX,

Formula IXX

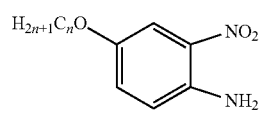

wherein n is 0, or an integer of 1-12,
comprising:
reacting a compound represented by Formula XXI with t-butyl bromoacetate under the action of an inorganic base or a Lewis base to give a compound represented by Formula XXII;

Formula XXI

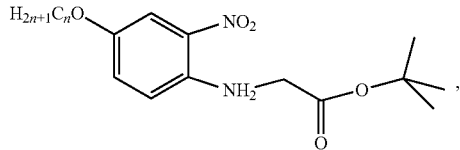

Formula XXII

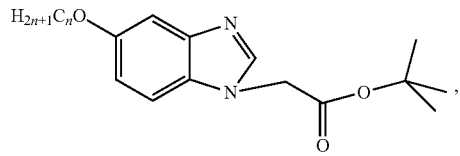

in Formulae XXI and XXII, n is 0, or an integer from 1 to 12;

2) subjecting the compound represented by Formula XXII to a reduction reaction in hydrogen under the catalysis of palladium on carbon, and then subjecting the resulting product to a ring-closing reaction with formamidine acetate to give a compound represented by Formula XXIII;

Formula XXIII

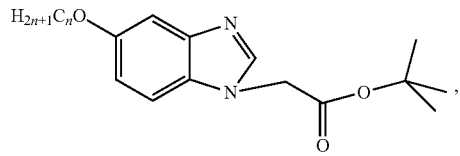

in Formula XXIII, n is 0, or an integer from 1 to 12;

3) heating the compound represented by Formula XXIII under reflux in hydrochloric acid or TFA to give a compound represented by Formula IXXV;

Formula IXXV

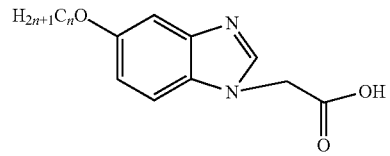

in Formula IXXV, n is 0, or an integer of 1-12; and 4) reacting the compound represented by the Formula IXXV with phosphorus trichloride in a phosphorous acid, sulfolane medium under reflux to give a compound represented by Formula IXX.

172. The method according to 171, wherein:
in step 1), the molar ratio of the compound represented by Formula XXI to the inorganic base or Lewis base and t-butyl bromoacetate is 1:(1-20):(0.2-15);
in step 1), the reaction is carried out at a temperature of 80-150° C. for a period of 1-96 h;
in step 2), the reduction reaction is carried out at a temperature of 0 to 100° C. for 0.5-24 h;
in step 2), the molar ratio of the compound represented by Formula XXII to formamidine acetate is 1:(0.2-10);
the ring-closing reaction is carried out in an organic solvent, preferably ethylene glycol monomethyl ether, at a temperature of 50-150° C. for a period of 1-24 h;
in step 3), the molar ratio of the compound represented by Formula XXIII to hydrochloric acid or TFA is 1:(1-100);
in step 3), the duration of the heating reflux is 0.5-96 h;
in step 4), the molar ratio of the compound represented by Formula IXXV to phosphorous acid and phosphorus trichloride is 1:(0.2-20):(0.2-20);
in step 4), the reaction is carried out for 0.5-96 h.

174. The use of a compound according to any one of 141-170 in the preparation of the following product:
1) a drug for the treatment of a metabolic bone disease;
2) a drug for the treatment of malaria;
3) an inhibitor of tumor cell proliferation of eukaryotic organism;
4) a drug for the prevention and/or treatment of a tumor;
5) a drug for immunotherapy;
6) an vaccines adjuvant;
7) a vaccine;
8) a product useful for inhibiting HsFPPs enzyme activity; or
9) a product useful for inhibiting PvGGPPs enzyme activity.

175. The use according to 174, wherein:
the eukaryotic organism is a mammal; the tumor cell is a cancer cell; the tumor is a cancer, and in particular, the cancer cell is a breast cancer cell; the cancer is a breast cancer, and preferably, the breast cancer cells may specifically be human breast cancer cell MDA-MB-231.

176. The immunogenic composition of 1, the HMG-CoA synthase inhibitor of 54, or the use of 98, wherein the HMG-CoA synthase is Hymeglusin (11-[3R-(hydroxymethyl)-4-oxo-2R-oxetanyl]-3,5,7R-trimethyl-2E,4E-undecadienoic acid).

Terms

In order to facilitate review of the various embodiments of this disclosure, the following explanations of terms are provided. Additional terms and explanations can be provided in the context of this disclosure.

Unless otherwise explained, all technical and scientific terms used herein have the same meaning as commonly understood by one of ordinary skill in the art to which this disclosure belongs.

The term "antigen" is used to indicate any molecule that can be specifically recognised by the adaptive elements of the immune response, i.e. by B cells or T cells, or both.

The antigen used in the present disclosure is preferably an immunogen, i.e. an antigen which activates immune cells to generate an autoimmune response.

The "immunogenic composition" is a composition of substance suitable for the administration to a human or animal subject (e.g., in an experimental setting) that is capable of eliciting a specific immune response, e.g., against a pathogen, such as hepatitis B virus. As such, an immunogenic composition includes one or more antigens (for example, whole purified virus or antigenic subunits, e.g., polypeptides thereof) or antigenic epitopes. An immunogenic composition can also include one or more additional components capable of eliciting or enhancing an immune response, such as an excipient, carrier, and/or adjuvant. In certain instances, immunogenic compositions are administered to elicit an immune response that protects the subject against symptoms or conditions induced by a pathogen. In some cases, symptoms or disease caused by a pathogen is prevented (or treated, e.g., reduced or ameliorated) by inhibiting replication of the pathogen (e.g., hepatitis B virus) following exposure of the subject to the pathogen. In the context of this disclosure, the term immunogenic composition will be understood to encompass compositions that are intended for administration to a subject or population of subjects for the purpose of eliciting a protective or palliative immune response, for example, against hepatitis B (that is, vaccine compositions or vaccines).

The "adjuvant" is an agent that enhances the production of an antigen-specific immune response as compared to administration of the antigen in the absence of the agent. Common adjuvants include aluminum containing adjuvants that include a suspensions of minerals (or mineral salts, such as aluminum hydroxide, aluminum phosphate, aluminum hydroxyphosphate) onto which antigen is adsorbed. In one case, the adjuvants are aluminum-(alum-)free adjuvants, which are formulated in the absence of any such aluminum salts. Alum-free adjuvants include oil and water emulsions, such as water-in-oil, and oil-in-water (and variants thereof, including double emulsions and reversible emulsions), liposaccharides, lipopolysaccharides, immunostimulatory nucleic acids (such as CpG oligonucleotides), liposomes, Toll-like Receptor agonists (particularly, TLR2, TLR4, TLR7/8 and TLR9 agonists), and various combinations of such components.

The "immune response" is a response of a cell of the immune system, such as a B cell, T cell, or monocyte, to a stimulus. An immune response can be a B cell response, which results in the production of specific antibodies, such as antigen specific neutralizing antibodies. An immune response can also be a T cell response, such as a CD4+ response or a CD8+ response. In some cases, the response is specific for a particular antigen (that is, an "antigen-specific response"). If the antigen is derived from a pathogen, the antigen-specific response is a "pathogen-specific response." A "protective immune response" is an immune response that inhibits a detrimental function or activity of a pathogen, reduces infection by a pathogen, or decreases symptoms (including death) that result from infection by the pathogen. A protective immune response can be measured, for example, by the inhibition of viral replication or plaque formation in a plaque reduction assay or ELISA-neutralization assay, or by measuring resistance to pathogen challenge in vivo.

The term "antibody" describes an immunoglobulin whether natural or partly or wholly synthetically produced. The term also covers any polypeptide or protein having a binding domain which is, or is homologous to, an antigen-binding domain.

A tumor antigen is an antigenic substance that is produced in a tumor cell, i.e. it may trigger an immune response in a host. A tumor antigen is a tumor marker useful in diagnostic tests for identifying tumor cells and are potential candidates for use in cancer therapy.

The term "Middle East Respiratory Syndrome (MERS)", also known as camel flu, is a viral respiratory infection caused by MERS-CoV. The symptoms can vary from mild to severe, including fever, cough, diarrhea and shortness of breath.

As used herein, the term "optionally" means that the subsequently described event(s) may or may not occur, and includes both event(s) that occur and event(s) that do not occur.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When enumerating the range of values, it is intended to include each of the values and sub-ranges within the range. For example, "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

As used herein, "aliphatic" or "aliphatic group" includes alkyl, alkenyl and alkynyl groups as defined below.

As used herein, "alkyl" is intended to include both branched and straight-chain saturated aliphatic hydrocarbon groups containing 1 to 20 carbons, preferably 1 to 12 carbons, preferably 1 to 11 carbons, preferably 1 to 10 carbons, preferably 1 to 9 carbons, more preferably 1 to 8 carbons, in the chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, preferably 2 to 11 carbons, preferably 2 to 10 carbons, preferably 2 to 9 carbons, and more preferably 1 to 8 carbons in the chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons, preferably 2 to 11 carbons, preferably 2 to 10 carbons, preferably 2 to 9 carbons, and more preferably 2 to 8 carbons in the chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl) and tricyclic alkyl, containing a total of 3 to 20 carbons forming the ring, preferably 3 to 10 carbons, forming the ring and which may be fused to 1 or 2 aromatic rings as described for aryl. The "cycloalkyl" containing one ring preferably contains 3 to 8 ring carbon atoms, preferably 3 to 7 ring carbon atoms, and more preferably 3 to 6 ring carbon atoms. The "cycloalkyl" includes cyclopropyl, cyclobutyl, cyclopentyl, cyclohexyl, cycloheptyl, cyclooctyl, cyclodecyl and cyclododecyl, cyclohexenyl,

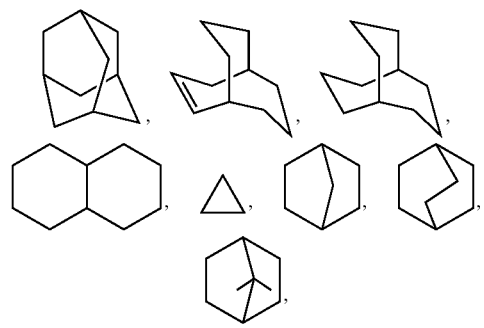

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $-C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

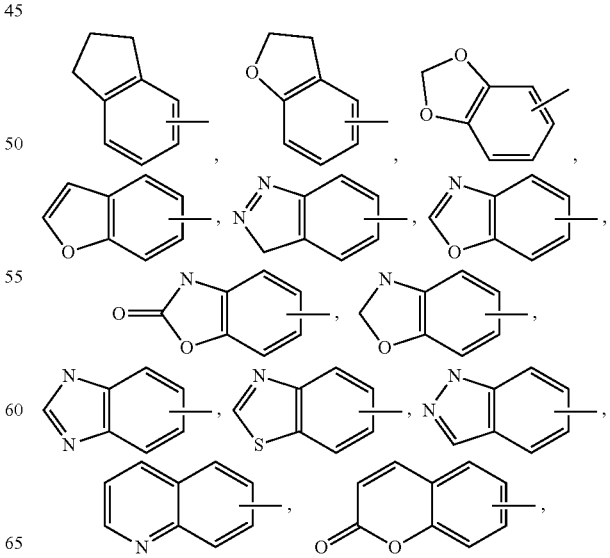

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroaryl alkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, aryl sulfinyl alkyl, arylsulfonylamino, or arylsulfonaminocarbonyl, and/or any of the alkyl substituents set out herein.

Unless otherwise indicated, the term "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that is unsubstituted or may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, or 4-diarylalkyl-1-piperazinyl, all of which may be optionally substituted with alkyl, alkoxy, alkylthio, halo, trifluoromethyl, or hydroxy.

Unless otherwise indicated, the term "alkylthio," "arylthio," or "aralkylthio" as employed herein alone or as part of another group includes any of the above alkyl, aralkyl, or aryl groups linked to a sulfur atom.

Unless otherwise indicated, the term "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, □-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl, benzimidazolyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the present disclosure, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, □-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the present disclosure, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "cyano" as used herein refers to a —CN group.

The term "nitro" as used herein refers to a —NO$_2$ group.

The term "hydroxy" as used herein refers to an —OH group.

The term "mercapto" as used herein refers to a —SH group.

The term "carbamoyl" as used herein refers to —C(=O)-amino, wherein the amino group is an optionally substituted amino group.

"Alkanoyl" means a RC(=O)— group, wherein R is an alkyl group as defined herein.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable salt" refers to a salt that retain the biological effectiveness and properties of the compounds of this invention and, which are not biologically or otherwise undesirable. In many cases, the compounds of the present disclosure are capable of forming acid and/or base salts by virtue of the presence of amino and/or carboxyl groups or groups similar thereto (e.g., phenol or hydroxyamic acid). Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present disclosure can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in *Remington's Pharmaceutical Sciences,* 20th ed., Mack Publishing Company, Easton, Pa., (1985), which is herein incorporated by reference.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the inventive compounds are also contemplated. The term "prodrug" denotes a compound which, upon administration to a subject, undergoes chemical conversion by metabolic or chemical processes to yield a compound as described herein, and/or a salt and/or solvate thereof. Any compound that will be converted in vivo to provide the bioactive agent is a prodrug within the scope and spirit of the invention. For example, compounds containing a carboxy group can form physiologically hydrolyzable esters which serve as prodrugs by being hydrolyzed in the body to yield compounds per se. Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. Particularly the $C_1$ to $C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the present disclosure.

Such prodrugs are preferably administered orally since hydrolysis in many instances occurs principally under the influence of the digestive enzymes. Parenteral administration may be used where the ester per se is active, or in those instances where hydrolysis occurs in the blood.

Various forms of prodrugs are well known in the art. For examples of such prodrug derivatives, see:
a) Design of Prodrugs, H. Bundgaard, ed., Elsevier (1985), and Methods in Enzymology, 112:309-396, K. Widder et al., eds., Academic Press (1985);
b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and
c) Bundgaard, H., Adv. Drug Deliv. Rev., 8:1-38 (1992), each of which is incorporated herein by reference.

Esters are typically compounds derived from acids (organic acids or inorganic acids) in which at least one —OH (hydroxy) group is replaced by an —O-alkyl (alkoxy) group. Esters are usually derived from carboxylic acids and alcohols.

The esters of the compounds of the present disclosure are preferably in vivo hydrolysable esters.

As used herein, the term "in vivo hydrolysable ester" is understood as meaning an in vivo hydrolysable ester of a compound of the present disclosure containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present disclosure containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present disclosure covers all such esters.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the present disclosure may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g., infant, child, adolescent) or adult subject (e.g., young adult, middle—aged adult or senior adult)) and/or a non-human animal, e.g., a mammal such as primates (e.g., cynomolgus monkeys, rhesus monkeys), cattle, pigs, horses, sheep, goats, rodents such as mice and rats, cats, and/or dogs. In certain embodiments, the subject is a human. In certain embodiments, the subject is a non-human animal. The terms "human," "patient," and "subject" are used interchangeably herein.

An "effective amount" means the amount of a compound that, when administered to a subject for treating or preventing a disease, is sufficient to effect such treatment or prevention. The "effective amount" can vary depending on the compound, the disease and its severity, and the age, weight, etc., of the subject to be treated. A "therapeutically effective amount" refers to the effective amount for therapeutic treatment. A "prophylatically effective amount" refers to the effective amount for prophylactic treatment.

"Preventing" or "prevention" or "prophylactic treatment" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; or (iii) relieving the disease, disorder, or condition, i.e., causing regression of the disease, disorder, and/or condition.

As used herein, the term "inhibition" or "inhibiting" refers to the reduction or suppression of a given condition, symptom, or disease, or a significant decrease in the baseline activity of a biological activity or process.

As used herein, the term "inhibitor" refers to a molecule which is capable of inhibiting (including partially inhibiting or allosteric inhibition) one or more of the biological activities of a target molecule, e.g., a farnesyl pyrophosphate synthase (FPPS). Inhibitors, for example, act by reducing or suppressing the activity of a target molecule and/or reducing or suppressing signal transduction.

The compounds described herein may exist in stereoisomeric forms (e.g., it contains one or more asymmetric carbon atoms). The individual stereoisomers (enantiomers and diastereomers) and mixtures of these are included within the scope of the present disclosure. Likewise, it is understood that the compounds described herein or salts thereof may exist in tautomeric forms other than that shown in the Formula and these are also included within the scope of the present disclosure. It is to be understood that the present disclosure includes all combinations and subsets of the particular groups defined hereinabove. The scope of the present disclosure includes mixtures of stereoisomers as well as purified enantiomers or enantiomerically/diastereomerically enriched mixtures. It is to be understood that the present disclosure includes all combinations and subsets of the particular groups defined hereinabove.

One enantiomer of the compounds described herein may exhibit superior activity as compared to another enantiomer. Therefore, all stereochemistry is considered as part of the present disclosure. The separation of racemic materials when desired may be achieved by using a chiral column for HPLC or by using a resolving agent such as camphanyl chloride for resolution (for example, as described by Young, S. D. et al., Antimicrobial Agents and Chemotherapy 1995, 2602-2605).

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the present disclosure and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, 31P, $^{32}P$, $^{35}S$, $^{18}F$, $^{36}Cl$, $^{123}I$, and $^{125}I$.

Compounds of the present disclosure and pharmaceutically acceptable salts of said compounds that contain the aforementioned isotopes and/or other isotopes of other atoms are within the scope of the present disclosure. Isotopically-labelled compounds of the present disclosure, for example those into which radioactive isotopes such as $^3H$ or $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

In particular, the present disclosure relates to the following embodiments.

In one embodiment, the present disclosure relates to an immunogenic composition comprising an adjuvant, wherein the adjuvant may include, but is not limited to, a thiolase (an acetoacetyl-CoA transferase) inhibitior, 2) a HMG-CoA synthase inhibitor, 3) a HMG-CoA reductase inhibitor, 4) a mevalonate kinase inhibitor, 5) a phosphomevalonate kinase inhibitor, 6) a mevalonate-5-pyrophosphate decarboxylase inhibitor, 7) an isopentenyl pyrophosphate isomerase inhibitor, 8) a farnesyl pyrophosphate synthase inhibitor, 9) a geranylgeranyl pyrophosphate synthase inhibitor, and 10) a geranylgeranyl transferase (I, II) inhibitor.

The thiolase (acetoacetyl-CoA transferase) inhibitor includes, but is not limited to, L-660631 described in biochemical and biophysical research communications, 1989, 163, 548-553.

The HMG-CoA synthase inhibitor includes, but is not limited to, L-659699 described in Biochem. J (1993) 289, 889-895, 1234A/F-244 described in Agric. Biol. Chem., 55 (12), 3129-3131, 1991, and Dihydroxerulin described in Tetrahedron, 2000, 56 (3), 479-487, and those compounds disclosed in the following documents: U.S. Pat. No. 5,064,856; EP0411703A1; Agric. Biol. Chem., 1991, 55 (12): 3129-3131; Bioorg. Med. Chem., 1998, 6:1255-1272; Biochem. Biophys. Res. Commun., 1999, 265:536-540, all of which are incorporated herein by reference.

The HMG-CoA reductase inhibitor includes, but is not limited to, those compounds disclosed in the following documents: U.S. Pat. No. 5,102,911-A; EP476493-A1; U.S. Pat. No. 5,091,378-A; EP465970-A; EP465265-A; EP464845-A; EP463456-A; EP456214-A1; EP591165-A; U.S. Pat. No. 5,049,577-A; EP445827-A2; EP442495-A; U.S. Pat. No. 5,025,000-A; EP435322-A2; U.S. Pat. No. 5,023,250-A; JP3112967-A; U.S. Pat. No. 5,017,716-A; U.S. Pat. No. 5,010,105-A; U.S. Pat. No. 5,011,947-A; EP424929-A1; EP422895-A1; EP420266-A2; EP419856-A2; EP418648-A1; EP416383-A2; U.S. Pat. No. 4,996,234-A; U.S. Pat. No. 4,994,494-A; EP415488-A; U.S. Pat. No. 4,992,429-A; EP411420-A2; EP409399-A1; EP408806-A1; DE3918364-A; EP401705-A; EP391185-A1; U.S. Pat. No. 4,957,940-A; U.S. Pat. No. 4,950,675-A; U.S. Pat. No. 4,946,860-A; U.S. Pat. No. 4,940,727-A; U.S. Pat. No. 4,939,143-A; U.S. Pat. No. 4,937,264-A; U.S. Pat. No. 4,937,263-A; EP402154-A1; EP375156-A2; U.S. Pat. No. 4,929,620-A; U.S. Pat. No. 4,927,851-A; U.S. Pat. No. 4,904,692-A; EP468974-A1; U.S. Pat. No. 4,904,646-A; WO9113616-A1; U.S. Pat. No. 4,897,402-A; U.S. Pat. No. 4,892,884-A; EP355846-A2; U.S. Pat. No. 4,885,314-A; EP349063-A; U.S. Pat. No. 4,876,280-A; EP346759-A2; EP422102-A1; EP344602-A1; DE3805884-A; EP330172-A; EP327166-A; EP327165-A; WO8905639-A; JP1068367-A; EP306264-A; U.S. Pat. No. 4,792,614-A; DE3632893-A1; U.S. Pat. No. 4,719,229-A; EP251625-A2; EP232997-A1; EP211416-A2; EP183132-A2; EP164049-A; FR2516087-A1; Wang K et al. J. Nat. Prod., 2015, 78: 1977-1989; Wess G et al. J Med. Chem., 1994, 37: 3240-3246; Procopiou P A et al. J Med. Chem., 1993, 36: 3655-3662; Pfefferkorn J A et al. J Med. Chem., 2008, 51: 31-45; Ahmad S et al. J Med. Chem., 2008, 51: 2722-2733; Sarver R W et al. J Med. Chem., 2008, 51: 3804-3813, all of which are incorporated herein by reference.

In a preferred embodiment, the HMG-CoA reductase inhibitor is a statin compound. Exemplary statin compounds are selected from the group consisting of: pravastatin, atorvastatin, rosuvastatin, fluvastatin, pitavastatin, mevastatin, lovastatin, simvastatin, cerivastatin, or a pharmaceutically acceptable salt, ester, prodrug, or solvate thereof. Preferred HMG-CoA reductase inhibitors are those that have been marketed, most preferably simvastatin, lovastatin and mevastatin, or a pharmaceutically acceptable salt, ester, prodrug and solvate thereof. Methods for preparing HMG-CoA reductase inhibitors are well known to those skilled in the art and include those are commercially available. A HMG-CoA reductase inhibitor may be used in its free acid form, its ester form, or a pharmaceutically acceptable salt thereof. These pharmaceutically acceptable salts include, for example, sodium salts, calcium salts, aluminum salts and ester salts. A HMG-CoA reductase inhibitor can be used in the form of racemic mixtures, or more active, appropriate stereoisomers.

The farnesyl pyrophosphate synthase inhibitor includes, but is not limited to, those compounds disclosed in the following documents: U.S. Pat. No. 7,462,733; US. 20080200679; WO.2006039721; U.S. Pat. Nos. 7,358,361;

7,745,422; US.20100316676; WO.2007109585; U.S. Pat. No. 7,687,482; WO. 2008128056; US. 20080255070; WO. 2010033980; WO. 2010033981; WO. 2008076417; U.S. Pat. No. 7,781,418; WO.2010033978; WO.2009068567; WO. 2010043584; WO.2009128918; ACS Med. Chem. Lett. 2013, 4:423-427; J. Am. Chem. Soc., 2009, 131:5153-62; Nat. Chem. Biol., 2010, 6:660-6; Bioorg. Med. Chem. Lett., 2008, 18:2878-82; J. Med. Chem., 2008, 51:2187-95; Proc. Natl. Acad. Sci. U.S.A, 2007, 104:10022-7; Tetrahedron Lett. 2011, 52:2285-87; Chem. Commun., 2010, 46:5340-5342; Expert Opin. Ther. Pat. 2011, 21(9): 1433-1451; J. Pharmacol. Exp. Ther., 2001, 296:235-42; J. Med. Chem. 2003, 46:5171-5183; J. Med. Chem. 2005, 48:2957-2963; J. Med. Chem. 2006, 49:5804-5814; J. Med. Chem. 2013, 56:7939-7950; J. Med. Chem. 2008, 51:2187-2195; ChemMed Chem 2015, 10:1884-1891; Biochim. Biophys. Acta, 2014, 1840 1840:1051-1062; J. Med. Chem. 2007; 50:5967-75, all of which are incorporated herein by reference.

In a further embodiment, the farnesyl pyrophosphate synthase inhibitor is a bisphosphonic acid compound or a pharmaceutically acceptable salt, ester, prodrug, or solvate thereof. The term "bisphosphonic acid (phosphonate)" refers to a compound characterized by two phosphonate groups linked by phosphoether bonds to a central (geminal) carbon atom. This P-C-P structure is shown in Formula I below. It should be noted that the term "bisphosphonic acids" as used herein in referring to the therapeutic agents of the present disclosure are meant to also encompass bisphosphonates, biphosphonic acids, and salts and derivatives thereof. Unless specifically indicated, the use of a specific nomenclature in referring to the biphosphonic acid or bisphosphonate is not meant to limit the scope of the present disclosure.

Bisphosphonates as pharmaceutical agents are described for example in EP-A-170,228, EP-A-197,478, EP-A-22,751, EP-A-252,504, EP-A-252,505, EP-A-258,618, EP-A-350, 002, EP-A-273,190, WO-A-90/00798, and the like, all of which are incorporated herein by reference.

"Bisphosphonic acids and pharmaceutically acceptable salts thereof" as pharmaceutical agents are described for example in U.S. Pat. Nos. 4,509,612, 4,666,895, 4,719,203, 4,777,163, 5,002,937, 4,971,958 and 4,958,839 and European Patent Applications 252,504 and 252,505, all of which are incorporated herein by reference.

Preferred bisphosphonic acids or pharmaceutically acceptable salts thereof are selected from the group consisting of alendronic acid, simma phosphonic acid, clodronic acid, EB-1053, tiludronic acid, etidronic acid, ibandronic acid, incadronic acid, minodronic acid, neridronic acid, olpadronic acid, risedronic acid, piridronic acid, pamidronic acid, zoledronic acid or an acceptable salt thereof, such as ibandronic acid monosodium salt monohydrate.

The geranylgeranyl pyrophosphate synthase inhibitor includes, but is not limited to, those compounds disclosed in the following documents: J. Med. Chem. 2009, 52:8025-37; Biochem. Biophys. Res. Commun., 2007, 353:921-925; J. Med. Chem. 2002, 45:2185-2196; Bioorg. Med. Chem. 2008, 16:390-399; J. Med. Chem., 2008, 51:5594-5607; ACS Med. Chem. Lett. 2015, 6:1195-1198; Proc. Natl. Acad. Sci. U.S.A, 2012, 109(11):4058-4063, all of which are incorporated herein by reference.

The geranylgeranyl transferase (I, II) inhibitor includes, but is not limited to, those compounds disclosed in the following documents: EP1165084A1; EP1165084A4; EP2014291A2; EP2014291B1; U.S. Pat. Nos. 6,103,487; 6,284,910; 6,355,643B1; U.S. Pat. No. 6,586,461B1; U.S. Pat. No. 6,638,962B2; U.S. Pat. No. 7,763,620B2; U.S. Pat. No. 8,093,274B2; U.S. Pat. No. 8,815,935B2; U.S. Pat. No. 9,040,563B2; US20030219847A1; US20040121985A1; US20060030624A1; US20070249010A1; US20100063114A1; US20110178138A1; US20120035184A1; US20130102639A1; WO1999006376A1; WO2000033826A1; WO2000051614A1; WO2007111948A2; WO2007118009A1; WO2010014054A1; WO2010088457A2; WO2012034038A2; WO2009106586; Angew. Chem. Int. Ed. 2011, 50, 4957-4961; J. Med. Chem. 2010, 53:3454-64; J. Biol. Chem. 2001, 276:48213-22; Bone. 2005, 37:349-58; J. Biol. Chem. 2009, 284:6861-8; Eur. J. Med. Chem., 2011, 46(10):4820-4826; Drug Discov. Today, 2015, 20:267-276; J. Med. Chem. 2012, 55, 8330-8340; J. Am. Chem. Soc. 2007, 129:5843-5845; J. Med. Chem. 2009, 52:8025-8037; J. Med. Chem. 1999, 42:1333-1340; PLoS ONE, 2011, 6:e26135; Bioorg. Med. Chem., 2005, 13:677-688; IL Farmaco, 2004, 59:857-861; Org. Biomol. Chem., 2006, 4, 1768-1784; J. Biol. Chem., 2006, 281(18):12445-12450; J. Biol. Chem., 2008, 283(15):9571-9579; and GGTI-298, which is described in McGuire et al (1996) Platelet-derived growth factor receptor tyrosine kinase phosphorylation requires protein geranylgeranylation but not farnesylation. J. Biol. Chem. 271 27402. PMID: 8910319, and has the following structure:

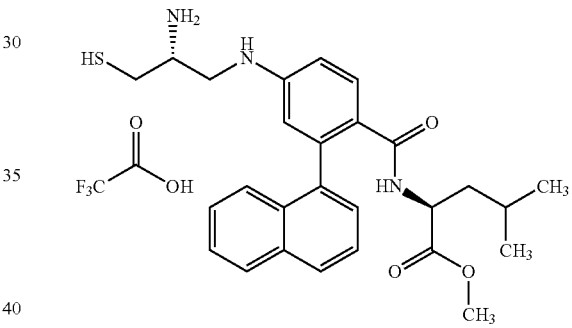

The Structure of GGTI-298 all of which are incorporated herein by reference.

In addition to the above-mentioned inhibitors, the present disclosure also relates to other substances which affect the geranylgeranylation of proteins, which may also be included as an adjuvant in the immunogenic composition.

In another aspect, the farnesyl pyrophosphate synthase inhibitor is a compound of the Formula (i.e., a TH-Z80 series compound) or a pharmaceutically acceptable salt, ester, prodrug, or solvate thereof:

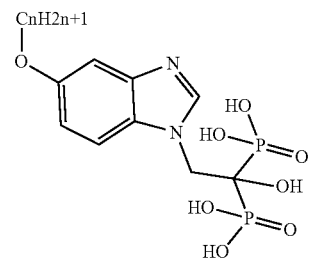

wherein n is an integer of 1 to 24, preferably n is an integer of 1 to 12.

In a further embodiment, n is an integer from 1 to 20. In a further embodiment, n is an integer from 1 to 15.

In a more specific embodiment, the compound is selected from the group consisting of:

| n= | Compound No. |
|---|---|
| 1 | TH-Z79 |
| 2 | TH-Z148 |
| 3 | TH-Z149 |
| 4 | TH-Z150 |
| 5 | TH-Z151 |
| 6 | TH-Z80 |
| 7 | TH-Z152 |
| 8 | TH-Z81 |
| 9 | TH-Z153 |
| 10 | TH-Z82 |
| 11 | TH-Z154 and |
| 12 | TH-Z155. |

Therefore, in one embodiment, the present mention relates to an immunogenic composition comprising an adjuvant selected from the group of TH-Z80 series of compounds described above or a pharmaceutically acceptable salt, an ester, a prodrug, a solvate thereof. In one embodiment, the present disclosure also relates to the use of the above-mentioned compounds or pharmaceutically acceptable salt, ester, prodrug and solvate thereof as adjuvants in the preparation of immunogenic compositions for the prevention or treatment of diseases.

In another aspect, the present disclosure also relates to novel bisphosphonic acid compounds (i.e., compounds of TH-Z97 series) or pharmaceutically acceptable salt, ester, prodrug, and solvate thereof as inhibitors of a farnesyl pyrophosphate synthase (FPPS), the compounds having the following formula:

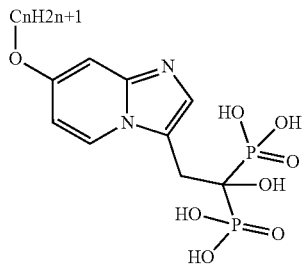

wherein n is an integer of 1 to 24, preferably n is an integer of 1 to 12.

In a further embodiment, n is an integer from 1 to 20. In a further embodiment, n is an integer from 1 to 15.

In a more specific embodiment, the compound is selected from the group consisting of:

| n= | Compound No. |
|---|---|
| 1 | TH-Z156 |
| 2 | TH-Z157 |
| 3 | TH-Z158 |
| 4 | TH-Z159 |
| 5 | TH-Z160 |
| 6 | TH-Z97 |
| 7 | TH-Z161 |
| 8 | TH-Z98 |

| n= | Compound No. |
|---|---|
| 9 | TH-Z162 |
| 10 | TH-Z99 |
| 11 | TH-Z198 and |
| 12 | TH-Z163. |

Therefore, in one embodiment, the present mention relates to an immunogenic composition comprising an adjuvant selected from the group of TH-Z97 series of compounds described above or a pharmaceutically acceptable salt, an ester, a prodrug, and a solvate thereof. In one embodiment, the present disclosure also relates to the use of the above-mentioned compounds or pharmaceutically acceptable salt, ester, prodrug and solvate thereof as adjuvants in the preparation of immunogenic compositions for the prevention or treatment of diseases.

In another aspect, the present disclosure also relates to a novel bisphosphonic acid compound or a pharmaceutically acceptable salt, ester, prodrug, or solvate thereof as an inhibitor of farnesyl pyrophosphate synthase (FPPS), said compound having the formula:

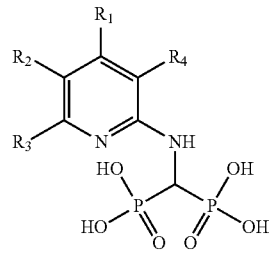

wherein $R_1$ is selected from the group consisting of hydrogen, alkyl, alkenyl, alkynyl, alkoxy, alkylamino, alkylthio, halogen, hydroxy, aryl and heteroaryl, wherein the alkyl group in said alkoxy group is optionally substituted with aryl, heteroaryl or heterocyclyl, wherein said aryl, heteroaryl or heterocyclyl is optionally substituted with alkyl or carbamoyl;

$R_2$ is selected from the group consisting of hydrogen, alkyl, alkoxy, alkylamino, alkylthio, halogen, hydroxy, aryl and heteroaryl;

$R_3$ is selected from the group consisting of hydrogen, alkyl, alkoxy, alkylamino, alkylthio, halogen, hydroxy, aryl and heteroaryl;

or $R_2$ and $R_3$ together with the carbon atom to which they are attached form an aromatic or heteroaromatic ring; and $R_4$ is selected from the group consisting of hydrogen, alkyl, alkoxy, alkylamino, alkylthio, halogen, hydroxy, aryl and heteroaryl.

In one embodiment, $R_1$ is selected from the group consisting of hydrogen, $C_{1-10}$ alkyl, $C_{1-10}$ alkynyl, $C_{1-10}$ alkylamino, $C_{1-10}$ alkylthio, halogen, hydroxy, indazolyl, $C_{1-10}$ alkoxy, $C_{1-10}$ alkoxy substituted with phenyl or pyridyl, wherein the pyridyl is optionally substituted with carbamoyl.

In a further embodiment, $R_1$ is selected from the group consisting of hydrogen, 4-methylphenylethoxy, 4,5,6,7-tetrahydro-2H-indazol-2-yl, (2-carbamoylpyridin-4-yl)methoxy, benzyloxy, hexyloxy, methylthio, octylamino, hexyl, octyl, decyl, oct-1-yn-1-yl, hydroxyl, bromo.

In one embodiment, $R_2$ is selected from the group consisting of hydrogen, $C_{1-10}$ alkoxy, halogen. In a further embodiment, $R_2$ is selected from the group consisting of hydrogen, octyloxy, and bromo.

In one embodiment, $R_3$ is selected from the group consisting of hydrogen, $C_{1-10}$ alkyl, $C_{1-10}$ alkoxy. In a further embodiment, $R_3$ is selected from the group consisting of hydrogen, methyl, and hexyloxy.

In one embodiment, $R_2$ and $R_3$ together with the carbon atom to which they are attached form a benzene ring.

In one embodiment, $R_4$ is selected from the group consisting of hydrogen and $C_{1-10}$ alkoxy. In a further embodiment, $R_4$ is selected from the group consisting of hydrogen, and octyloxy.

In a further embodiment, the compound is selected from the group consisting of:

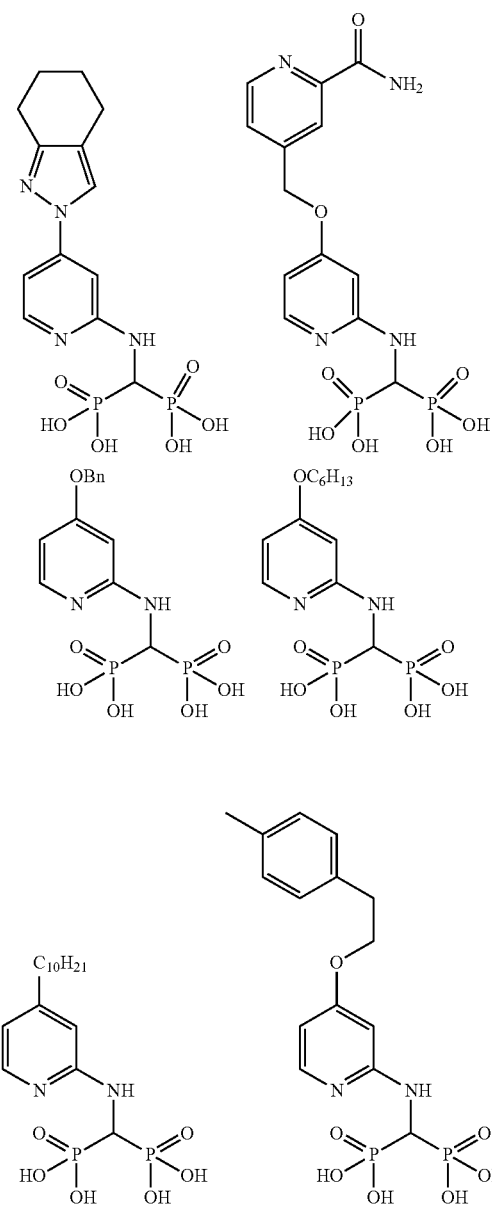

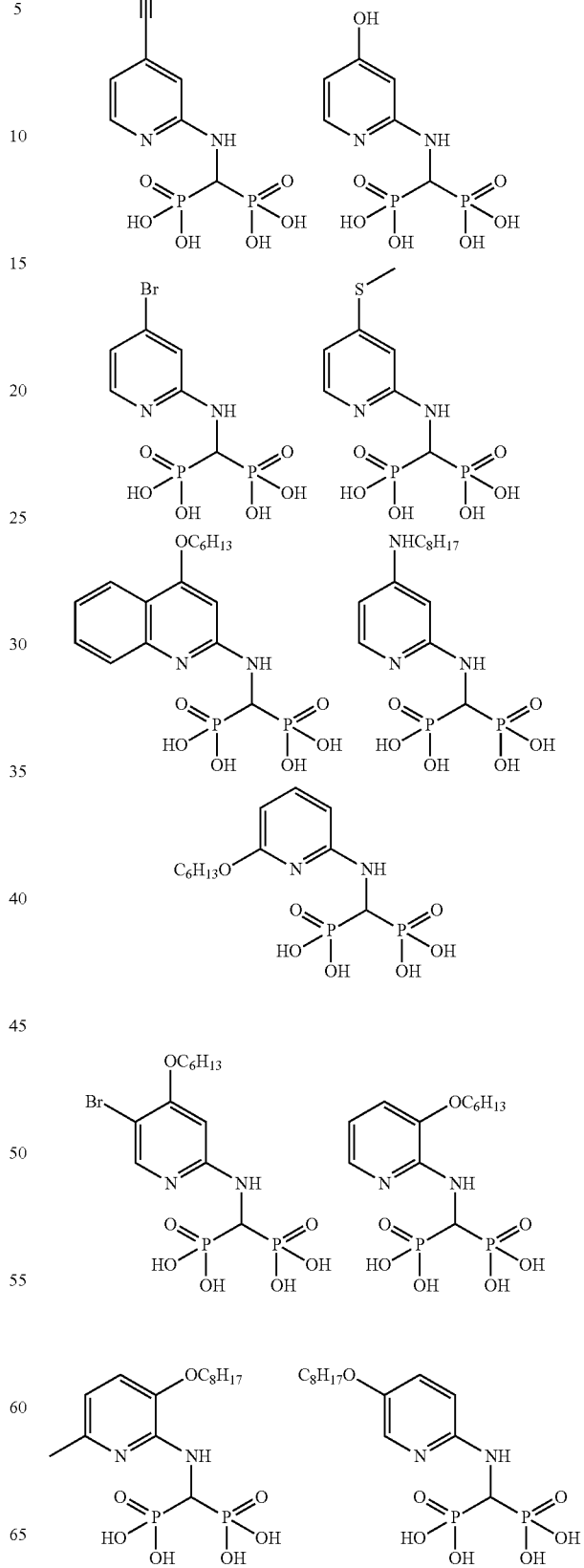

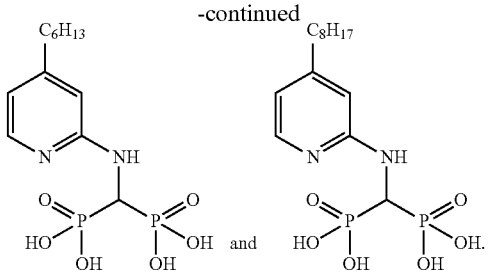

Therefore, in one embodiment, the present disclosure relates to an immunogenic composition comprising an adjuvant selected from the group consisting of the above-mentioned o-aminopyridine compounds or a pharmaceutically acceptable salt, ester, prodrug, or solvate thereof. In one embodiment, the present disclosure also relates to the use of the above-mentioned compounds or pharmaceutically acceptable salt, ester, prodrug and solvate thereof as adjuvants in the preparation of immunogenic compositions for the prevention or treatment of diseases.

In another aspect, the present disclosure also relates to a novel bisphosphonic acid compound or a pharmaceutically acceptable salt, ester, prodrug, or solvate thereof as an inhibitor of farnesyl pyrophosphate synthase (FPPS), said compound having the formula:

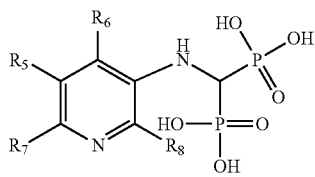

wherein:
$R_5$ is selected from the group consisting of hydrogen, alkyl, alkenyl, alkynyl, alkoxy, alkylamino, alkylthio, halogen, hydroxy, aryl and heteroaryl;
$R_6$ is selected from the group consisting of hydrogen, alkyl, alkenyl, alkynyl, alkoxy, alkylamino, alkylthio, halogen, hydroxy, aryl and heteroaryl;
$R_7$ is selected from the group consisting of hydrogen, alkyl, alkenyl, alkynyl, alkoxy, alkylamino, alkylthio, halogen, hydroxy, aryl and heteroaryl; and
$R_8$ is selected from the group consisting of hydrogen, alkyl, alkenyl, alkynyl, alkoxy, alkylamino, alkylthio, halogen, hydroxy, aryl and heteroaryl.

In one embodiment, $R_5$ is selected from $C_{1-10}$ alkoxy.

In a further embodiment, the compound is selected from the group consisting of:

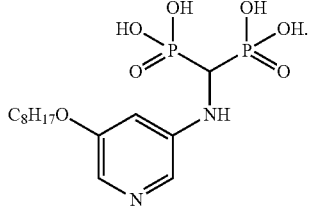

Therefore, in one embodiment, the present disclosure relates to an immunogenic composition comprising an adjuvant selected from the group consisting of the above-mentioned m-aminopyridine compounds or a pharmaceutically acceptable salt, ester, prodrug, or solvate thereof. In one embodiment, the present disclosure also relates to the use of the above-mentioned compounds or pharmaceutically acceptable salt, ester, prodrug and solvate thereof as adjuvants in the preparation of immunogenic compositions for the prevention or treatment of diseases.

In another aspect, the present disclosure also relates to a novel bisphosphonic acid compound or a pharmaceutically acceptable salt, ester, prodrug, or solvate thereof as an inhibitor of geranylgeranyl pyrophosphate synthase, said compound having the formula:

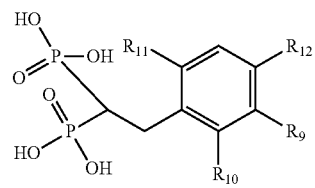

wherein:
$R_9$ is selected from the group consisting of hydrogen, alkyl, alkenyl, alkynyl, alkoxy, alkylamino, alkylthio, halogen, hydroxy, aryl and heteroaryl;
$R_{10}$ is selected from the group consisting of hydrogen, alkyl, alkenyl, alkynyl, alkoxy, alkylamino, alkylthio, halogen, hydroxy, aryl and heteroaryl;
$R_{11}$ is selected from the group consisting of hydrogen, alkyl, alkenyl, alkynyl, alkoxy, alkylamino, alkylthio, halogen, hydroxy, aryl and heteroaryl; and
$R_{12}$ is selected from the group consisting of hydrogen, alkyl, alkenyl, alkynyl, alkoxy, alkylamino, alkylthio, halogen, hydroxy, aryl and heteroaryl.

In one embodiment, $R_9$ is selected from $C_{1-10}$ alkoxy.

In a further embodiment, the compound is selected from the group consisting of:

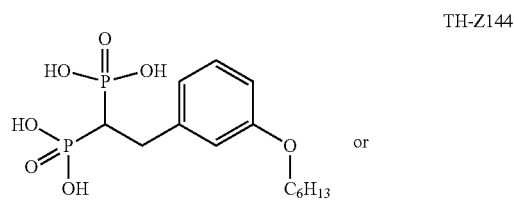

TH-Z144

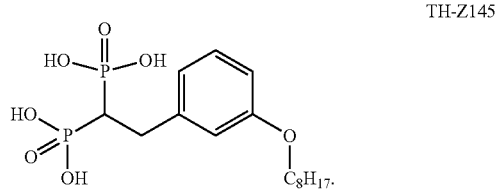

TH-Z145

Therefore, in one embodiment, the present disclosure relates to an immunogenic composition comprising an adjuvant selected from the group consisting of the above-mentioned benzyl bisphosphonic acid compound or a pharmaceutically acceptable salt, ester, prodrug, or solvate thereof. In one embodiment, the present disclosure also relates to the use of the above-mentioned compounds or pharmaceutically acceptable salt, ester, prodrug and solvate thereof as adjuvants in the preparation of immunogenic compositions for the prevention or treatment of diseases.

Bisphosphonic Acid Compounds

As early as 40 years ago, Fleisch et al. found that pyrophosphate has the effect of inhibiting ectopic calcification. But the pyrophosphate is unstable and is easily inactivated by enzymatic hydrolysis. Later, the P-O-P group which may be easily hydrolyzed by an enzyme in the pyrophosphate structure was transformed into a P-C-P group which is stable to the enzyme. And then a series of bisphosphonates were developed, and these compounds play good effects in the treatment of osteoporosis. Representative drugs include sodium etidronate as the first generation, sodium clodronate, sodium pamidronate and sodium tiludronate as the second generation, and current sodium alendronate, sodium neridronate, sodium olpadronate, sodium risedronate, and sodium ibandronate, sodium zoledronate and the like as the third generation. Unlike the first-generation bisphosphonates, the second and third generation bisphosphonates predominantly act through the protonation of N to the key enzyme FPPS (farnesyl pyrophosphate synthase) in the terpene biosynthetic pathway, leading to osteoclast apoptosis.

The zoledronic acid as a representative third generation drug has excellent effect in the treatment of osteoporosis, and also has some but mild effects in the treatment of bone metastases of cancers caused by abnormal bone metabolism, which is in turn caused by bone metastases of multiple myeloma, breast cancer, prostate cancer and lung cancer and other malignant tumors.

One embodiment of the present disclosure relates to novel bisphosphonic acid compounds as described above, which are useful for the preparation of drugs for the treatment of metabolic bone diseases, drugs for the treatment of malaria, inhibitors of tumor cell proliferation of eukaryotic organism, drugs for the prevention and/or treatment of a tumor, drugs for immunotherapy, and vaccines adjuvants.

In the drugs for the treatment of metabolic bone diseases, drugs for the treatment of malaria, inhibitors of tumor cell proliferation of eukaryotic organism, drugs for the prevention and/or treatment of a tumor, or drugs for immunotherapy, the compound represented by Formula I has a content of 0.001 to 90% by weight.

In the vaccine, the compound represented by Formula I has a content of 0.001 to 90% by weight.

The drugs for the treatment of metabolic bone diseases, drugs for the treatment of malaria, inhibitors of tumor cell proliferation of eukaryotic organism, drugs for the prevention and/or treatment of a tumor, drugs for immunotherapy, and vaccines can be administered by injection, ejection, nasal drops, eye drops, osmosis, absorption, physical or chemical-mediated method into the body such as muscle, intradermal, subcutaneous, intravenous, mucosal tissue; or can be administered into the body after being mixed or wrapped in other substances.

In the bisphosphonic acid compound of the present disclosure, bisphosphonic acid which is asymmetric at the 4, 5, 6 and 7 positions of benzimidazole is first synthesized by improving the modification of the terminal carboxyl group. The bisphosphonic acid compound of the present disclosure retains the activity of imidazophosphonic acid to FPPS and also has a good inhibitory effect on GGPPS, malaria and tumor cell proliferation, and in particular, has a good effect as a vaccine adjuvant and an immunotherapeutic agent. The bisphosphonic acid compound of the present disclosure can be used for the preparation of drugs for the treatment of metabolic bone diseases, drugs for the treatment of malaria, inhibitors of tumor cell proliferation of eukaryotic organism, drugs for the prevention and/or treatment of a tumor, and drugs for immunotherapy, and can be used as a vaccine adjuvant for preparing a vaccine.

Antigen

In one embodiment, the immunogenic composition of the present disclosure comprises an antigen derived from a bacteria, a virus, a parasite or a tumor. In certain aspects, the one or more antigens are each independently a microbial antigen, an autoantigen, a tumor antigen, an allergen or an addictive substance. The antigens of the present disclosure also include those described in International Patent Application WO2011/148356.

The antigen may be obtained by recombinant means or peptide synthesis, or from natural sources or extracts and may be derived from any living or non-living organisms.

The antigen may be derived from bacteria, such as, for example anthrax, *campylobacter*, cholera, diphtheria, enterotoxigenic *E. coli*, giardia, gonococcus, *Helicobacter pylori*, Hemophilus influenza B, Hemophilus influenza of an unknown type, meningococcus, pertussis, pneumococcus, *salmonella, shigella, Streptococcus* B, group A *Streptococcus*, tetanus, *Vibrio cholerae, yersinia, Staphylococcus, Pseudomonas* species and Clostridia species.

Alternatively, the antigen may be derived from viruses, such as, for example adenovirus, dengue serotypes 1 to 4, ebola (Jahrling et al., Arch Virol Suppl, 11:135-140, 1996), enterovirus, hepatitis serotypes A to E (Blum, Digestion 56:85-95, 1995; Katkov, Med Clin North Am 80:189-200, 1996; Lieberman and Greenberg, Adv Pediatr Infect Dis 11:333-3631996; Mast et al., Annu Rev Med 47:257-266, 1996) herpes simplex virus 1 or 2, human immunodeficiency virus (Deprez et al., Vaccine 14:375-382, 1996), influenza, Japanese equine encephalitis, measles, Norwalk, papilloma virus, parvovirus B19, polio, rabies, rotavirus, rubella, rubeola, vaccinia, vaccinia constructs containing genes coding for other antigens such as malaria antigens, varicella, and yellow fever. Alternatively, the antigen may be derived from a parasite. The parasites include, for example: *Entamoeba histolytica* (Zhang et al., Infect Immun 63:1349-1355); *Plasmodium* (Bathurst et al., Vaccine 11:449-456, 1993), Toxoplasmosis, and the Helminths.

Alternatively, the antigen may be a tumor specific antigen (TSA) or a tumor associated antigen (TAA). The tumor specific antigen refers to a new antigen that is expressed only on the surface of a tumor cell and does not exist on normal cells, and thus is also known as a unique tumor antigen. Such tumor associated antigen is known in the art. Common tumor specific antigens include (1) α-fetoprotein (AFP); (2) carcinoembryonic antigen (CEA); (3) CA-125; (4) MUC-1; (5) epithelial cell tumor antigen (ETA); (6) tyrosinase; (7) melanoma-associated antigen (MAGE); (8) tumor testicular antigen; (9) prostate specific antigen (PSA); (10) gp100; (11) Melan A; (12) GAGE, G antigen 12B/C/D/E; (13) BAGE, B melanoma antigen; (14) GM2, ganglioside. The tumor associated antigens are antigens that are highly correlated with certain tumor cells. They are not usually found, or are found to a lesser extent, on normal cells. Such tumor associated antigens are known in the art and common tumor associated antigens include those listed in International Patent Application WO 2010/009124, for example, (1) BMPR1B; (2) E16; (3) STEAP1; (4) 0772P; (5) MPF; (6) Napi3b; (7) Sema 5b; (8) PSCA hlg; (9) ETBR; (10) MSG783; (11) STEAP2; (12) TrpM4; (13) CRIPTO; (14) CD21; (15) CD79b; (16) FcRH2; (17) HER2; (18) NCA; (19) MDP; (20) IL20Rα; (21) Brevican; (22) EphB2R; (23) ASLG659; (24) PSCA; (25) GEDA; (26) BAFF-R; (27) CD22; (28)

CD79a; (29) CXCR5; (30) HLA-DOB; (31) P2X5; (32) CD72; (33) LY64; (34) FcRH1; (35) IRTA2; and (36) TENB2, which are incorporated herein by reference.

In a further embodiment, the antigen is derived from Middle East Respiratory Syndrome (Mers) virus, hepatitis B virus, and melanoma.

In another aspect, the immunogenic composition of the present disclosure further comprises another adjuvant. The other vaccine adjuvants include, but are not limited to, aluminum adjuvants, complete Freund's adjuvant, incomplete Freund's adjuvant, MF59, AS01, AS02, AS03, AS04, AS15, CAF01, ISCOMs (immunostimulatory complex), Virosomes (virus particles), GLA-SE, liposomes, edible oils, saponins, AF03, TLR agonists.

In a further embodiment, the other adjuvant is selected from TLR agonists. Exemplary TLR agonists are: TLR1 stimulants (such as triacyl lipoprotein), TLR2 stimulants (e.g., peptidoglycans, zymosan, HMGB1 (high mobility group protein 1), lipoteichoic acid), TLR3 stimulants (double-stranded RNA such as PolyI: C), TLR4 stimulants (e.g., LPS, MPL, RC529, GLA, E6020), TLR5 stimulants (flagellin), TLR6 stimulants (e.g., triacyl lipoprotein, lipoteichoic acid), TLR7/8 stimulants (single-stranded RNA, imiquimod), TLR9 stimulants (DNA, such as CPG ODN), C-lectin ligands (e.g., kelp polysaccharides), CD1d ligands (e.g., α-galactosylceramide).

Applied Vaccine

The adjuvants and immunogenic compositions described herein can be used in a variety of vaccines including, but not limited to, BCG vaccine, hepatitis A vaccine, hepatitis B vaccine, hepatitis C vaccine, hepatitis D vaccine, hepatitis E vaccine, influenza vaccine, polio vaccine, DPT vaccine, measles vaccine, vaccinum encephalitidis epidemicae, rabies vaccine, hemorrhage fever vaccine, pneumonia vaccine, epidemic menigitis vaccine, hepatitis A vaccine, mumps vaccine, influenza vaccine, rubella vaccine, varicella vaccine, AIDS vaccine, malaria vaccine, and vaccines for the treatment and prevention of cancers, including but not limited to melanoma therapeutic vaccines, melanoma prophylactic vaccines, lung cancer therapeutic vaccines, lung cancer prophylactic vaccines, bladder cancer prophylactic vaccines, bladder cancer therapeutic and prophylactic vaccines, cervical cancer therapeutic vaccines, cervical cancer prophylactic vaccines, bladder cancer therapeutic vaccines, bladder cancer prophylactic vaccines, breast cancer therapeutic vaccines, breast cancer prophylactic vaccines, liver cancer therapeutic vaccines, liver cancer prophylactic vaccines, prostate cancer therapeutic vaccines, and prostate cancer prophylactic vaccines.

Indications

The immunogenic compositions of the present disclosure are useful in the treatment of various diseases or conditions, including diseases caused by bacteria, viruses, fungi, and parasites.

In aspects of the present disclosure, a bacteria includes, but is not limited to, *Aceinetobacter calcoaceticus*, *Acetobacter paseruianus*, *Actinobacillus actinomycetemcomitans*, *Actinobacillus pleuropneumonias*, *Actinomyces israelli*, *Actinomyces viscosus*, *Aeromonas hydrophila*, *Alcaliges eutrophus*, *Alicyclobacillus acidocaldarius*, *Arhaeglobus fulgidus*, *Bacillus* species, *Bacillus antracis*, *Bacillus pumilus*, *Bacillus stearothermophillus*, *Bacillus subtilis*, *Bacillus thermocatenulatus*, *Bacteroides* species, *Bordetella* species, *Bordetella bronchiseptica*, *Borrelia burgdorferi*, *Brucella* species, *Burkholderia cepacia*, *Burkholderia glumae*, *Brachyspira* species. *Brachyspira hyodysenteria*, *Brachyspira pilosicoli*, *Camphylobacter* species, *Campylobacter coli*, *Campylobacter fetus*, *Campylobacter hyointestinalis*, *Campylobacter jejuni*, *Chlamydia psittaci*, *Chlamydia trachomatis*, *Chlamydophila* species, *Chromobacterium viscosum*, *Clostridium* species, *Clostridium botulinum*, *Clostridium difficile*, *Clostridium perfringens*, *Clostridium tetani*, *Corynebacterium* species, *Corynebacterium diphtherias*, *Ehrlichia canis*, *Enterobacter* species, *Enterobacter aerogenes*, *Enterococcus* species, *Erysipelothrix rhusiopathieae*, *Escherichia* species, *Escherichia coli*, *Fusobacterium nucleatum*, *Haemophilus* species, *Haemophilus influenzae*, *Haemophilus somnus*, *Helicobacter* species, *Helicobacter pylori*, *Helicobacter suis*, *Klebsiella* species, *Klebsiella pneumoniae*, *Lactobacillus acidophilis*, *Lawsonia intracellularis*, *Legionella* species, *Legionella pneumophilia*, *Leptospira* species, such as *Leptospira canicola*, *Leptospira grippotyposa*, *Leptospira hardjo*, *Leptospira borgpetersenii hardjo-bovis*, *Leptospira borgpetersenii hardjo-prajitno*, *Leptospira interrogans*, *Leptospira icterohaemorrhagiae*, *Leptospira pomona*, *Leptospira*, *Leptospira bratislava*, *Listeria* species, *Listeria monocytogenes*, *Meningococcal bacteria*, *Moraxella* species, *Mycobacterium* species, *Mycobacterium bovis*, *Mycobacterium tuberculosis*, *Mycobacterium avium*, *Mycobacterium intracellulare*, *Mycobacterium kansaii*, *Mycobacterium gordonae*, *Mycoplasma* species, such as, *Mycoplasma hyopneumoniae*, *Mycoplasma synoviae*, *Mycoplasma hyorhinis*, *Mycoplasma pneumoniae*, *Mycoplasma mycoides* subsp. *mycoides* LC, *Neisseria* species, *Neisseria gonorrhoeae*, *Neisseria meningitidis*, *Odoribacter denticanis*, *Pasteurella* species, *Pasteurella* (*Mannheimia*) *haemolytica*, *Pasteurella multocida*, *Photorhabdus luminescens*, *Porphyromonas gingivalis*, *Porphyromonas gulae*, *Porphyromonas salivosa*, *Propionibacterium acnes*, *Proteus* species, *Proteus vulgaris*, *Pseudomonas* species, *Pseudomnas wisconsinensis*, *Pseudomonas aeruginosa*, *Pseudomonas fluorescens* C9, *Pseudomonas fluorescens* SIKW 1, *Pseudomonas fragi*, *Pseudomonas luteola*, *Pseudomonas oleovorans*, *Pseudomonas* sp B11-1, *Psychrobacter immobilis*, *Rickettsia* spp, *Rickettsia prowazekii*, *Rickettsia rickettsia*, *Salmonella* species, *Salmonella bongori*, *Salmonella choleraeuis*, *Salmonella dublin*, *Salmonella enterica*, *Salmonella newport*, *Salmonella typhimurium*, *Salmonella typhi*, *Serratia marcescens*, *Shigella* species, *Spirlina platensis*, *Staphylococci* species, *Staphlyoccocus aureus*, *Staphyloccoccus epidermidis*, *Staphylococcus hyicus*, *Streptococcus* species, *Streptobacillus moniliformis*, beta-hemolytic *Streptococcus*, *Streptococcus pyogenes* (Group A *Streptococcus*), *Streptococcus agalactiae* (Group B *Streptococcus*), *Streptococcus* (*viridans* group), *Streptococcus faecalis*, *Streptococcus bovis*, *Streptococcus uberis*, *Streptococcus dysgalactiae*, *Streptococcus* (anaerobic sps.), *Streptococcus pneumoniae*, *Streptococcus mutans*, *Streptococcus sobrinus*, *Streptococcus sanguis*, *Streptomyces albus*, *Streptomyces cinnamoneus*, *Streptomyces exfoliates*, *Streptomyces scabies*, *Sulfolobus acidocaldarius*, *Syechocystis* sp., *Treponena* species, *Treponema denticola*, *Treponema minutum*, *Treponema palladium*, *Treponema pertenue*, *Treponema phagedenis*, *Treponema refringens*, *Treponema vincentii*, *Vibrio* species, *Vibrio cholerae*, *Yersinia* species and combinations thereof.

In some aspects, the virus is one that infects animals including, but not limited to, Avian herpesvirus, Avian influenza, Avian leukosis virus, Avian paramyxoviruses, Border disease virus, Bovine coronavirus, Bovine ephemeral fever virus, Bovine herpes viruses, Bovine immunodeficiency virus, Bovine leukemia virus, Bovine parainfluenza virus 3, Bovine respiratory syncytial virus, Bovine viral diarrhea virus (BVDV), BVDV Type I, BVDV Type II, Canine adenovirus, Canine coronavirus (CCV), Canine distemper virus, Canine herpes viruses, Equine herpes viruses, Canine influenza virus, Canine parainfluenza virus, Canine parvovirus, Canine respiratory coronavirus, Classical swine fever virus, Eastern Equine encephalitis virus (EEE), Equine infectious anemia virus, Equine influenza virus, West nile virus, Feline Calicivirus, Feline enteric coronavirus, Feline immunodeficiency virus, Feline infectious peritonitis virus, Feline herpes Virus, Feline influenza virus, Feline leukemia virus (FeLV), Feline viral rhinotracheitis virus, Lentivirus, Marek's disease virus, Newcastle Disease virus, Ovine herpesviruses, Ovine parainfluenza 3, Ovine progressive pneumonia virus, Ovine pulmonary adenocarcinoma virus, Pantropic CCV, Porcine circovirus (PCV) Type I, PCV Type II, Porcine epidemic diarrhea virus, Porcine hemagglutinating encephalomyletitis virus, Porcine herpesviruses, Porcine parvovirus, Porcine reproductive and respiratory syndrome (PRRS) Virus, Pseudorabies virus, Rabies, Rotovirus, Rhinoviruses, Rinderpest virus, Swine influenza virus, Transmissible gastroenteritis virus, Turkey coronavirus, Venezuelan equine encephalitis virus, Vesicular stomatitis virus, West Nile virus, Western equine encephalitis virus and combinations thereof.

In some aspects, the virus is one that infects humans, including, but not limited to, Adenoviridae (most adenoviruses); Arena viridae (hemorrhagic fever viruses); Astroviruses; Bungaviridae (e.g., Hantaan viruses, bunga viruses, phleboviruses and Nairo viruses); Calciviridae (e.g., strains that cause gastroenteritis); Coronoviridae (e.g., coronaviruses); Filoviridae (e.g., ebola viruses); Flaviridae (e.g., hepatitis C virus, dengue viruses, encephalitis viruses, yellow fever viruses); Hepadnaviridae (Hepatitis B virus); Herpesviridae (herpes simplex virus (HSV) 1 and 2, varicella zoster virus, cytomegalovirus (CMV), herpes virus); Iridoviridae (e.g., African swine fever virus); Norwalk and related viruses; Orthomyxoviridae (e.g., influenza viruses); Papovaviridae (papilloma viruses, polyoma viruses); Paramyxoviridae (e.g., parainfluenza viruses, mumps virus, measles virus, respiratory syncytial virus); Middle East Respiratory Syndrome (Mers) virus; Parvovirida (parvoviruses); Picornaviridae (e.g., polio viruses, hepatitis A virus; enteroviruses, human Coxsackie viruses, rhinoviruses, echoviruses); Poxviridae (variola viruses, vaccinia viruses, pox viruses); Reoviridae (e.g., reoviruses, orbiviurses and rotaviruses); Retroviridae (e.g. human immunodeficiency viruses, such as HIV-1 or HIV-2 (also referred to as HTLV-III, LAV or HTLV-III/LAV, or HIV-III; and other isolates, such as HIV-LP); Rhabdoviradae (e.g., vesicular stomatitis viruses, rabies viruses); Togaviridae (e.g., equine encephalitis viruses, rubella viruses); and Unclassified viruses (e.g., the etiological agents of Spongiform encephalopathies, the agent of delta hepatitis (thought to be a defective satellite of hepatitis B virus).

In aspects of the present disclosure, a fungus includes, but is not limited to, spores, molds and yeasts (for example, *Candida* species).

In aspects of the present disclosure, a parasite includes, but is not limited to, a protein from *Anaplasma, Fasciola hepatica* (liver fluke), *Coccidia, Eimeria* spp., *Neospora caninum, Toxoplasma gondii, Giardia, Dirofilaria* (heartworms), *Ancylostoma* (hookworms), *Trypanosoma* spp., *Leishmania* spp., *Trichomonas* spp., *Cryptosporidium parvum, Babesia, Schistosoma, Taenia, Strongyloides, Ascaris, Trichinella, Sarcocystis, Hammondia,* or *Isopsora*, and combinations thereof. In aspects, a parasite includes, but is not limited to, ticks, including *Ixodes, Rhipicephalus,* *Dermacentor, Amblyomma, Boophilus, Hyalomma,* or *Haemaphysalis* species, and combinations thereof.

In aspects of the present disclosure, the cancer may be a malignant or non-malignant cancer. Cancers or tumors include, but are not limited to, biliary tract cancer; bladder cancer; brain cancer; breast cancer; cervical cancer; choriocarcinoma; colon cancer; colorectal cancer; endometrial cancer; esophageal cancer; gastric cancer; gliobastoma; intraepithelial neoplasms; lymphomas (for example, follicular lymphoma); liver cancer; lung cancer (for example, small cell and non-small cell); leukemia (for example, hairy cell leukemia, chronic myelogenous leukemia, cutaneous T-cell leukemia); melanoma (for example, malignant melanoma); multiple myeloma; neuroblastomas; oral cancer; ovarian cancer; pancreas cancer; prostate cancer; rectal cancer; renal cancer; sarcomas; skin cancer; testicular cancer; thyroid cancer; and renal cancer, as well as other carcinomas and sarcomas (for example, squamous cell carcinoma, renal cell carcinoma, prostate carcinoma, bladder cell carcinoma, or colon carcinoma).

Administration Mode and Dose

For use in therapy, an effective amount of one or more immunogenic compositions may be administered to a subject. Administering the pharmaceutical composition of the present disclosure may be accomplished by any means known to the skilled artisan. Preferred routes of administration include but are not limited to parenteral (for example, intramuscular, subcutaneous, intradermal, intravenous injection), topical to the skin (for example, transdermal) or mucosal (for example, oral, intranasal, intravaginal, intrarectal, trans-buccal, intraocular or sublingual). In the case of treatment of cancers, this may include intra-tumor administrations.

In some aspects of the present disclosure, an "effective amount" of an immunogenic composition refers to an amount that is necessary or sufficient to achieve the desired biological effect. For example, an effective amount of an immunogenic composition for treating a condition may be an amount necessary to eliminate a microbial infection or a tumor. An effective amount for use as a vaccine adjuvant may be an amount that can be used to enhance the immune response of a subject to a vaccine. The effective amount may vary depending on the following parameters: the disease or condition to be treated, the particular immunogenic composition administered, the age of the subject or the severity of the disease or condition. One of ordinary skill in the art can empirically determine the effective amount of a particular immunogenic composition without undue experimentation.

The immunogenic composition may be administered in a single dosage regimen, or preferably in a plurality of dosage regimens. That is, the main process of inoculating the immunogenic composition is 1-10 individual doses and subsequent administration of other doses at subsequent intervals according to the need to maintain and/or enhance the immune response, for example, a second dose after 1-4 months, and, if desired, a subsequent dose after a few months or years. The medication regimen is also determined at least in part by the needs of the individual and depends on the judgment of the medical staff. Examples of suitable immunization regimens include: a first dose, followed by a second dose between day 7 and month 6, and optionally a third dose between month 1 and year 2 after the first inoculation; or other schemes that are sufficient to elicit a virus neutralizing antibody titer which is desirable for imparting protective immunity, for example, correspond to an established inoculation scheme for a pediatric immunogenic composition. Satisfactory protective immunity can be maintained by supplementing the enhanced dose given at specific intervals (e.g., every two years).

The immunogenic compositions of the present disclosure can be prepared in various forms such as injections, tablets, powders, granules, capsules, oral solutions, unguentums, creams and the like. The above-mentioned various dosage forms of the medicament may be prepared according to conventional methods in the field of pharmacy. One or more pharmaceutically acceptable carriers may also be added to the formulations described above. The carrier includes conventional diluents, excipients, fillers, binders, wetting agents, disintegrating agents, absorption enhancers, surfactants, adsorption carriers, lubricants and the like in the pharmaceutical field.

When it is desired to systemically deliver one or more immunogenic compositions, they may be formulated for parenteral administration by injection (e.g., bolus or instillation). For example, the subject's sole, subcutaneous, muscle, abdominal and nasal mucosa can be injected to immunize. The formulation for injection may be presented in unit dosage form, for example, in an ampoule or in a multi-dose container with the added preservative. For example, the compositions may take the form of suspensions, solutions or emulsions in oily or aqueous vehicles and may contain formulation agents such as suspending agents, stabilizers and/or dispersing agents.

EXAMPLES

The present disclosure is further illustrated by reference to the following examples. It should be noted, however, that, as with the embodiments described above, these examples are exemplary and should not be construed as limiting the scope of the invention in any way.

In the present application, unless otherwise stated, the following abbreviations are used:
FPPS farnesyl pyrophosphate synthase
GGPPS geranylgeranyl pyrophosphate synthase
SQS squalene synthase
GGPP geranylgeranyl pyrophosphate
GGOH geranylgeraniol
OVA ovalbumin
IgM immunoglobulin M
IgG immunoglobulin G
PBS Phosphate Buffered Saline
PBST Phosphate Buffered Saline+Tween
BSA bovine serum albumin
HRP horseradish peroxidase
OPD o-phenylenediamine
DMSO dimethyl sulfoxide
min minute
h hour
DMAPP dimethylallyl pyrophosphate
IPP isopentenyl pyrophosphate
PEI polyethyleneimine
IFA incomplete Freund's adjuvant
CFA complete Freund's adjuvant
LPS lipopolysaccharide
DC dendritic cells
BMDC bone marrow-derived dendritic cells
FITC fluorescein isothiocyanate
Mers Middle East Respiratory Syndrome
KLH keyhole limpet hemocyanin
TLR Toll-like receptors In the biology experiments, unless otherwise stated, the experimental animals used were mice, and the strain of the mice was C57B/6. Mice were purchased from Beijing Vital River Laboratory Animal Technology Co., Ltd., and were housed in the SPF Animal Room of Tsinghua University Biomedical Testing Center.

Biological Examples

We for the first time discovered and demonstrated that enzymes associated with the mevalonate pathway can serve as targets for the rational design of adjuvant, and proposed that all substances that affect geranylgeranylation of proteins, such as inhibitors of all the enzymes involved in the mevalonate pathway, can be used as adjuvants for use in the preparation of vaccines or immunogenic compositions. We have demonstrated this view through the following biology experiments.

Example 1

Determination of Effect of a HMG-CoA Reductase Inhibitors (Statin Compounds) as Adjuvants in Mice In the mevalonate pathway, HMG-CoA reductase catalyzes the reduction of 3-hydroxy-3-methylglutaryl coenzyme A (HMG-CoA) to mevalonate, whereas HMG-CoA reductase inhibitors (i.e., statin compounds) inhibit the action of HMG-CoA reductase.

We used statin compounds as examples to demonstrate the effects of HMG-CoA reductase inhibitors as adjuvants. In this assay, the effects of statin compounds as adjuvants for immunizing mice were investigated.

In this assay, 8 statin drugs commonly used in clinical practice were used. These 8 statin drugs are: pravastatin, atorvastatin, rosuvastatin, fluvastatin, pitavastatin, mevastatin, lovastatin, simvastatin.

Material source: simvastatin was purchased from Tianjin Heowns Biochemical Technology Co., Ltd.; mevastatin and lovastatin were purchased from Aladdin company; pravastatin and atorvastatin were purchased from Energy Chemical company, fluvastatin, pitavastatin and rosuvastatin were purchased from Huazhong Weihai company; and the OVA (Ovalbumin) antigen was purchased from Sigma-Aldrich.

OVA evaluation system was used to determine adjuvant activity in antibody titer. Ovalbumin, which is also known as chicken egg albumin, consists of 386 amino acids, has a molecular weight of about 43 kD, and is usually used as a tool protein to study antibody titer.

Experimental method: each of the statins was mixed with the OVA antigen at 1:1, with the concentrations of both the statin and OVA are 10 mg/ml. Mice of C57B/6 strain were used. The mice in the experimental group were injected with the obtained mixture of each of the statins and OVA antigen through soles injection, with 20 µl for each mouse. The mice in the control group were injected with a 1:1 mixture of PBS or DMSO (10 µl) and 10 µl OVA antigen (PBS or DMSO is 10 µl, respectively, and the antigen is 10 µl) through soles injection, with 20 µl for each mouse. On Day 7 and Day 14 after immunization, blood was taken from the mice's orbits, with 100 µl was taken from each mouse. The obtained blood was left at 4° C. overnight, and centrifuged at 6000 rpm for 8 min. The supernatant serum was removed and the titers of anti-OVA IgM and IgG antibodies in the serum were determined.

Test of the OVA antibody titer: The OVA protein was diluted to a concentration of 2 µg/ml with a carbonate solution of pH 9.6, coated in a 96-well ELISA plate at 50 µl per well, and left at 4° C. overnight. The ELISA plate was washed five times with PBS containing 0.05% Tween 20, blocked with 1% BSA solution at 200 µl per well, and incubated at room temperature for 2 h. The ELISA plate was washed five times with PBST (Phosphate Buffered Saline with Tween), a 2-fold serial dilution of the mouse serum after immunized with OVA was added at 50 µl per well and incubated at room temperature for 2 h. After the ELISA plate was washed five times with PBST, HRP (horseradish peroxidase)-labeled goat-anti-mouse IgM or IgG antibody was added and incubated at room temperature for 45 min. The ELISA plate was washed five times with PBST, and a color developing solution of sodium citrate OPD (o-phenylenediamine) was added. After 10 min of color development in the dark, sulfuric acid was added to terminate the reaction. The reading was performed with ELIASA OD490. The maximum serum dilution factor, when the ratio of light absorptions of the experimental group to the control group was ≥2.0, was the titer of the anti-OVA antibody in the serum.

As shown in the results in FIG. 2, in mice treated with statin drugs such as fluvastatin, pitavastatin, rosuvastatin, simvastatin, lovastatin and mevastatin, IgM and IgG antibodies with significantly higher titers were produced as compared to PBS or DMSO treated mice in the control group, wherein especially simvastatin, lovastatin and mevastatin had the most significant adjuvant effects. The effects of some statin compounds were not significant, possibly due to poor bioavailability in vivo, such as poor solubility or absorption. Better effects can be achieved by adjusting pharmacokinetic properties of these compounds (e.g., forming salts, esters or prodrugs, or forming aluminum salts).

Therefore, the above study demonstrates that HMG-CoA reductase inhibitors can be used as adjuvants to enhance the specific immune response induced by the antigen.

Example 2

Determination of Effect of FPPS Inhibitors as Adjuvants in Mice

In the mevalonate pathway, farnesyl pyrophosphate synthase (FPPS) catalyzes the formation of farnesyl pyrophosphate (FPP) from dimethyl allyl pyrophosphate (DPP), whereas FPPS inhibitors inhibit the action of FPPS. We investigated the effect of FPPS inhibitors as adjuvants for immunizing mice. It is well known that bisphosphonic acid compounds are potent inhibitors of FPPS. In the following assays, adjuvant effects of various bisphosphonic acid compounds were investigated.

(1) Effects of TH-Z80 Series of Compounds as Adjuvants in Mice

The TH-Z80 series of compounds were newly synthesized bisphosphonic acid compounds, the structures of which were shown below.

First, inhibitory activities of the TH-Z80 series of compound against FPPS target were determined by referring to the purification method for humanized farnesyl pyrophosphate synthase (HsFPPS) in the reference (Sanders, J. M., et al., Pyridinium-1-yl bisphosphonates are potent inhibitors of farnesyl diphosphate synthase and bone resorption. Journal of medicinal chemistry, 2005. 48(8): p. 2957-2963.) and the enzymatic activity test method in the reference (Zhang, Y., et al., Lipophilic Bisphosphonates as Dual Farnesyl/Geranylgeranyl Diphosphate Synthase Inhibitors: An X-ray and NMR Investigation. Journal of the American Chemical Society, 2009. 131(14): p. 5153-5162.).

The measurement method is briefly described as follows: the expression of HsFPPS with 6 consecutive His at the N-terminus was induced in vitro, collected, and purified by Ni column. An in vitro HsFPPS enzyme activity assay was performed in a 96-well plate with 200 µl of solution per well. The buffer of the system was 25 mM HEPES, 2.5 mM $MgCl_2$, pH 7.4. Using DMAPP and IPP as reaction substrates, the change of the UV value at a wavelength of 360 nm was monitored in real time in a phosphate lyase system. The ORIGIN 8.0 software was used to plot and fit. The $IC_{50}$ values for the inhibition of FPPS by the TH-Z80 series of compounds were shown in the following table, in micromoles per liter (µM).

| n = | Compound No. | $IC_{50}$ for inhibition of PPS (µM) |
|---|---|---|
| 1 | TH-Z79 | 0.1-0.3 |
| 2 | TH-Z148 | 0.068 |
| 3 | TH-Z149 | 0.27 |
| 4 | TH-Z150 | 0.14 |
| 5 | TH-Z151 | 0.12 |
| 6 | TH-Z80 | 0.11 |
| 7 | TH-Z152 | 0.14 |
| 8 | TH-Z81 | 0.48 |
| 9 | TH-Z153 | 4.9 |
| 10 | TH-Z82 | 9.5 |
| 11 | TH-Z154 | >5 |
| 12 | TH-Z155 | >5 |

It can be seen from the above data that the TH-Z80 series of compounds can effectively inhibit the activity of FPPS, and are potent inhibitors of FPPS.

Subsequently, we used the OVA evaluation system as described in Example 1 to determine adjuvant effects of the TH-Z80 series of compounds and the compound BPH-266 without side chain substitution on the same parent core in mice. Each test compound was formulated at a concentration of 2 mg/ml and the concentration of OVA antigen was 2 mg/ml. Each compound was mixed with OVA at 1:1. Each C57B/6 mouse in the experimental group was injected with 100 µl of the mixture (containing 50 µl of the antigen and 50 µl of the compound) by intramuscular injection at the right thigh. On Day 7 and Day 14 after immunization, blood was taken from the mice's orbit, and 100 µl was taken for each mouse. The obtained blood was allowed to stand at 4° C. overnight, and centrifuged at 6000 rpm for 8 min. The supernatant serum was removed, and the titers of anti-OVA IgM and IgG antibodies in the serum were determined. The results of the experiment are shown in FIG. 3.

Wherein the BPH-266 compound (See compound 8 in the reference: Ling, Y., et al., Bisphosphonate Inhibitors of *Toxoplasma gondi* Growth: In Vitro, QSAR, and In Vivo Investigations. Journal of Medicinal Chemistry, 2005. 48(9): p. 3130-3140.] has the following structure:

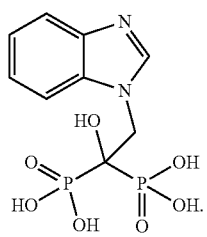 [SMILES: O=P(O)(O)C(O)(Cn1cnc2ccccc21)P(=O)(O)O]

Figure 3:
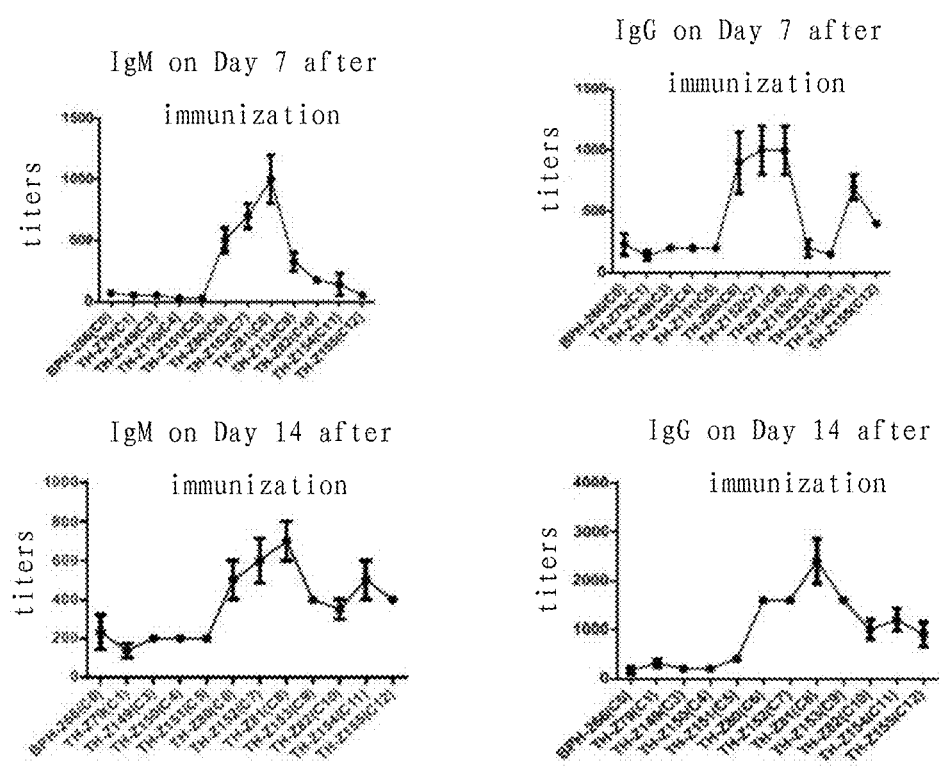
FIG. 3 shows adjuvant activities of the TH-Z80 series of compounds in OVA antibody titer assay, expressed as antibody titers of IgM and IgG on Day 7 and Day 14 after immunization.

As shown in FIG. 3, mice treated with the TH-Z80 series of compounds produced IgM and IgG antibodies with significantly higher titers, wherein especially TH-Z80, TH-Z81, TH-Z152, and TH-Z153 had the most significant adjuvant effects.

Therefore, the above assay confirmed that the potent inhibitors of FPPS, i.e., the TH-Z80 series of compounds of the present application, can act as adjuvants to enhance specific immune responses induced by the antigen.

(2) Effects of TH-Z97 Series of Compounds as Adjuvants in Mice

The TH-Z97 series of compounds were newly synthesized bisphosphonic acid compounds, the structure of which are shown below.

First, we performed a HsFPPS (humanized farnesyl pyrophosphate synthase) activity assay and determined the inhibitory activities of the TH-Z97 series of compounds against the FPPS target. The same method as for testing the TH-Z80 series of compounds as described above was used. The $IC_{50}$ values of the TH-Z97 series compounds to inhibit FPPS were shown in the following table, in micromoles per liter.

| n = | Compound No. | $IC_{50}$ for inhibition of FPPS (μM) |
|---|---|---|
| 1 | TH-Z156 | 0.16 |
| 2 | TH-Z157 | 0.08 |
| 3 | TH-Z158 | 0.13 |
| 4 | TH-Z159 | 0.06 |
| 5 | TH-Z160 | 0.07 |
| 6 | TH-Z97 | 0.06 |
| 7 | TH-Z161 | 0.17 |
| 8 | TH-Z98 | 0.15 |
| 9 | TH-Z162 | 5.0 |
| 10 | TH-Z99 | >5 |
| 11 | TH-Z198 | >5 |
| 12 | TH-Z163 | >5 |

It can be seen from the above data that the TH-Z97 series of compounds can effectively inhibit the activity of FPPS, and are potent inhibitors of FPPS.

Subsequently, we used the OVA evaluation system as described in Example 1 to determine adjuvant effects of the TH-Z97 series of compounds in mice. The results were shown in FIG. 4.

Figure 4:
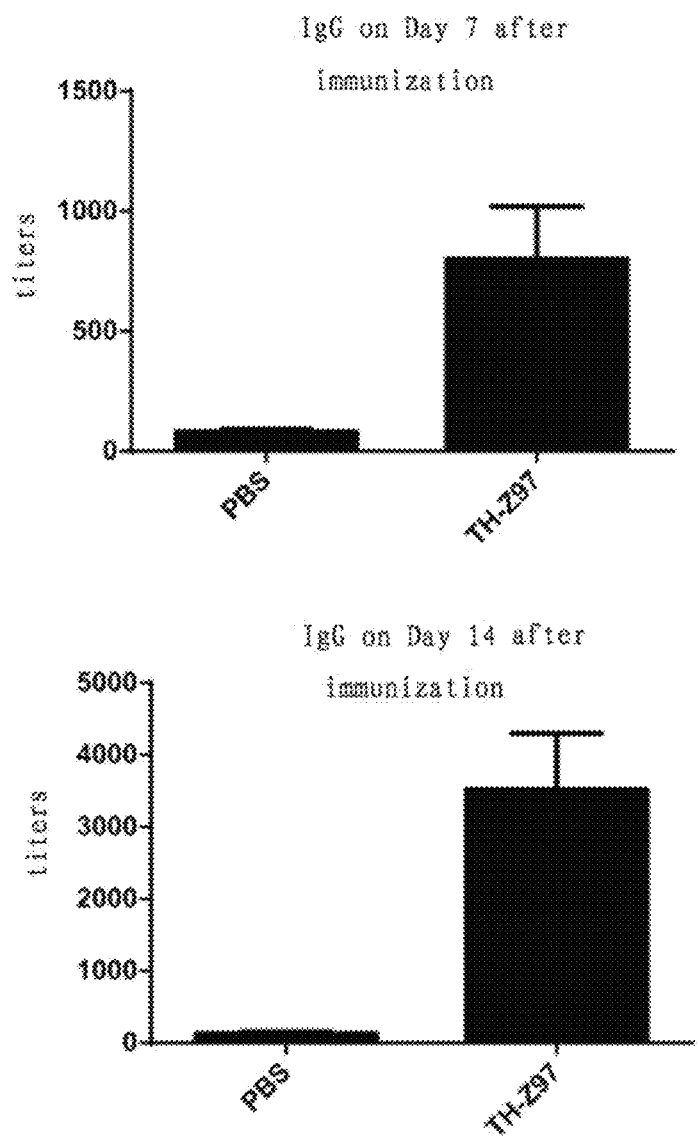
FIG. 4 shows adjuvant activity of the FPPS inhibitor TH-Z97 in OVA antibody titer assay, expressed as antibody titers of IgG on Day 7 and Day 14 after immunization.

As shown in FIG. 4, mice treated with TH-Z97 produced the IgG antibody with significantly higher titers relative to PBS treated mice in the control group.

Therefore, the above assay confirmed that the potent inhibitors of FPPS, i.e., the TH-Z97 series of compounds of the present application, can act as adjuvants to enhance the specific immune responses induced by the antigen.

(3) O-Aminopyridine Compounds and the Test Data of their Activity Against HsFPPS (Humanized Farnesyl Pyrophosphate Synthase)

We tested the activity of some newly synthesized o-aminopyridine bisphosphonic acid compounds against the HsFPPS (humanized farnesyl pyrophosphate synthase) and determined the inhibitory activities of these compounds against the FPPS target. The same method as for testing the TH-Z80 series of compounds as described above was used. The $IC_{50}$ values of these compounds to inhibit FPPS were shown in the following table, in micromoles per liter (μM).

| No. | Structure | $IC_{50}$ (μM) |
|---|---|---|
| TH-Z93 | $OC_6H_{13}$ pyridine-aminobisphosphonate | 0.100 |
| TH-Z106 | OBN pyridine-aminobisphosphonate | 0.108 |
| TH-Z108 | tetrahydroindazole-pyridine-aminobisphosphonate | 0.112 |

-continued

| No. | Structure | IC$_{50}$ (µM) |
|---|---|---|
| TH-Z109 | (structure shown) | 0.643 |

It can be seen from the above data that the o-aminopyridine bisphosphonic acid compounds can effectively inhibit the activity of FPPS, and are potent inhibitors of FPPS.

The adjuvant effect of such o-aminopyridine bisphosphonic acid compounds (e.g., TH-Z93) in mice was shown in the following test (4).

(4) Effects of Other FPPS Inhibitor Compounds as an Adjuvant in Mice

In this assay, the OVA evaluation system as described in Example 1 was used to determine the adjuvant effects of 8 bisphosphonic acid compounds commonly used in clinical practice and the TH-Z80 and TH-Z93 compounds of the present disclosure in mice. And the adjuvant activity of the novel bisphosphoric acid compounds synthesized in the present disclosure was compared with the commercially available bisphosphonic acid drugs. The 8 bisphosphonic acid compounds were zoledronic acid (zoledronate), pamidronic acid (pamidronate), alendronic acid (alendronate), ibandronic acid (ibandronate), neridronic acid (neridronate), risedronic acid (risedronate), olpadronic acid (olpadronate), and minodronic acid (minodronate). These compounds were synthesized with reference to the following document: Zhang, Yonghui, Annette Leon, Yongcheng Song, Danielle Studer, Christa Haase, Lukasz A. Koscielski and Eric Oldfield. "Activity of Nitrogen-Containing and Non-Nitrogen-Containing Bisphosphonates on Tumor Cell Lines." *Journal of Medicinal Chemistry*, 2006: 5804-5814, which was hereby incorporated by reference in its entirety.

Method: each of the test compounds (the 10 bisphosphonates as described above) was mixed with the OVE antigen at 1:1, and the concentrations of bisphosphonic acid and OVA were both 10 mg/ml. Mice of C57B/6 strain were used. The mice in the experimental group were injected with the mixture of each of the test compounds and OVA antigen through soles injection, with 20 µl for each mouse, and wherein the amounts of OVA antigen and each of the test compounds were both 100 µg. The mice in the control group were injected with a 1:1 mixture of 10 µl PBS and 10 µl OVA antigen through sole injection. On Day 7 and Day 14 after immunization, blood was taken from the mice's orbits, and 100 µl was taken from each mouse. The obtained blood was left at 4° C. overnight, and centrifuged at 6000 rpm for 8 min. The supernatant serum was removed, and the titers of anti-OVA IgM and IgG antibodies in the serum were determined.

As shown in the results in FIG. 5, in mice treated with test compounds, IgM and IgG antibodies with higher titers were produced relative to PBS treated mice in the control group, wherein among these bisphosphonic acid compounds, the TH-Z80 and TH-Z93 compounds of the present disclosure showed the most significant adjuvant effects. For example, it can be seen from FIG. 5 that, on Day 7 and Day 14 after immunization, the titers of IgM and IgG antibodies in mice treated with the TH-Z80 and TH-Z93 compounds of the present disclosure were more than five times higher than the antibody titers in PBS treated mice in the control group. In addition, the adjuvant effects of the TH-Z80 and TH-Z93 compounds of the present disclosure were much higher than any of the 8 commercially available bisphosphonic acid compounds which are commonly used in clinical practice.

The assays (1) to (4) showed that the FPPS inhibitors can serve as adjuvants and enhance the specific immune responses induced by the antigen.

Example 3

(1) Determination of the Effects of GGPPS Inhibitors as Adjuvants in Mice

In the mevalonate pathway, geranylgeranyl pyrophosphate synthase (GGPPS) catalyzes the formation of geranylgeranyl pyrophosphate (GGPP) from FPP. We investigated the role of GGPPS inhibitors as adjuvants for immunizing mice.

The compounds TH-Z144 and TH-Z145 were new bisphosphonic acid compounds synthesized by us, the structures of which were as shown above.

The inhibitory activities of compounds TH-Z144 and TH-Z145 on GGPPS (geranylgeranyl pyrophosphate synthase) were tested by referring to the expression and purification method for HsGGPPS (humanized geranylgeranyl pyrophosphate synthase) in the reference (Szabo, C. M., et al., Inhibition of Geranylgeranyl Diphosphate Synthase by Bisphosphonates and Diphosphates: A Potential Route to New Bone Antiresorption and Antiparasitic Agents. Journal of Medicinal Chemistry, 2002. 45(11): p. 2185-2196.) and the method for testing enzyme activity in the reference (Zhang, Y., et al., Lipophilic Bisphosphonates as Dual Farnesyl/Geranylgeranyl Diphosphate Synthase Inhibitors: An X-ray and NMR Investigation. Journal of the American Chemical Society, 2009. 131(14): p. 5153-5162.) The data of the activity test were as follows:

| No. | Structure of compound | IC$_{50}$ (µM) |
|---|---|---|
| TH-Z144 | (structure shown) | 2.76 |

| No. | Structure of compound | IC$_{50}$ (μM) |
|---|---|---|
| TH-Z145 | 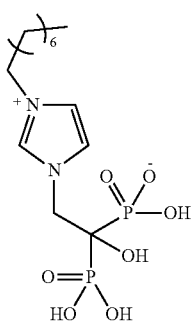 | 0.66 |

It can be seen from the above data that the compounds TH-Z144 and TH-Z145 can effectively inhibit the activity of GGPPS, and are potent inhibitors of GGPPS.

Subsequently, we used the OVA evaluation system as described in Example 1 to investigate the adjuvant effects of TH-Z144 and TH-Z145.

Method: TH-Z144 and TH-Z145 were prepared at the concentration of 10 mg/ml, the concentration of OVA antigen was also 10 mg/ml, and the compound and the antigen were mixed at 1:1. Mice of C57B/6 strain were used. Each mice in the experimental group was injected with a 20 μl mixture of the test compound and OVA antigen at right sole, i.e. 100 μg (10 μl) of adjuvant and 100 μg (10 μl) of antigen OVA. Mice in the control group were injected with a 1:1 mixture of 10 μl of PBS and 10 μl of OVA antigen through sole injection. On Day 7 and Day 14 after immunization, blood was taken from the mice's orbits, and 100 μl was taken for each mouse. The taken blood was left at 4° C. overnight, and then the serum was separated. The titers of anti-OVA IgM and IgG antibodies in the serum were determined. The results were shown in FIG. 6.

As shown in the results in FIG. 6, in mice treated with test compounds TH-Z144 and TH-Z145 IgM and IgG antibodies with significantly higher titers were produced relative to PBS treated mice in the control group. It demonstrates that GGPPS inhibitors can act as adjuvants and enhance specific immune responses induced by the antigen.

(2) Effect of Dual Inhibitors of FPPS and GGPPS as Adjuvants in Mice

Compounds BPH-716 and BPH-1222 have been reported as dual inhibitors of FPPS and GGPPS (references: Zhang, Y., et al., Lipophilic pyridinium bisphosphonates: potent γδ T cell stimulators. Angewandte Chemie, 2010. 122(6): p. 1154-1156., Zhang, Y., et al., Chemo-Immunotherapeutic Antimalarials Targeting Isoprenoid Biosynthesis. ACS Medicinal Chemistry Letters, 2013. 4(4): p. 423-427), which have the following structures:

BPH-1222

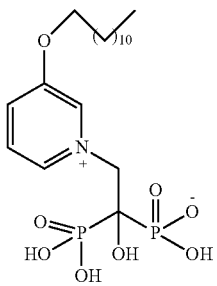

BPH-716

We used the OVA evaluation system as described in Example 1 to investigate the adjuvant effects of BPH-716 and BPH-1222. The results are shown in FIGS. 7A-D.

As shown in FIGS. 7A-D, on Day 7 and Day 14 after immunization, in mice treated with BPH-716 and BPH-1222 IgM and IgG antibodies with significantly higher titers were produced relative to PBS treated mice in the control group (the antigens used for testing BPH-1222 and BPH-716 is a hapten, 4-hydroxy-3-nitrophenylacetyl (abbreviated as NP), mice were immunized with NP33-KLH (nitrobenzene attached to Keyhole limpet hemocyanin (KLH)) mixed with BPH-1222 and BPH-716; and on Day 7 and Day 14 after immunization, the titer of specific antibody against NP in the serum was measured with NP33-BSA (nitrobenzene attached to bovine serum albumin (BSA)). Specific implementation and testing methods were the same as those for OVA immunization and test).

Therefore, the assay demonstrates that dual inhibitors for FPPS and GGPPS both increase the titer of immunoglobulin, can exert a good effect as an adjuvant, and can enhance specific immune responses induced by the antigen.

Example 4

Comparison of Activities of HMG-CoA Reductase Inhibitor, FPPS Inhibitor, and GGPPS Inhibitor as Adjuvants with the Existing Adjuvants Using the OVA evaluation system as described in Example 1, the differences in adjuvant effects of a HMG-CoA reductase inhibitor (simvastatin), FPPS inhibitors (TH-Z80 and TH-Z93), and a GGPPS inhibitor (TH-Z145) with known common adjuvants (PEI, imiquimod, aluminum adjuvant, MF59, IFA and CFA) were compared. In particular, in mice treated with these adjuvants IgG titers and antibody affinities were tested after boost.

Antibody affinity refers to the strength of an antibody to bind to the epitope of an antigen, which is a very important indicator when evaluating an antibody. It is due to gene mutations of antibody-forming cells themselves and selective activation of antigens for B cell clones. The functional state of the body is the result of long-term evolution and continuous adaptation to the external environment, which is of great significance to the defense of the body and the maintenance of autoimmune monitoring. In an in vitro test, the affinity of an antibody is determined by disrupting the antigen-antibody binding by sodium thiocyanate. The determination of antibody affinity is based on the fact that sodium thiocyanate can disrupt the binding of antigen and antibody, and the stronger the affinity of the antibody, the higher the concentration of sodium thiocyanate is required to dissociate the antigen and antibody. From another aspect if the affinity of the antibody is stronger, the effect of an adjuvant is better.

Material source: PEI (polyethyleneimine) was purchased from Lebost (Beijing) Technology Co., Ltd., imiquimod was purchased from Yeasen Biological Technology Co., Ltd., Shanghai, aluminum adjuvant was purchased from Thermo Scientific, and IFA (incomplete Freund's adjuvant) and CFA (complete Freund's adjuvant) were purchased from Sigma-Aldrich. MF59 was produced by our laboratory, and the production method can refer to the literature "The adjuvant effect of MF59 is due to the oil-in-water emulsion formulation, none of the individual components induce a comparable adjuvant effect.", Calabro S1, Tritto E, Pezzotti A, Taccone M, Muzzi A, Bertholet S, De Gregorio E, O'Hagan D T, Baudner B, Seubert A. Vaccine. 2013 Jul. 18; 31(33): 3363-9, which is incorporated by reference herein in its entirety.

Method: Each of the test adjuvants was mixed with the OVA antigen at 1:1, with the concentration of OVA antigens is 2 mg/ml and in a volume of 50 μl. Simvastatin, TH-Z80, TH-Z93, TH-Z145, PEI and imiquimod were each used at 100 μg; aluminum adjuvant, MF59, IFA (incomplete Freund's adjuvant) and CFA (complete Freund's adjuvant) were each used at 50 μl. The antigen and adjuvant were mixed beforehand and left overnight at 4° C. before being used to immunize mice. Mice in the experiment group were immunized by intramuscular injection with 100 μl of a mixture of each of the test adjuvants and the OVA antigen. Mice in the control group were injected intramuscularly with 50 μl of PBS and 50 μl of OVA antigen mixed in a ratio of 1:1. On Day 7 and Day 14 after immunization, 50 μg of OVA protein was used for booster immunization, respectively. On the 7th day after the third immunization, the mice were sacrificed, the blood was taken to separate the serum and the IgG titer in the serum was measured.

The OVA protein was diluted to a concentration of 2 μg/ml with a carbonate solution of pH 9.6, coated in a 96-well ELISA plate at 50 μl per well, and left at 4° C. overnight. The ELISA plate was washed five times with PBS containing 0.05% Tween 20, blocked with 1% BSA solution at 200 μl per well, and incubated at room temperature for 2 h. The ELISA plate was washed five times with PBST and the serum with certain dilution was added. Specifically, for the dilutions, the PBS group was not diluted, the simvastatin group was diluted 16-fold, the TH-Z80 group was diluted 16-fold, the TH-Z93 group was diluted 32-fold, the TH-Z145 group was diluted 16-fold, the imiquimod group was diluted 8-fold, the PEI group was diluted 8-fold, the aluminum adjuvant group was diluted 8-fold, the MF59 group was diluted 16-fold, the incomplete Freund's adjuvant group was diluted 32-fold, and the complete Freund's adjuvant group was diluted 64-fold. Before adding sodium thiocyanate, the amount of anti-OVA IgG type antibody in the diluted serum was the same, 50 μl per well, and incubated for 2 h at room temperature. After washing the ELISA plate with PBST for five times, 10 mM, 9.5 mM, 9 mM, 8.5 mM, 8 mM, 7.5 mM, 7 mM, 6.5 mM, 6 mM, 5.5 mM, 5 mM, 4.5 mM, 4 mM, 3.5 mM, 3 mM, 2.5 mM, 2 mM, 1.5 mM, and 0.5 mM sodium thiocyanate were added to each well at 50 μl per well, and incubated for 30 min at room temperature. After washing the ELISA plate for five times with PBST, HRP-labeled goat-anti-mouse antibody was added to each well at 50 μl per well and incubated for 45 min at room temperature. The ELISA plate was washed for five times with PBST, and a color developing solution of sodium citrate OPD was added. After 10 min of color development in the dark, sulfuric acid was added to terminate the reaction. According to the readings of ELIASA, the Prism software was used to calculate the $IC_{50}$ of sodium thiocyanate. The higher the IC50 value, the stronger the antibody affinity produced by the immunization.

Figure 8:
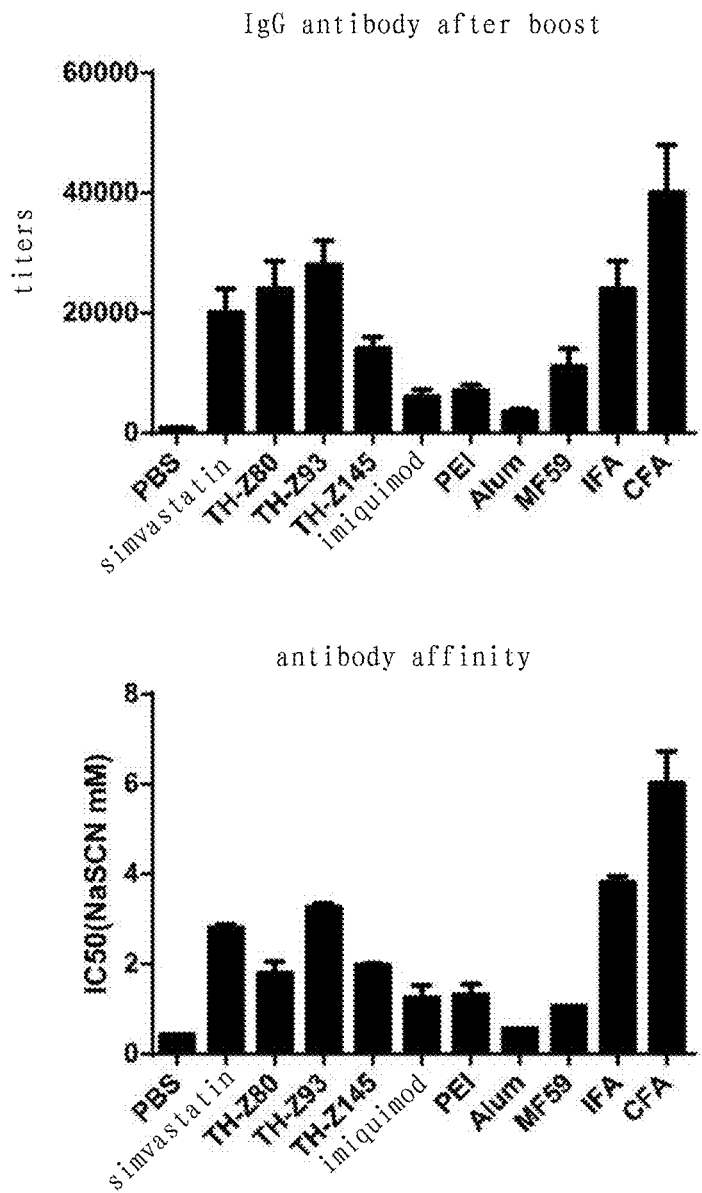
FIG. 8 shows the comparison of adjuvant activities of the three inhibitors (namely, the HMG-CoA reductase inhibitor, FPPS inhibitor, GGPPS inhibitor) of the present disclosure with the existing adjuvants. The above figure shows the antibody titer of IgG after boost, and the figure below shows the antibody affinity index.
Figure 13:
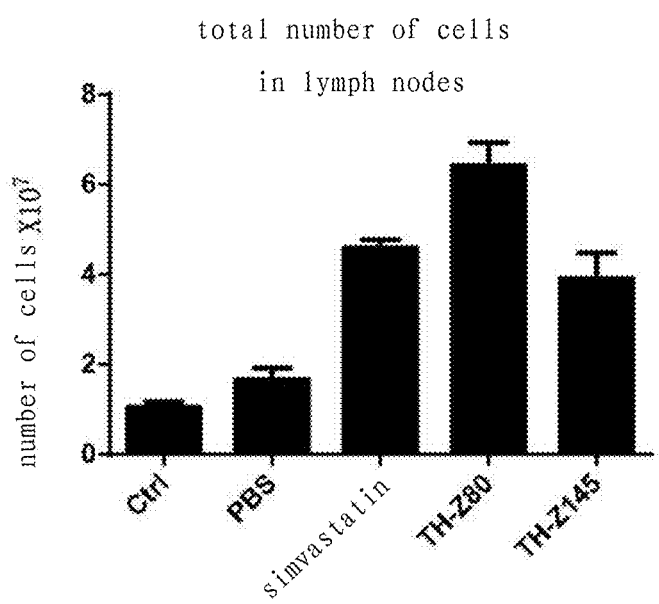
FIG. 13 shows the total number of cells in lymph nodes after 24 h immunization of mice with simvastatin, TH-Z80, TH-Z145 described herein as adjuvants, where Ctrl represents mice that are not subjected to any treatment.
Figure 14:
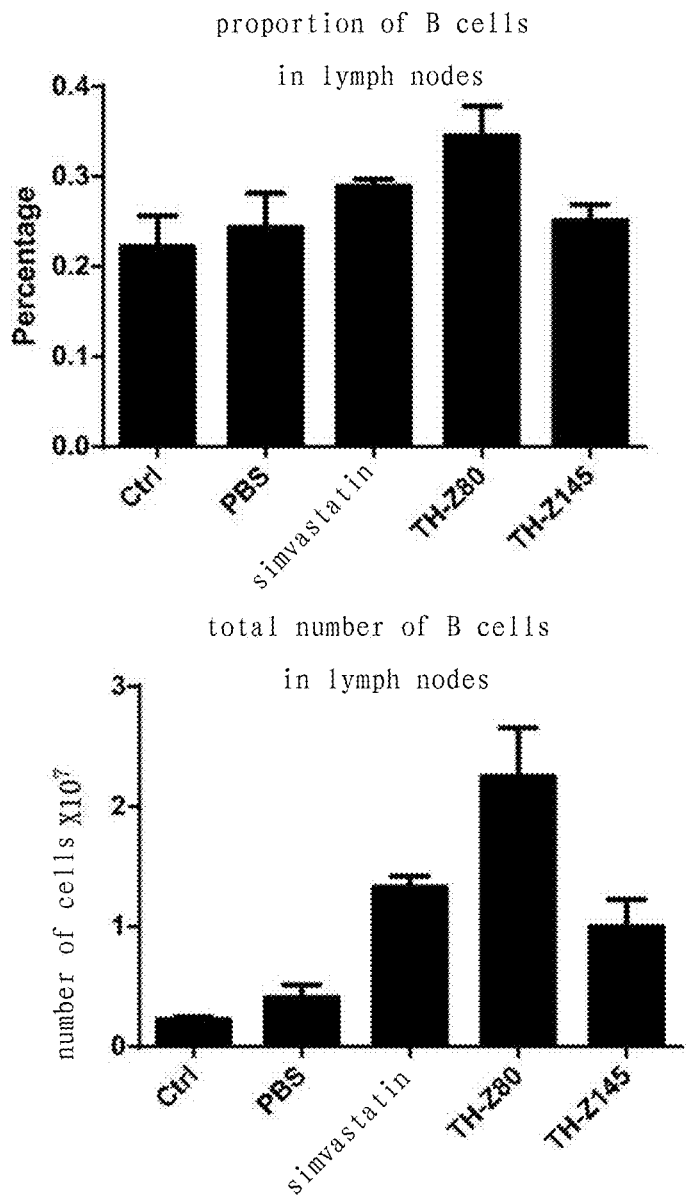
FIG. 14 shows the proportion and number of B lymphocytes in lymph nodes after 24 h immunization of mice with simvastatin, TH-Z80, TH-Z145 described herein as adjuvants, where Ctrl represents mice that are not subjected to any treatment.
Figure 15:
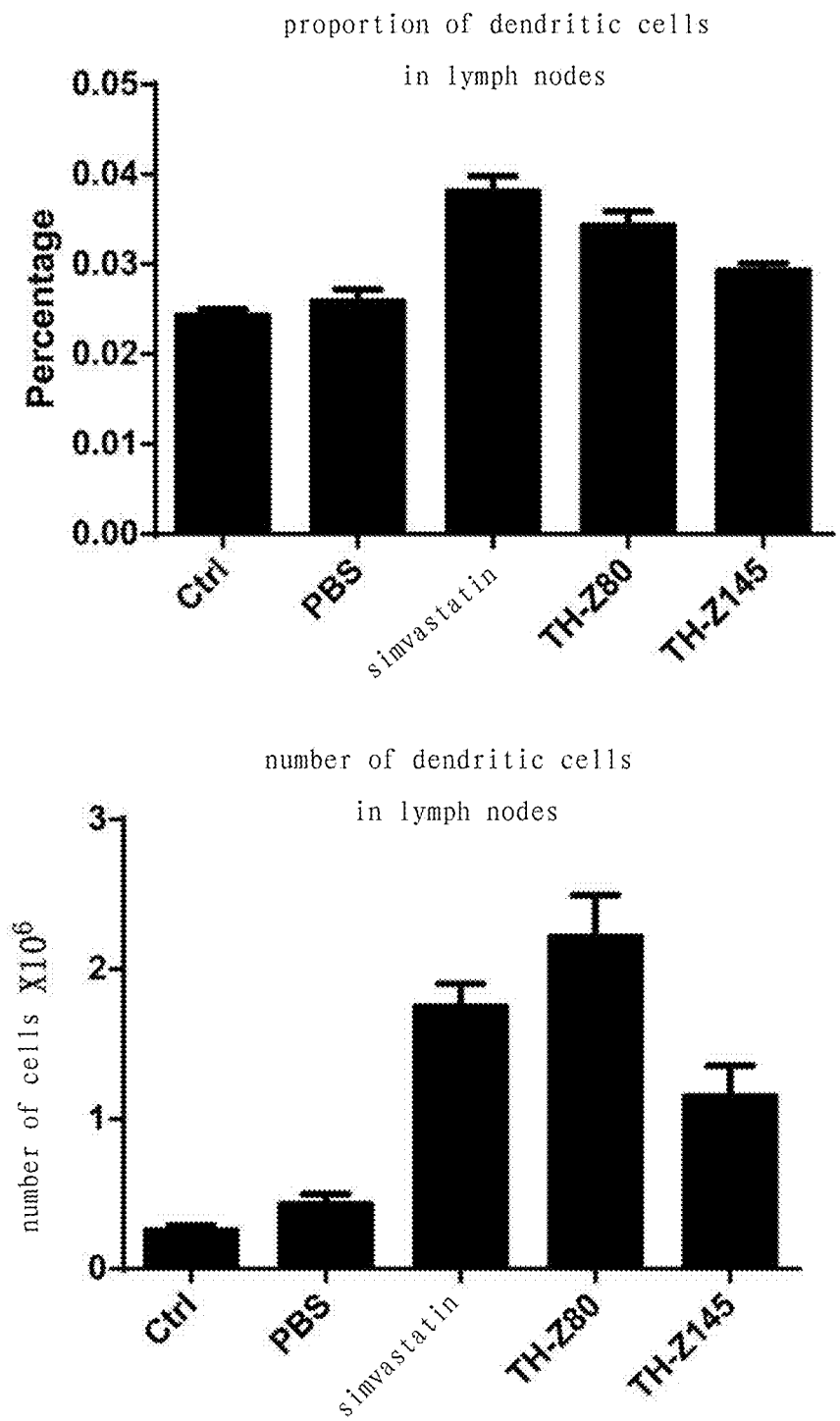
FIG. 15 shows the proportion and number of dendritic cells in lymph nodes after 24 h immunization of mice with simvastatin, TH-Z80, TH-Z145 described herein as adjuvants, where Ctrl represents mice that are not subjected to any treatment.
Figure 16:
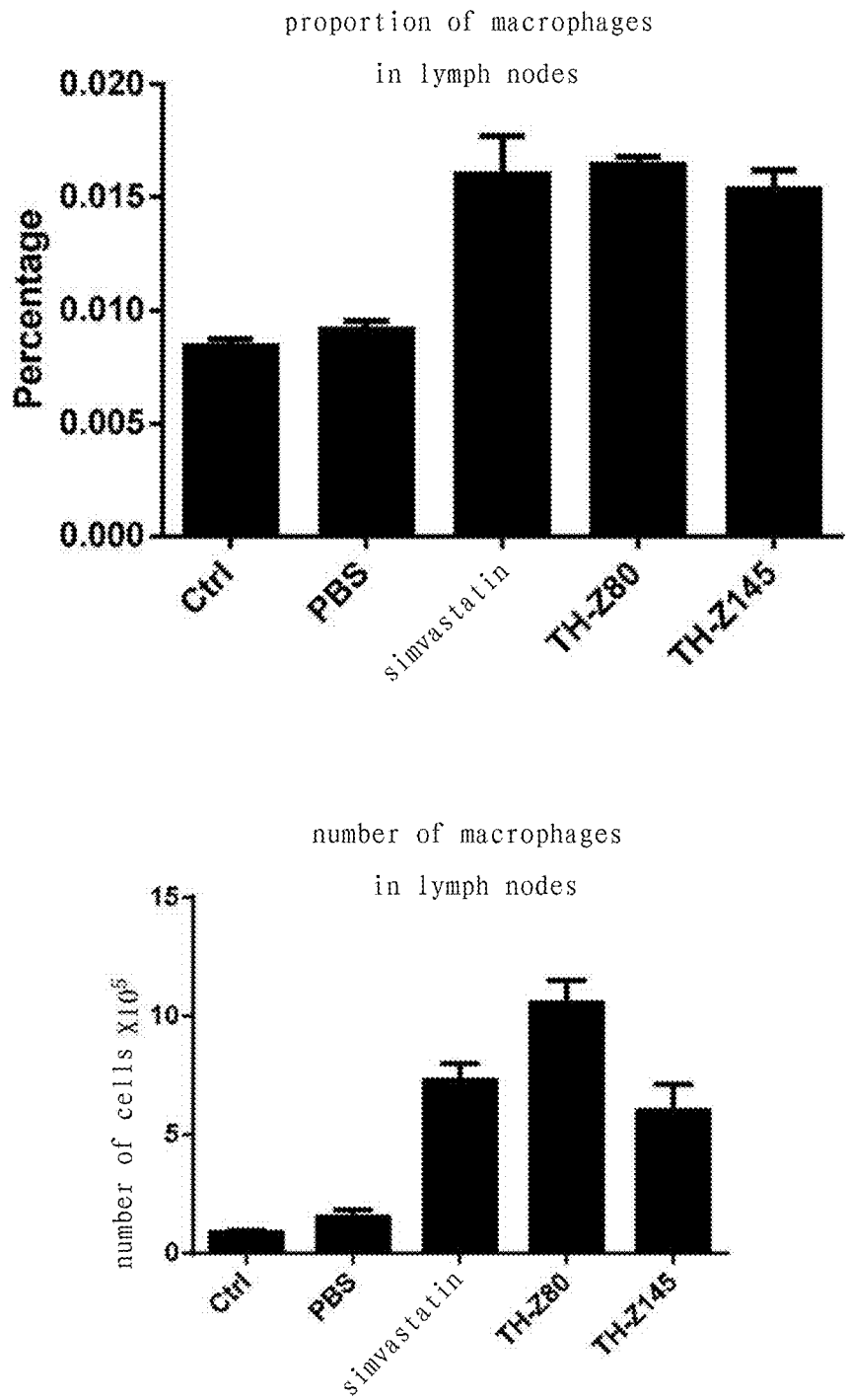
FIGS. 16A-B show the proportion and number of macrophages in lymph nodes after 24 h immunization of mice with simvastatin, TH-Z80, TH-Z145 described herein as adjuvants, where Ctrl represents mice that are not subjected to any treatment.
Figure 17:
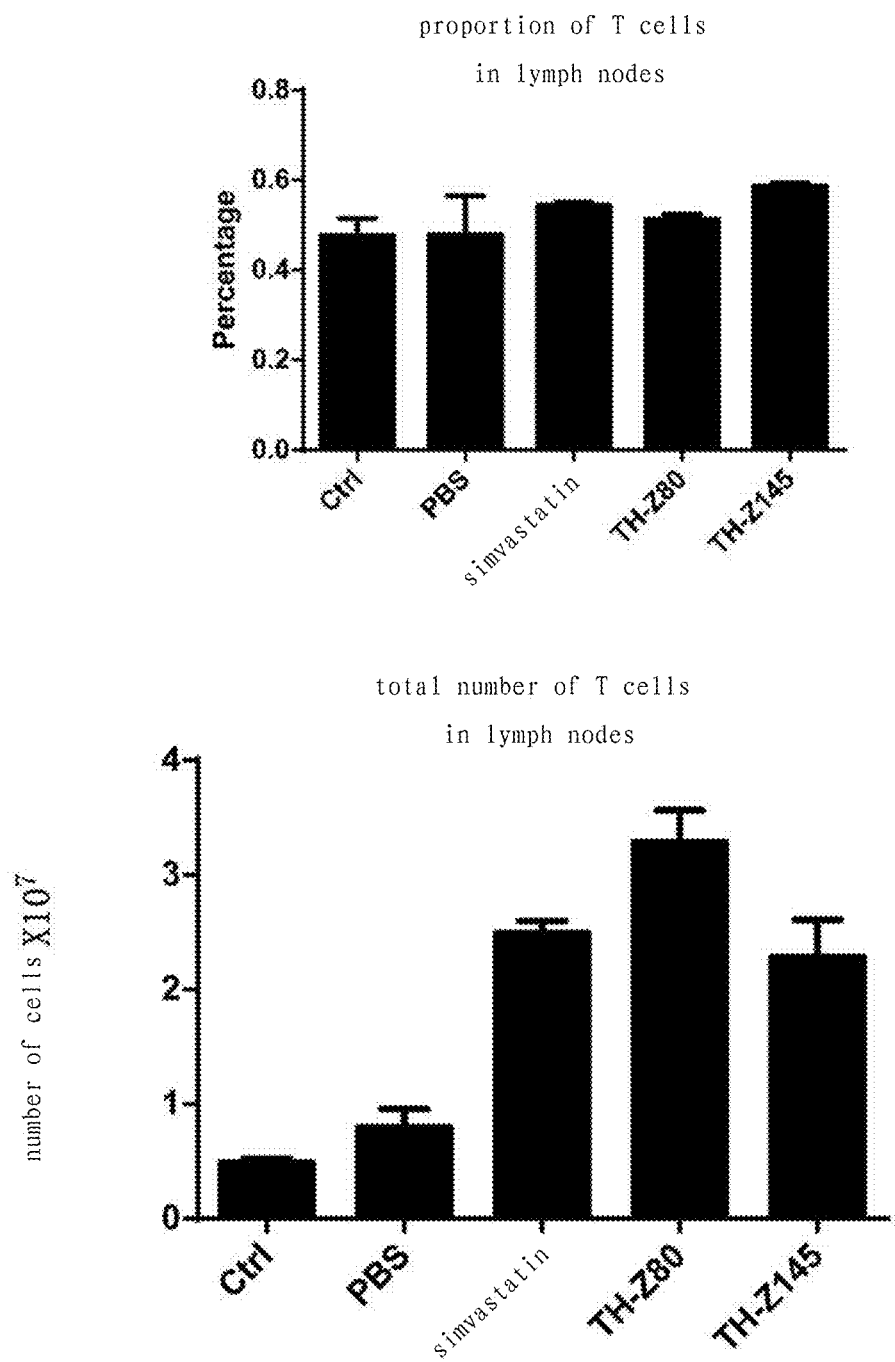
FIG. 17 shows the proportion and number of T lymphocytes in lymph nodes after 24 h immunization of mice with simvastatin, TH-Z80, TH-Z145 described herein as adjuvants, where Ctrl represents mice that are not subjected to any treatment.
Figure 18:
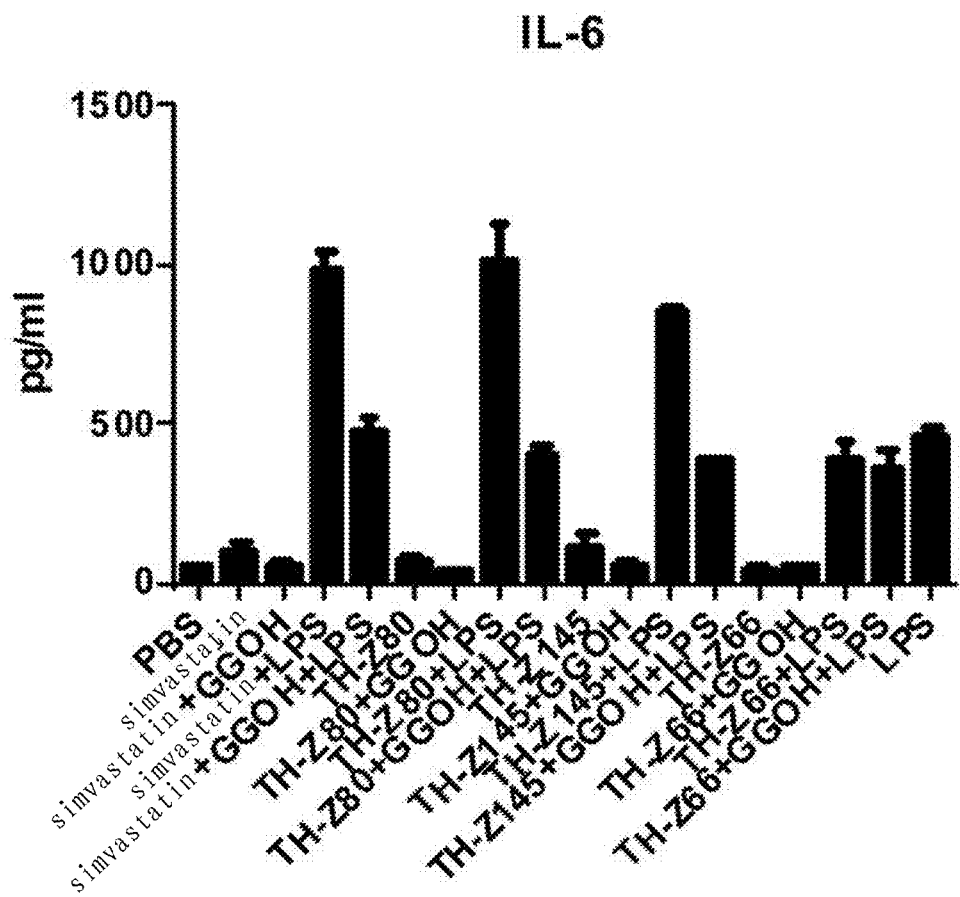
FIGS. 18-21 respectively show the concentrations of IL-6, TNF-α, IL-1β and IL-12p70 after treatment of mice bone marrow cells containing GM-CSF and IL-4 with 1 μM of simvastatin, TH-Z80, TH-Z145 and TH-Z66 followed by stimulation with 100 ng/ml LPS.
Figure 19:
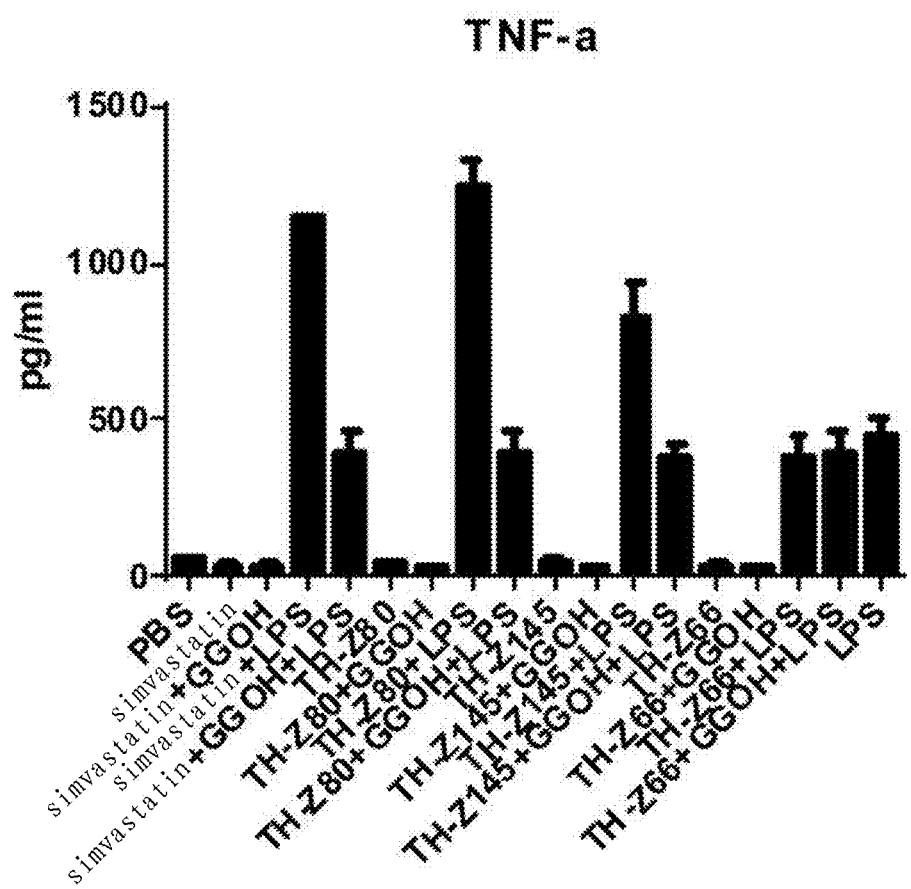
Figure 20:
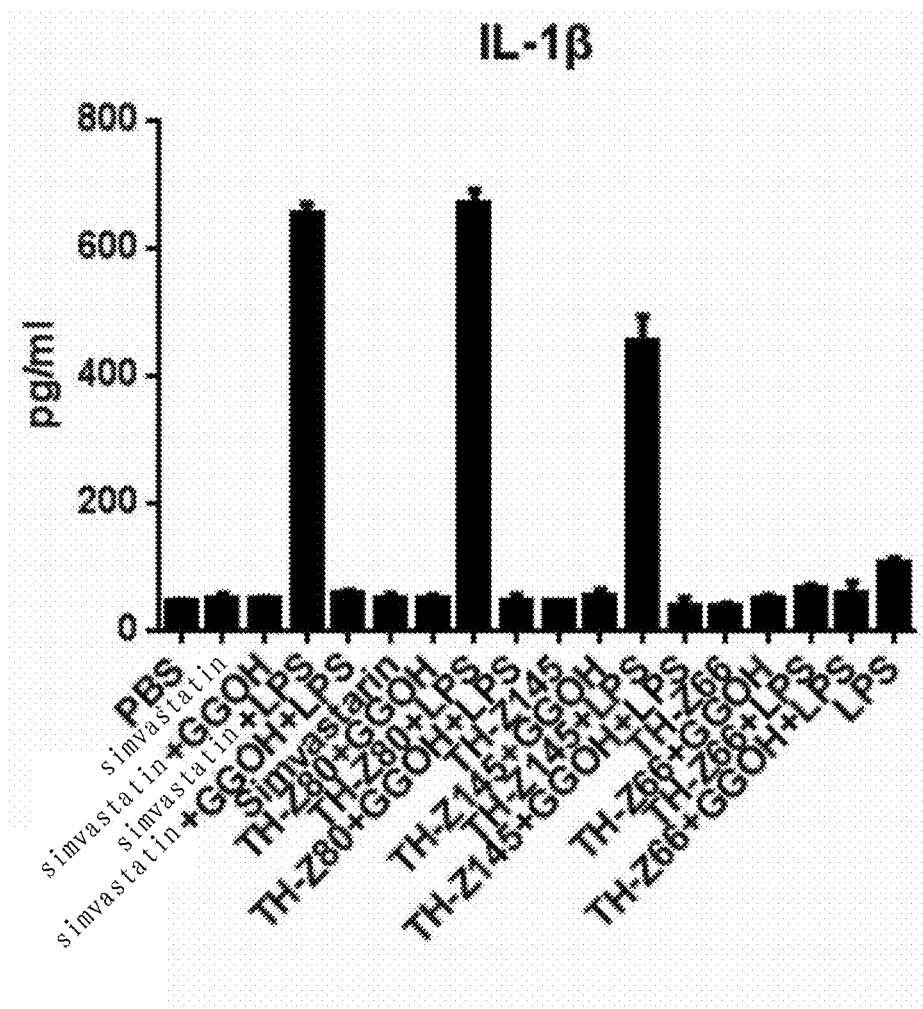
Figure 21:
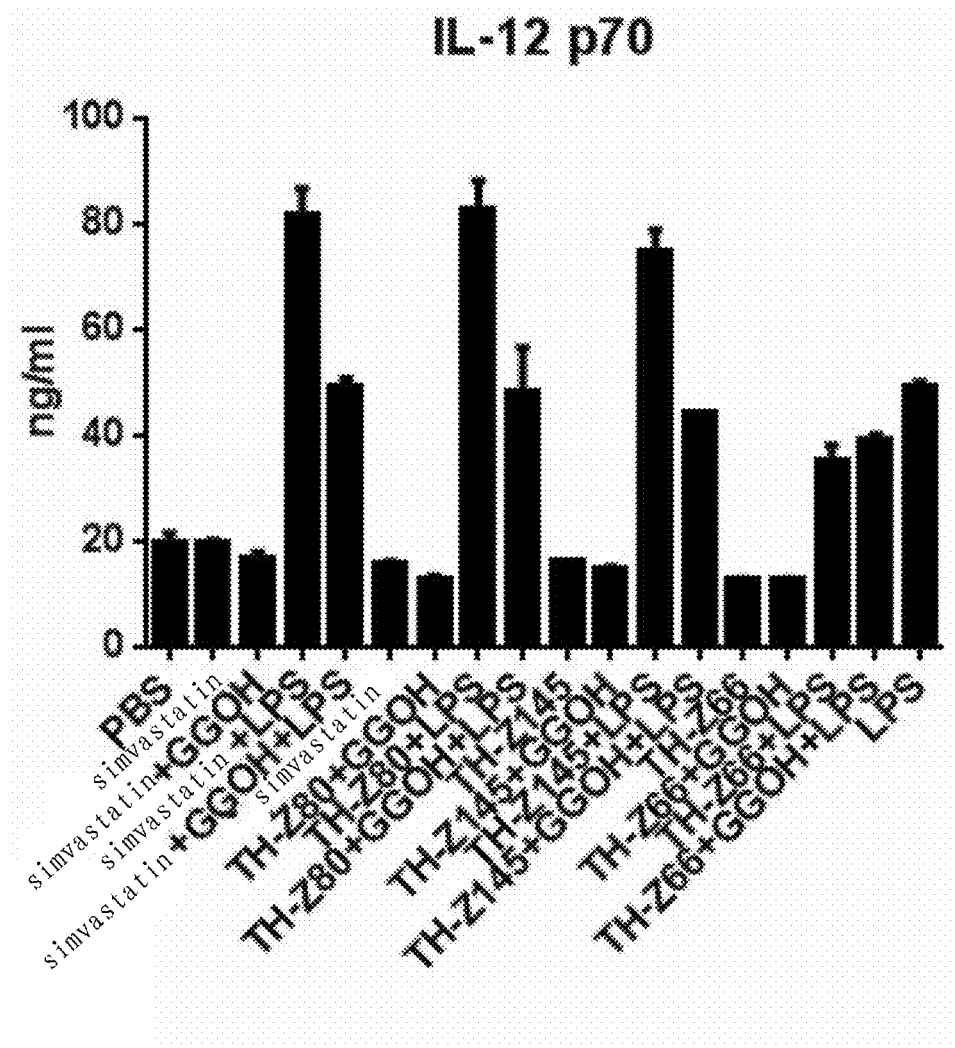

As can be seen from FIG. 8, compared with the PBS treated mice in the control group, in mice treated with the three types of inhibitors of the present disclosure (simvastatin, TH-Z80, TH-Z93, and TH-Z145) as adjuvants IgG antibodies with significantly high titers and antibody affinities were produced. In addition, it is particularly notable that the inhibitors of the present disclosure were even superior to known common adjuvants such as PEI, imiquimod, aluminum adjuvant, and MF59, both for IgG antibody titers and for antibody affinity. We believe this result will promote the development of more effective adjuvants in the art.

Examples 1-4 sufficiently demonstrate that compounds capable of inhibiting the activities of HMG-CoA reductase, FPPS, GGPPS in the mevalonate pathway can act as adjuvants in immunogenic compositions. In other words, HMG-CoA reductase inhibitors, FPPS inhibitors, GGPPS inhibitors can act as adjuvants to enhance the specific immune responses induced by antigens. We believe that inhibitors of other enzymes in the mevalonate pathway can also act as adjuvants. These enzymes include but are not limited to thiolase (acetoacetyl-CoA transferase), HMG-CoA synthase, mevalonate kinase, phosphomevalonate kinase, mevalonate-5-pyrophosphate decarboxylase, isopentenyl pyrophosphate isomerase and geranylgeranyl transferase (I, II).

Example 5

Validation that Various Adjuvants of the Present Disclosure Function Through the Mechanism of Inhibiting Geranylgeranylation of Proteins As mentioned above, we found that the HMG-CoA reductase inhibitors such as statins, farnesyl pyrophosphate synthetase inhibitors such as bisphosphonates, and geranylgeranyl pyrophosphate synthase inhibitors such as bisphosphonic acid compounds in the mevalonate pathway significantly increased the titer of IgG antibodies and antibody affinity relative to the negative control group, and can serve as adjuvants in immunogenic compositions. The geranylgeranyl pyrophosphate synthase is a downstream enzyme in the mevalonate pathway, and our experiments revealed that inhibition of geranylgeranyl pyrophosphate synthase can exert a good adjuvant effect. Therefore, we further speculated that these inhibitors exerted the adjuvant effect by inhibiting the geranylgeranylation of proteins in the mevalonate pathway. It is to be understood that if the signal transduction is carried out through post-translational modification (i.e., geranylgeranylation) of proteins in the mevalonate pathway, relevant biological behavior can be restored by the geranylgeranylated substrate, i.e., geranylgeranyl pyrophosphate (GGPP) or geranylgeraniol (GGOH); that is, once the geranylgeranylated substrates (i.e., GGPP and GGOH) are additionally added externally, these inhibitors do not effectively exert their inhibitory effect and thus can not prevent the formation of the prenylated protein.

To demonstrate our hypothesis, we designed adjuvant+OVA+GGPP (or GGOH) to verify whether various inhibitors of the present disclosure function as adjuvants through the mechanism of inhibiting geranylgeranylation. In particular, we investigated the effect of GGOH and GGPP on the adjuvant activity of simvastatin (HMG-CoA reductase inhibitor), TH-Z93 (FPPS inhibitor), and TH-Z145 (GGPPS inhibitor).

A. Rescue Experiment of GGPP and GGOH

Method: Simvastatin, TH-Z93 and TH-Z145 were formulated at a concentration of 10 mg/ml; the concentration of OVA antigen was 20 mg/ml; and GGOH and GGPP were formulated into a series of solutions at concentrations of 200 mg/ml, 100 mg/ml, 40 mg/ml and 20 mg/ml, respectively. For the experimental group, on the one hand, titers of antibodies were measured when immunization was performed without adding GGOH or GGPP while only mixing 10 μl of test compound and 5 μl of OVA antigen. On the other hand, titers of antibodies were measured when immunization was performed after adding GGOH or GGPP; specifically, 10 μl of test compound, 5 μl of OVA antigen and 5 μl of each concentration of GGOH or GGPP (total volume of 20 μl) were mixed and used for immunization in mice by injection at the sole of the right feet. Mice in the control group were treated with PBS and the antigen only, without addition of test compounds and GGOH or GGPP. On Day 7 and Day 14 after immunization, blood was taken from the mice's orbit, and 100 μl was taken for each mouse. The obtained blood was left at 4° C. overnight. The serum was separated, and titers of anti-OVA IgM and IgG antibodies in the serum were determined.

As can be seen from FIGS. 9-11, compared with titers in PBS-treated mice in the control group, IgG and IgM antibody titers were significantly higher in mice treated with simvastatin, TH-Z93, TH-Z145 of the present disclosure as adjuvant without addition of GGPP or GGOH, confirming their potent effects as adjuvants. However, after the addition of GGPP or GGOH, the titers of IgG and IgM antibodies produced in mice treated with the test compounds as adjuvants decreased significantly, and the greater amount of GGPP or GGOH added, the more the titers decreased. After the addition of 1 mg GGPP, the antibody titers even decreased to the same level as the titers in the control group treated with PBS alone.

It can be seen that both geranylgeranylated substrates GGPP and GGOH can effectively inhibit adjuvant effects of simvastatin, TH-Z93 and TH-Z145, indicating that the compounds function as adjuvants through the mechanism of inhibiting geranylgeranylation of proteins. That is, once geranylgeranylated substrates GGPP and GGOH are additionally added exogenously, the compounds of the present application can not prevent the formation of prenylated protein and thus can not function as adjuvants.

B. Study on Adjuvant Activity of Selective Squalene Synthase Inhibitors

In the mevalonate pathway, there are many different downstream pathways starting from the generation of FPP, such as the formation of cholesterol. It is known in the art that the HMG-CoA reductase inhibitor acts by blocking the intracellular mevalonate pathway and thus blocking the synthesis of cholesterol. There is such a doubt that whether various enzyme inhibitors of the present disclosure in the mevalonate pathway exert an adjuvant effect is due to the suppressed geranylgeranylation in the downstream of the mevalonate pathway or is due to the inhibition of other downstream pathways such as cholesterol synthesis. To this end, we investigated adjuvant effect of selective squalene synthase (SQS) inhibitor TH-Z66 in order to determine whether the compounds of the present application act by inhibiting cholesterol formation. It is well known that squalene synthase (SQS) inhibitors can inhibit the in vivo biosynthesis of cholesterol.

The selective squalene synthase (SQS) inhibitor TH-Z66 is BPH-652 described in the following reference: Liu C I et al. A cholesterol biosynthesis inhibitor blocks *Staphylococcus aureus* virulenc, Science, 2008 Mar. 7; 319(5868): 1391-4. This reference had demonstrated that BPH-652 is a selective squalene synthase (SQS) inhibitor that may inhibit in vivo biosynthesis of cholesterol. Its disclosure is incorporated herein by reference in its entirety. TH-Z66 was synthesized according to the method described in this reference.

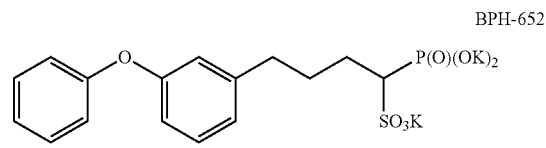

BPH-652

Method: TH-Z66 was formulated at a concentration of 10 mg/ml and OVA antigen was also formulated at a concentration of 10 mg/ml and the two were mixed in a 1:1 ratio. Each mouse was injected with 20 which contains 100 μg of TH-Z66 and 100 μg of the antigen. The mice used were of C57B/6 strain. The mice in the experimental group were injected at the sole of the right feet. Mice in the control group were treated similarly except that TH-Z66 was replaced with the same volume of PBS. On Day 7 and Day 14 after immunization, 100 μl of blood was taken from the orbit of the mouse. The obtained blood was left at 4° C. overnight, and then the serum was separated. The titers of anti-OVA IgM and IgG antibodies in the serum were determined.

As shown in FIG. 12, this study showed that titers of IgG and IgM antibodies produced in mice treated with the SQS inhibitor TH-Z66 did not differ significantly from titers in PBS-treated mice in the control group. Moreover, 7 days after immunization, titers of IgG antibody produced in mice treated with SQS inhibitor TH-Z66 were lower than those in mice in the control group. This showed that TH-Z66 does not have an adjuvant effect, thereby excluding the influence of the cholesterol lowering effect of the compounds of the present application on the adjuvant effect. From this, it can be seen that the inhibitors of the present disclosure in the mevalonate pathway do not exert the adjuvant effects by inhibiting cholesterol synthesis.

The experiments A and B above sufficiently demonstrated that inhibitors of the present disclosure in the mevalonate pathway do not exert the adjuvant effects by inhibition of cholesterol synthesis, but rather by inhibition of geranylgeranylation of proteins.

Through the studies of examples 1-5, we confirmed that inhibitors of various enzymes in the mevalonate pathway can act as adjuvants to enhance the specific immune response elicited by the antigen, and such adjuvant effects are achieved by inhibiting geranylgeranylation of the proteins.

Example 6

Recruitment of Cells in the Lymph Nodes after Immunization with Inhibitors of the Present Application as Adjuvants Lymph nodes are important places for immune responses. The lymph nodes are rich in various types of immune cells, which facilitates the capture of antigens, transmission of the information of antigens, and activation of cell proliferation. Normally, B lymphocytes, T lymphocytes, macrophages, and dendritic cells are recruited to lymph nodes after immunization. Here, we studied the recruitment of cells in lymph nodes after immunization with the inhibitors of the present disclosure as adjuvants.

Method: Following an similar procedure of example 1, OVA was used as antigen and three inhibitor compounds, simvastatin, TH-Z80, and TH-Z145 were added as adjuvants, respectively. The OVA antigen and adjuvant were mixed at 1:1 and used for immunizing mice by subcutaneous injection. 24 hours after immunization, inguinal lymph nodes ipsilateral to the immunization were removed and separated through a 100 mesh screen into single-cell suspension. Flow cytometry was used to determine changes of the proportions and numbers of B lymphocytes, T lymphocytes, macrophages and dendritic cells in lymph nodes. The marker of the B lymphocyte was B220, the marker of the T lymphocyte was CD3, the markers of the macrophage were CD11b and F4/80, and the marker of the dendritic cell was CD11c.

As shown in FIGS. 13-17, after the addition of the adjuvant, compared with mice in the control group (Ctrl) without any treatment and PBS-treated mice in the control group, the proportions and numbers of these four cells in the lymph nodes of mice treated with the three compounds (simvastatin, TH-Z80, TH-Z145) of the present disclosure as adjuvants were significantly increased. This indicates that all of these adjuvants of the present application can greatly facilitate the migration of these cells into lymph nodes 24 hours after immunization, indicating that the compounds of the present application enhance immune responses as adjuvants.

Example 7

Inhibitors of the Mevalonate Pathway Enhance DC Responses to LPS

Dendritic cells (DCs) are among the most potent antigen-presenting cells in the body and bridge the gap between innate immunity and adaptive immunity. Dendritic cells have highly expressed antigen presenting molecules (MHC-I and MHC-II), costimulatory molecules (such as CD80 and CD86) and the like on the surface, and thus become powerful antigen-presenting cells. Dendritic cells can activate naive T cells and play an important role in immune responses. Tumors can be treated by the following method: dendritic cells in peripheral blood of patients are extracted, or mononuclear cells in peripheral blood are separated and then induced to differentiate into dendritic cells by adding cytokines; and then tumor antigens, inactivated tumor cells, tumor cell lysates, plasmids containing DNA of tumor antigens, RNA, or the like are introduced into dendritic cells, some stimulants are added to stimulate and activate these dendritic cells to express more co-stimulatory molecules, and then the treated dendritic cells are delivered back into the patients.

The adjuvant of the present disclosure can enhance the stimulation of dendritic cells by LPS in vitro and also can be applied to dendritic cell vaccines. The following can be used as novel DC vaccines: Dendritic cells are pre-treated with these adjuvants, followed by the addition of tumor antigens, inactivated tumor cells, tumor cell lysates, plasmids containing DNA of tumor antigen, RNA of tumor antigen; or, these antigens and adjuvants are used to stimulate dendritic cells together, or, dendritic cells are treated with these antigens, and then the adjuvant is added.

Method: bone marrow cells of mice were removed and 10 ng/ml recombinant mouse GM-CSF and IL-4 were added. The mixture was used after in vitro induction for 7 days. The differentiated bone marrow-derived dendritic cells (BMDC) of mice were treated with 1 µM of simvastatin, TH-Z80, TH-Z145 and TH-Z66 for 24 h. 100 ng/ml LPS was then added to stimulate. After 24 hours of stimulation, the supernatants were harvested and assayed for TNF-α, IL-6, IL-12p70 and IL-10 therein. Simvastatin, TH-Z80, TH-Z93, TH-Z145 at 1 µM or these adjuvants mixed with 2 µM of GGOH were added to BMDC in a 96-well plate, with 50,000 cells per well. After 24 hours, 50 000 OT-I CD8+ T cells or OT-II CD4+ T cells and 100 µg/ml OVA protein were added and cultured for 72 h. After 72 h, the supernatant of the cells was collected and secreted cytokines IL-6, IFN-γ and TNF-α in the supernatant were measured.

The cytokine assay reference kit was purchased from ebioscience, and the assay method followed the product manual. Capture antibodies for these cytokines were coated on a 96-well ELISA plate at 4° C. overnight with 100 µl per well. After wash with PBST for five times, blocking was performed with blocking solution at room temperature for 2 hours. After washing with PBST for five times, 2-fold diluted cell supernatant was added and incubated for 2 h at room temperature. After washing with PBST for five times, the detection antibody was added and incubated for 1 h at room temperature. After washing with PBST for five times, avidin-conjugated horseradish peroxidase was added and incubated for 45 min at room temperature. After washing with PBST for five times, a solution of 3,3",5,5"-tetramethylbenzidine was added to develop color for 15 min. 2 Mol of sulfuric acid was added to terminate the reaction. Reading was performed with ELIASA OD450, and the concentrations of cytokines in the supernatant were calculated according to the standard.

The results showed that these adjuvants had no stimulating effect on mouse bone marrow-derived dendritic cells (BMDC), but could enhance the stimulation of DCs by LPS. In particular, these adjuvants could assist LPS to stimulate DC to produce IL-10 (FIG. 18-21, and FIG. 38), indicating that inhibitors of the present application enhance the immune responses and can be used in dendritic cell vaccines.

Example 8

Uptake of OVA by Antigen-Presenting Cells in Lymph Nodes after Immunization with Inhibitors of the Present Application as Adjuvants In the process of immune responses, in addition to the central role of T cells and B cells, monocytes/macrophages and dendritic cells also play roles, primarily processing and presenting antigens, so they are called antigen presenting cells (APCs), also known as accessory cells or A cells. APC can ingest and process antigens by phagocytosis or pinocytosis, and bind the treated antigen epitope-containing polypeptide fragments with MHC class II molecules and then express it on the cell surface for presentation to CD4+ TH cells. There are mainly three types of cells that have antigen presenting function: monocyte/macrophage, dendritic cell and B cell. Here we investigated the uptake of OVA antigen by antigen-presenting cells after immunization with the inhibitors of the present disclosure as adjuvants.

Method: OVA was labeled with FITC (fluorescein isothiocyanate). The FITC-labeled OVA was mixed with three compounds of the present disclosure (simvastatin, TH-Z80, and TH-Z145). Mice were immunized subcutaneously following similar procedures as described in example 1. 24 hours after immunization, lymph nodes ipsilateral to the immunization were removed and separated into single cell suspensions. Flow cytometry was used to determine the proportion of FITC-OVA cells contained in the three antigen-presenting cells in the lymph nodes. The marker of the B lymphocyte was B220, the marker of the T lymphocyte was CD3, the markers of the macrophage were CD11b and F4/80, and the marker of the dendritic cell was CD11c.

Figure 22A:
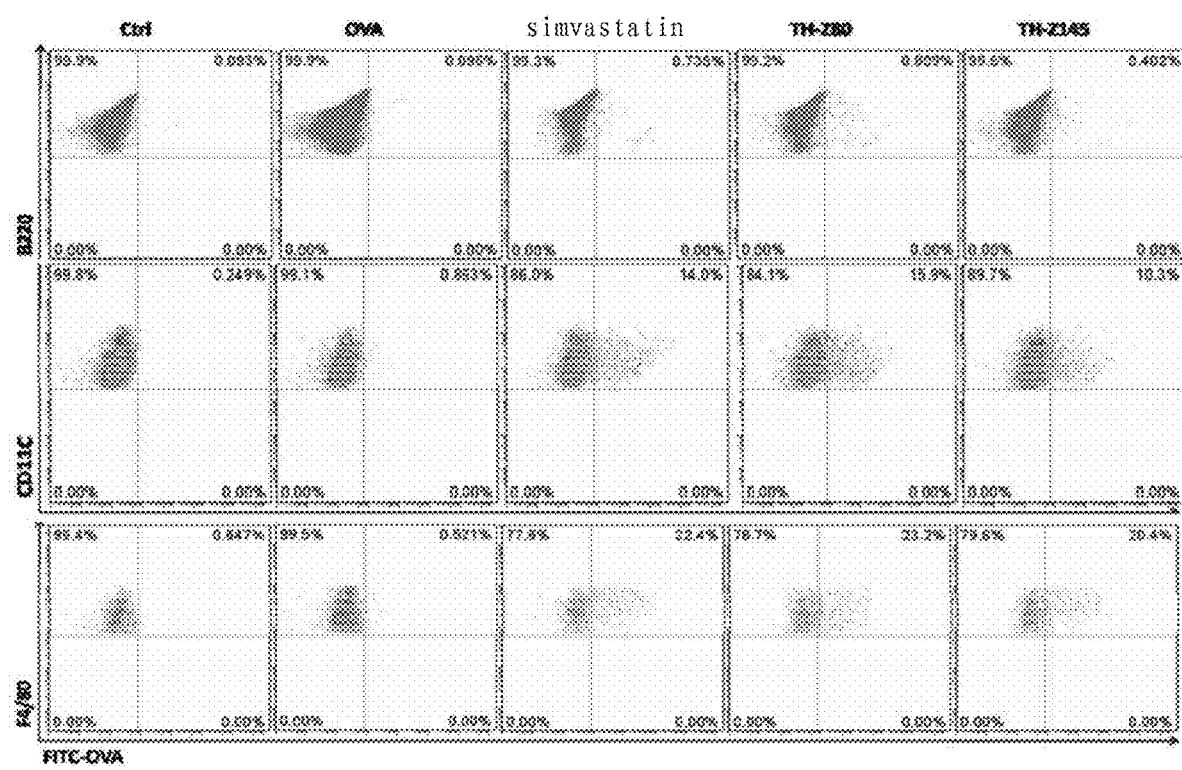
Figure 22D:
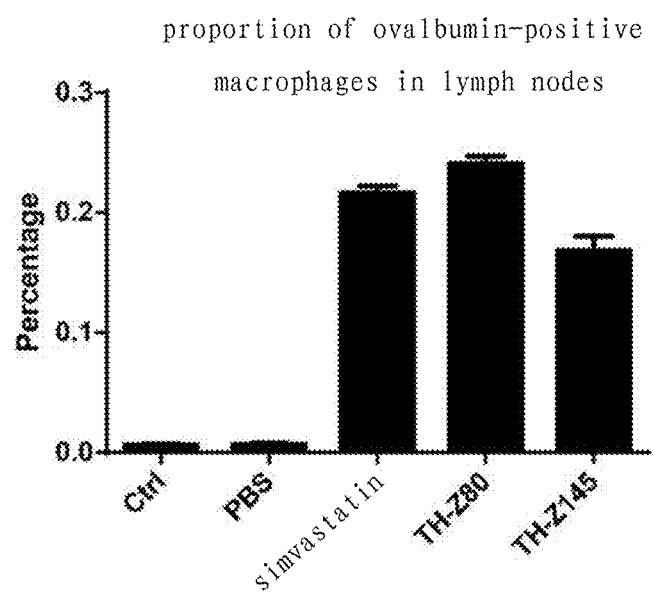
Figure 25A:
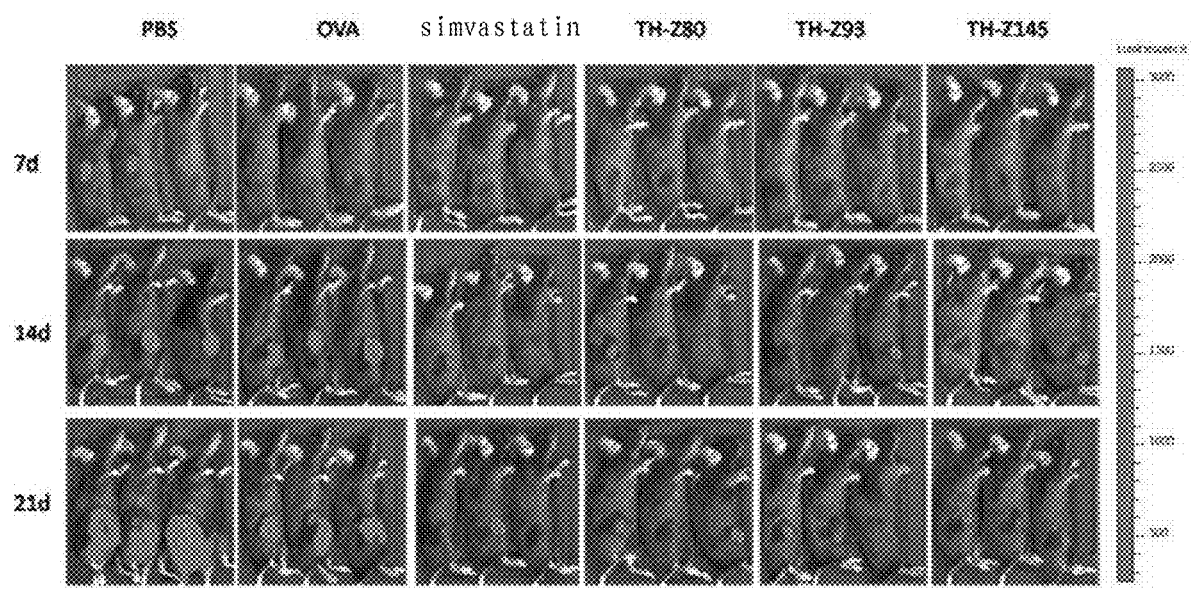
Figure 25D:
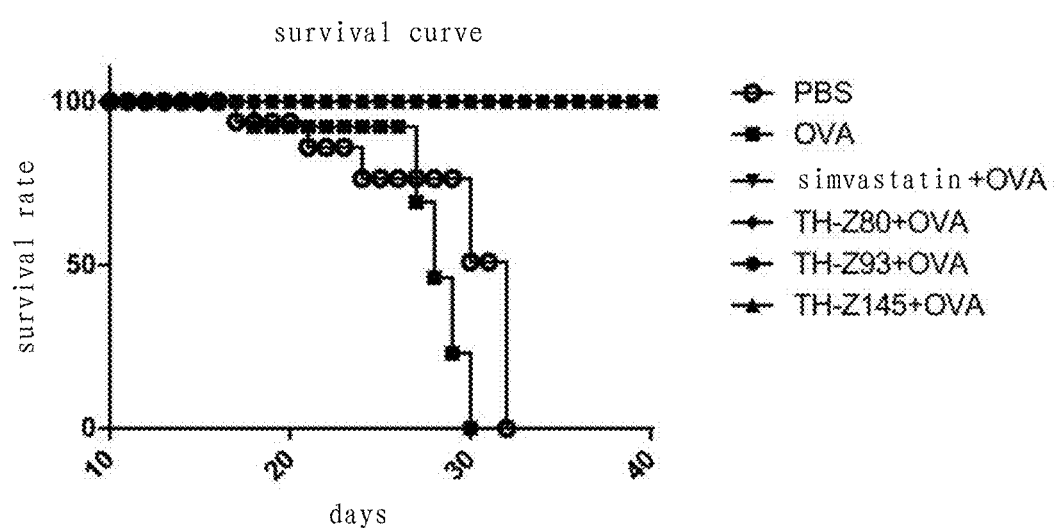

As can be seen from FIG. 22, compared with mice in the control group (Ctrl) without any treatment and PBS-treated mice in the control group, in the lymph nodes of mice treated with the three compounds of the present disclosure as adjuvants in the experiment group, the proportions of FITC-positive cells (B220, CD11c, F4/80) were elevated, demonstrating that all of the inhibitors of the present disclosure are capable of promoting antigen uptake of antigen-presenting cells or migration of antigen-presenting cells into lymph nodes, reflecting that the compounds of the present application enhance immune responses as adjuvants.

The examples 6-8 demonstrated that the adjuvant effects of the inhibitors of the present disclosure were manifested not only by an increase in antibody titer but also by various aspects of immune responses, for example, by enhancing the recruitments of B lymphocytes, T lymphocytes, macrophages, and dendritic cells in the lymph nodes, assisting LPS in stimulating DC to produce IL-10, and promoting the uptake of antigens by antigen presenting cells.

In the following experiments, we investigated the adjuvant effects of the inhibitors of the present disclosure on several specific antigens.

Example 9

The Three Inhibitors can Act as Mucosal Adjuvants to Prompt Mers Protein to Produce More Antibodies In Vivo The Mers protein (expression and purification of the protein referred to Jiang L et al, Potent neutralization of MERS-CoV by human neutralizing monoclonal antibodies to the viral spike glycoprotein. Sci Transl Med. 2014 Apr. 30) was used in an amount of 20 μg, and each of the three compounds (simvastatin, TH-Z80, TH-Z144) of the present disclosure was added as an adjuvant in an amount of 100 μg. Mice were immunized through nasal mucosa according to a procedure similar to that of Example 1. 100 μs of C48/80 (a mast cell stimulator commonly used as a mucosal adjuvant) was used as a comparison. On Day 7 and Day 14 after immunization, titers of IgM and IgG antibodies to Mers protein of Middle East Respiratory Syndrome virus in mouse serum were tested.

As can be seen from FIG. 23, the antibodies titers of all three adjuvant in mice treated with the three compounds of the present disclosure as adjuvants in the experiment group were significantly increased compared to PBS treated mice in the control group, demonstrating that the inhibitors of the present disclosure are capable of assisting the Mers protein to produce more antibodies, suggesting that they may be used as adjuvants in the vaccines of the Middle East Respiratory Syndrome virus.

Example 10

The Three Inhibitors can Prompt Hepatitis B Surface Antigen HbsAg to Produce More Antibodies 20 μg of hepatitis B surface antigen (HBsAg, a gift from Tiantan Biological Products Co., Ltd., Beijing) was used as antigen. 100 μg of each of the three compounds (simvastatin, TH-Z80, TH-Z144) of the present disclosure was added as an adjuvant. Mice were immunized by intramuscular injection following similar procedures as Example 1. On Day 7 and Day 14 after immunization, titers of anti-HBsAg protein IgM and IgG in mouse serum were measured.

It can be seen from FIG. 24 that antibodies titers of all three adjuvant in mice treated with the three compounds of the present disclosure as adjuvants in the experiment group were significantly increased compared to PBS treated mice in the control group, demonstrating that the inhibitors of the present disclosure can assisst hepatitis B surface antigen to produce more antibodies, suggesting that they can be used as adjuvants in hepatitis B vaccines.

Example 11

Preparation of Prophylactic Vaccines for Melanoma

Simvastatin, TH-Z80, TH-Z93 and TH-Z145 of the present disclosure were used as adjuvants and mixed with OVA. Mice were immunized following similar procedures as Example 1. The mixture used for the primary immunization each contained 100 μg of OVA protein and 100 μg of adjuvant (i.e., the above four substances). The subcutaneous injection was performed at the base of the tail. After two weeks upon the immunization, boost was performed by subcutaneously injecting 50 μg of antigen at the tail base without use of the adjuvant. After two weeks upon the second immunization, boost was performed again by subcutaneously injecting 50 μg of antigen at the tail base. After two weeks upon the third immunization, $3*10^5$ B16-OVA (B16 melanoma cells stably expressing OVA, a gift from Biomedical Research Institute of Suzhou University) was inoculated subcutaneously in the right groin of mice. Mice were tested for body weight and tumor volume changes every two days. Tumor volume was calculated using the Formula length*width*width/2.

Cells were stably transfected to express luciferase prior to inoculation. Specific methods were as follows: 293T cells were transfected with a viral plasmid expressing luciferase, and after 48 hours upon transfection, virus-containing 293T cell culture supernatant was collected. After culturing the B16-OVA cells with virus-containing supernatant, the virus in the supernatant infected B16-OVA cells and expressed luciferase. Using flow cytometry, cells expressing luciferase were sorted and expanded.

On Day 7, Day 14 and Day 21 after inoculation, three mice were randomly taken from each group, and injected with fluorescein substrate at 3 mg/mouse. After 8 min upon injection, mice were anesthetized. The tumor volume was observed with an in vivo imager.

The results were shown in FIG. 25. The melanoma volume was significantly decreased in the mice treated with the four compounds of the present disclosure as adjuvants in the experiment group compared to PBS treated mice in the control group, suggesting that the four compounds of the present disclosure could be used as adjuvants in prophylactic vaccines for melanoma.

Example 12

Preparation of therapeutic vaccines for melanoma cells $3*10^5$ (i.e., 300000) B16-OVA tumor cells (also donated by the Biomedical Research Institute of Suzhou University) were inoculated subcutaneously into the right groin of C57B/6 mice. On Day 5 after inoculation, the mice were subcutaneously injected at the tail base with a mixture containing 100 μg of OVA protein and 100 μg of adjuvant (i.e., simvastatin, TH-Z80, TH-Z93, and TH-Z145 as described above). After seven days upon the first immunization, boost was performed by subcutaneously injecting 50

µg of antigen at the tail base without the use of the adjuvant. After seven days upon the second immunization, boost was performed again with 50 µg of antigen. Mice were tested for body weight and tumor volume changes every two days. Tumor volume was calculated using the Formula length*width*width/2.

The same method as described in example 11 was used to allow cells to stably transfect and express luciferase prior to inoculation.

On Day 7, Day 14 and Day 21 after inoculation, three mice were randomly taken from each group, and injected with fluorescein substrate at 3 mg/mouse. After 8 min upon injection, mice were anesthetized. The tumor volume was observed with an in vivo imager.

Figure 26A:
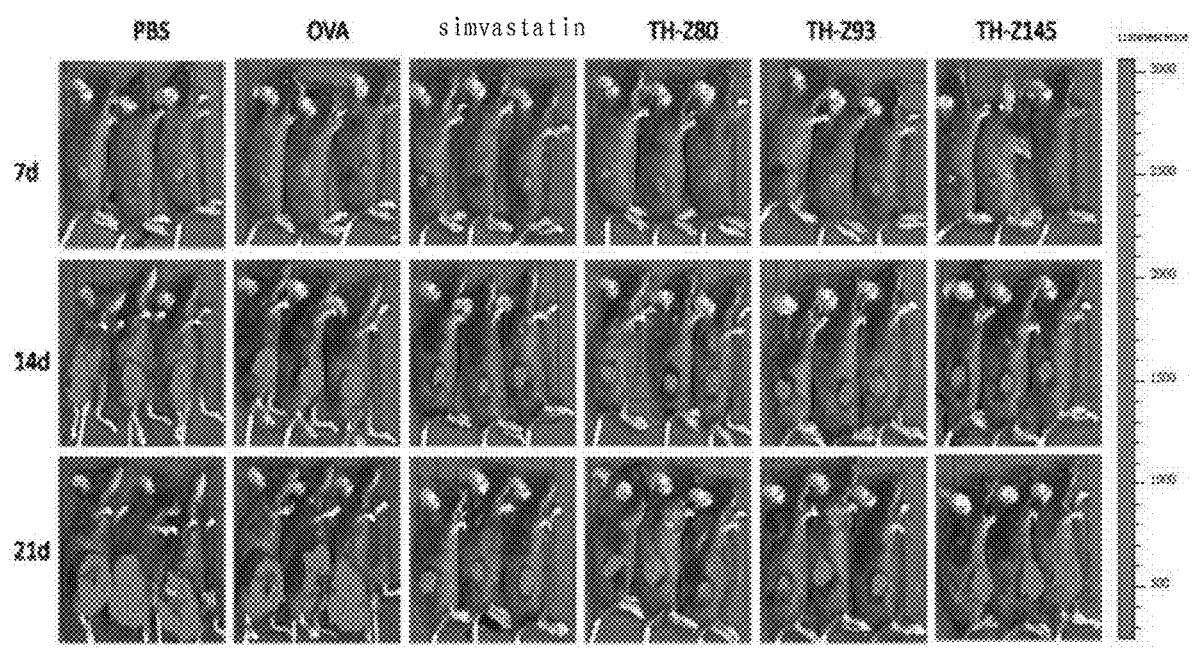
Figure 26D:
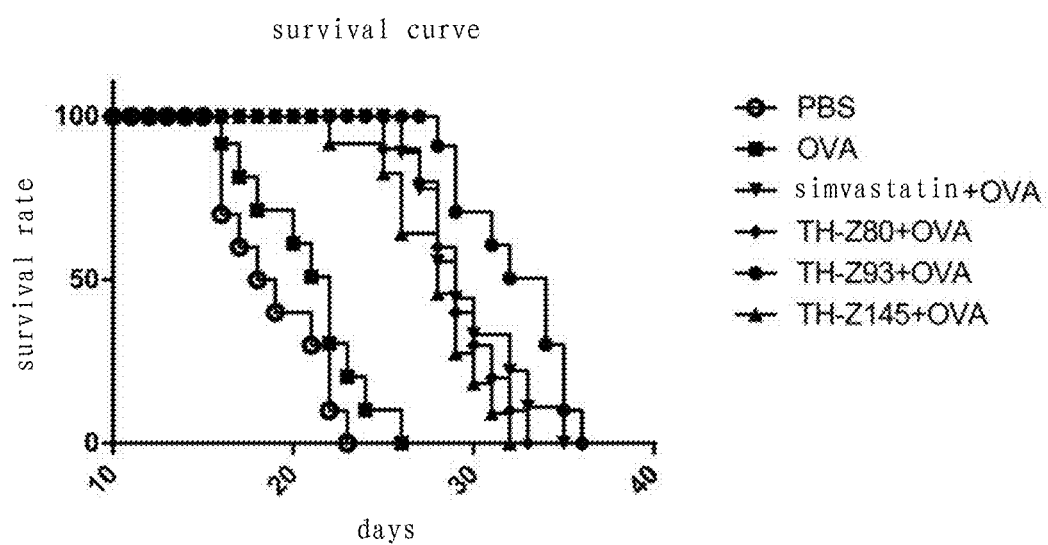

The results were shown in FIG. 26. The melanoma volume was significantly reduced in the mice treated with the four compounds of the present disclosure as adjuvants in the experiment group compared to PBS treated mice in the control group, suggesting that the four compounds of the present disclosure could be used as adjuvants in therapeutic vaccines for melanoma.

The example 9-12 demonstrated that the inhibitors of the present disclosure can be used as adjuvants in clinical vaccines such as those of the Middle East Respiratory Syndrome virus, hepatitis B vaccines, therapeutic and prophylactic vaccines of melanoma, suggesting that the inhibitors of the present disclosure have broad prospects for clinical application.

Example 13

Adjuvant Effects at Different Immunization Sites

The OVA antigen was mixed with the TH-Z80 of the present disclosure as adjuvant to immunize mice at different parts. The immunization sites were soles of the feet, subcutaneous, muscle, abdominal and nasal mucosa of the mice, respectively. For the soles of the feet and nasal mucosa, 20 µl systems were used for immunization. The concentration of TH-Z80 was 10 mg/ml and the concentration of OVA protein was 10 mg/ml. The adjuvant and antigen were mixed in a ratio of 1:1, i.e., 10 µl of the adjuvant and 10 µl of the antigen. For musclar, subcutaneous and intraperitoneal immunization, 100 µl systems are used. The concentration of TH-Z80 was 2 mg/ml and the concentration of OVA protein was 2 mg/ml. The adjuvant and antigen were mixed in a ratio of 1:1, i.e., 50 µl of adjuvant and 50 µl of antigen. Mice in the control group were immunized with the same volume of PBS mixed with OVA antigen. On Day 7 and Day 14 after immunization, titers of anti-OVA IgM and IgG antibodies in the serum were determined following similar procedures as in Example 1.

Figure 27:
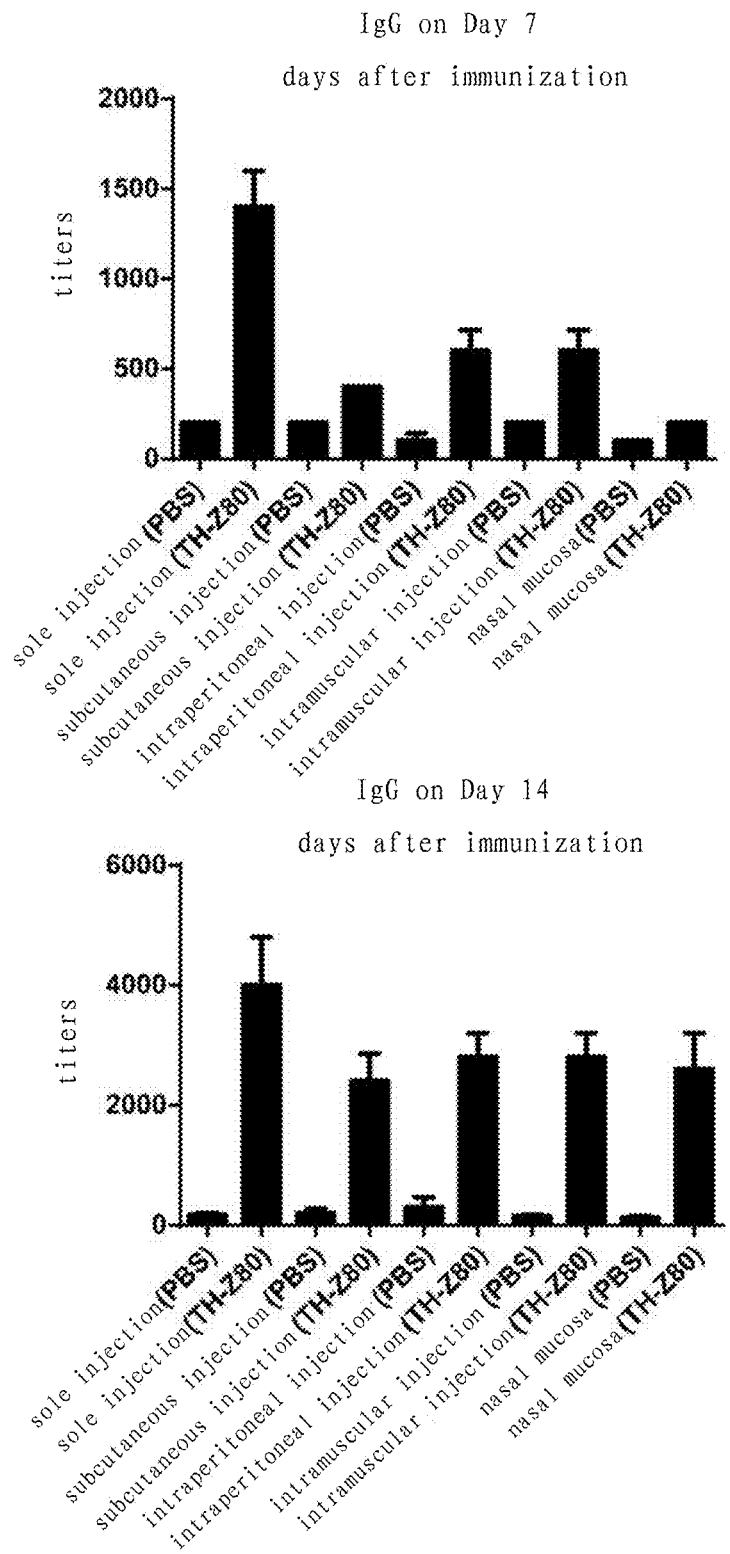

As can be seen from FIG. 27, the antibody titers of TH-Z80 group were significantly increased as compared to PBS-treated mice in the control group, regardless of the site used for immunization. It demonstrates that the compounds of the present disclosure can achieve good adjuvant effect by injection at various sites.

Example 14

Combined Adjuvant Effect of FPPS Inhibitor and TLR Agonist

In this assay we investigated the combined effect of the inhibitor of the present disclosure and other adjuvants known in the art, wherein the other adjuvant employed was imiquimod (a TLR agonist).

Two compounds, TH-Z93 and Imiquimod, were formulated at a concentration of 4 mg/ml, and OVA antigen at a concentration of 10 mg/ml. When used alone, 5 µl of TH-Z93 or imiquimod was added as an adjuvant and mixed with 10 µl of antigen and 5 µl of PBS. When two adjuvants were used in combination, each of the adjuvants were added in an amount of 5 µl and mixed with 10 µl of antigen, and the total volumes were 20 µl. The mice used are of C57B/6 strain. An equal volume of PBS without any adjuvant was used for mice in the control group. The mice was injected at the soles of the right feet. On Day 7 and Day 14 after immunization, blood was taken from the mice's orbits, and 100 µl was taken for each mouse. The obtained blood was left at 4° C. overnight, and then the serum was separated. The titers of anti-OVA IgM and IgG antibodies in the serum were determined.

As can be seen from FIG. 28, compared with PBS-treated mice in the control group, in the mice treated with TH-Z93 or imiquimod alone antibody with significant high titers were produced. Antibody titers of mice treated with TH-Z93 alone were significantly superior to those of mice treated with imiquimod alone. In addition, when two adjuvants were used in combination, a synergistic effect occurred in the body. This study showed that various inhibitors of the present disclosure can be used in combination with other adjuvants known in the art to play a greater degree of the adjuvant effect of increasing the immune response.

Example 15

Activity Test of Compounds of Formula IXX
Test of Activity Against Targets
a: Test of activity against HsFPPS (humanized farnesyl pyrophosphate synthase)

HsFPPs with 6 consecutive His at the N-terminus was induced to express in vitro, collected, and purified by Ni column. In vitro HsFPPs enzymatic activity assay was performed in a 96-well plate at 200 µl of solution per well. The buffer of the system was 25 mM HEPES, 2.5 mM $MgCl_2$, pH 7.4. Using DMAPP and IPP as reaction substrates, the changes of UV at 360 nm were monitored in real-time in phosphate lyase system. ORIGIN 8.0 software was used to plot and fit.

b: Test of activity against PvGGPPS (geranylgeranyl pyrophosphate synthase from *plasmodium*)

PvGGPPs with 6 consecutive His at the N-terminus was induced to express in vitro, collected, and purified by Ni column. In vitro PvGGPPs enzymatic activity assay was performed in a 96-well plate at 200 µl of solution per well. The buffer of the system was 25 mM HEPES, 2.5 mM $MgCl_2$, pH 7.4. Using GPP and IPP as reaction substrates, a 360 nm continuous spectrophotometric detection was performed in a phosphate lyase system. ORIGIN 8.0 software was used to plot and fit. The results were shown in the table below:

TABLE

Activity results of synthetic compounds on different targets

| Compound | HsFPPS ($IC_{50}/\mu M$) | PvGGPPS ($IC_{50}/\mu M$) | Malaria ($IC_{50}/\mu M$) |
|---|---|---|---|
| TH-Z79 | 0.1-0.3 | 0.61 | 0.96 |
| TH-Z148 | 0.068 | 0.56 | 1.86 |
| TH-Z149 | 0.27 | 0.47 | 0.92 |
| TH-Z150 | 0.14 | 0.28 | 0.78 |
| TH-Z151 | 0.12 | 0.46 | 1.25 |

TABLE-continued

Activity results of synthetic compounds on different targets

| Compound | HsFPPS ($IC_{50}/\mu M$) | PvGGPPS ($IC_{50}/\mu M$) | Malaria ($IC_{50}/\mu M$) |
| --- | --- | --- | --- |
| TH-Z80 | 0.11 | 0.37 | 1.76 |
| TH-Z152 | 0.14 | 0.95 | 1.21 |
| TH-Z81 | 0.48 | 2.07 | 1.95 |
| TH-Z153 | 4.9 | 1.09 | 1.28 |
| TH-Z82 | 9.5 | 3.05 | 0.83 |
| TH-Z154 | >5 | 5.16 | 0.75 |
| TH-Z155 | >5 | 10.23 | 3.26 |
| II-7 | 0.16 | 0.82 | 0.69 |

Zoledronic acid as a positive control compound has an $IC_{50}$ value of about 100 nM for HsFPPS. Many compounds of the present disclosure have $IC_{50}$ values of about 100 nM for HsFPPS. Meanwhile, the compounds of the present disclosure have good inhibitory effect on both PvGGPPS and malaria.

Test of Cell Activity:

A: Test of *Plasmodium* Activity,

*Plasmodium falciparum* 3D7 was cultured with IPEM1640 medium mixed with 10% human O-type blood serum and 25 mM HEPES. The cultivation process was maintained in a carbon dioxide incubator under 5% carbon dioxide. In vitro drug testing experiments were performed on a 96-well plate. The test drug was dissolved in PBS and pre-diluted with complete medium. Infected erythrocytes were cultured in triplicate for 72 hours in 3-fold serial dilutions of drug. Then an equal amount of SYBR-GREEN1 was added to each well. The detection was then performed at 485 nm for excitation light and 538 nm for emitted light. Comparisons were observed with artemisinin and a control group without any drug. ORIGIN 8.0 software was used to plot and fit. The results were shown in Table 1.

B: Test of MDA-MB-231 Activity

Reagents and Equipments

DMEM medium was purchased from Gibco; Fetal bovine serum (FBS) was purchased from BI; the double-antibiotics was purchased from Beyotime; 0.25% trypsin-EDTA was purchased from Gibco; MTT was purchased from Ameresco; the centrifuge was purchased from Anhui Chibest Technology Co., Ltd., 4° C. refrigerator was purchased from Haier, −80° C. refrigerator was purchased from Thermo company;

DMEM Complete Medium 10 ml of fetal calf serum was added per 90 ml DMEM medium. The double-antibiotics was added in accordance with 1:100 to make a complete culture medium, and stored at 4° C.

1. Resuscitation, Passage and Cryopreservation of MDA-MB-231 Passage Cells

Cell resuscitation: The cryopreservation tube was quickly removed from the liquid nitrogen tank, immediately immersed in water at 37° C. under the clamping of tweezer to accelerate the thawing, and transferred to a clean bench after completely melted. The cell suspension was aspirated and 3 ml of DMEM containing the double-antibiotics and 10% FBS was added. After mixing well, centrifugation was performed at 4° C. for 3 min at 1000 r/min. The supernatant was discarded, an appropriate amount of DMEM medium containing 10% FBS was added for dilution, and cells were seeded in a culture flask at a density of $0.5 \times 10^6$ cells/cm². After gently mixing, the cells were placed in a 37° C., 5% $CO_2$ incubator for culturing. Two days after the cell resuscitation, the cell morphology was observed under a microscope. The medium was replaced once and cultured to three days. Before passage, the cells were observed under the microscope to confirm full cells and strong refraction. The cells in their logarithmic growth phase were tested.

Cell passage: For cell passage, the medium was first discarded, and then the cells were washed once with pre-warmed PBS at room temperature and then digested with 0.01% trypsin-EDTA in a 5% $CO_2$ incubator at 37° C. for 1-3 min. The cells were detached from the bottom wall of the flask by gently tapping the sides of the flask. 2 ml of DMEM medium containing serum was added to terminate digestion. The cell suspension was transferred to a 15 ml glass centrifuge bottle and gently aspirated into a single cell suspension. Centrifugation was performed at 4° C. for 3 min at 1000 r/min. The supernatant was discarded and cells were resuspended with an appropriate amount of medium. 50 µl of cell suspension was taken and mixed well with 50 µl phthalocyanine blue. Living cells were counted by a cell counting plate. Cells were introduced into a culture flask at a density of $0.5 \times 10^6$ cells/cm², mixed well with an appropriate amount of medium, and then placed in a 37° C., 5% $CO_2$ incubator and allowed to stand for culture.

Cell cryopreservation: Cells were collected in a glass centrifuge tube and counted. The supernatant was discarded, and the cell cryopreservation solution was prepared with the ratio of DMSO to serum of 1:9. Cells were resuspended in cell cryopreservation solution at a concentration of $1-2 \times 10^6$ cells/ml. 1 ml of the suspension was then dispensed into each cryopreservation tube, placed in a −80° C. freezer overnight, and transferred to liquid nitrogen. Cells can be stored for years.

2. Steps of Drug Screening Test:

Drug dissolution: A certain amount of bisphosphonate drug was weighed, a small amount of NaOH or $NaHCO_3$ was added to dissolve the drug, and the drug was stored at a concentration of 10 µM;

Drug dilution: The prepared bisphosphonate stock solution was diluted with DMEM complete medium. The maximum concentration was 1 mM. The dilution was performed serially in a ratio of 1:3.2 with a total of 11 concentration gradients;

a. MDA-MB-231 cells were digested the day before. Centrifugation was performed at 1000 rmp for 3 min. The cells were counted. The cells were seeded into a 96-well plate at 3000 cells/well in a volume of 100 µl per well and cultured for 14-16 h. It should be noted that the cell count should be accurate, and the amount of cells seeded per well should be consistent. The cell suspension can be gently shaken in the intermittence of plating, or a row of cells were plated and the cell suspension was pipetted gently with a pipette. The speed of pipetting into the 96-well plate with a pipette should not be too fast or too slow, in order to avoid uneven distribution of cells in the plate, affecting the experiments; the wells at the fringe of the 96-well plate will evaporate slightly faster and the concentration of the solution will change slightly faster. Under normal situation, the central 60 wells should be selected for stimulation. Also, the pipetted liquid should be prevented from creating bubbles.

b. After the cells had adhered, the liquid in the 96-well plate was pipetted out and discarded. The above prepared solution was added to the cell culture plate in which cells had been plated the day before (the total volume of the final cells for treatment was 100 µl), and at the same time the blank control group (adding medium alone) was set, with each group of 6 replicates;

c. 72 hours after the action of drug, the prepared MTT solution (immediately before use, a certain amount of MTT powder was weighed and dissolved in PBS at 5 mg/ml, under dark, filter with 0.22 filter membrane) was added directly to each well with 20 µl per well and continued to culture for 4 hours;

d. The filter paper (which can be replaced by an absorbent paper) was laid, and the plate was inverted gently (be careful to prevent the crystal in the well from dropping). After the liquid in the wells was removed, 150 µl of DMSO was added to dissolve the crystals, and the mixture was shaken thoroughly with a shaker for a period of time just to dissolve the crystals. The absorbance (OD value) of each well was measured at 570 nm with ELIASA. The mean value of blank control was calculated as OD Blank. OD value for each well=OD measured–OD Blank. ODNT mean value was calculated. Relative percentage of cell death calculated using the ODNT mean value=(1−OD/ODNT)*100% (or relative percentage of cell survival=OD/ODNT*100%). Mean and standard error were then calculated. The mean and standard error of each group of drug concentration (uM) and corresponding drug inhibition rate were fitted by Graph Prism software to obtain the $IC_{50}$ of the drug. The results are shown in the table below:

TABLE

Inhibitory activity of compounds with different carbon chain lengths on proliferation of MDA-MB-231

| Drug name | TH-Z79 | TH-Z80 | TH-Z81 | TH-Z82 | TH-Z148 |
|---|---|---|---|---|---|
| $IC_{50}$ (µM) | 50.93 | 75.46 | 59.63 | 63.09 | 7.302 |
| Drug name | TH-Z149 | TH-Z150 | TH-Z151 | TH-Z152 | TH-Z153 |
| $IC_{50}$ (µM) | 36.07 | 127.5 | 406.4 | 428.2 | 234.5 |

Biological Experiments as Adjuvants:

I. Immunization and Serum Isolation in Mice

During the immunization, the antigen we used was ovalbumin (OVA). Mice were c57bl/6 female mice at the age of 8 weeks. OVA was formulated at a concentration of 1 mg/ml and bisphosphonate concentration was 1 mg/ml. OVA and bisphosphonates were mixed at a ratio of 1:1 at the time of immunization. Mice were injected intramuscularly with 100 µl, i.e. 100 µg of OVA and 100 µg of bisphosphonate per mouse. 14 days after immunization, 100 µl of orbital blood was taken from each mouse.

The whole blood which had been obtained was placed in a 4° C. freezer overnight. The next day, the whole blood at 4° C. was centrifuged at a speed of 6000 rpm at a temperature of 4° C. for 5 minutes. After the centrifugation, the upper serum was carefully taken out and centrifuged again at a speed of 6000 rpm at a temperature of 4° C. for 5 minutes. The upper serum was taken again. Serum was frozen and stored at −20° C. and thawed when tested.

II. Potential Monitoring

1. Coating: antigen OVA was diluted to a protein content of 2 µg/ml with 0.05M pH 9.6 carbonate coating buffer. Each reaction well of a polystyrene plate was coated with 50 µl of the solution overnight at 4° C. or 2 h at 37° C. The next day, the solution in the wells was discarded and washing was performed for five times with wash buffer PBST.

2. Blocking: blocking was performed with 150 µl of 2% BSA at 37° C. for 2h, and washing was performed for five times with wash buffer PBST.

3. Serum incubation: serum was diluted with a dilution solution at a 1:200 ratio, and then 2-fold diluted. 50 µl of the diluted serum was added to each well and incubated at 37° C. for 2 hours. Washing was performed for five times with wash buffer PBST (simultaneously for blank wells and negative control wells). The dilution solution was 0.1% BSA.

4. Addition of enzyme labeled secondary antibody: in each reaction well, 50 µl of freshly diluted HRP-labeled goat-anti-mouse IgM or goat-anti-mouse IgM was added (1:5000) and incubated at 37° C. for 1 h. Washing was performed for five times with wash buffer PBST.

5. Addition of a substrate to develop color: in each reaction well, 50 ml of pre-formulated OPD color-developing reagent was added.

6. Termination of reaction: after developing for 10 min, 50 µl of 2 M sulfuric acid was added to each reaction well.

7. On an ELISA detector, the OD value was read at 490 nm. Titers of serum antibody were calculated. Serum dilutions were calculated as titers of serum antibody based on an OD value greater than or equal to 1.5 times of the reading of the negative control well.

Figure 29:
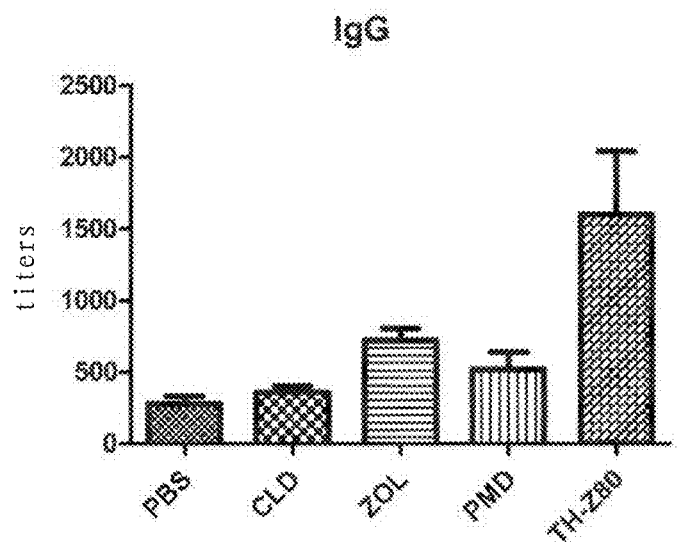

FIG. 29 is a graph showing the effect of injection of 100 µg different bisphosphonates on production of the antibodies in mice.

As can be seen from FIG. 29, compared to conventional bisphosphonates, TH-Z80 was capable of producing higher titers of antibodies than conventional bisphosphonates.

Figure 30:
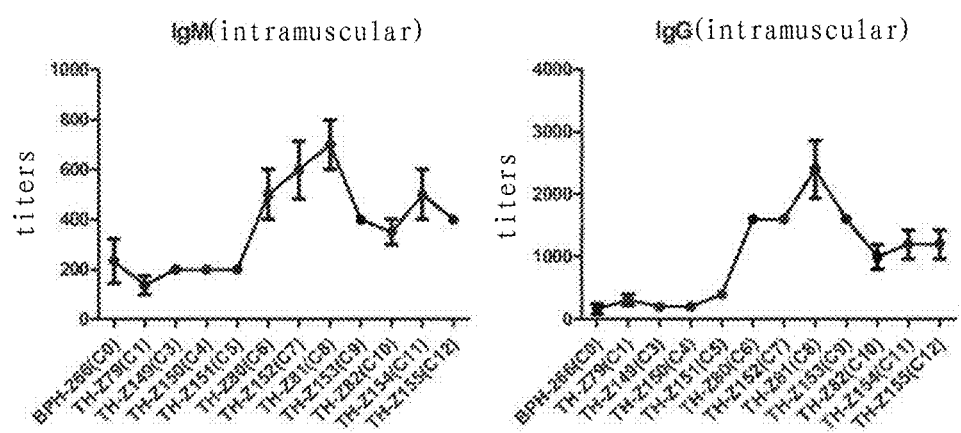

FIG. 30 is a graph showing the effect of bisphosphonic acids with different carbon chain lengths of the side chain as adjuvants.

As can be seen from FIG. 30, the adjuvant effect changes a little when the carbon chain length of the side chain increased from 1 to 5, whereas the adjuvant effect increased significantly when the carbon chain length of the side chain increased from 6 to 8, but the adjuvant effect decreased again when the carbon chain length of the side chain is longer than 8. The compound TH-Z81 had the strongest effect as an adjuvant.

The antibody affinity refers to the strength of an antibody to bind to the epitope of an antigen, which is a very important indicator to evaluate the antibody. It is due to gene mutations of antibody-forming cells themselves and selective activation of B cell clones by antigens. The functional state of the body is the result of long-term evolution and continuous adaptation to the external environment, which is of great significance to the defense of the body and the maintenance of autoimmune monitoring.

In an in vitro test, the affinity of the antibody was determined by disrupting the binding of the antigen to the antibody by NaSCN. The procedure was as follows: a 96-well ELISA plate was coated with 2 µg/ml OVA, and blocked with 2% BSA. Serum was added and incubated for 2 h at 37° C., where the serum had the same titer after dilution and was from mice 7 days after OVA primary immunization with TH-Z80 as adjuvant and boosting. After PBS-T washing, different dilutions of sodium thiocyanate (NaSCN) were added with 50 µl per well, and incubated at 37° C. for 0.5 h; After washing with PBS-T, 1:5000 diluted HRP-labeled goat-anti-mouse IgG was added and incubated at 37° C. for 1 h. Washing was performed for five times with PBS-T. Color development was performed with OPD-phosphate citrate buffer system (pH9.6). The reaction was terminated with 2M $H_2SO_4$ solution. Absorbance values at OD 490 nm were read. The $IC_{50}$ values of NaSCN inhibition were calculated. The higher the $IC_{50}$ value of NaSCN, the stronger the antibody affinity by the immunization.

Figure 31:
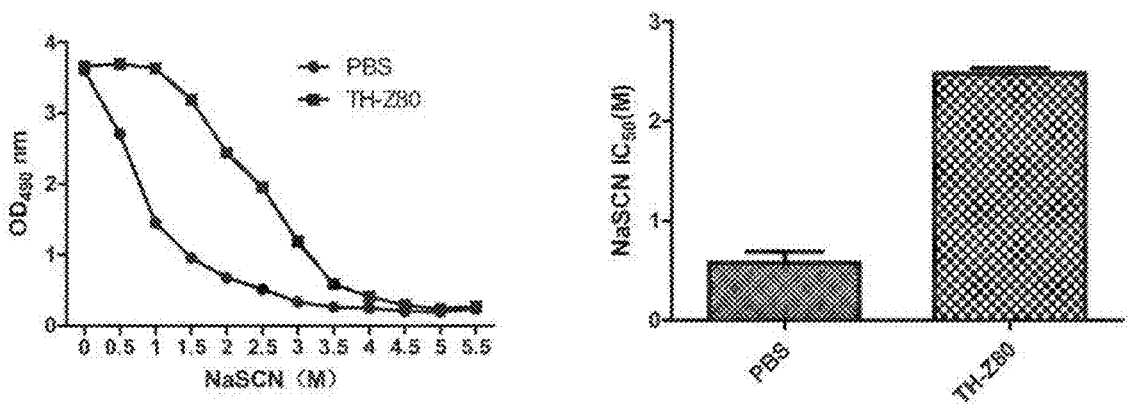

FIG. 31 shows the effect of TH-Z80 for increasing antibody affinity.

As can be seen in FIG. 31, TH-Z80 significantly increased the affinity of the antibody to its antigen compared to PBS.

Human peripheral blood mononuclear cells (PBMCs) were prepared from healthy volunteers by Ficoll-Hypaque density gradient centrifugation. In a 96-well round bottom plate, $1 \times 10^5$ PBMCs were seeded in 0.2 mL of medium, and 4 μM of tested bisphosphonates and 200 U/mL of rIL-2 were added, with zoledronic acid as a positive control. Cells were harvested on day 12 and stained with FITC-anti-CD3 (Miltenyi Biotec) and PE-anti-Vδ2 (Miltenyi Biotec) monoclonal antibodies. Flow cytometry was used for detection. Prism 5.0 was used to analyze the data.

Figure 32:
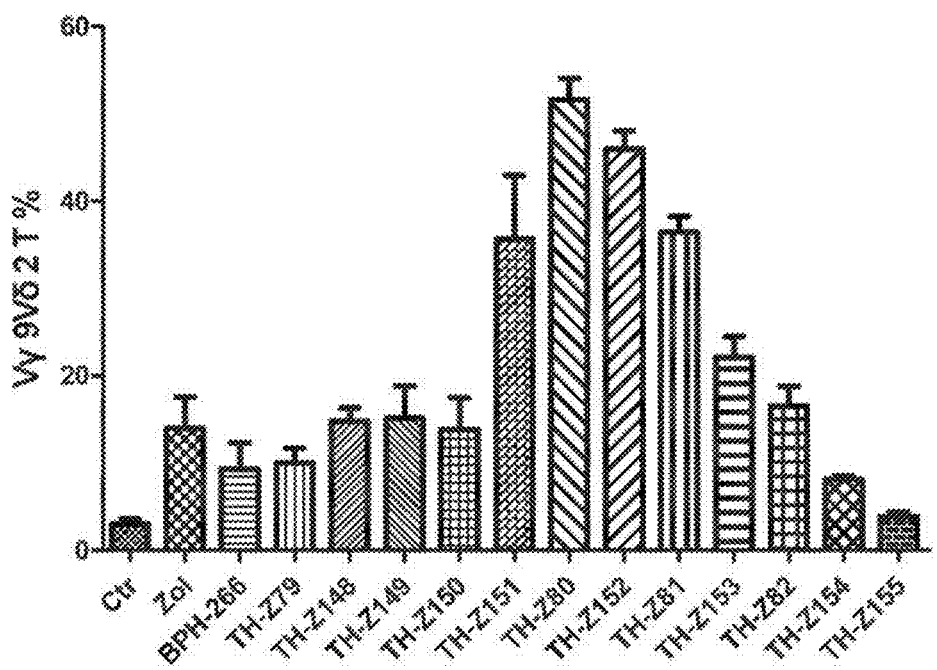

FIG. 32 shows the amplification effect of benzimidazole bisphosphonates with different carbon chain lengths on δγT cells.

It can be clearly seen from the figure that the carbon chain length significantly affects Vγ9Vδ2 T cells, and the compound TH-Z80 has the best amplification effect on Vγ9Vδ2 T cells.

Figure 33:
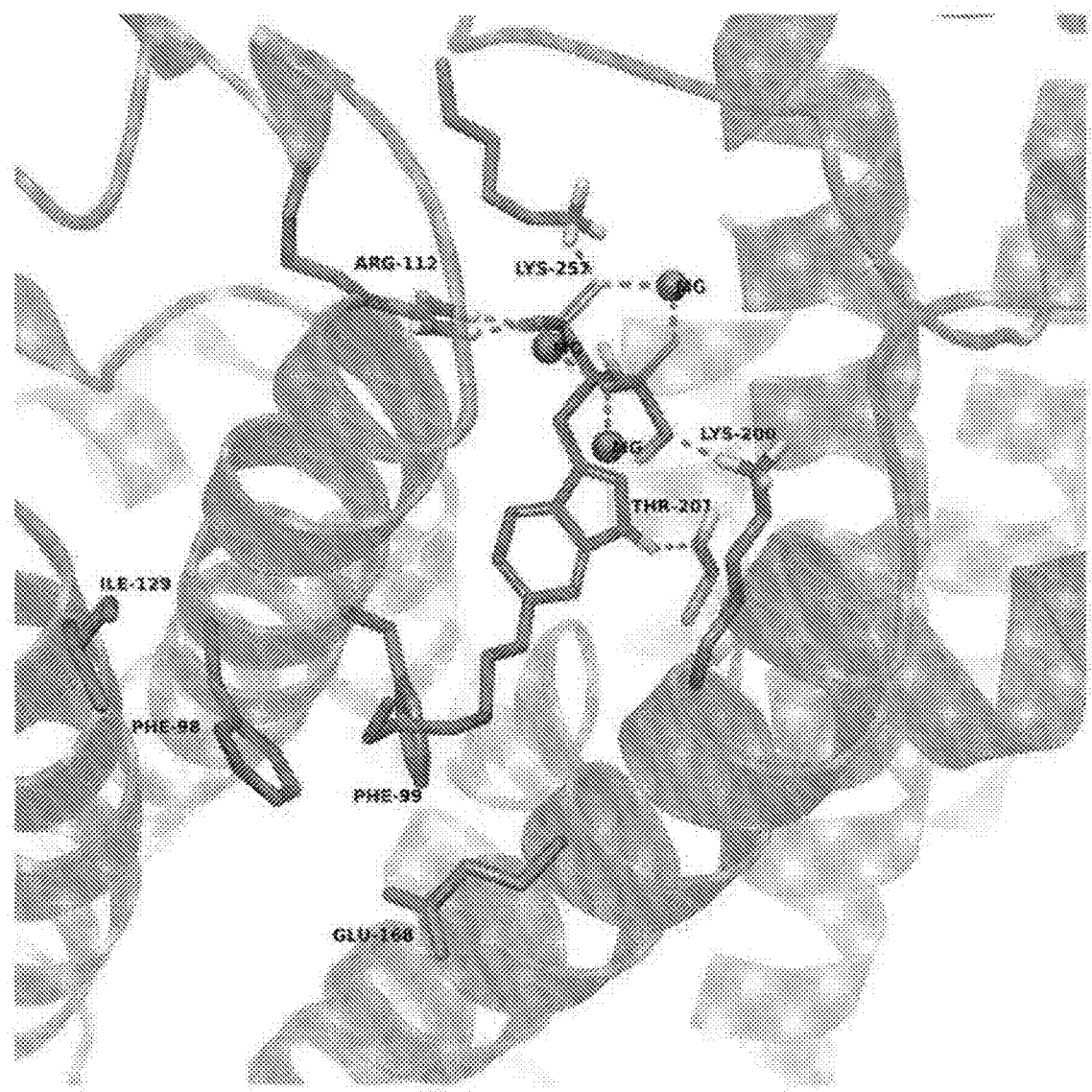

FIG. 33 is a schematic representation (plot with pymol) of crystal structures of the compound TH-Z80 and HsFPPS.

It can be clearly seen from the figure that the main driving force for the binding of the TH-Z80 bisphosphonate to FPPS lies in the chelation of the bisphosphonate with metal ions while the long carbon chain is in a hydrophobic cavity. The benzene ring and phenol ether in benzimidazole had no obvious effect on FPPS. The results showed that the introduction of N heteroatom into the benzene ring of benzimidazole does not have significant effect on the binding activity of the compound to FPPS. By introducing a long carbon chain into the side chain of the aza-benzbenzimidazole compound, its hydrophobic interaction with FPPS was enhanced, and the binding of the compound to FPPS was enhanced.

Figure 34:
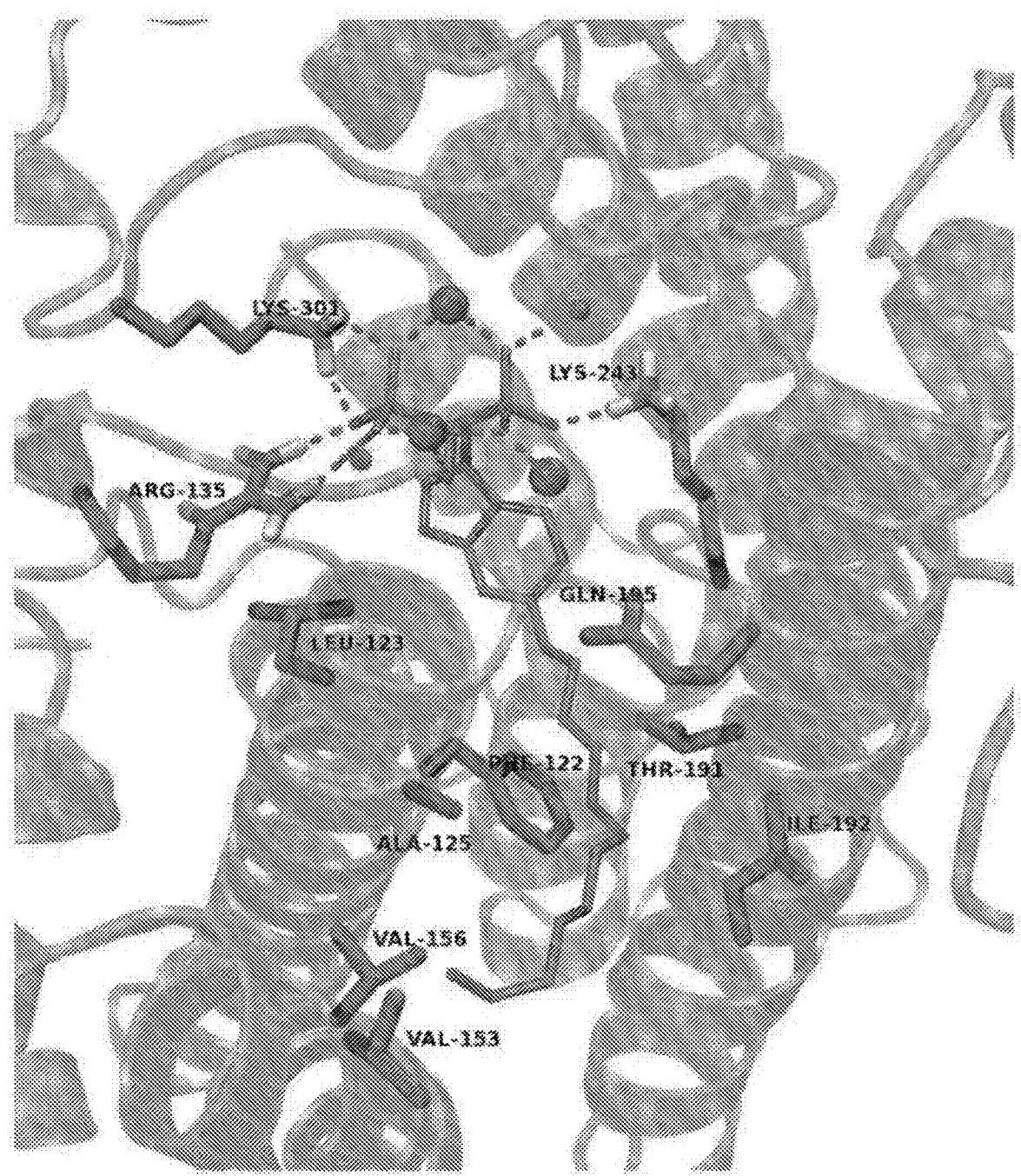
Figure 38:
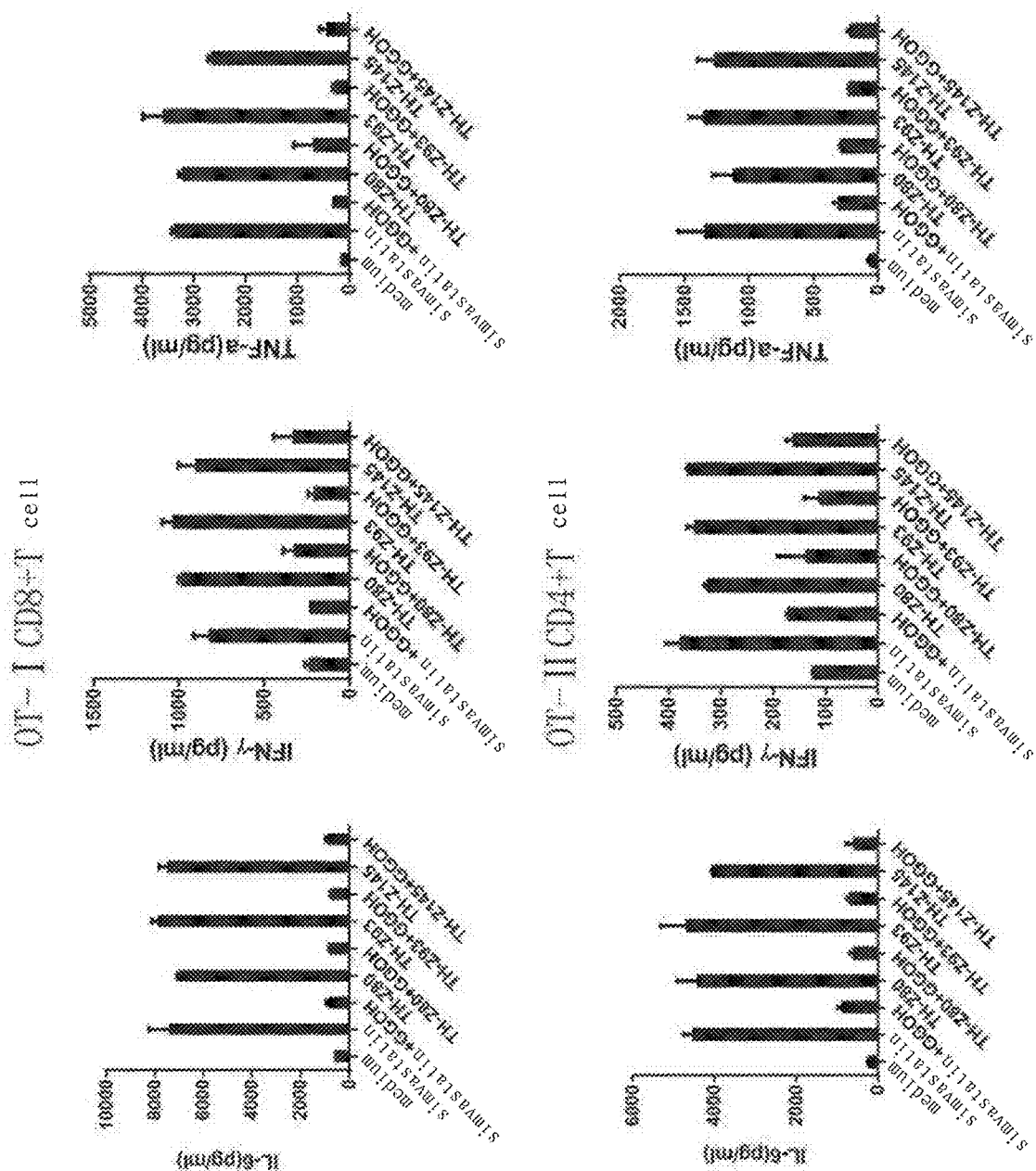

FIG. 34 is a schematic representation (plot wtih pymol) of crystal structures of the compound TH-Z82 and PvGGPPS.

It can be clearly seen from the figure that similar to the crystal structures of TH-Z80 and HsFPPS, the main driving force for binding of the TH-Z82 bisphosphonates to PvGGPPS lies in the chelation of the bisphosphonate with metal ions and the hydrophobic effect of its long carbon chain. The benzene ring and phenol ether in benzimidazole also do not have significant effect on PvGGPPS. This result indicated that the introduction of N heteroatom into the benzene ring of benzimidazole does not have significant effect on the binding activity of the compound to PvGGPPS. By introducing a long carbon chain into the side chain of aza-benzbenzimidazole compound, its hydrophobic interaction with GGPPS was enhanced and the binding of the compound to GGPPS was enhanced.

According to crystal structures (calculated results), FPPS and GGPPS both have a hydrophobic cavity. Therefore, alkoxy groups on the side chains can be replaced by other hydrophobic groups. Therefore, we also claim aza-benzimidazole compounds substituted with other hydrophobic group.

Example 16

Effects of Simvastatin, TH-Z80, TH-Z93 and TH-Z145 on PR8 Influenza Virus

Method: 5 micrograms of hemagglutinin protein (HA1) in the PR8 influenza virus was added to phosphate buffer, 20 micrograms of simvastatin, 20 micrograms of TH-Z80, 20 micrograms of TH-Z93 and 20 micrograms of TH-Z145, respectively. And mice were injected intramuscularly for immunization on day 0, day 14 and day 21. Nasal mucosa of mice was inoculated with PR8 virus on day 28. And then the weight of the mice was weighed daily and the death of the mice was observed.

Result: As shown in FIG. 35, mice without being treated simvastatin, TH-Z80, TH-Z93 and TH-Z145 had been losing weight after being vaccinated with the virus and died within 5 to 10 days. However, mice treated with simvastatin, TH-Z80, TH-Z93 and TH-Z145 did not lose weight nor died.

Example 17

Inhibition of B16-OVA Tumor by Anti-PD1 Antibody in Combination with Four Adjuvants and Ovalbumin Method: 300000 tumor cells were inoculated subcutaneously into the right groin of C57B/6 mice. On Day 5 after inoculation, the mice were injected subcutaneously at the base of the tail with a mixture containing 100 μg of OVA protein and 100 μg of adjuvant, namely simvastatin, TH-Z80, TH-Z93 and TH-Z145, respectively. Seven days after the initial immunization, 50 μg of antigen without the adjuvant was administered subcutaneously at the base of the tail to boost. Seven days after the second immunization, boost was again performed with 50 μg of antigen. At the same time, 100 microliters of anti-PD1 antibody was injected on days 8, 11, 15, 18, 22 and 25 after tumor inoculation. Mice were tested for body weight and tumor volume changes every two days. Tumor volume was calculated using the Formula length*width*width/2.

Result: As shown in FIG. 36, anti-PD1 antibody in combination with the four adjuvants and ovalbumin showed an inhibitory effect on B16-OVA tumors.

Example 18

Adjuvant Activity of HMG-CoA Synthase Inhibitor Hymeglusin in OVA Antibody Titer Test Method: Hymeglusin, a HMG-CoA synthase inhibitor, was formulated to a concentration of 10 mg/ml and the concentration of OVA antigen was also 10 mg/ml. The compound and antigen were mixed at 1:1. The mice used were of C57B/6 strain. Each mouse in the experimental group was injected intramuscularly with 20 μl of a mixture of the test compound and OVA antigen, i.e., 100 μg Hymeglusin (10 μl) and 100 μg (10 μl) antigen OVA. Mice in the control group were intramuscularly injected with 10 μl of PBS and 10 μl of OVA antigen mixed at 1:1. Fourteen days after immunization, 100 μl of blood was taken from the orbit of the mouse. After standing overnight at 4° C., the serum was separated. Titers of anti-OVA IgG antibodies in the serum were determined.

Result: As shown in FIG. 37, IgG antibodies with significantly higher titers were produced in mice treated with the HMG-CoA synthase inhibitor Hymeglusin relative to PBS-treated mice in the control group, sufficiently demonstrating that compounds that can inhibit the activity of HMG-CoA reductase in the mevalonate pathway can serve as adjuvants in immunogenic compositions.

Example of Preparation of Compounds

The NMR data for all compounds were obtained on a Bruker Avance DRX-400 spectrometer. Chemical shifts (δ in ppm) were given with reference to $D_2O$ at 4.79 ppm, $CDCl_3$ at 7.26 ppm and MeOD at 3.31 ppm. Pattern of nuclear magnetic resonance peaks was respectively expressed as d, t, q, m, that is, doublet, triplet, quartet, multiplet. The coupling constant was in Hertz. High-resolution mass spectrometry was performed on a Waters Xevo G2 QT using ESI as an ion source.

Starting materials were obtained from commercial sources or prepared by established literature procedures known to those skilled in the art.

Example 1

Preparation of TH-Z97 Series of Compounds

Preparation of TH-Z97 (n=6) ((1-hydroxy-2-(7-n-hexyloxyimidazo[1,2-a]pyridin-3-yl)ethane-1,1-diyl) bisphosphonic Acid)

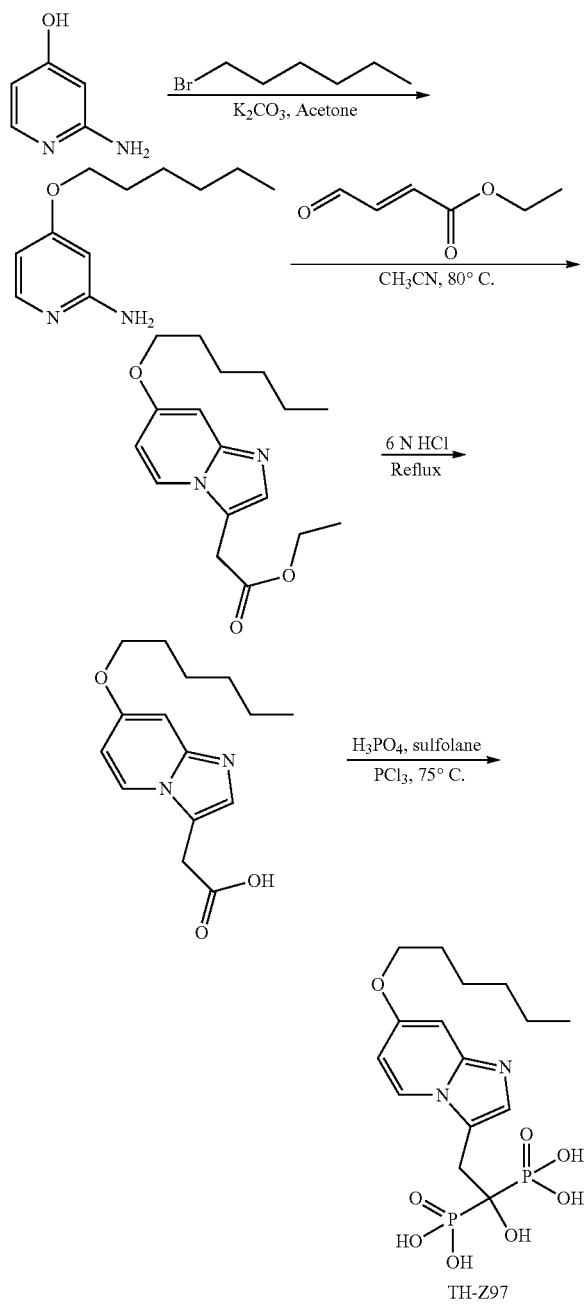

Step 1: 10 mmol (1.11 g) of 2-amino-4-hydroxypyridine was dissolved in 50 mL of acetone. 30 mmol of anhydrous potassium carbonate was added. After heating to reflux under $N_2$ protection, 12 mmol (1.67 mL) of bromohexane was added. After overnight, the insoluble matter was filtered and the organic phase was rotary evaporated to dryness. The crude product was loaded on a column and purified by petroleum ether/ethyl acetate to give 7.8 mmol (1.51 g) of 4-hexyloxy-2-amino-pyridine (yield: 78%).

Step 2: 5 mmol (0.97 g) of 4-hexyloxy-2-amino-pyridine was reacted with 5.5 mmol (0.71 g) trans-ethyl 4-oxo-2-butenoate in 20 mL of acetonitrile at 80° C. overnight. The mixture was then rotary evaporated to dryness. The crude product was loaded on a column and purified by petroleum ether/ethyl acetate to give 4.1 mmol (1.13 g) of ethyl 2-(7-(n-hexyloxy)imidazo[1,2-a]piperidin-3-yl)acetate (yield 82%).

Step 3: 3 mmol of ethyl 2-(7-(n-hexyloxy)imidazo[1,2-a]piperidin-3-yl)acetate in 6 N HCl was refluxed for 6 h, rotary evaporated to dryness and then dried to constant weight. The crude product obtained was used directly in the next reaction.

Step 4: The resulting 2-(7-(n-hexyloxy)imidazo[1,2-a]piperidin-3-yl)acetic acid was dissolved with 9 mmol (0.74 g) of phosphorous acid and 6 mL of sulfolane at 75° C. 10.2 mmol (1068 μL) of $PCl_3$ was then added dropwise. After 3.5 hours of reaction, 1 mL of water was added. The reaction was heated to reflux for 2h and then cooled. The precipitated solid was filtered and ultrafiltered with methanol three times. The resulting light yellow solid was dried to constant weight and then weighed to give 228 mg of the target product (yield 18%).

Characterization data of structure: $^1$H NMR (400 MHz, $D_2O$), δ (ppm): 8.49 (d, J1=7.2 Hz 1H), 7.39 (s, 1H), 6.79-6.75 (m, 2H), 4.02 (t, J=6.0 Hz, 2H), 3.47 (m, 2H), 1.95 (m, 2H), 1.39-1.25 (m, 2H), 1.47 (m, 6H), 0.79 (t, J=6.4 Hz, 3H), $^{31}$P NMR (162 MHz, $D_2O$), δ (ppm): 17.22

Compounds TH-Z157, TH-Z158, TH-Z159, TH-Z160, TH-Z97, TH-Z161, TH-Z98, TH-Z162, TH-Z99, TH-Z198 and TH-Z163 were prepared according to a similar procedure to TH-Z97 described above using the corresponding bromoalkanes and 2-amino-4-hydroxypyridine.

TH-Z156 was prepared step-by-step according to synthesis steps 2-4 of TH-Z97 using 2-amino-4-methoxypyridine directly as the starting material.

The characterization data of these compounds were as follows:

TH-Z98: characterization data of structure: $^1$H NMR (400 MHz, $D_2O$), δ (ppm): 8.58 (d, J=7.6 Hz, 1H, 7.37 (s, 1H), 6.86 (s, 1H), 6.65 (d, J=7.2 Hz, 1H), 4.12 (t, J=6.4 Hz, 2H,), 3.57 (t, J=12.0 Hz, 2H), 1.81 (m, 2H), 1.48-1.44 (m, 2H), 1.27 (m, 8H), 0.79 (t, J=6.4 Hz, 3H), $^{31}$P NMR (162 MHz, $D_2O$), δ (ppm): 17.92

TH-Z99: characterization data of structure: $^1$H NMR (400 MHz, $D_2O$), δ (ppm): 8.51 (d, J=7.6 Hz, 1H), 7.37 (s, 1H), 6.87 (s, 1H), 6.65 (d, J=7.2 Hz, 1H), 4.12 (t, J=6.4 Hz, 2H,), 3.55 (t, J=12.0 Hz, 2H), 1.95 (m, 2H), 1.46-1.44 (m, 2H), 1.27 (m, 10H), 0.79 (t, J=6.8 Hz, 3H), $^{31}$P NMR (162 MHz, $D_2O$), δ (ppm): 17.70

TH-Z156: characterization data of structure: $^1$H NMR (400 MHz, $D_2O$), δ (ppm): 8.60 (d, J=7.6 Hz, 1H, 7.37 (s, 1H), 6.87 (s, 1H), 6.65 (d, J=7.6 Hz, 1H), 3.58 (t, J=12.0 Hz, 2H), $^{31}$P NMR (162 MHz, $D_2O$), δ (ppm): 17.97

TH-Z157: characterization data of structure: $^1$H NMR (400 MHz, $D_2O$), δ (ppm): 8.59 (d, J=7.2 Hz, 1H), 7.37 (s, 1H), 6.85 (d, J=1.6 Hz, 1H), 6.63 (dd, J1=7.6 Hz, J2=1.8 Hz, 1H), 4.16 (q, J=7.2 Hz, 2H,),3.57 (t, J=11.6 Hz, 2H), 1.41 (t, J=6.8 Hz, 2H), $^{31}$P NMR (162 MHz, $D_2O$), δ (ppm): 18.00

TH-Z158: characterization data of structure: $^1$H NMR (400 MHz, $D_2O$), δ (ppm): 8.61 (d, J=7.6 Hz, 1H), 7.37 (s, 1H), 6.87 (s, 1H), 6.65 (d, J=7.2 Hz, 1H), 4.12 (t, J=6.4 Hz, 2H,), 3.55 (t, J=12.0 Hz, 2H), 1.95 (m, 2H), 0.97 (t, J=6.8 Hz, 3H), $^{31}$P NMR (162 MHz, D$_2$O), δ (ppm): 16.76

TH-Z159: characterization data of structure: $^1$H NMR (400 MHz, D$_2$O), δ (ppm): 8.64 (d, J=7.6 Hz, 1H), 7.55 (s, 1H), 6.99 (d, J=7.6 Hz, 1H), 6.96 (s, 1H), 4.13 (t, J=6.4 Hz, 2H), 3.61 (t, J=12.0 Hz, 2H), 1.80 (m, 2H), 1.49 (m, 2H), 0.96 (t, J=7.2 Hz, 3H), $^{31}$P NMR (162 MHz, D$_2$O), δ (ppm): 16.56

TH-Z160: characterization data of structure: $^1$H NMR (400 MHz, D$_2$O), δ (ppm): 8.61 (d, J=7.2 Hz, 1H), 7.38 (s, 1H), 6.88 (d, J=2.1 Hz, 1H), 6.66 (dd, J1=7.6 Hz, J2=2.2 Hz, 1H), 4.14 (t, J=6.4 Hz, 2H), 3.59 (t, J=11.7 Hz, 2H), 1.50-1.34 (m, 4H), 0.92 (t, J=7.2 Hz, 3H), $^{31}$P NMR (162 MHz, D$_2$O), δ (ppm): 17.18

TH-Z161: characterization data of structure: $^1$H NMR (400 MHz, D$_2$O), δ (ppm): 8.46 (d, J=7.6 Hz, 1H), 7.38 (s, 1H), 6.89 (s, 1H), 6.68 (d, J=8.0 Hz, 1H), 4.13 (t, J=6.4 Hz, 2H), 3.54 (t, J=11.7 Hz, 2H), 1.82 (m, 2H), 1.48-1.29 (m, 6H), 0.92 (t, J=7.2 Hz, 3H), $^{31}$P NMR (162 MHz, D$_2$O), δ (ppm): 17.52

TH-Z162: characterization data of structure: $^1$H NMR (400 MHz, D$_2$O), δ (ppm): 8.53 (d, J=7.6 Hz, 1H), 7.40 (s, 1H), 6.90 (s, 1H), 6.68 (d, J=7.2 Hz, 1H), 4.15 (t, J=6.4 Hz, 2H), 3.58 (t, J=11.6 Hz, 2H), 1.83 (m, 2H), 1.48-1.28 (m, 12H), 0.86 (t, J=6.0 Hz, 3H), $^{31}$P NMR (162 MHz, D$_2$O), δ (ppm): 17.74

TH-Z163: characterization data of structure: $^1$H NMR (400 MHz, D$_2$O), δ (ppm): 8.63 (d, J=7.2 Hz, 1H), 7.40 (s, 1H), 6.89 (s, 1H), 6.67 (d, J=6.4 Hz, 1H), 4.15 (t, J=6.4 Hz, 2H), 3.60 J=11.6 Hz, 2H), 1.83 (m, 2H), 1.48-1.28 (m, 18H), 0.86 (t, J=6.0 Hz, 3H), $^{31}$P NMR (162 MHz, D$_2$O), δ (ppm): 18.05

TH-Z198: characterization data of structure: $^1$H NMR (400 MHz, D$_2$O), δ (ppm): 8.39 (d, J=6.8 Hz, 1H), 7.27 (s, 1H), 6.77 (s, 1H), 6.56 (d, J=6.4 Hz, 1H), 4.02 (t, J=6.4 Hz, 2H), 3.45 (t, J=11.0 Hz, 2H), 1.71 (brs, 2H), 1.36-1.16 (m, 16H), 0.73 (brs, 3H), $^{31}$P NMR (162 MHz, D$_2$O), δ (ppm): 17.67

Example 2

Preparation of (((4-(hexyloxy)pyridin-2-yl)amino)methylene)bisphosphonic Acid (TH-Z93)

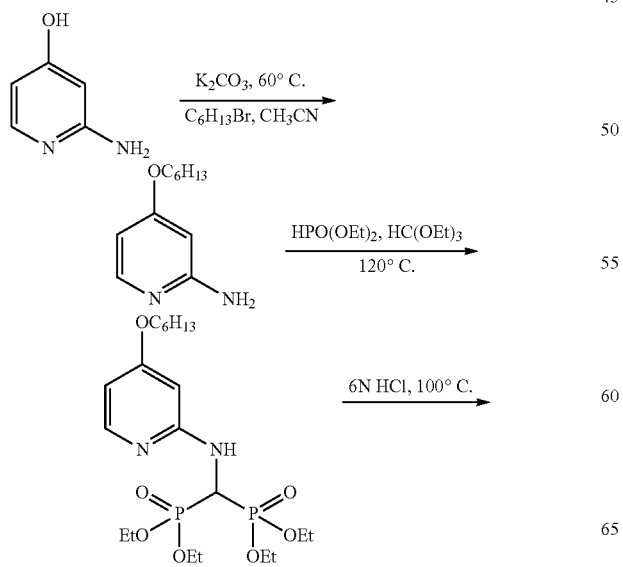

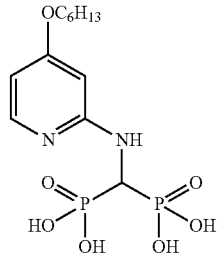

Step 1: 10 mmol of 2-amino-4-hydroxypyridine was weighed and dissolved in 100 mL of acetonitrile. 20 mmol of potassium carbonate and 12 mmol of 1-bromo-n-hexane were added. The mixture was allowed to react overnight at 60° C. under nitrogen. The reaction was monitored by TLC until the starting material was completely reacted. After cooling the reaction solution, potassium carbonate was filtered off, and the filtrate was concentrated under reduced pressure. The pure product was purified by column chromatography on silica gel (200-300 mesh) with petroleum ether/ethyl acetate (1:1) in 75% yield.

Step 2: 6 mmol of the product of the first step was weighed and dissolved in 20 mL of toluene. 15 mmol of diethyl phosphite and 24 mmol of triethyl orthoformate were added and reacted at 120° C. for 10 h. The pure product was purified by column chromatography on silica gel (200-300 mesh) with petroleum ether/ethyl acetate (1:1). Toluene was distilled off under reduced pressure. The pure product was purified by column chromatography on silica gel (200-300 mesh) with ethyl acetate:methanol (30:1) in 78% yield.

Step 3: 50 mL of 6N hydrochloric acid was added to the product of the step 2 and reacted at 100° C. for 10 hours. Hydrochloric acid was distilled off under reduced pressure. The crude product was washed once with acetone under ultrasonic sound, and then washed three times with methanol under ultrasonic sound to obtain pure product in 95% yield.

Characterization data of TH-Z93:

1H NMR (400 MHz, D$_2$O): δ 7.62-7.63 (d, 1H, J=8.0 Hz), 6.04-6.1 (m, 2H), 4.01-4.04 (t, 2H, J=6.4 Hz), 1.64-1.69 (m, 2H), 1.24-1.35 (m, 6H), 0.77-0.80 (t, 3H, J=6.4 Hz). $^{31}$P NMR (162 MHz, D$_2$O): δ15.12.

HRMS (ESI): C12H22N2O7P2 Calculated: 369.0980; Measured: 369.0969.

Example 3

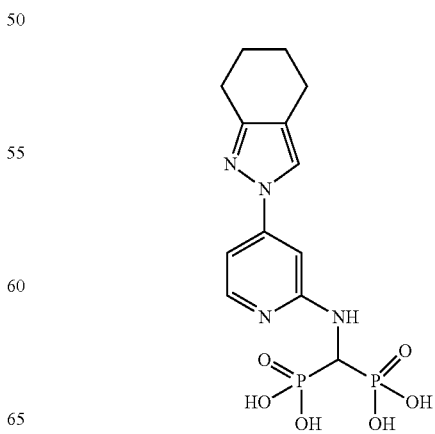

125
(((4-(4,5,6,7-tetrahydro-2H-indazol-2-yl)pyridin-2-yl)amino)methylene)bisphosphonic Acid

126
(((4-((2-carbamoylpyridin-4-yl)methoxy)pyridin-2-yl)amino)methylene)bisphosphonic Acid

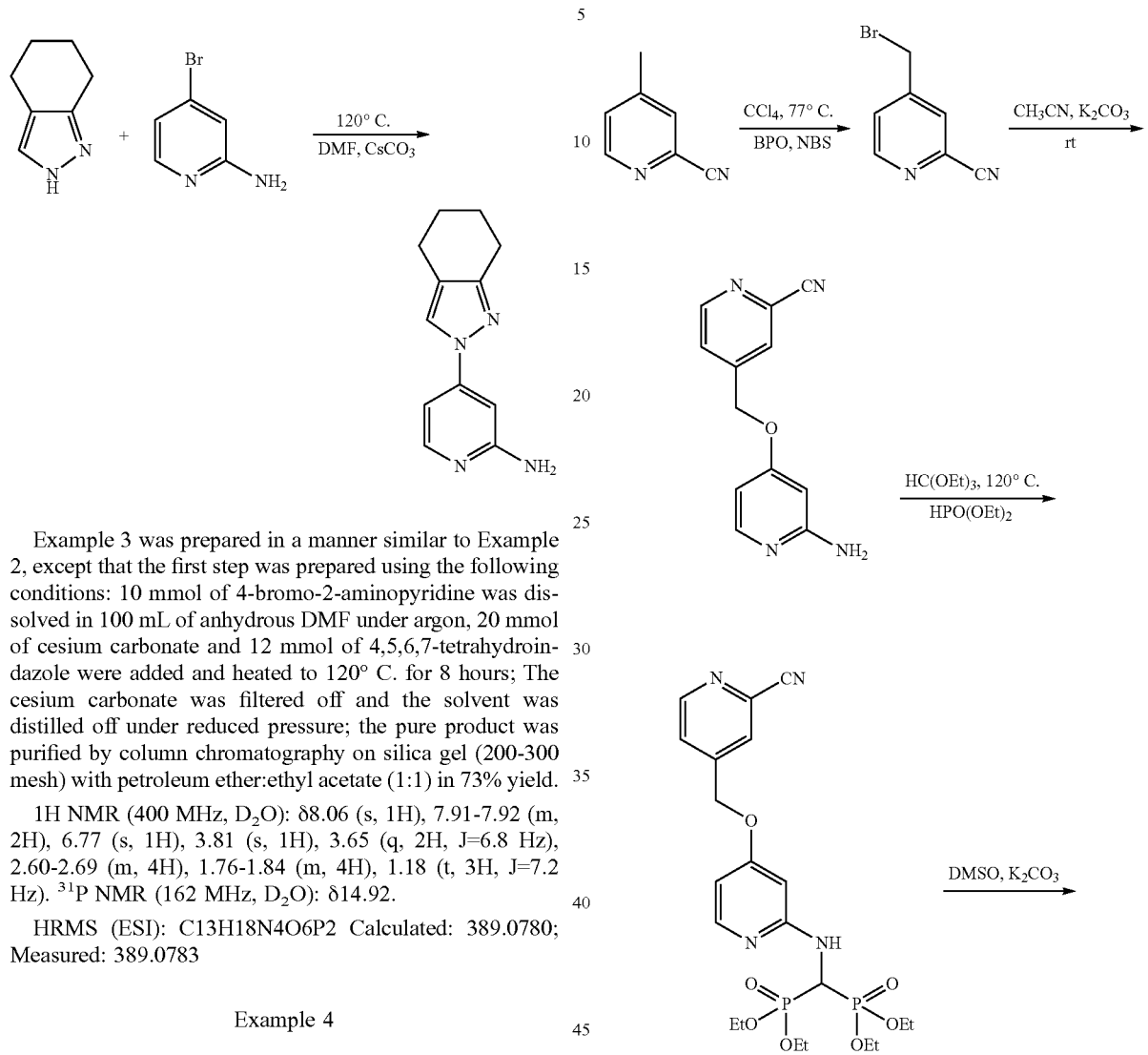

Example 3 was prepared in a manner similar to Example 2, except that the first step was prepared using the following conditions: 10 mmol of 4-bromo-2-aminopyridine was dissolved in 100 mL of anhydrous DMF under argon, 20 mmol of cesium carbonate and 12 mmol of 4,5,6,7-tetrahydroindazole were added and heated to 120° C. for 8 hours; The cesium carbonate was filtered off and the solvent was distilled off under reduced pressure; the pure product was purified by column chromatography on silica gel (200-300 mesh) with petroleum ether:ethyl acetate (1:1) in 73% yield.

1H NMR (400 MHz, D$_2$O): δ8.06 (s, 1H), 7.91-7.92 (m, 2H), 6.77 (s, 1H), 3.81 (s, 1H), 3.65 (q, 2H, J=6.8 Hz), 2.60-2.69 (m, 4H), 1.76-1.84 (m, 4H), 1.18 (t, 3H, J=7.2 Hz). $^{31}$P NMR (162 MHz, D$_2$O): δ14.92.

HRMS (ESI): C13H18N4O6P2 Calculated: 389.0780; Measured: 389.0783

Example 4

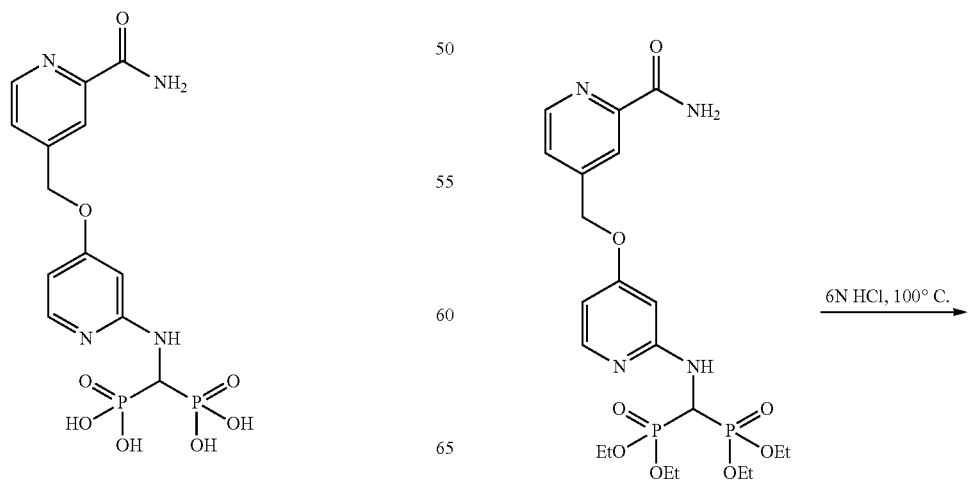

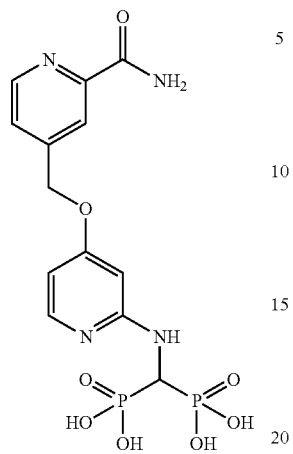

Step 1: 10 mol of 2-cyano-4-methylpyridine was dissolved in 100 mL of carbon tetrachloride. 11 mol of benzoyl peroxide and 11 mol of bromosuccinimide were added and reacted at 77° C. for 4 hours. The solvent was distilled off under reduced pressure. The pure product was purified by column chromatography on silica gel (200-300 mesh) with petroleum ether:ethyl acetate (3:1) in 67% yield.

Step 2: 6 mmol of the product from the step 1 was dissolved in 50 mL of solvent. 12 mmol of potassium carbonate and 7.2 mmol of 4-hydroxy-2-aminopyridine were added and allowed to react overnight at room temperature. The potassium carbonate solid was filtered off and the acetonitrile solvent was distilled off under reduced pressure. The pure product was purified by column chromatography on silica gel (200-300 mesh) with petroleum ether:ethyl acetate (1:1) in 43% yield.

Step 3: 2.5 mmol of the product of the step 2, 6 mmol of diethyl phosphite and 10 mmol of triethyl orthoformate were dissolved in 20 mL of toluene and reacted at 120° C. overnight. Excess solvent was evaporated under reduced pressure. The pure product was purified by column chromatography on silica gel (200-300 mesh) with ethyl acetate: methanol (30:1) in 82% yield.

Step 4: 2.0 mmol of the product of the step 3 was dissolved in 10 mL of DMSO. 20 mL of 30% hydrogen peroxide and 3.0 mmol of potassium carbonate were added and the reaction was carried out at room temperature for 4 hours. The reaction mixture was extracted with ethyl acetate. The organic layer was dried over magnesium sulfate and filtered, and ethyl acetate was evaporated under reduced pressure. The resulting product was directly subjected to next reaction without isolation.

Step 5 is the same as Step 3 in example 2 with 78% overall yield in two steps.

$^1$H NMR (400 MHz, D$_2$O): δ8.71 (bs, 1H), 8.09 (bs, 2H), 7.67 (bs, 1H), 6.58 (bs, 2H), 5.39 (bs, 1H), 3.86-3.95 (t, 1H, 17.2 Hz). $^{31}$P NMR (162 MHz, D$_2$O): δ12.19.

HRMS (ESI): C13H16N4O8P2 Calculated: 419.0522; Measured: 419.0518

Example 5

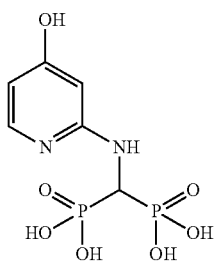 [SMILES: O=P(O)(O)C(Nc1cc(O)ccn1)P(=O)(O)O]

(((4-hydroxypyridin-2-yl)amino)methylene)bisphosphonic Acid

Example 5 was prepared in a manner similar to Example 2, except that benzyl bromide was used in the first step instead of hexyl bromide as a starting material and reacted at room temperature.

1H NMR (400 MHz, D$_2$O): δ7.41 (s, 1H), 5.88 (s, 1H), 5.69 (s, 1H), 3.51-3.60 (t, 2H, J=19.2 Hz)$^{31}$P NMR (162 MHz, D$_2$O): δ15.27.

HRMS (ESI): C6H10N2O7P2 Calculated: 284.0051; Measured: 284.0059

Example 6

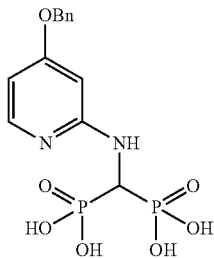 [SMILES: O=P(O)(O)C(Nc1cc(OCc2ccccc2)ccn1)P(=O)(O)O]

(((4-(benzyloxy)pyridin-2-yl)amino)methylene) bisphosphonic Acid

Example 6 was prepared in a manner similar to Example 5, except that trimethylsilyl bromide was used instead of 6N hydrochloric acid in the third step and hydrolysis was carried out in methylene chloride at room temperature.

1H NMR (400 MHz, D$_2$O): δ7.70-7.71 (d, 1H, J=6.0 Hz), 7.39-7.50 (m, 5H), 6.19-6.22 (m, 2H), 5.18 (s, 2H), 3.76 (bs, 1H). $^{31}$P NMR (162 MHz, D$_2$O): δ15.33.

HRMS (ESI): C13H16N2O7P2 Calculated: 375.0511; Measured: 375.0519.

Example 7

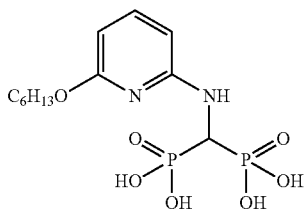

(((6-(hexyloxy)pyridin-2-yl)amino)methylene)bisphosphonic Acid

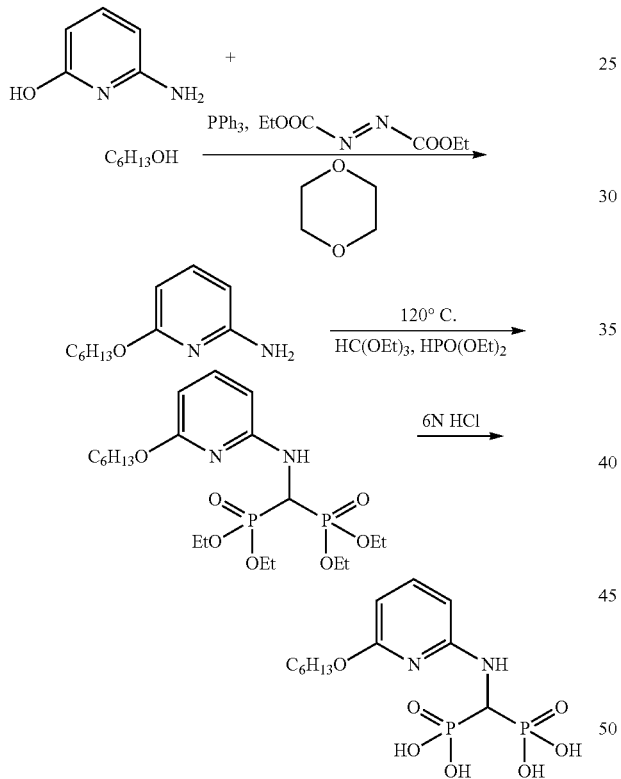

Example 7 was prepared in a manner similar to that of example 2 except for the first step.

Step 1: At room temperature, 10 mmol of 6-hydroxy-4-aminopyridine were dissolved in 100 mL of dioxane. 12 mmol of triphenylphosphine and diethyl azodicarboxylate were added, followed by the slow addition of 20 mmol of n-hexanol. After 4 hours of reaction, the reaction mixture was distilled under reduced pressure to remove the solvent. The pure product was purified by column chromatography on silica gel (200-300 mesh) with petroleum ether:ethyl acetate (2:1) in 85% yield.

The other reaction steps were the same as Example 2.

1H NMR (400 MHz, D$_2$O): δ7.62 (d, 1H, J=2.4 Hz), 7.43 (dd, 1H, J1=9.2 Hz, J2=2.4 Hz), 7.62 (d, 1H, J=9.2 Hz), 4.03 (t, 2H, J=6.4 Hz), 3.96 (t, 1H, J=19.2 Hz), 1.71-1.78 (m, 2H), 1.43-1.46 (m, 2H), 1.33-1.34 (m, 4H), 0.89 (t, 3H, J=6.8 Hz). $^{31}$P NMR (162 MHz, D$_2$O): δ13.5.

HRMS (ESI): C12H22N2O7P2 Calculated: 369.0980; Measured: 369.0973.

Example 8

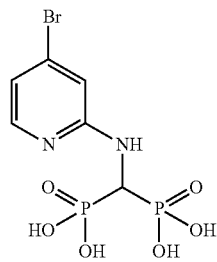 [SMILES: O=P(O)(O)C(Nc1cc(Br)ccn1)P(=O)(O)O]

(((4-bromopyridin-2-yl)amino)methylene)bisphosphonic Acid

Example 8 was prepared in a manner similar to Example 2, except that 2-amino-4-bromopyridine was used as the starting material in the first step.

1H NMR (400 MHz, D$_2$O): δ7.67 (s, 1H), 7.09-7.13 (m, 1H), 6.84-6.86 (m, 1H), 4.06 (t, 1H, J=19.2 Hz). $^{31}$P NMR (162 MHz, D$_2$O): δ13.5.

HRMS (ESI): C6H9BrN2O6P2 Calculated: 347.9143; Measured: 347.9145.

Example 9

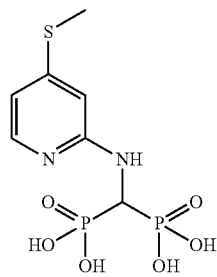 [SMILES: CSc1ccnc(NC(P(=O)(O)O)P(=O)(O)O)c1]

(((4-(methylthio)pyridin-2-yl)amino)methylene)bisphosphonic Acid

Example 9 was prepared in a manner similar to Example 2, except that 2-amino-4-thiopyridine and methyl iodide were used as starting materials in the first step.

1H NMR (400 MHz, D$_2$O): δ7.36 (s, 1H), 6.61 (s, 1H), 6.51 (s, 1H), 3.82 (t, 1H, J=16.0 Hz), 2.46 (s, 3H). $^{31}$P NMR (162 MHz, D$_2$O): δ13.0.

HRMS (ESI): C7H12N2SO6P2 Calculated: 314.9969; Measured: 314.9969.

Example 10

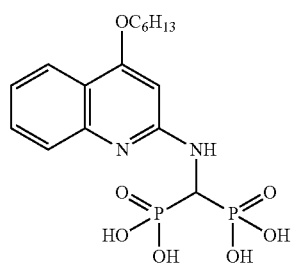

(((4-(hexyloxy)quinolin-2-yl)amino)methylene)bisphosphonic Acid

Example 10 was prepared in a manner similar to Example 2, except that 2-amino-4-hydroxyquinoline was used as the starting material in the first step.

1H NMR (400 MHz, D$_2$O): δ7.98 (d, 1H, J=8.0 Hz), 7.58 (d, 1H, J=8.0 Hz), 7.51 (t, 1H, J=8.0 Hz), 7.21 (t, 1H, J=8.0 Hz), 6.0 (s, 1H), 4.1 (t, 2H, J=6.4 Hz), 3.80 (t, 1H, J=20.0 Hz), 1.90-2.04 (m, 2H), 1.52-1.54 (m, 2H), 1.37-1.38 (m, 2H), 1.23-1.25 (m, 4H), 0.92 (s, 3H, J=6.4 Hz). $^{31}$P NMR (162 MHz, D$_2$O): δ13.1.

HRMS (ESI): C16H24N2O7P2 Calculated: 419.1137; Measured: 419.1145.

Example 11

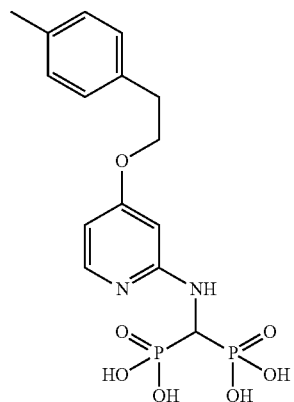 [SMILES: Cc1ccc(CCOc2ccnc(NC(P(=O)(O)O)P(=O)(O)O)c2)cc1]

(((4-(4-methylphenethoxy)pyridin-2-yl)amino)methylene)bisphosphonic Acid

Example 11 was prepared in a manner similar to Example 2, except that 1-(2-bromo-ethyl)-4-methyl-benzene was used as the starting material in the first step.

1H NMR (400 MHz, D$_2$O): δ7.49 (d, 1H, J=6.0 Hz), 7.20-7.27 (m, 5H), 6.34 (s, 1H), 6.23 (d, 1H, J=6.0 Hz), 4.37 (t, 1H, J=6.0 Hz), 3.80 (t, 1H, J=18.4 Hz), 3.07 (t, J=5.6 Hz), 2.30 (s, 3H), 2.21 (s, 3H). $^{31}$P NMR (162 MHz, D$_2$O): δ13.1.

HRMS (ESI): C15H20N2O7P2 Calculated: 403.0824; Measured: 403.0829.

Example 12

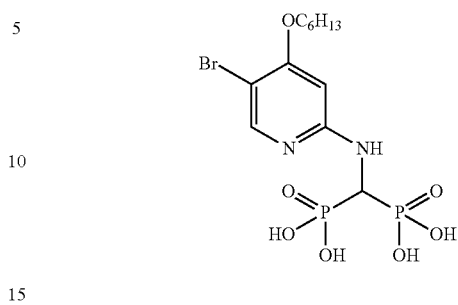

(((5-bromo-4-(hexyloxy)pyridin-2-yl)amino)methylene)bisphosphonic Acid

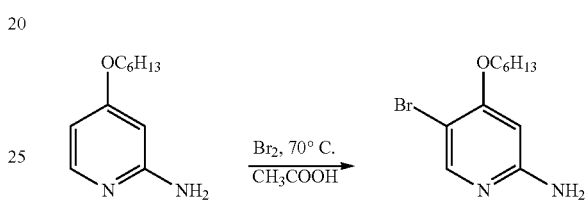

Example 12 was prepared in a manner similar to Example 2, except that the intermediate 4-hexyloxy-2-aminopyridine in example 2 was subjected to bromination. The operation were as follows: 10 mmol of 4-hexyloxy-2-aminopyridine was dissolved in 30 mL of glacial acetic acid; 11 mmol of bromine was added at room temperature and heated to 70° C. for 4 hours; the reaction was then quenched with saturated sodium thiosulfate solution and extracted with ethyl acetate; the organic layer was dried over anhydrous magnesium sulfate and concentrated under reduced pressure; the pure product was purified by column chromatography on silica gel (200-300 mesh) with petroleum ether:ethyl acetate (1:1) in 73% yield.

1H NMR (400 MHz, D$_2$O): δ7.75 (s, 1H), 6.10 (s, 1H), 4.06 (t, 2H, J=8.0 Hz), 3.68 (bs, 1H), 1.66-1.73 (m, 2H), 1.34-1.35 (m, 2H), 1.22 (s, 4H), 0.76 (t, 3H, J=6.8 Hz). $^{31}$P NMR (162 MHz, D$_2$O): δ15.5.

HRMS (ESI): C12H21BrN2O7P2 Calculated: 448.0032; Measured: 448.0033.

Example 13

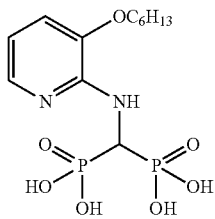

(((3-(hexyloxy)pyridin-2-yl)amino)methylene)bisphosphonic Acid

Example 13 was prepared in a manner similar to Example 2, except that 2-amino-3-hydroxypyridine was used as the starting material in the first step.

1H NMR (400 MHz, D$_2$O): δ7.39 (d, 1H, J=6.4 Hz), 7.29 (d, 1H, J=8.0 Hz), 6.82 (t, J=7.2 Hz), 4.18 (t, 2H, J=6.8 Hz), 4.10 (t, 1H, J=20.4 Hz), 1.81-1.88 (m, 2H), 1.44 (s, 2H), 1.32 (s, 4H), 0.87 (t, 3H, J=6.8 Hz). $^{31}$P NMR (162 MHz, D$_2$O): δ11.1.

HRMS (ESI): C12H22N2O7P2 Calculated: 369.0980; Measured: 369.0978.

Example 14

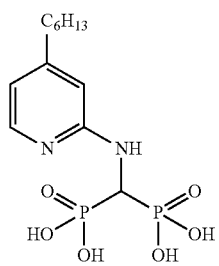

(((4-hexylpyridin-2-yl)amino)methylene)bisphosphonic Acid

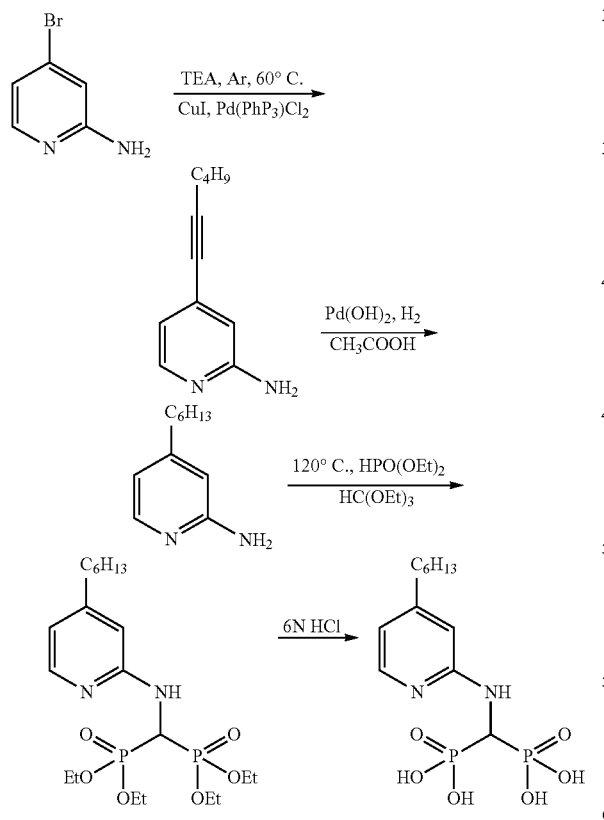

Step 1: 10 mmol of 2-amino-4-bromopyridine was dissolved in 100 mL of dry tetrahydrofuran. 10 ml of triethylamine, 15 mmol of 1-hexyne, 0.5 mmol of cuprous iodide, and 1 mmol of triphenylphosphinepalladium chloride were added, and the reaction was carried out at 60° C. for 4 hours under argon. The solvent was distilled off under reduced pressure. The pure product was purified by column chromatography on silica gel (200-300 mesh) with petroleum ether:ethyl acetate (3:1) in 88% yield.

Step 2: 8.8 mmol of the product of the first step was dissolved in 50 mL of acetic acid. After adding 200 mg of palladium hydroxide, the hydrogen reduction reaction was carried out for 24 hours. The palladium hydroxide was filtered through celite and the acetic acid was evaporated under reduced pressure. The pure product was purified by column chromatography on silica gel (200-300 mesh) with petroleum ether:ethyl acetate (2:1) in 95% yield.

The other reaction steps were similar to the second and third steps in Example 2.

1H NMR (400 MHz, D$_2$O): δ7.63 (d, 1H, J=6.0 Hz), 6.90 (s, 1H), 6.73 (d, J=5.6 Hz), 4.04 (t, 1H, J=19.6 Hz), 2.64 (s, 2H), 1.62 (s, 2H), 1.28 (s, 6H), 0.84 (s, 3H). $^{31}$P NMR (81 MHz, D$_2$O): δ11.7.

HRMS (ESI): C12H22N2O6P2 Calculated: 353.1031; Measured: 353.1037

Example 15

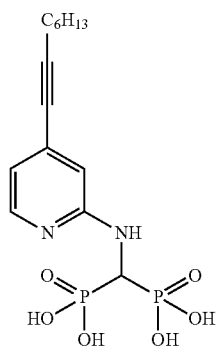

(((4-(oct-1-yn-1-yl)pyridin-2-yl)amino)methylene) bisphosphonic Acid

Example 15 was prepared in a manner similar to Example 14, except that 1-octyne was used as the starting material in the first step. The third step of the reaction was carried out in the absence of the hydrogen reduction of the second step.

1H NMR (400 MHz, D$_2$O): δ7.64 (d, 1H, J=5.6 Hz), 7.03 (s, 1H), 6.63 (d, J=6.0 Hz), 4.06 (t, 2H, J=19.6 Hz), 2.45 (s, 2H), 1.56-1.58 (m, 2H), 1.41 (s, 2H), 1.29 (s, 4H), 0.86 (s, 3H). $^{31}$P NMR (162 MHz, D$_2$O): δ11.6.

HRMS (ESI): C14H22N2O6P2 Calculated: 377.1031; Measured: 377.1033.

Example 16

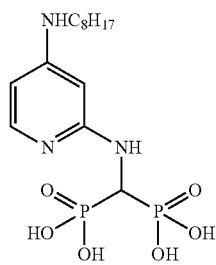

(((4-(octylamino)pyridin-2-yl)amino)methylene)bisphosphonic Acid

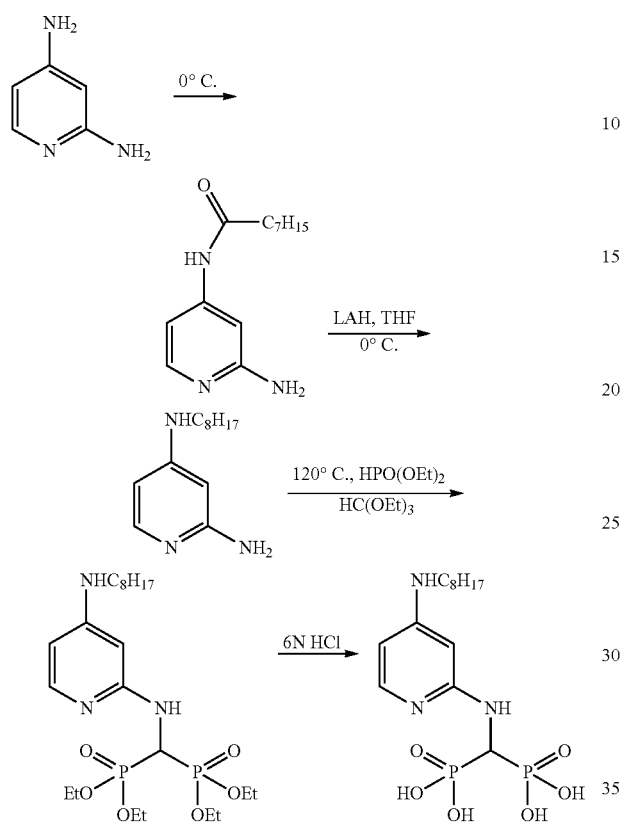

Step 1: 10 mmol 2,4-diaminopyridine was dissolved in 100 mL pyridine and cooled to 0° C. Octyl chloride was slowly added dropwise to the reaction solution. After 4 hours of reaction, the solvent was removed under reduced pressure. The pure product was purified by column chromatography on silica gel (200-300 mesh) with petroleum ether: ethyl acetate (1:1) in 37% yield.

Step 2: The product of the first step (3 mmol) was dissolved in 50 mL of anhydrous tetrahydrofuran and cooled to 0° C. 5 mmol of lithium aluminum hydride was slowly added and the reaction was continued for 2 hours. The reaction was quenched with saturated ammonium chloride solution and extracted with 150 mL of ethyl acetate. The organic phase was dried over anhydrous magnesium sulfate and concentrated under reduced pressure. The pure product was purified by column chromatography on silica gel (200-300 mesh) with petroleum ether:ethyl acetate (1:1) in 89% yield.

Reactions of Step 3 and Step 4 were similar to those of Step 2 and Step 3 in example 2.

1H NMR (400 MHz, D$_2$O): δ7.72 (s, 1H), 7.62 (s, 1H), 7.05 (s, 1H), 4.11 (t, 2H, J 6.8 Hz), 3.55 (t, 1H, J=14.4 Hz), 1.76-1.79 (m, 2H), 1.43-1.45 (m, 2H), 1.29-1.33 (m, 8H), 0.89 (t, 3H, J=6.8 Hz). $^{31}$P NMR (162 MHz, D$_2$O): δ13.5.

HRMS (ESI): C14H27N3O6P2 Calculated: 396.1463; Measured: 396.1471.

Example 17

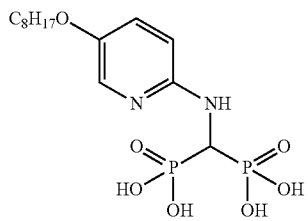

(((5-(octyloxy)pyridin-2-yl)amino)methylene)bisphosphonic Acid

Example 17 was prepared in a manner similar to Example 2, except that 5-hydroxy-2-aminopyridine and n-octanol were used as starting materials in the first step.

1H NMR (400 MHz, D$_2$O): δ7.76-7.71 (M, 2H), 6.89-6.91 (m, 1H), 4.02 (t, 2H, J=8.0 Hz), 3.88 (t, 1H, J=20.0 Hz), 1.78-1.85 (m, 2H), 1.45-1.49 (m, 2H), 1.34-1.36 (m, 8H), 0.91 (t, 3H, J=6.4 Hz). $^{31}$P NMR (162 MHz, D$_2$O): δ13.5.

HRMS (ESI): C14H26N2O7P2 Calculated: 397.1293; Measured: 397.1298.

Example 18

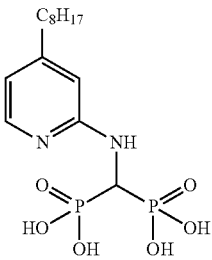

(((4-octylpyridin-2-yl)amino)methylene)bisphosphonic Acid

Example 18 was prepared in a manner similar to Example 14, except that 1-octyne was used as the starting material in the first step.

1H NMR (400 MHz, D$_2$O): δ7.65 (d, 1H, J=6.0 Hz), 6.92 (s, 1H), 6.75 (d, J=5.6 Hz), 4.06 (t, 1H, J=19.6 Hz), 2.65 (s, 2H), 1.64 (s, 2H), 1.29 (s, 10H), 0.85 (s, 3H). $^{31}$P NMR (162 MHz, D$_2$O): δ11.8.

HRMS (ESI): C14H26N2O6P2 Calculated: 381.1316; Measured: 381.1320.

Example 19

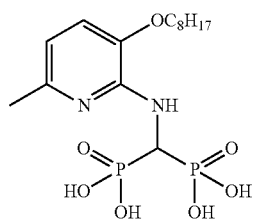

(((6-methyl-3-(octyloxy)pyridin-2-yl)amino)methylene)bisphosphonic Acid

Example 19 was prepared in a similar manner to Example 2, except that 2-amino-3-hydroxy-6-methylpyridine was used as a starting material in the first step.

1H NMR (400 MHz, D$_2$O): δ7.37 (d, 1H, J=7.2 Hz), 7.21 (d, 1H, J=7.2 Hz), 4.02 (t, 2H, J=8.0 Hz), 3.88 (t, 1H, J=20.0 Hz), 2.43 (s, 3H), 1.78-1.85 (m, 2H), 1.45-1.49 (m, 2H), 1.34-1.36 (m, 12H), 0.91 (t, 3H, J=6.4 Hz). $^{31}$P NMR (162 MHz, D$_2$O): δ13.5.

HRMS (ESI): C15H29N2O7P2 Calculated: 411.1421; Measured: 411.1417.

Example 20

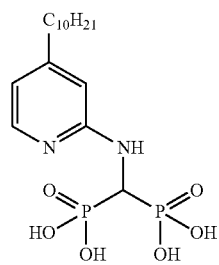

(((4-decylpyridin-2-yl)amino)methylene)bisphosphonic Acid

This compound was synthesized analogously to the method of example 20, except that in the first step 1-decyne was used as starting material.

1H NMR (400 MHz, D$_2$O): δ7.63 (d, 1H, J=6.0 Hz), 6.89 (s, 1H), 6.72 (d, J=5.6 Hz), 4.02 (t, 1H, J=19.6 Hz), 2.61 (s, 2H), 1.61 (s, 2H), 1.27 (s, 14H), 0.82 (s, 3H). $^{31}$P NMR (162 MHz, D$_2$O): δ11.5.

HRMS (ESI): C16H30N2O6P2 Calculated: 410.1657; Measured: 410.1663.

Example 21

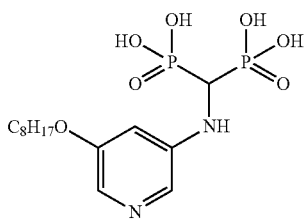

(((5-(octyloxy)pyridin-3-yl)amino)methylene)bisphosphonic Acid

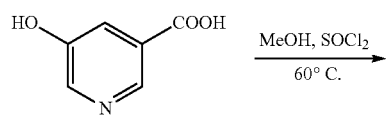

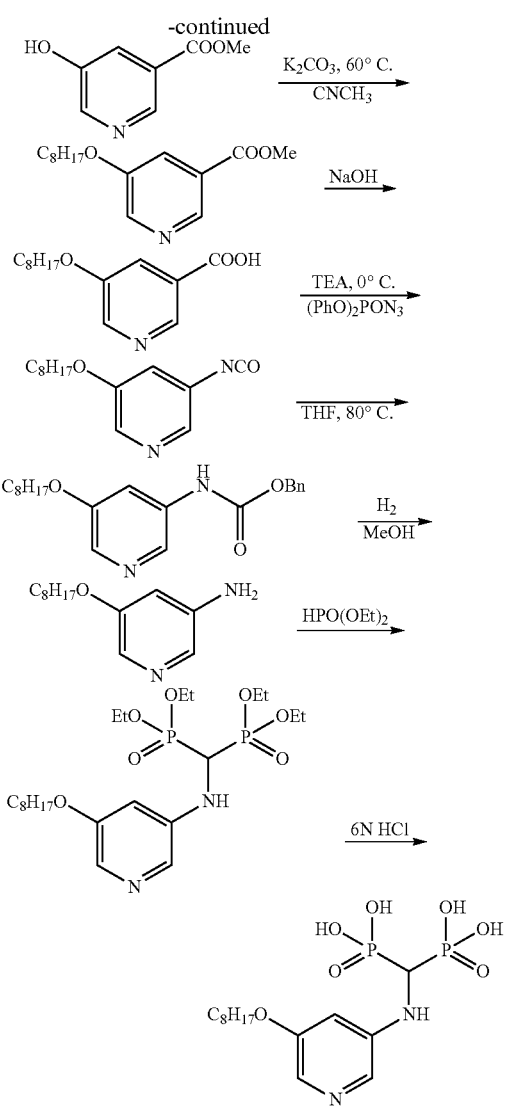

Step 1: 10 mmol of 5-hydroxy-3-carboxypyridine was dissolved in 100 mL of methanol. 5 mL of thionyl chloride was slowly added and reacted at 60° C. for 4 hours. The solvent was distilled off under reduced pressure. The resulting product was used in the next reaction without purification.

Step 2: The product of the first step was dissolved in 150 mL of acetonitrile. 30 mmol of potassium carbonate was added and reacted at 60° C. overnight. The solid was filtered off and the solvent was distilled off under reduced pressure. The pure product was purified by column chromatography on silica gel (200-300 mesh) with petroleum ether:ethyl acetate (1:1) in 73% yield over two steps.

Step 3: 7.3 mmol of product was dissolved in 100 mL of dioxane. 20 mL of 4N NaOH was added and reacted for 8 hours at room temperature. After the reaction was completed, the pH was adjusted to 6 with dilute hydrochloric acid. The mixture was extracted with 200 mL of ethyl acetate, and the organic phase was dried over anhydrous magnesium sulfate. The solvent was distilled off under reduced pressure. The crude product was used directly in the next reaction without purification.

Step 4: The crude product of the step 3 was dissolved in 150 mL of dichloromethane. 10 mL of triethylamine was added at 0° C. and 8 mmol of diphenyl azidophosphate was slowly added dropwise. After 4 hours, the reaction reached room temperature. The solvent was distilled off under reduced pressure. The product was used in the next reaction without isolation.

Step 5: In a pressure tube, the crude product from the previous step was dissolved in 100 mL of tetrahydrofuran. 10 mL of benzyl alcohol was added and reacted at 90° C. for 8 hours. The solvent was distilled off under reduced pressure. The pure product was purified by column chromatography on silica gel (200-300 mesh) with petroleum ether:ethyl acetate (3:1) in a total yield of 78% over three steps.

Step 6: The product from the previous step was dissolved in 100 mL of methanol. 500 mg of palladium on carbon was added and the reaction was reduced with hydrogen for 24 hours at room temperature. The palladium on carbon was filtered off through celite and the filtrate was concentrated under reduced pressure. The pure product was purified by column chromatography on silica gel (200-300 mesh) with petroleum ether:ethyl acetate (1:1) in 97% yield.

The remaining two reaction steps were the same as steps 2 and 3 in Example 2.

1H NMR (400 MHz, D$_2$O): δ7.62 (s, 1H), 7.42 (s, 1H), 6.73 (s, 1H), 4.11 (t, 2H, J 6.8 Hz), 3.55 (t, 1H, J=14.4 Hz), 1.76-1.79 (m, 2H), 1.43-1.45 (m, 2H), 1.29-1.33 (m, 8H), 0.89 (t, 3H, J=6.8 Hz). $^{31}$P NMR (162 MHz, D$_2$O): δ13.5.

HRMS (ESI): C14H26N2O7P2 Calculated: 397.1293; Measured: 397.1298.

Example 22

Preparation of TH-Z144

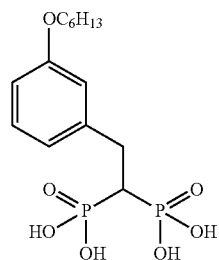

(2-(3-(hexyloxy)phenyl)ethane-1,1-diyl)bisphosphonic Acid

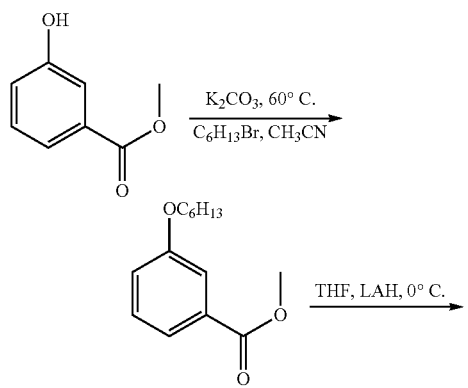

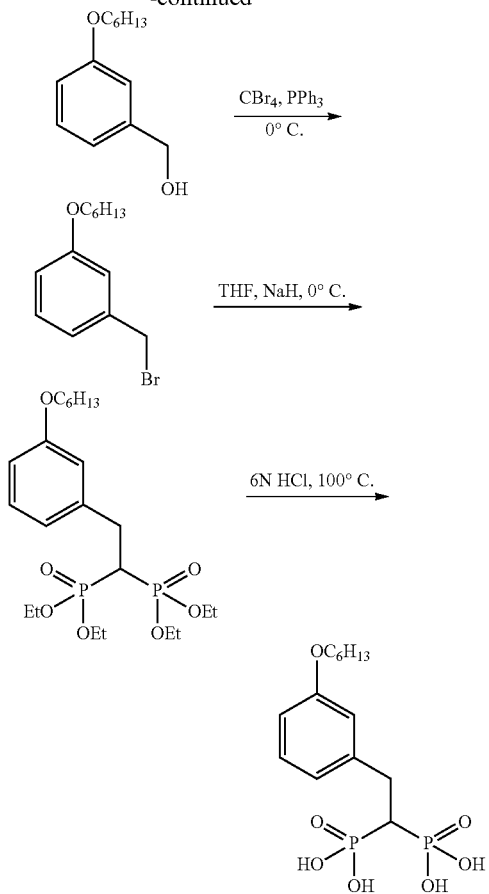

Step 1: 10 mmol of starting material methyl 3-hydroxybenzoate was dissolved in 100 mL of acetonitrile. 20 mmol of potassium carbonate and 12 mmol of 1-bromo-n-hexane were added. The mixture was allowed to react overnight at 60° C. under nitrogen. The reaction was cooled to room temperature. The potassium carbonate was filtered off and the filtrate was concentrated under reduced pressure. The crude product was used for the next reaction without column separation.

Step 2: The product of the previous step was dissolved in 200 mL of anhydrous tetrahydrofuran at 0° C. 20 mmol of lithium aluminum hydride was added in portions and the reaction was continued at 0° C. for 4 hours. By TLC, it was found that the starting material reacted almost completely. The reaction was quenched with saturated ammonium chloride and extracted with 200 mL of ethyl acetate. The organic phase was dried over anhydrous magnesium sulphate. The pure product was purified by column chromatography on silica gel (200-300 mesh) with petroleum ether:ethyl acetate (8:1) in a yield of 90% over two steps.

Step 3: The product from the previous step was dissolved in 100 mL of anhydrous dichloromethane. At 0° C., 10.8 mmol of triphenylphosphine was added, and then a solution of 10.8 mmol of carbon tetrabromide in dichloromethane was slowly added dropwise. The reaction was continued for 4 hours and TLC showed complete reaction of the starting material. The methylene chloride was distilled off under reduced pressure. The pure product was purified by column chromatography on silica gel (200-300 mesh) with petroleum ether:ethyl acetate (30:1) in 95% yield.

Step 4: 6 mmol of tetraethyl methylenebis(phosphonate) were dissolved in 100 mL of anhydrous tetrahydrofuran. 7 mmol of sodium hydride was added at 0° C. After the reaction was carried out for 30 minutes, 8 mmol of the product from the previous step was dissolved in 10 mL of anhydrous tetrahydrofuran and added dropwise to the above mixture. The reaction reached room temperature. Thin layer chromatography showed that most of the raw materials reacted. 100 mL of saturated sodium chloride solution was added, and the mixture was extracted with 200 mL of ethyl acetate. The organic phase was dried over anhydrous magnesium sulphate. The pure product was purified by column chromatography on silica gel (200-300 mesh) with petroleum ether:ethyl acetate (3:1) in 75% yield.

Step 5: 50 mL of 6 N hydrochloric acid was added to the product of the previous step, and reacted at 100° C. for 10 hours. Hydrochloric acid was distilled off under reduced pressure. The crude product was washed three times with acetone under ultrasonic sound to give the pure product in 93% yield.

1H NMR (400 MHz, MeOD): δ7.13-7.17 (t, 1H, J=8.0 Hz), 6.88-6.90 (m, 2H), 6.71-6.74 (dd, J1=8.0 Hz, J2=2.4 Hz), 3.93-3.97 (t, 2H, J=6.4 Hz), 3.14-3.24 (td, 2H, J1=16.8 Hz, J2=6.0 Hz), 2.43-2.58 (m, 1H), 1.72-1.79 (m, 2H), 1.44-1.51 (m, 2H), 1.34-1.37 (m, 4H), 0.91-0.94 (t, 3H, J=8.0 Hz). $^{31}$P NMR (162 MHz, MeOD): δ21.78. HRMS (ESI): C16H28O7P2 Calculated: 367.1080; Measured: 367.1081

Example 23

Preparation of TH-Z145

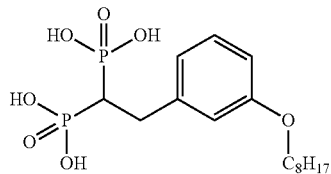

(2-(3-(octyloxy)phenyl)ethane-1,1-diyl)bisphosphonic Acid

TH-Z145 was prepared in a manner similar to H-Z144, except that 1-bromo-n-octane was used in the first step instead of 1-bromo-n-hexane as a starting material and reacted at 60° C.

1H NMR (400 MHz, MeOD): δ7.13-7.18 (t, 1H, J=8.0 Hz), 6.86-6.88 (m, 2H), 6.70-6.73 (dd, J1=8.0 Hz, J2=2.4 Hz), 3.90-3.94 (t, 2H, J=6.4 Hz), 3.12-3.22 (td, 2H, J1=16.8 Hz, J2=6.0 Hz), 2.40-2.55 (m, 1H), 1.70-1.77 (m, 2H), 1.42-1.49 (m, 2H), 1.33-1.36 (m, 8H), 0.90-0.93 (t, 3H, J=8.0 Hz). $^{31}$P NMR (162 MHz, MeOD): δ21.67. HRMS (ESI): C14H24O7P2 Calculated: 395.1393; Measured: 395.1387.

Example 24

Preparation of TH-Z80: TH-Z80 was Prepared According to the Following Synthetic Route

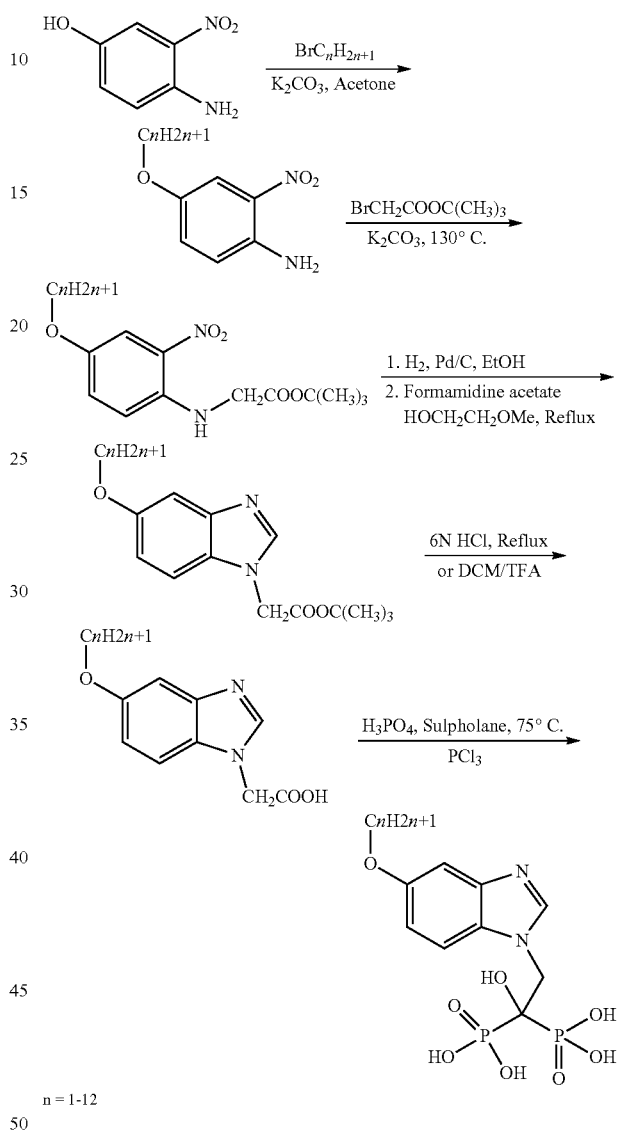

n = 1-12

Step 1: 10 mmol (1.54 g) of 3-nitro-4-aminophenol was dissolved in 50 mL of acetone. 30 mmol of anhydrous potassium carbonate was added. After heating to reflux under N2 protection, 12 mmol (1.67 mL) of bromohexane was added. After reacting overnight, the insolubles were filtered and the organic phase was rotary evaporated to dryness. The crude product was loaded and purified by petroleum ether/ethyl acetate to give 7.3 mmol (1.74 g) of 4-hexyloxy-2-nitro-aniline (yield: 73%).

Step 2: 5 mmol (1.19 g) of 4-hexyloxy-2-nitro-aniline, 60 mmol (9.69 mL) of tert-butyl bromoacetate and 7.5 mmol (1.04 g) of anhydrous potassium carbonate were reacted at 110° C. for 12 h under N2 protection. Insolubles in the reaction solution were filtered, and the filtrate was rotary evaporated to dryness. The crude product was loaded and purified by petroleum ether/ethyl acetate to give 2.1 mmol (0.74 g) of tert-butyl (4-(hexyloxy)-2-nitrophenyl)glycinate in 42% yield.

Step 3: 2 mmol (0.70 g) of tert-butyl (4-(hexyloxy)-2-nitrophenyl)glycinate was dissolved in 10 mL of ethanol. 0.1 g of 5% palladium on carbon was added and reacted for 4 h under $H_2$. The mixture was filtered through celite and the organic phase was rotary evaporated to dryness. The resulting crude was dissolved in 10 mL of ethylene glycol monomethyl ether. 7 mmol (0.72 g) of formamidine acetate was added and heated to reflux for 4 h and then cooled. The reaction was rotary evaporated to dryness. The crude product was loaded on a column and passed through the column to give 0.7 mmol (0.23 g) of tert-butyl 2-(5-(hexyloxy)-1H-benzo[d]imidazol-1-yl)acetate in a total yield of 35% over two steps.

Step 4: 0.6 mmol (0.2 g) of tert-butyl 2-(5-(hexyloxy)-1H-benzo[d]imidazol-1-yl)acetate in 6 N HCl was heated to reflux for 6 h, rotary evaporated to dryness, and dried to constant weight. The crude product obtained was used directly in the next reaction.

Step 5: The resulting 2-5-(hexyloxy)-1H-benzo[d]imidazol-1-yl)acetic acid was dissolved with 1.8 mmol (0.15 g) of phosphorous acid and 1 mL of sulfolane at 75° C. 2 mmol (178 μL) of $PCl_3$ was then added dropwise. After 3.5 hours of reaction, 1 mL of water was added. The mixture was heated to reflux for 2h and then cooled. The precipitated solid was filtered and ultrafiltered with methanol three times. The resulting light yellow solid was dried to constant weight and then weighed to give 38 mg of the title product (15% yield).

Characterization data of structure: 1H NMR (400 MHz, $D_2O$), δ (ppm): 8.19 (s, 1H), 7.76 (d, J=8.9 Hz, 1H), 7.26 (d, J=2.2 Hz, 1H), 7.04 (dd, J1=8.9 Hz, J2=2.3 Hz, 1H,), 4.77 (m, 2H), 4.14 (t, J=6.6 Hz, 2H,), 1.79 (m, 2H), 1.47 (m, 2H), 1.33 (m, 4H), 0.88 (t, J=7.1 Hz, 3H), $^{13}C$ NMR (100 MHz, $D_2O$), δ(ppm): 154.18, 147.63, 142.09, 131.10, 113.20, 112.78, 102.72, 77.79, 76.49, 75.19, 69.96, 50.51, 30.80, 28.40, 24.91, 21.94, 13.32, $^{31}P$ NMR (162 MHz, $D_2O$), δ (ppm): 15.67

Referring to the above preparation method, the present disclosure also prepared compounds of the following Formula wherein n=1, 2, 3, 4, 5, 7, 8, 9, 10, 11 and 12, respectively:

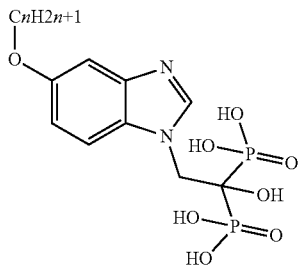

which were designated as TH-Z79, TH-Z148, TH-Z149, TH-Z150, TH-Z151, TH-Z152, TH-Z81, TH-Z153, TH-Z82, TH-Z154 and TH-Z155, respectively.

The starting material 4-hexyloxy-2-nitro-aniline from step 2 in the preparation of TH-Z80 was replaced with 4-hydroxy-2-nitroaniline, and the steps 2, 3, 4 and 5 were sequentially performed to obtain BPH-266 (corresponding to the compound of Formula I wherein R1, R2, R4 and R5=H, m=1, X=OH, M=H, n=0).

Except that TH-Z79 directly used 2-amino-4-methoxyaniline as starting material, other TH-Z80 series of compounds were synthesized according to the synthetic steps of TH-Z80.

The characterization data of the TH-Z80 series of compounds were as follows:

TH-Z79: characterization data of structure: $^1H$ NMR (400 MHz, $D_2O$), δ (ppm): 8.32 (s, 1H), 7.70 (d, J=7.6 Hz, 1H), 7.19 (s, 1H), 6.97 (d, J=7.6 Hz, 1H), 4.70 (s, 2H), 3.83 (t, J=7.0 Hz, 3H), $^{31}P$ NMR (162 MHz, $D_2O$), δ (ppm): 15.33

TH-Z81: characterization data of structure: $^1H$ NMR (400 MHz, $D_2O$), δ (ppm): 8.40 (s, 1H), 7.78 (d, J=9.0 Hz, 1H), 7.27 (s, 1H), 7.05 (d, J=9.0 Hz, 1H), 4.70 (s, 2H), 4.16 (t, 6.4 Hz, 2H), 1.81 (m, 2H), 1.47 (m, 2H), 1.29 (m, 8H), 0.87 (t, J=6.8 Hz, 3H)$^{31}P$ NMR (162 MHz, $D_2O$), δ (ppm): 15.60

TH-Z82: characterization data of structure: $^1H$ NMR (400 MHz, $D_2O$), δ (ppm): 8.40 (s, 1H), 7.78 (d, J=9.0 Hz, 1H), 7.27 (s, 1H), 7.05 (d, J=9.0 Hz, 1H), 4.72 (s, 2H), 4.16 (t, 6.4 Hz, 2H), 1.81 (m, 2H), 1.47 (m, 2H), 1.28 (m, 8H), 0.86 (t, J=6.8 Hz, 3H)$^{31}P$ NMR (162 MHz, $D_2O$), δ (ppm): 15.58

TH-Z148: characterization data of structure: $^1H$ NMR (400 MHz, $D_2O$), δ (ppm): 8.65 (s, 1H), 7.82 (d, J=9.0 Hz, 1H), 7.19 (s, 1H), 7.13 (d, J=9.0 Hz, 1H), 4.84 (s, 2H), 4.17 (q, 6.7 Hz, 2H),1.43 (t, J=6.8 Hz, 3H), $^{31}P$ NMR (162 MHz, $D_2O$), δ (ppm): 14.82

TH-Z149: characterization data of structure: $^1H$ NMR (400 MHz, $D_2O$), δ (ppm): 8.90 (s, 1H), 7.86 (d, J=9.0 Hz, 1H), 7.27 (s, 1H), 7.05 (d, J=9.0 Hz, 1H), 4.70 (s, 2H), 4.16 (t, 6.4 Hz, 2H), 1.81 (m, 2H), 1.47 (m, 2H), 1.29 (m, 8H), 0.87 (t, J=6.8 Hz, 3H), $^{31}P$ NMR (162 MHz, $D_2O$), δ (ppm): 15.60

TH-Z150: characterization data of structure: $^1H$ NMR (400 MHz, $D_2O$), δ (ppm): 8.39 (s, 1H), 7.77 (d, J=8.9 Hz, 1H), 7.28 (s, 1H), 7.05 (d, J=8.4 Hz, 1H), 4.74 (s, 2H), 4.15 (t, J=6.4 Hz, 2H), 1.78 (m, 2H), 1.48 (m, 2H), 0.96 (t, J=7.2 Hz, 3H), $^{31}P$ NMR (162 MHz, $D_2O$), δ (ppm): 15.60

TH-Z151: characterization data of structure: $^1H$ NMR (400 MHz, $D_2O$), δ (ppm): 8.37 (s, 1H), 7.76 (d, J=8.9 Hz, 1H), 7.26 (s, 1H), 7.05 (d, J=9.0 Hz, 1H), 4.73 (s, 2H), 4.14 (t, J=6.5 Hz, 2H), 1.79 (m, 2H), 1.46 (m, 2H), 1.36 (m, 2H), 0.90 (t, J=7.2 Hz, 3H)$^{31}P$ NMR (162 MHz, $D_2O$), δ (ppm): 14.02

TH-Z152: characterization data of structure: $^1H$ NMR (400 MHz, $D_2O$), δ (ppm): 8.34 (s, 1H), 7.74 (d, J=9.0 Hz, 1H), 7.27 (s, 1H), 7.06 (d, J=9.0 Hz, 1H), 4.72 (s, 2H), 4.14 (t, 6.4 Hz, 2H), 1.80 (m, 2H), 1.47 (m, 2H), 1.31 (m, 8H), 0.86 (t, J=6.4 Hz, 3H)$^{31}P$ NMR (162 MHz, $D_2O$), δ (ppm): 15.32

TH-Z153: characterization data of structure: $^1H$ NMR (400 MHz, $D_2O$), δ (ppm): 8.40 (s, 1H), 7.78 (d, J=9.0 Hz, 1H), 7.27 (s, 1H), 7.05 (d, J=9.0 Hz, 1H), 4.75 (s, 2H), 4.15 (t, 5.6 Hz, 2H), 1.80 (m, 2H), 1.47 (m, 2H), 1.29 (m, 10H), 0.87 (t, J=6.2 Hz, 3H)$^{31}P$ NMR (162 MHz, $D_2O$), δ (ppm): 15.41

TH-Z154: characterization data of structure: $^1H$ NMR (400 MHz, $D_2O$), δ (ppm): 8.32 (s, 1H), 7.76 (d, J=8.8 Hz, 1H), 7.29 (s, 1H), 7.07 (d, J=8.9 Hz, 1H), 4.73 (s, 2H), 4.16 (t, 6.4 Hz, 2H), 1.81 (m, 2H), 1.48 (m, 2H), 1.28 (m, 14H), 0.85 (t, J=6.4 Hz, 3H)$^{31}P$ NMR (162 MHz, $D_2O$), δ (ppm): 15.33

TH-Z155: characterization data of structure: $^1H$ NMR (400 MHz, $D_2O$), δ (ppm): 8.37 (s, 1H), 7.78 (d, J=8.9 Hz, 1H), 7.28 (s, 1H), 7.05 (d, J=9.0 Hz, 1H), 4.72 (s, 2H), 4.16 (t, 6.4 Hz, 2H), 1.81 (m, 2H), 1.47 (m, 2H), 1.29 (m, 16H), 0.86 (t, J=6.8 Hz, 3H)$^{31}P$ NMR (162 MHz, $D_2O$), δ (ppm): 15.39

This application refers to various issued patents, published patent applications, journal articles, and other publications, all of which are incorporated herein by reference. If any of the references cited conflict with this description, the present specification shall control. In addition, any particular embodiment of the present disclosure that falls within the purview of the prior art may be expressly excluded from any one or more of the claims. As the described embodiments are to be considered as known to those skilled in the art, they can be excluded, even if the exclusion is not explicitly listed in this application. Any particular embodiment of the present disclosure may be excluded from any claim for any reason in the presence or absence of the prior art.

Using only routine experimentation, one of ordinary skill in the art will recognize, or be able to determine many equivalents to the specific embodiments described herein. The scope of the embodiments of the present disclosure described herein is not intended to be limited to the above description, but rather as set forth in the appended claims. It will be understood by those skilled in the art that various changes and modifications to the description can be made without departing from the spirit or scope of the invention as defined by the claims.

What is claimed is:

1. A method for enhancing the specific immune responses induced by antigens in a subject, wherein the method comprises administering to the subject an immunogenic composition comprising an adjuvant, wherein the adjuvant is a compound of the following Formula or a pharmaceutically acceptable salt, ester, prodrug, or solvate thereof:

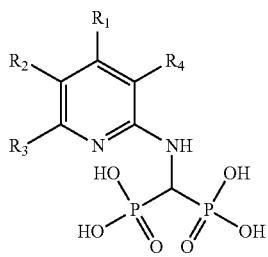

wherein:
   $R_1$ is selected from the group consisting of alkenyl, alkynyl, alkoxy, alkylamino, alkylthio, and cycloalkyl, with a proviso that $R_1$ is not methoxy, wherein the alkyl group in said alkoxy group is optionally substituted with aryl, heteroaryl or heterocyclyl, wherein said aryl, heteroaryl or heterocyclyl is optionally substituted with alkyl or carbamoyl;
   $R_2$ is selected from the group consisting of hydrogen, alkyl, alkoxy, alkylamino, alkylthio, halogen, hydroxy, cycloalkyl, heterocyclyl, aryl and heteroaryl;
   $R_3$ is selected from the group consisting of hydrogen, alkyl, alkoxy, alkylamino, alkylthio, halogen, hydroxy, cycloalkyl, heterocyclyl, aryl and heteroaryl;
   or $R_2$ and $R_3$ together with the carbon atom to which they are attached form an aromatic or heteroaromatic ring; and
   $R_4$ is selected from the group consisting of hydrogen, alkyl, alkoxy, alkylamino, alkylthio, halogen, hydroxy, cycloalkyl, heterocyclyl, aryl and heteroaryl, wherein the antigen is derived from anthrax, *campylobacter*, cholera, diphtheria, enterotoxigenic *Escherichia coli*, giardia, *Neisseria gonorrhoeae*, *Helicobacter pylori*, *Haemophilus influenzae* type B, *haemophilus* influenza of an unknown type, meningitis cocci, pertussis, pneumococcus, *salmonella, shigella, streptococcus* B, *streptococcus* of a group A, tetanus, *Vibrio cholerae, yersinia, staphylococcus, pseudomonas* species, *clostridium* species, adenovirus, dengue serotype 1 to 4, ebola virus, enterovirus, hepatitis serotype A to E, herpes simplex virus 1 or 2, human immunodeficiency virus, influenza, Japanese equine encephalitis, measles, norwalk, papilloma virus, parvovirus B19, poliomyelitis, rabies, rotavirus, rubella, measles, vaccinia lymph, vaccinia lymph constructs containing genes encoding other antigens selected from malaria antigens, chickenpox, and yellow fever, *entamoeba histolytica*, malaria parasite, toxoplasmosis, worms, or tumors.

2. The method of claim 1, wherein the adjuvant is:

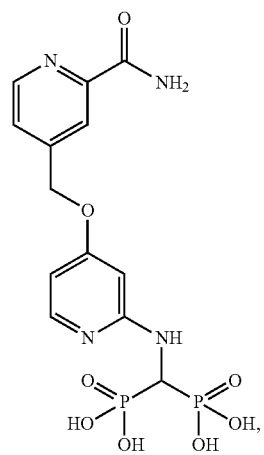 [SMILES: NC(=O)c1cc(COc2ccnc(NC(P(=O)(O)O)P(=O)(O)O)c2)ccn1]

or a pharmaceutically acceptable salt, ester, prodrug, or solvate thereof.

3. The method of claim 1, wherein the adjuvant is:

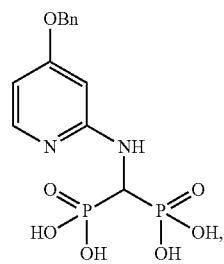 [SMILES: O=P(O)(O)C(Nc1cc(OCc2ccccc2)ccn1)P(=O)(O)O]

or a pharmaceutically acceptable salt, ester, prodrug, or solvate thereof.

4. The method of claim 1, wherein the adjuvant is:

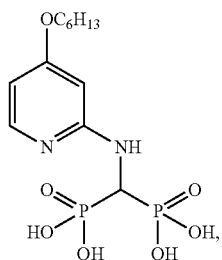

or a pharmaceutically acceptable salt, ester, prodrug, or solvate thereof.

5. The method of claim 1, wherein the adjuvant is:

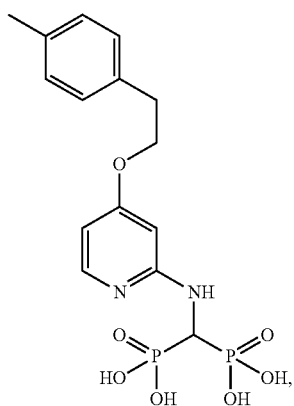 [SMILES: Cc1ccc(CCOc2ccnc(NC(P(=O)(O)O)P(=O)(O)O)c2)cc1]

or a pharmaceutically acceptable salt, ester, prodrug, or solvate thereof.

6. The method of claim 1, wherein the adjuvant is:

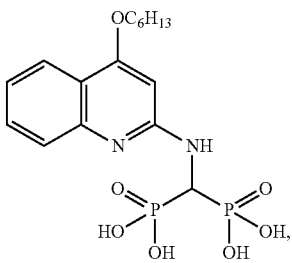

or a pharmaceutically acceptable salt, ester, prodrug, or solvate thereof.

7. The method of claim 1, wherein the adjuvant is:

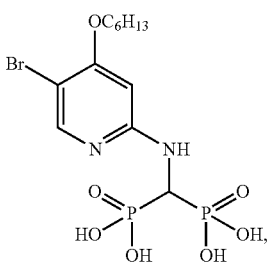

or a pharmaceutically acceptable salt, ester, prodrug, or solvate thereof.

* * * * *